US010196434B2

(12) United States Patent
Kumar et al.

(10) Patent No.: US 10,196,434 B2
(45) Date of Patent: Feb. 5, 2019

(54) ALK4:ACTRIIB HETEROMULTIMERS AND USES THEREOF

(71) Applicant: Acceleron Pharma Inc., Cambridge, MA (US)

(72) Inventors: Ravindra Kumar, Acton, MA (US); Asya Grinberg, Lexington, MA (US); Dianne Sako, Medford, MA (US); Robert Scott Pearsall, North Reading, MA (US); Roselyne Castonguay, Watertown, MA (US)

(73) Assignee: ACCELERON PHARMA INC., Cambridge, MA (US)

(*) Notice: Subject to any disclaimer, the term of this patent is extended or adjusted under 35 U.S.C. 154(b) by 51 days.

(21) Appl. No.: 15/092,573

(22) Filed: Apr. 6, 2016

(65) Prior Publication Data
US 2016/0289292 A1 Oct. 6, 2016

Related U.S. Application Data

(60) Provisional application No. 62/220,836, filed on Sep. 18, 2015, provisional application No. 62/143,579, filed on Apr. 6, 2015.

(51) Int. Cl.
C07K 14/705 (2006.01)
C07K 14/71 (2006.01)

(52) U.S. Cl.
CPC ............ C07K 14/705 (2013.01); C07K 14/71 (2013.01); C07K 2319/30 (2013.01)

(58) Field of Classification Search
CPC ... C07K 14/705; C07K 14/71; C07K 2319/30
See application file for complete search history.

(56) References Cited

U.S. PATENT DOCUMENTS

| 5,731,168 | A | 3/1998 | Carter et al. |
| 5,932,448 | A | 8/1999 | Tso et al. |
| 6,248,516 | B1 | 6/2001 | Winter et al. |
| 7,183,076 | B2 | 2/2007 | Arathoon et al. |
| 7,612,041 | B2 | 11/2009 | Knopf et al. |
| 7,709,605 | B2 | 5/2010 | Knopf et al. |
| 7,820,620 | B2 | 10/2010 | Vale et al. |
| 7,842,663 | B2 | 11/2010 | Knopf et al. |
| 8,067,360 | B2 | 11/2011 | Knopf et al. |
| 8,216,997 | B2 | 7/2012 | Seehra et al. |
| 8,293,881 | B2 | 10/2012 | Seehra et al. |
| 8,343,933 | B2 | 1/2013 | Knopf et al. |
| 8,361,957 | B2 | 1/2013 | Seehra et al. |
| 8,592,562 | B2 | 11/2013 | Kannan et al. |
| 8,629,109 | B2 | 1/2014 | Knopf et al. |
| 8,734,760 | B2 | 5/2014 | O'Connor-McCourt et al. |
| 9,163,075 | B2 | 10/2015 | Knopf et al. |
| 9,181,533 | B2 | 11/2015 | Seehra et al. |
| 9,399,669 | B2 | 7/2016 | Knopf et al. |
| 9,611,306 | B2 | 4/2017 | Hinck et al. |
| 9,809,638 | B2 | 11/2017 | Sun et al. |
| 2009/0010879 | A1 | 1/2009 | Stahl et al. |
| 2010/0330657 | A1 | 12/2010 | Miyazono et al. |
| 2011/0236309 | A1 | 9/2011 | O'Connor-Mccourt et al. |
| 2012/0302737 | A1 | 11/2012 | Christensen et al. |
| 2013/0171095 | A1 | 7/2013 | Bernett et al. |
| 2016/0289298 | A1 | 10/2016 | Kumar et al. |
| 2016/0297867 | A1 | 10/2016 | Kumar et al. |
| 2016/0298093 | A1 | 10/2016 | Kumar et al. |
| 2017/0240639 | A1 | 8/2017 | Kumar et al. |
| 2017/0306027 | A1 | 10/2017 | Knopf et al. |
| 2018/0008672 | A1 | 1/2018 | Chalothorn et al. |
| 2018/0072791 | A1 | 3/2018 | Sun et al. |
| 2018/0111991 | A1 | 4/2018 | Miller et al. |
| 2018/0148491 | A1 | 5/2018 | Han et al. |

FOREIGN PATENT DOCUMENTS

| EP | 3 101 029 A1 | 12/2016 |
| WO | WO-93/11162 A1 | 6/1993 |
| WO | WO-94/11502 A2 | 5/1994 |
| WO | WO-00/43781 A2 | 7/2000 |
| WO | WO 2004/039948 A2 | 5/2004 |
| WO | WO 2005/028433 A2 | 3/2005 |
| WO | WO-2006/012627 A2 | 2/2006 |
| WO | WO-2007/147901 A1 | 12/2007 |

(Continued)

OTHER PUBLICATIONS

Tsuchida et al., Activin signaling as an emerging target for therapeutic interventions. Cell Communication and Signaling 7:15, 2009.*
Issued U.S. Pat. No. 8,058,229 (U.S. Appl. No. 12/583,177).
Issued U.S. Pat. No. 9,505,813 (U.S. Appl. No. 13/750,249).
Pending U.S. Appl. No. 15/336,363.
Issued U.S. Pat. No. 8,216,997 (U.S. Appl. No. 12/856,420).
Issued U.S. Pat. No. 8,703,927 (U.S. Appl. No. 13/542,269).
Issued U.S. Pat. No. 9,439,945 (U.S. Appl. No. 14/201,192).
Pending U.S. Appl. No. 15/221,341.
Pending U.S. Appl. No. 15/790,400.
Allendorph, et al., "Structure of the ternary signaling complex of a TGF-β superfamily member," Proceedings of the National Academy of Sciences, vol. 103(20): 7643-7648 (2006).

(Continued)

Primary Examiner — Ruixiang Li
(74) Attorney, Agent, or Firm — White & Case LLP

(57) ABSTRACT

In certain aspects, the disclosure provides soluble heteromeric polypeptide complexes comprising an extracellular domain of an ALK4 receptor and an extracellular domain of ActRIIB. In certain aspects, such soluble ALK4:ActRIIB complexes may be used to regulate (promote or inhibit) growth of tissues or cells including, for example, muscle, bone, cartilage, fat, neural tissue, tumors, and/or cancerous cells. In certain aspects, such ALK4:ActRIIB complexes are can be used to improve muscle formation, bone formation, metabolic parameters, and disorders associated with these tissues, cellular networks, kidney, and endocrine systems.

31 Claims, 29 Drawing Sheets
(25 of 29 Drawing Sheet(s) Filed in Color)
Specification includes a Sequence Listing.

(56) References Cited

FOREIGN PATENT DOCUMENTS

| | | |
|---|---|---|
| WO | WO-2008/073351 A2 | 6/2008 |
| WO | WO-2008/097541 A2 | 8/2008 |
| WO | WO-2009/089004 A1 | 7/2009 |
| WO | WO-2010/019261 A1 | 2/2010 |
| WO | WO-2010/083034 A1 | 7/2010 |
| WO | WO-2010/151426 A1 | 12/2010 |
| WO | WO-2011/034605 A2 | 3/2011 |
| WO | WO 2011/056497 A1 | 5/2011 |
| WO | WO 2013/000234 A1 | 1/2013 |
| WO | WO-2016/164497 A1 | 10/2016 |
| WO | WO 2016/205570 A1 | 12/2016 |
| WO | WO 2017/037634 A1 | 3/2017 |
| WO | WO 2018/009624 A1 | 1/2018 |
| WO | WO 2018/075747 A1 | 4/2018 |

OTHER PUBLICATIONS

Ashmore, et al., "Comparative Aspects of Muscle Fiber Types in Fetuses of the Normal and "Double-Muscled" Cattle," Growth, vol. 38: 501-506 (1974).

Attie, et al., "A phase 1 study of Ace-536, a regulator of erythroid differentiation, in healthy volunteers," American Journal of Hematology, vol. 89(7): 766-770 (2014).

Attisano, et al., "Novel Activin Receptors: Distinct Genes and Alternative mRNA Splicing Generate a Repertoire of Serine/Threonine Kinase Receptors," Cell, vol. 68: 97-108 (1992).

Bogdanovich, et al., "Functional improvement of dystrophic muscle by myostatin blockade," Nature, vol. 420: 418-421 (2002).

Brown, et al., "Physicochemical Activation of Recombinant Latent Transforming Growth Factor-beta's 1, 2, and 3," Growth Factors, vol. 3: 35-43 (1990).

Calvanese, et al., "Structural insights into the interaction between the Cripto CFC domain and the ALK4 receptor," Journal of Peptide Science, vol. 15: 175-183 (2009).

Cantini, et al., "Profibrotic Role of Myostatin in Peyronie's Disease," Journal of Sexual Medicine, vol. 5: 1607-1622 (2008).

Clouthier, et al., "Hepatic Fibrosis, Glomerulosclerosis, and a Lipodystrophy-like Syndrome in Pepck-TGF-β1 Transgenic Mice," Journal of Clinical Investigation, vol. 100(11): 2697-2713 (1997).

Das, et al., "Macromolecular Modeling with Rosetta," Annual Review of Biochemistry, vol. 77: 363-382 (2008).

Davis, et al., "SEEDbodies: fusion proteins based on strand-exchange engineered domain (SEED) CH3 heterodimers in an Fc analogue platform for asymmetric binders or immunofusions and bispecific antibodies," Protein Engineering, Design & Selection, vol. 23(4): 195-202 (2010).

DePaolo, et al., "Follistatin and Activin: A Potential Intrinsic Regulatory System with Diverse Tissues," Proceedings of the Society for Experimental Biology and Medicine: 500-512 (1991).

Dyson, et al., "Activin signalling has a necessary function in Xenopus early development," Current Biology, vol. 7(1): 81-84 (1997).

Fenn, et al., "Crystal Structure of an Anti-Ang2 CrossFab Demonstrates Complete Structural and Functional Integrity of the Variable Domain," PLoS One, vol. 8(4): e61953 (2013).

Gamer, et al., "A Novel BMP Expressed in Developing Mouse Limb, Spinal Cord, and Tail Bud Is a Potent Mesoderm Inducer in Xenopus Embryos," Developmental Biology, vol. 208: 222-232 (1999).

Gamer, et al., "Gdf11 Is a Negative Regulator of Chrondrogenesis and Myogenesis in the Developing Chick Limb," Developmental Biology, vol. 229: 407-420 (2001).

Gonzalez-Cadavid, et al., "Organization of the human myostatin gene and expression in healthy men and HIV-infected men with muscle wasting," Proceedings of the National Academy of Sciences, vol. 95: 14938-14943 (1998).

Goumans, et al., "Activin Receptor-like Kinase (ALK)1 Is an Antagonistic Mediator of Lateral TGFβ/ALK5 Signaling," Molecular Cell, vol. 12: 817-828 (2003).

Greenwald, et al., "Three-finger toxin fold for the extracellular ligand-binding domain of the type II activin receptor serine kinase," Nature Structural Biology, vol. 6(1): 18-22 (1999).

Grobet, et al., "A deletion in the bovine myostatin gene causes the double-muscled phenotype in cattle," Nature Genetics, vol. 17: 71-74 (1997).

Gunasekaran, et al., "Enhancing Antibody Fc Heterodimer Formation through Electrostatic Steering Effects," The Journal of Biological Chemistry, vol. 285(25): 19637-19646 (2010).

Hardy, et al., "The activin a antagonist follistatin inhibits cystic fibrosis-like lung inflammation and pathology," Immunology and Cell Biology, vol. 93: 567-574 (2015).

Harrison, et al., "Identification of a Functional Binding Site for Activin on the Type I Receptor ALK4," The Journal of Biological Chemistry, vol. 278: 21129-21135 (2003).

Hedger, et al., "The activins and their binding protein, follistatin—Diagnostic and therapeutic targets in inflammatory disease and fibrosis," Cytokine & Growth Factor Reviews, vol. 24: 285-295 (2013).

Hildén, et al., "Expression of Type II Activin Receptor Genes During Differentiation of Human K562 Cells and cDNA Cloning of the Human Type IIB Activin Receptor," Blood, vol. 83(8): 2163-2170 (1994).

Hinck, "Structural studies of the TGF-β5 and their receptors—insights into evolution of the TGF-β superfamily," Federation of European Biochemical Societies Letters, vol. 586: 1860-1870 (2012).

Kabat, et al., "Sequences of Proteins of Immunological Interest," Fifth Edition, Public Health Service National Institutes of Health, NIH Publication No. 91-3242: 688-696 (1991).

Kambadur, et al., "Mutations in myostatin (GDF8) in Double-Muscled Belgian Blue and Piedmontese Cattle," Genome Research, vol. 7: 910-915 (1997).

Klahr, et al., "Obstructive nephropathy and renal fibrosis," American Journal of Physiology-Renal Physiology, vol. 283: F861-F875 (2002).

Klein, et al., "Progress in overcoming the chain association issue in bispecific heterodimeric IgG antibodies," mAbs, vol. 4(6): 653-663 (2012).

Kubiczkova, et al., "TGF-β—an excellent servant but a bad master," Journal of Translational Medicine, vol. 10(183): 24 pages (2012).

Lewis, et al., "Generation of bispecific IgG antibodies by structure-based design of an orthogonal Fab interface," Nature Biotechnology, vol. 32(2): 191-198 (2014).

Li, et al., "Transforming Growth Factor-β Controls Development, Homeostasis, and Tolerance of T Cells by Regulatory T Cell-Dependent and -Independent Mechanisms," Immunity, vol. 25: 455-471 (2006).

Lin, et al., "The structural basis of TGF-β, bone morphogenetic protein, and activin ligand binding," Reproduction, vol. 132: 179-190 (2006).

Macías-Silva, et al., "Specific Activation of Smad1 Signaling Pathways by the BMP7 Type I Receptor, ALK2*," The Journal of Biological Chemistry, vol. 273(40): 25628-25636 (1998).

Massagué, "How Cells Read TGF-β Signals," Nature Reviews Molecular Cell Biology, vol. 1(3): 169-178 (2000).

McPherron, et al., "Double muscling in cattle due to mutations in the myostatin gene," Proceedings of the National Academy of Sciences, vol. 94: 12457-12461 (1997).

McPherron, et al., "Regulation of skeletal muscle mass in mice by a new TGF-β superfamily member," Nature, vol. 387: 83-90 (1997).

McPherron, et al., "Regulation of anterior/posterior patterning of the axial skeleton by growth/differentiation factor 11," Nature Genetics, vol. 22: 260-264 (1999).

Merchant, et al., "An efficient route to human bispecific IgG," Nature Biotechnology, vol. 16: 677-681 (1998).

Miyazono, et al., "Latent High Molecular Weight Complex of Transforming Growth Factor β1," The Journal of Biological Chemistry, vol. 263(13): 6407-6415 (1998).

Nakashima, et al., "Expression of growth/differentiation factor 11, a new member of the BMP/TGFβ superfamily during mouse embryogenesis," Mechanisms of Development, vol. 80: 185-189 (1999).

(56) References Cited

OTHER PUBLICATIONS

Pack, et al., "Miniantibodies: Use of Amphipathic Helices to Produce Functional, Flexibly Linked Dimeric Fv Fragments with High Avidity in Escherichia coli," Biochemistry, vol. 31(6): 1579-1584 (1992).
Pack, et al., "Improved Bivalent Miniantibodies, with Identical Avidity as Whole Antibodies, Produced by High Cell Density Fermentation of *Escherichia coli*," Bio/Technology, vol. 11: 1271-1277 (1993).
Pistilli, et al., "Targeting the Activin Type IIB Receptor to Improve Muscle Mass and Function in the mdx Mouse Model of Duchenne Muscular Dystrophy," the American Journal of Pathology, vol. 178(3): 1287-1297 (2011).
Recombinant Human Activin a Receptor, Type 1B (ACVR1 B), GIBCO, Publication Part No. MAN0004539, Jun. 16, 2011, 2 pages, downloaded Nov. 6, 2017.
Rider, et al., "Bone morphogenetic protein and growth differentiation factor cytokine families and their protein antagonists," Biochemical Journal, vol. 429: 1-12 (2010).
Ridgway, et al., "Knobs-into-holes' engineering of antibody CH3 domains for heavy chain heterodimerization," Protein Engineering, vol. 19(7): 617-621 (1996).
Romano, et al., "Toward a better understanding of the interaction between TGF-β family members and their ALK receptors," Journal of Molecular Modeling, vol. 18: 3617-3625 (2012).
Sakuma, et al., "Inhibition of Nodal signalling by Lefty mediated through interaction with common receptors and efficient diffusion," Genes to Cells, vol. 7: 401-412 (2002).
Schaefer et al., "Immunoglobulin domain crossover as a genetic approach for the production of bispecific IgG antibodies," Proceedings of the National Academy of Sciences, vol. 108(27): 11187-11192 (2011).
Schuelke, et al., "Myostatin Mutation Associated with Gross Muscle Hypertrophy in a Child," The New England Journal of Medicine, vol. 350(26): 2682-2688 (2004).
Spiess, et al., "Alternative molecular formats and therapeutic applications for bispecific antibodies," Molecular Immunology, vol. 67: 95-106 (2015).
Swatland, et al., "Fetal Development of the Double Muscled Condition in Cattle," Journal of Animal Science, vol. 38(4): 752-757 (1974).
Thompson, et al., "Structures of an ActRIIB: activin a complex reveal a novel binding mode for TGF-β ligand: receptor interactions," The EMBO Journal, vol. 22(7): 1555-1566 (2003).
Wakefield, et al., "Latent Transforming Growth Factor-β from Human Platelets," The Journal of Biological Chemistry, vol. 263(16): 7646-7654 (1988).
Weiss, et al., "The TGFbeta Superfamily Signaling Pathway," Developmental Biology, vol. 2: 47-63 (2013).
Woodruff, "Regulation of Cellular and System Function by Activin," Biochemical Pharmacology, vol. 55: 953-963 (1998).
Wranik, et al., "LUZ-Y, a Novel Platform for the Mammalian Cell Production of Full-length IgG-bispecific Antibodies," The Journal of Biological Chemistry, vol. 287(52): 43331-43339 (2012).
Wu, et al., "Autoregulation of Neurogenesis by GDF11," Neuron, vol. 37: 197-207 (2003).
Zimmers, et al., "Induction of Cachexia in Mice by Systemically Administered Myostatin," Science, vol. 296: 1486-1488 (2002).
Pending U.S. Appl. No. 14/849,313.
Pending U.S. Appl. No. 15/201,031.
Pending U.S. Appl. No. 15/092,609.
Pending U.S. Appl. No. 15/092,577.
Qin et al., "A novel highly potent trivalent TGF-β receptor trap inhibits early-stage tumorigenesis and tumor cell invasion in murine Pten-deficient prostate glands," Oncotarget, Advance Publications: 1-16 (2016).
Zwaagstra et al., "Engineering and Therapeutic Application of Single-Chain Bivalent TGF-β Family Traps," Molecular Cancer Therapeutics; vol. 11(7): 1477-1487 (2012).
Zhou et al., "Truncated Activin Type I Receptor Alk4 Isoforms are Dominant Negative Receptors Inhibiting Activin Signaling," Molecular Endocrinology, vol. 14(12): 2066-2075 (2000).
Pending U.S. Appl. No. 15/726,255.
Pending U.S. Appl. No. 16/158,661.
Issued U.S. Pat. No. 7,709,605 (U.S. Appl. No. 11/190,202).
Issued U.S. Pat. No. 8,252,900 (U.S. Appl. No. 12/751,868).
Issued U.S. Pat. No. 9,138,459 (U.S. Appl. No. 13/588,468.
Pending U.S. Appl. No. 14/836,684.
Issued U.S. Pat. No. 7,612,041 (U.S. Appl. No. 11/603,485).
Issued U.S. Pat. No. 7,951,771 (U.S. Appl. No. 12/284,864).
Issued U.S. Pat. No. 8,067,360 (U.S. Appl. No. 12/284,862).
Issued U.S. Pat. No. 8,629,109 (U.S. Appl. No. 13/176,864).
Issued U.S. Pat. No. 9,163,075 (U.S. Appl. No. 14/027,542).
Issued U.S. Pat. No. 10,071,135 (U.S. Appl. No. 14/849,313).
Pending U.S. Appl. No. 16/054,107.
Issued U.S. Pat. No. 7,842,663 (U.S. Appl. No. 12/012,652).
Issued U.S. Pat. No. 8,343,933 (U.S. Appl. No. 12/893,976).
Issued U.S. Pat. No. 9,399,669 (U.S. Appl. No. 13/730,418).
Allowed U.S. Appl. No. 15/201,031.
Allowed U.S. Appl. No. 15/092,609.
Pending U.S. Appl. No. 15/480,726.
Pending U.S. Appl. No. 15/092,600.
Allowed U.S. Appl. No. 15/092,577.
Issued U.S. Pat. No. 8361957 (U.S. Appl. No. 13/247,748).
Issued U.S. Pat. No. 8,293,881 (U.S. Appl. No. 12/796,307).
Issued U.S. Pat. No. 9,181,533 (U.S. Appl. No. 13/657,649).

* cited by examiner

```
ActRIIa    ILGRSETQEC LFFNANWEKD RTNQTGVEPC YGDKDKRRHC FATWKNISGS
ActRIIb    GRGEAETREC IYYNANWELE RTNQSGLERC EGEQDKRLHC YASWRNSSGT

IEIVKQGCWL DDINCYDRTD CVEKKDSPEV YFCCCEGNMC NEKFSYFPEM
           IELVKKGCWL DDFNCYDRQE CVATEENPQV YFCCCEGNFC NERFTHLPEA

EVTQPTSNPV TPKPPT
           GGPEVTYEPP PTAPT
```

FIG. 3

```
IgG1    --------THTCPPCPAPELLGGPSVFLFPPKPKDTLMISRTPEVTCVVVDVSHEDPEVKF  53
IgG4    ----ESKYGPPCPSCPAPEFLGGPSVFLFPPKPKDTLMISRTPEVTCVVVDVSQEDPEVQF  57
IgG2    --------VECPPCPAPPVAG-FSVFLFPPKPKDTLMISRTPEVTCVVVDVSHEDPEVQF  51
IgG3    EPKSCDTPPPCPRCPAPELLGGPSVFLFPPKPKDTLMISRTPEVTCVVVDVSHEDPEVQF  60
                  **  ****  . *  ************************* ***** *

IgG1    NWYVDGVEVHNAKTKPREEQYNSTYRVVSVLTVLHQDWLNGKEYKCKVSNKALPAPIEKT  113
IgG4    NWYVDGVEVHNAKTKPREEQFNSTYRVVSVLTVLHQDWLNGKEYKCKVSNKGLPSSIEKT  117
IgG2    NWYVDGVEVHNAKTKPREEQFNSTFRVVSVLTVVHQDWLNGKEYKCKVSNKGLPAPIEKT  111
IgG3    KWYVDGVEVHNAKTKPREEQYNSTFRVVSVLTVLHQDWLNGKEYKCKVSNKALPAPIEKT  120
        :******************:***:*******:********************.** :.****

IgG1    ISKAKGQPREPQVYTLPPSREEMTKNQVSLTCLVKGFYPSDIAVEWESNGQPENNYKTTP  173
IgG4    ISKAKGQPREPQVYTLPPSQEEMTKNQVSLTCLVKGFYPSDIAVEWESNGQPENNYKTTP  177
IgG2    ISKTKGQPREPQVYTLPPSREEMTKNQVSLTCLVKGFYPSDIAVEWESNGQPENNYKTTP  171
IgG3    ISKTKGQPREPQVYTLPPSREEMTKNQVSLTCLVKGFYPSDIAVEWESSGQPENNYNTTP  180
        ***.*************** .***************************.******* .***

IgG1    PVLDSDGSFFLYSKLTVDKSRWQQGNVFSCSVMHEALHNHYTQKSLSLSPGK  225
IgG4    PVLDSDGSFFLYSRLTVDKSRWQEGNVFSCSVMHEALHNHYTQKSLSLSLGK  229
IgG2    PMLDSDGSFFLYSKLTVDKSRWQQGNVFSCSVMHEALHNHYTQKSLSLSPGK  223
IgG3    PMLDSDGSFFLYSKLTVDKSRWQQGNIFSCSVMHEALHNRFTQKSLSLSPGK  232
        *:***********:********* ***:**********:  *********  **
```

ALK4:ACTRIIB HETEROMULTIMERS AND USES THEREOF

CROSS-REFERENCE TO RELATED APPLICATIONS

This application claims the benefit of priority to U.S. provisional application Ser. No. 62/143,579, filed Apr. 6, 2015; and U.S. provisional application Ser. No. 62/220,836, filed Sep. 18, 2015. The disclosures of each of the foregoing applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on May 25, 2016, is named PHPH109101_SL.txt and is 122,692 bytes in size.

BACKGROUND OF THE INVENTION

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is divided into two general phylogenetic clades: the more recently evolved members of the superfamily, which includes TGF-betas, activins, and nodal and the clade of more distantly related proteins of the superfamily, which includes a number of BMPs and GDFs [Hinck (2012) FEBS Letters 586:1860-1870]. TGF-beta family members have diverse, often complementary biological effects. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass [Grobet et al. (1997) Nat Genet 17(1):71-4]. Furthermore, in humans, inactive alleles of GDF8 are associated with increased muscle mass and, reportedly, exceptional strength [Schuelke et al. (2004) N Engl J Med 350:2682-8].

Changes in fibrosis, muscle, bone, fat, red blood cells, and other tissues may be achieved by enhancing or inhibiting intracellular signaling (e.g., SMAD 1, 2, 3, 5, and/or 8) that is mediated by ligands of the TGF-beta family. Thus, there is a need for agents that regulate the activity of various ligands of the TGF-beta superfamily.

SUMMARY OF THE INVENTION

As described herein, it has been discovered that an ALK4:ActRIIB heterodimer protein complex is a unique antagonist of ligands of the TGF-beta superfamily, exhibiting a different ligand-binding profile/selectivity compared to corresponding ActRIIB and ALK4 homodimers. In particular, an exemplary ALK4:ActRIIB heterodimer displays enhanced binding to activin B compared to either homodimer, retains strong binding to activin A, GDF8, and GDF11 as observed with ActRIIB homodimer, and exhibits substantially reduced binding to BMP9, BMP10, and GDF3. In fact, the ALK4:ActRIIB heterodimer displays low to no observable affinity for BMP9, whereas this ligand binds strongly to ActRIIB homodimer. See FIG. 6. These results therefore demonstrate that ALK4:ActRIIB heterodimers are a more selective antagonists (inhibitors) of certain ligands of the TGF-beta superfamily compared to ActRIIB homodimers. Accordingly, an ALK4:ActRIIB heterodimer will be more useful than an ActRIIB homodimer in certain applications where such selective antagonism is advantageous. Examples include therapeutic applications where it is desirable to antagonize one or more of activin (e.g., activin A, activin B, activin AB, activin AC), GDF8, and GDF11 with decreased antagonism of one or more of BMP9, BMP10, and GDF3.

Moreover, ALK4:ActRIIB heterodimer produced certain biological effects strikingly similar to those of an ActRIIB homodimer despite differential ligand selectivity of the two complexes. For example, ALK4:ActRIIB heterodimer exerts beneficial anabolic effects on skeletal muscle and bone as well as catabolic effects on adipose tissue, very similar to those of an ActRIIB-Fc homodimer. However, unlike ActRIIB homodimer, ActRIIB:ALK4 heterodimer exhibits only low-affinity or transient binding to BMP9 and BMP10 and so should have little to no concurrent inhibition on processes mediated by those ligands, such as angiogenesis. This novel selectivity may be useful, for example, in treating patients in need of stimulatory effects on muscle and bone, and/or inhibitory effects on fat, but not in need of altered angiogenesis. In addition, ALK4:ActRIIB heterodimer had various beneficial effects in a mouse model of kidney disease, particularly on treating or preventing kidney damage, inflammation, and fibrosis. Therefore, while not wishing to be bound to a particular mechanisms of action, it is expected that ALK4:ActRIIB heteromultimers, as well as variants thereof, that bind to/inhibit at least one or more of activin (e.g., activin A, activin B, activin AB, and activin AC), GDF8, and/or GDF11 will be useful agents for promoting beneficial anabolic effects on skeletal muscle and bone, catabolic effects on adipose tissue, and beneficial effects on kidney disease. Furthermore, it is expected that other antagonists (inhibitors), or combinations of antagonists, that mimic the binding/inhibitory properties of the ALK4:ActRIIB heterodimers described herein as well as agents that directly or indirectly antagonize ALK4 and/or ActRIIB receptors, agents that directly or indirectly antagonize ALK4- and/or ActRIIB-binding ligands, agents that directly or indirectly antagonize downstream signaling mediators (e.g., Smads), and/or agents that directly or indirectly antagonize TGF-beta superfamily co-receptors will have similar biological effects in vivo including, for example, stimulatory effects on muscle and bone and inhibitory effects on fat. These antagonistic mimetic are collectively referred to herein as "ALK4:ActRIIB antagonists" or "ALK4:ActRIIB inhibitors".

Therefore, the present disclosure provides, in part, heteromultimer complexes (heteromultimers) comprising at least one ALK4 polypeptide and at least one ActRIIB polypeptide (ALK4:ActRIIB heteromultimers). Preferably, ALK4 polypeptides comprise a ligand-binding domain of an ALK4 receptor, for example, a portion of the ALK4 extracellular domain. Similarly, ActRIIB polypeptides generally comprise a ligand-binding domain of an ActRIIB receptor, for example, a portion of the ActRIIB extracellular domain. Preferably, such ALK4 and ActRIIB polypeptides, as well as resultant heteromultimers thereof, are soluble.

In certain aspects, an ALK4:ActRIIB heteromultimer comprises an ALK4 amino acid sequence that is at least 70% identical to a polypeptide that begins at any one of amino acids 24-34 of SEQ ID NO: 9 (e.g., amino acids 24, 25, 26, 27, 28, 29, 30, 31, 32, 33, and 34) and ends at any one of amino acids 101-126 of SEQ ID NO: 9 (e.g., amino acids 101, 102, 103, 104, 105, 106, 107, 108, 109, 110, 111, 112, 113, 114, 115, 116, 117, 118, 119, 120, 121, 122, 123, 124, 125, and 126). For example, ALK4:ActRIIB heteromultimers may comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 34-101 of SEQ ID NO: 9. In some embodiments, ALK4:ActRIIB heteromultimers may comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 24-126 of SEQ ID NO: 9. In other embodiments, ALK4:ActRIIB heteromultimers may comprise an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 10. In still other embodiments, ALK4:ActRIIB heteromultimers may comprise an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 20.

In certain aspects, an ALK4:ActRIIB heteromultimer comprises an ActRIIB amino acid sequence that is at least 70% identical to a polypeptide that begins at any one of amino acids 20-29 of SEQ ID NO: 1 (e.g., amino acids 20, 21, 22, 23, 24, 25, 26, 27, 28, and 29) and ends at any one of amino acids 109-134 (109, 110, 111, 112, 113, 114, 115, 116, 117, 118, 119, 120, 121, 122, 123, 124, 125, 126, 127, 128, 129, 130, 131, 132, 133, and 134) of SEQ ID NO: 1. For example, ALK4:ActRIIB heteromultimers may comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 29-109 of SEQ ID NO: 1. In some embodiments, ALK4:ActRIIB heteromultimers may comprise an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 25-131 of SEQ ID NO: 1. In other embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 2. In still other embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 3. In even other embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 5. In still even other embodiments, ALK4:ActRIIB heteromultimers may comprise an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 6. In certain preferred embodiments, ALK4:ActRIIB heteromultimers do not comprise an ActRIIB polypeptide comprising an acidic amino acid (e.g., the naturally occurring amino acids E or D or an artificial acidic amino acid) at the position corresponding to L79 of SEQ ID NO: 1.

Various combinations of the ALK4 and ActRIIB polypeptides described herein are also contemplated with respect to ALK4:ActRIIB heteromultimers. For example, in certain aspects, an ALK4:ActRIIB heteromultimer may comprise a) a polypeptide comprising, consisting essentially of, or consisting of an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 34-101 of SEQ ID NO: 9; and b) a polypeptide comprising, or consisting essentially of, or consisting of an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 29-109 of SEQ ID NO: 1. In certain aspects, an ALK4:ActRIIB heteromultimer may comprise a) a polypeptide comprising, consisting essentially of, or consisting of an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 24-126 of SEQ ID NO: 9; and b) a polypeptide comprising, or consisting essentially of, or consisting of an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 25-131 of SEQ ID NO: 1. In other aspects, an ALK4:ActRIIB heteromultimer may comprise a) a polypeptide comprising, consisting essentially of, or consisting of an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 10; and b) a polypeptide comprising, or consisting essentially of, or consisting of an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 2. In other aspects, an ALK4:ActRIIB heteromultimer may comprise a) a polypeptide comprising, consisting essentially of, or consisting of an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 20; and b) a polypeptide comprising, or consisting essentially of, or consisting of an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 2. In even other aspects, an ALK4:ActRIIB heteromultimer may comprise a) a polypeptide comprising, consisting essentially of, or consisting of an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 10; and b) a polypeptide comprising, or consisting essentially of, or consisting of an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 3. In even other aspects, an ALK4:ActRIIB heteromultimer may comprise a) a polypeptide comprising, consisting essentially of, or consisting of an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 20; and b) a polypeptide comprising, or consisting essentially of, or consisting of an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 3. In still other aspects, an ALK4:ActRIIB heteromultimer may comprise a) a polypeptide comprising, consisting essentially of, or consisting of an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 10; and b) a polypeptide comprising, or consisting essentially of, or consisting of an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 5. In still other aspects, an ALK4:ActRIIB heteromultimer may comprise a) a polypeptide comprising, consisting essentially of, or consisting of an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 20; and b) a polypeptide comprising, or consisting essentially of, or consisting of an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 5. In still even other aspects, an ALK4:ActRIIB heteromultimer may comprise a) a polypeptide comprising, consisting essentially of, or consisting of an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 10; and b) a polypeptide comprising, or consisting essentially of, or consisting of an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 6. In still even other aspects, an ALK4:ActRIIB heteromultimer may comprise a) a polypeptide comprising, consisting essentially of, or consisting of an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 20; and b) a polypeptide comprising, or consisting essentially of, or consisting of an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 6.

As described herein, ALK4:ActRIIB heteromultimer structures include, for example, heterodimers, heterotrimers, heterotetramers, heteropentamers, and higher order heteromultimer complexes. See, e.g., FIGS. 1, 2, and 8-10. In certain preferred embodiments, ALK4:ActRIIB heteromultimers are heterodimers.

In certain aspects, ALK4 and/or ActRIIB polypeptides may be fusion proteins. For example, in some embodiments, an ALK4 polypeptide may be a fusion protein comprising an ALK4 polypeptide domain and one or more heterologous (non-ALK4) polypeptide domains. Similarly, in some embodiments, an ActRIIB polypeptide may be a fusion protein comprising an ActRIIB polypeptide domain and one or more heterologous (non-ActRIIB) polypeptide domains.

Optionally, ALK4 polypeptides are connected directly (fused) to one or more heterologous domains, or an intervening sequence, such as a linker, may be positioned between the amino acid sequence of the ALK4 polypeptide and the one or more heterologous domains. Similarly, the ActRIIB polypeptide may be connected directly (fused) to one or more heterologous domains, or an intervening sequence, such as a linker, may be positioned between the amino acid sequence of the ActRIIB polypeptide and the one or more heterologous domains. Linkers may correspond to the roughly 15 amino acid unstructured region at the C-terminal end of the extracellular domain of ActRIIB or ALK4 (the "tail"), or it may be an artificial sequence of between 5 and 15, 20, 30, 50, 100 or more amino acids that are relatively free of secondary structure. A linker may be rich in glycine and proline residues and may, for example, contain repeating sequences of threonine/serine and glycines. Examples of linkers include, but are not limited to, the sequences TGGG (SEQ ID NO: 17), SGGG (SEQ ID NO: 18), TGGGG (SEQ ID NO: 15), SGGGG (SEQ ID NO: 16), GGGGS (SEQ ID NO: 58), GGGG (SEQ ID NO: 14), and GGG (SEQ ID NO: 13). In some embodiments, the one or more heterologous domains that provide a desirable property to the ALK4 and/or ActRIIB fusion proteins including, for example, improved pharmacokinetics, easier purification, targeting to particular tissues, etc. For example, a heterologous domain of a fusion protein may enhance one or more of in vivo stability, in vivo half-life, uptake/administration, tissue localization or distribution, formation of protein complexes, multimerization of the fusion protein, and/or purification. An ALK4 or ActRIIB fusion protein may include an immunoglobulin Fc domain (wild-type or mutant) or a serum albumin. In some embodiments, ALK4 and/or ActRIIB polypeptides may comprise a purification subsequence, such as an epitope tag, a FLAG tag, a polyhistidine sequence, and a GST fusion.

In certain embodiments, ALK4:ActRIIB heteromultimers described herein comprise an ALK4 polypeptide covalently, or non-covalently, associated with an ActRIIB polypeptide wherein the ALK4 polypeptide comprises an ALK4 domain and an amino acid sequence of a first member (or second member) of an interaction pair and the ActRIIB polypeptide comprises an ActRIIB polypeptide and an amino acid sequence of a second member (or first member) of the interaction pair. Interaction pairs described herein are designed to promote dimerization or form higher order multimers. See, e.g., FIGS. 1, 2, and 8-10 In some embodiments, the interaction pair may be any two polypeptide sequences that interact to form a complex, particularly a heterodimeric complex although operative embodiments may also employ an interaction pair that forms a homodimeric sequence. The first and second members of the interaction pair may be an asymmetric pair, meaning that the members of the pair preferentially associate with each other rather than self-associate (i.e., guided interaction pairs). Accordingly, first and second members of an asymmetric interaction pair may associate to form a heterodimeric complex. Alternatively, the interaction pair may be unguided, meaning that the members of the pair may associate with each other or self-associate without substantial preference and thus may have the same or different amino acid sequences. Accordingly, first and second members of an unguided interaction pair may associate to form a homodimer complex or a heterodimeric complex. Optionally, the first member of the interaction action pair (e.g., an asymmetric pair or an unguided interaction pair) associates covalently with the second member of the interaction pair. Optionally, the first member of the interaction action pair (e.g., an asymmetric pair or an unguided interaction pair) associates non-covalently with the second member of the interaction pair. Optionally, the first member of the interaction action pair (e.g., an asymmetric pair or an unguided interaction pair) associates through both covalent and non-covalent mechanisms with the second member of the interaction pair.

In some embodiments, ALK4 polypeptides are fusion proteins that comprise an Fc domain of an immunoglobulin.

Similarly, in some embodiments, ActRIIB polypeptides are fusion proteins that comprise an Fc domain of an immunoglobulin. Traditional Fc fusion proteins and antibodies are examples of unguided interaction pairs, whereas a variety of engineered Fc domains have been designed as asymmetric interaction pairs [Spiess et al (2015) Molecular Immunology 67(2A): 95-106]. Therefore, a first member and/or a second member of an interaction pair described herein may comprise a constant domain of an immunoglobulin, including, for example, the Fc portion of an immunoglobulin. For example, a first member of an interaction pair may comprise an amino acid sequence that is derived from an Fc domain of an IgG (IgG1, IgG2, IgG3, or IgG4), IgA (IgA1 or IgA2), IgE, or IgM immunoglobulin. Such immunoglobulin domains may comprise one or more amino acid modifications (e.g., deletions, additions, and/or substitutions) that promote ALK4:ActRIIB heteromultimer formation. For example, the first member of an interaction pair may comprise, consist essentially of, or consist of an amino acid sequence that is at least 70%, 75%, 80%, 85%, 90%, 91%, 92%, 93%, 94%, 95%, 96%, 97%, 98%, 99% or 100% identical to any one of SEQ ID NOs: 23-37. Similarly, a second member of an interaction pair may comprise an amino acid sequence that is derived from an Fc domain of an IgG (IgG1, IgG2, IgG3, or IgG4), IgA (IgA1 or IgA2), IgE, or IgM. Such immunoglobulin domains may comprise one or more amino acid modifications (e.g., deletions, additions, and/or substitutions) that promote ALK4:ActRIIB heteromultimer formation. For example, the second member of an interaction pair may comprise, consist essentially of, or consist of an amino acid sequence that is at least 70%, 75%, 80%, 85%, 90%, 91%, 92%, 93%, 94%, 95%, 96%, 97%, 98%, 99% or 100% identical to any one of SEQ ID NOs: 23-37. In some embodiments, a first member and a second member of an interaction pair comprise Fc domains derived from the same immunoglobulin class and subtype. In other embodiments, a first member and a second member of an interaction pair comprise Fc domains derived from different immunoglobulin classes or subtypes. In some embodiments, an ALK4:ActRIIB heterodimer comprises i) an ALK4 polypeptide comprising, consisting essentially of, or consisting of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 44, and ii) an ActRIIB polypeptide comprising, consisting essentially of, or consisting of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 41. In other embodiments, an ALK4:ActRIIB heterodimer comprises i) an ALK4 polypeptide comprising, consisting essentially of, or consisting of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 48, and ii) an ActRIIB polypeptide comprising, consisting essentially of, or consisting of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 46.

Optionally, a first member and/or a second member of an interaction pair (e.g., an asymmetric pair or an unguided interaction pair) comprise a modified constant domain of an immunoglobulin, including, for example, a modified Fc portion of an immunoglobulin. For example, protein complexes of the disclosure may comprise a first modified Fc portion of an IgG comprising, consisting essentially of, or consisting of an amino acid sequence that is at least 80%, 85%, 90%, 91%, 92%, 93%, 94%, 95%, 96%, 97%, 98%, or 99% identical to an amino acid sequence selected from the group: SEQ ID NOs: 23-37 and a second modified Fc portion of an IgG, which may be the same or different from the amino acid sequence of the first modified Fc portion of the IgG, comprising, consisting essentially of, or consisting of an amino acid sequence that is at least 80%, 85%, 90%, 91%, 92%, 93%, 94%, 95%, 96%, 97%, 98%, or 99% identical to an amino acid sequence selected from the group: SEQ ID NOs: 23-37. In some embodiments, ALK4:ActRIIB heteromultimers comprise: a) an ALK4 (or ActRIIB) fusion protein comprising an immunoglobulin domain that comprises, consisting essentially of, or consisting of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 23, optionally wherein the immunoglobulin domain comprises a positively charged amino acid (e.g., K, R, or H) at the positions corresponding to residues 134 and 177 of SEQ ID NO: 23, and further optionally wherein the immunoglobulin domain does not comprise a positively charged amino acid (e.g., K, R, or H) at the position corresponding to residue 225 of SEQ ID NO: 23, and b) an ActRIIB (or ALK4) fusion protein comprising an immunoglobulin domain that comprises, consisting essentially of, or consisting of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 24, optionally wherein the immunoglobulin domain comprises a negatively charged (e.g., D or E) amino acid at the positions corresponding to residues 170 and 187 of SEQ ID NO: 24, and further optionally wherein the immunoglobulin domain comprises a positively charged amino acid (e.g., K, R, or H) at the position corresponding to residue 225 of SEQ ID NO: 24. In other embodiments, ALK4:ActRIIB heteromultimers comprise: a) an ALK4 (or ActRIIB) fusion protein comprising an immunoglobulin domain that comprises, consisting essentially of, or consisting of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 27, optionally wherein the immunoglobulin domain comprises a C at the position corresponding to residue 132 of SEQ ID NO: 27 and a W at the position corresponding to residue 144 of SEQ ID NO: 27, and further optionally wherein the immunoglobulin domain does not comprise a positively charged amino acid (e.g., K, R, or H) at the position corresponding to residue 225 of SEQ ID NO: 27, and b) an ActRIIB (or ALK4) fusion protein comprising an immunoglobulin domain that comprises, consisting essentially of, or consisting of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 28, optionally wherein the immunoglobulin domain comprises a S at the position corresponding to residue 144 of SEQ ID NO: 28, an A at the position corresponding to residue 146 of SEQ ID NO: 28, and a V at the position corresponding to residue 185 of SEQ ID NO: 28, and further optionally wherein the immunoglobulin domain does not comprises a positively charged amino acid (e.g., K, R, or H) at the position corresponding to residue 225 of SEQ ID NO: 28.

In certain aspects, an ALK4:ActRIIB heteromultimer comprises, consists essentially of, or consists of an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 39. In some embodiments, an ALK4:ActRIIB heteromultimer comprises, consists essentially of, or consists of an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 41. In certain aspects, an ALK4:ActRIIB heteromultimer comprises, consists essentially of, or consists of an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 42. In some embodiments, an ALK4:ActRIIB heteromultimer comprises, consists essentially of, or consists of an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 44. Various combinations of the ALK4 and ActRIIB fusion polypeptides described herein are also contemplated with respect to ALK4:ActRIIB heteromultimers. For example, in some embodiments, an ALK4:ActRIIB heteromultimer may comprise a) a polypeptide comprising, consisting essentially of, or consisting of an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 44; and b) a polypeptide comprising, or consisting essentially of, or consisting of an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 41. In some embodiments, an ALK4:ActRIIB heteromultimer may comprise a) a polypeptide comprising, consisting essentially of, or consisting of an ALK4 amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 48; and b) a polypeptide comprising, or consisting essentially of, or consisting of an ActRIIB amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 46.

Optionally, an ALK4 and/or ActRIIB polypeptide comprises one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. ALK4 and/or ActRIIB polypeptides may comprise at least one N-linked sugar, and may include two, three or more N-linked sugars. Such polypeptides may also comprise O-linked sugars. ALK4 and/or ActRIIB polypeptides may be produced in a variety of cell lines that glycosylate the protein in a manner that is suitable for patient use, including engineered insect or yeast cells, and mammalian cells such as COS cells, CHO cells, HEK cells and NSO cells. In some embodiments an ALK4 and/or ActRIIB polypeptide is glycosylated and has a glycosylation pattern obtainable from a Chinese hamster ovary cell line. Preferably ALK4:ActRIIB heteromultimer complexes of the disclosure exhibit a serum half-life of at least 4, 6, 12, 24, 36, 48, or 72 hours in a mammal (e.g., a mouse or a human). Optionally, ALK4:ActRIIB heteromultimers may exhibit a serum half-life of at least 6, 8, 10, 12, 14, 20, 25, or 30 days in a mammal (e.g., a mouse or a human).

In certain aspects, ALK4:ActRIIB heteromultimers of the disclosure bind to one or more TGF-beta superfamily ligands. Optionally, ALK4:ActRIIB heteromultimers bind to one or more of these ligands with a $K_D$ of less than or equal to $10^{-8}$, $10^{-9}$, $10^{-10}$, $10^{-11}$, or $10^{-12}$M. For example, in some embodiments, ALK4:ActRIIB heteromultimers bind to activin B. In some embodiments, ALK4:ActRIIB heteromultimers bind to activin A. In some embodiments, ALK4:ActRIIB heteromultimers bind to activin AB. In some embodiments, ALK4:ActRIIB heteromultimers bind to activin C. In some embodiments, ALK4:ActRIIB heteromultimers bind to activin AC. In some embodiments, ALK4:ActRIIB heteromultimers bind to activin BC. In some embodiments, ALK4:ActRIIB heteromultimers bind to activin BC. In some embodiments, ALK4:ActRIIB heteromultimers bind to activin BE. In some embodiments, ALK4:ActRIIB heteromultimers bind to GDF11. In some embodiments, ALK4:ActRIIB heteromultimers bind to GDF8. In some embodiments, ALK4:ActRIIB heteromultimers bind to BMP6. In some embodiments, ALK4:ActRIIB heteromultimers bind to GDF3. In some embodiments, ALK4:ActRIIB heteromultimers bind to BMP10. In some embodiments, ALK4:ActRIIB heteromultimers do not bind to, or do not substantially bind to, BMP9. In some embodiments, ALK4:ActRIIB heteromultimers bind to activin B with stronger affinity compared to a corresponding ActRIIB homomultimer. In some embodiments, ALK4:ActRIIB heteromultimers bind to GDF3 with weaker affinity compared to a corresponding ActRIIB homomultimer. In some embodiments, ALK4:ActRIIB heteromultimers bind to BMP10 with weaker affinity compared to a corresponding ActRIIB homomultimer. In some embodiments, ALK4:ActRIIB heteromultimers bind to BMP9 with weaker affinity compared to a corresponding ActRIIB homomultimer.

In general, ALK4:ActRIIB heteromultimers of the disclosure antagonize (inhibit) one or more activities of at least one TGF-beta superfamily ligand, and such alterations in activity may be measured using various assays known in the art, including, for example, a cell-based assay such as those described herein. In certain aspects, ALK4:ActRIIB heteromultimers may be used to inhibit signaling (e.g., Smad 2/3 and/or Smad 1/5/8 signaling) mediated by one or more TGFβ superfamily ligands in, for example, a cell-based assay. For example, in some embodiments, ALK4:ActRIIB heteromultimers inhibit activin signaling in a cell-based assay. In some embodiments, ALK4:ActRIIB heteromultimers inhibit activin signaling in a cell-based assay. In some embodiments, ALK4:ActRIIB heteromultimers inhibit activin A signaling in a cell-based assay. In some embodiments, ALK4:ActRIIB heteromultimers inhibit activin B signaling in a cell-based assay. In some embodiments, ALK4:ActRIIB heteromultimers inhibit activin AB signaling in a cell-based assay. In some embodiments, ALK4:ActRIIB heteromultimers inhibit activin C signaling in a cell-based assay. In some embodiments, ALK4:ActRIIB heteromultimers inhibit activin AC signaling in a cell-based assay. In some embodiments, ALK4:ActRIIB heteromultimers inhibit activin BC signaling in a cell-based assay. In some embodiments, ALK4:ActRIIB heteromultimers inhibit activin E signaling in a cell-based assay. In some embodiments, ALK4:ActRIIB heteromultimers inhibit activin AE signaling in a cell-based assay. In some embodiments, ALK4:ActRIIB heteromultimers inhibit activin CE signaling in a cell-based assay. In some embodiments, ALK4:ActRIIB heteromultimers inhibit GDF11 signaling in a cell-based assay. In some embodiments, ALK4:ActRIIB heteromultimers inhibit GDF8 signaling in a cell-based assay. In some embodiments, ALK4:ActRIIB heteromultimers inhibit BMP6 signaling in a cell-based assay. In some embodiments, ALK4:ActRIIB heteromultimers inhibit GDF3 signaling in a cell-based assay. In some embodiments, ALK4:ActRIIB heteromultimers inhibit BMP10 signaling in a cell-based assay. In some embodiments, ALK4:ActRIIB heteromultimers does not inhibit, or does not substantially inhibit, BMP9 signaling in a cell-based assay. In some embodiments, ALK4:ActRIIB heteromultimers are stronger inhibitors of activin B signaling in a cell-based assay. In some embodiments, ALK4:ActRIIB heteromultimers are weaker inhibitors of GDF3 signaling in a cell-based assay. In some embodiments, ALK4:ActRIIB heteromultimers are weaker inhibitors of BMP10 signaling in a cell-based assay. In some embodiments, ALK4:ActRIIB heteromultimers are weaker inhibitors of BMP9 signaling in a cell-based assay.

Any of the ALK4:ActRIIB heteromultimers as well as ALK4:ActRIIB antagonists described herein may be formulated as a pharmaceutical preparation (compositions). In some embodiments, pharmaceutical preparations comprise a pharmaceutically acceptable carrier. A pharmaceutical preparation will preferably be pyrogen-free (meaning pyrogen free to the extent required by regulations governing the quality of products for therapeutic use). A pharmaceutical preparation may also include one or more additional compounds such as a compound that is used to treat a disorder/condition described herein. In general, ALK4:ActRIIB heteromultimer pharmaceutical preparations are substantially free of ALK4 and/or ActRIIB homomultimers. For example, in some embodiments, ALK4:ActRIIB heteromultimer pharmaceutical preparations comprise less than about 10%, 9%, 8%, 7%, 6%, 5%, 4%, 3%, 2%, or less than about 1% ALK4 homomultimers. In some embodiments, ALK4:ActRIIB heteromultimer pharmaceutical preparations comprise less than about 10%, 9%, 8%, 7%, 6%, 5%, 4%, 3%, 2%, or less than about 1% ActRIIB homomultimers.

In certain aspects, the disclosure provides nucleic acids encoding an ALK4 or ActRIIB polypeptide as described herein. For example, an ActRIIB nucleic acid may comprise, consists essentially of, or consists of a nucleic acid that is at least 70%, 75%, 80%, 85%, 86%, 87%, 88%, 89%, 90%, 91%, 92%, 93%, 94%, 95%, 96%, 97%, 98%, 99%, or 100% identical to the sequence of 73-396 of SEQ ID NO: 7 or one that hybridizes under stringent conditions to the complement of nucleotides 73-396 of SEQ ID NO: 7. Such an nucleic acid may be one that comprises the sequence of SEQ ID NOs: 8 or 40. In some embodiments, an ActRIIB nucleic acids comprises, consists essentially of, or consists of a nucleotide sequence that is at least 70%, 75%, 80%, 85%, 86%, 87%, 88%, 89%, 90%, 91%, 92%, 93%, 94%, 95%, 96%, 97%, 98%, 99%, or 100% identical to any one of SEQ ID Nos: 7, 8, and 40. Similarly, an ALK4 nucleic acid may comprise, consists essentially of, or consists of a nucleic acid that is at least 70%, 75%, 80%, 85%, 86%, 87%, 88%, 89%, 90%, 91%, 92%, 93%, 94%, 95%, 96%, 97%, 98%, 99%, or 100% identical to the sequence of 70-378 of SEQ ID NO: 11 or one that hybridizes under stringent conditions to the complement of nucleotides 70-378 of SEQ ID NO: 11. Such an ALK4 nucleic acid may be one that comprises the sequence of SEQ ID NOs: 12, 22, or 43. In some embodiments, an ALK4 nucleic acids comprises, consists essentially of, or consists of a nucleotide sequence that is at least 70%, 75%, 80%, 85%, 86%, 87%, 88%, 89%, 90%, 91%, 92%, 93%, 94%, 95%, 96%, 97%, 98%, 99%, or 100% identical to any one of SEQ ID NOs: 11, 12, 21, 22, and 43.

In certain aspects, the present disclosure provides nucleic acids sequence comprising a coding sequence for and ALK4 polypeptide and a coding sequence for the ActRIIB polypeptide. For example, in some embodiments, nucleic acids of the disclosure a) comprises, consists essentially of, or consists of a nucleotide sequence that is at least 70%, 75%, 80%, 85%, 86%, 87%, 88%, 89%, 90%, 91%, 92%, 93%, 94%, 95%, 96%, 97%, 98%, 99%, or 100% identical to any one of SEQ ID NOs: 11, 12, 21, 22, and 43, and b) comprises, consists essentially of, or consists of a nucleotide sequence that is at least 70%, 75%, 80%, 85%, 86%, 87%, 88%, 89%, 90%, 91%, 92%, 93%, 94%, 95%, 96%, 97%, 98%, 99%, or 100% identical to any one of SEQ ID Nos: 7, 8, and 40. Preferably, ALK4 and/or ActRIIB nucleic acids are isolated and/or recombinant nucleic acids. Nucleic acids disclosed herein may be operably linked to a promoter for expression. The present disclosure further provides vectors comprising such ALK4 and/or ActRIIB polynucleotides as well as cells (e.g., CHO cells), preferably cells isolated from a human or other vertebrate species, comprising such ALK4 and/or ActRIIB polynucleotides as well as vectors comprising such ALK4 and/or ActRIIB polynucleotides.

In certain aspects, an ALK4 polypeptides and/or ActRIIB polypeptides may be expressed in a mammalian cell line, optionally a cell line that mediates suitably natural glycosylation of the ActRIIB or ALK4 protein so as to diminish the likelihood of an unfavorable immune response in a patient (including the possibility of veterinary patients). Human and CHO cell lines have been used successfully, and it is expected that other common mammalian expression vectors will be useful. Thus the disclosure provides cultured cells comprising any of the nucleic acids disclosed herein. Such cells may be mammalian cells, including CHO cells, NSO cells, HEK cells and COS cells. Other cells may be chosen depending on the species of the intended patient. Other cells are disclosed herein. Cultured cells are understood to mean cells maintained in laboratory or other man-made conditions (e.g., frozen, or in media) and not part of a living organism.

In certain aspects, the disclosure provides methods for making any of the ALK4 and ActRIIB polypeptides described herein as well as ALK4:ActRIIB heteromultimer complexes comprising such polypeptides. Such a method may include expressing any of the nucleic acids disclosed herein in a suitable cell (e.g., CHO cell or a COS cell). For example, in some embodiments a method of making a heteromultimer comprising an ALK4 polypeptide and an ActRIIB polypeptide comprises: a) culturing a cell under conditions suitable for expression of an ALK4 polypeptide and an ActRIIB polypeptide, wherein the cell comprises an ALK4 polynucleotide and an ActRIIB polynucleotide; and b) recovering the heteromultimer so expressed. Alternatively, a method of making a heteromultimer comprising an ALK4 polypeptide and an ActRIIB polypeptide may comprise: a) culturing a first cell under conditions suitable for expression of an ALK4 polypeptide, wherein the first cell comprises an ALK4 polynucleotide; b) recovering the ALK4 polypeptide so expressed; c) culturing a second cell under conditions suitable for expression of an ActRIIB polypeptide, wherein the second cell comprises an ActRIIB polynucleotide; d) recovering the ActRIIB polypeptide so expressed; e) combining the recovered ALK4 polypeptide and the recovered ActRIIB polypeptide under conditions suitable for ALK4:ActRIIB heteromultimer formation; and f) recovering the ALK4:ActRIIB heteromultimer. In certain embodiments, ALK4 and/or ActRIIB polypeptides are expressed using a TPA leader sequence (e.g., SEQ ID NO: 38). In certain embodiments, ALK4 and/or ActRIIB polypeptides are expressed in a CHO cell. ALK4 and ActRIIB polypeptides described herein, as well as protein complexes of the same, may be recovered as crude, partially purified, or highly purified fractions using any of the well-known techniques for obtaining protein from cell cultures. In general, such methods result in ALK4:ActRIIB heteromultimers that substantially free of ALK4 and/or ActRIIB homomultimers.

For example, in some embodiments, methods for producing ALK4:ActRIIB heteromultimers result in less than about 10%, 9%, 8%, 7%, 6%, 5%, 4%, 3%, 2%, or less than about 1% ALK4 homomultimers. In some embodiments, methods for producing ALK4:ActRIIB heteromultimers result in less than about 10%, 9%, 8%, 7%, 6%, 5%, 4%, 3%, 2%, or less than about 1% ActRIIB homomultimers. In some embodiments, methods for producing ALK4:ActRIIB heteromultimers result in less than about 10%, 9%, 8%, 7%, 6%, 5%, 4%, 3%, 2%, or less than about 1% ALK4 homomultimers and less than about 10%, 9%, 8%, 7%, 6%, 5%, 4%, 3%, 2%, or less than about 1% ActRIIB homomultimers.

The disclosure further provides methods and ALK4:ActRIIB antagonists (e.g., ALK4:ActRIIB heteromultimers) for use in the treatment or prevention of various ALK4:ActRIIB-associated diseases and conditions associated with, for example, muscle, bone, fat, red blood cells, and other tissues. Such disease and disorders include, but are not limited to, disorders associated with muscle loss or insufficient muscle growth (e.g., muscle atrophy; muscular dystrophy, including Duchenne muscular dystrophy, Becker muscular dystrophy, and facioscapulohumeral muscular dystrophy; amyotrophic lateral sclerosis; and cachexia) and disorders associated with undesirable weight gain (e.g., obesity, type 2 diabetes or non-insulin dependent diabetes mellitus (NIDDM), cardiovascular disease, hypertension, osteoarthritis, stroke, respiratory problems, and gall bladder disease). In some embodiments, ALK4:ActRIIB antagonists (e.g., heteromultimers) may be used to decrease body fat content or reduce the rate of increase in body fat content in a subject in need thereof. In some embodiments, ALK4:ActRIIB antagonists (e.g., heteromultimers) may be used to reduce cholesterol and/or triglyceride levels in a patient. In some embodiments, ALK4:ActRIIB antagonists (e.g., heteromultimers) may be used to treat or prevent fibrosis or a fibrosis-associated disorder or condition (e.g., renal failure, chronic renal disease, cystic fibrosis, and myelofibrosis).

The disclosure further provides methods and ALK4:ActRIIB antagonists for use in the treatment or prevention of various ALK4:ActRIIB—associated diseases and conditions associated with, for example, the kidney. Such diseases or conditions include, for example, chronic kidney disease or failure, acute kidney disease or failure, patients that have stage 1 kidney disease, patients that have stage 2 kidney disease, patients that have stage 3 kidney disease, patients that have stage 4 kidney disease, patients that have stage 5 kidney disease, non-diabetic kidney diseases, glomerulonephritis, interstitial nephritis, diabetic kidney diseases, diabetic nephropathy, glomerulosclerosis, rapid progressive glomerulonephritis, renal fibrosis, Alport syndrome, IDDM nephritis, mesangial proliferative glomerulonephritis, membranoproliferative glomerulonephritis, crescentic glomerulonephritis, renal interstitial fibrosis, focal segmental glomerulosclerosis, membranous nephropathy, minimal change disease, pauci-immune rapid progressive glomerulonephritis, IgA nephropathy, polycystic kidney disease, Dent's disease, nephrocytinosis, Heymann nephritis, autosomal dominant (adult) polycystic kidney disease, autosomal recessive (childhood) polycystic kidney disease, acute kidney injury, nephrotic syndrome, renal ischemia, podocyte diseases or disorders, proteinuria, glomerular diseases, membranous glomerulonephritis, focal segmental glomerulonephritis, pre-eclampsia, eclampsia, kidney lesions, collagen vascular diseases, benign orthostatic (postural) proteinuria, IgM nephropathy, membranous nephropathy, sarcoidosis, diabetes mellitus, kidney damage due to drugs, Fabry's disease, aminoaciduria, Fanconi syndrome, hypertensive nephrosclerosis, interstitial nephritis, Sickle cell disease, hemoglobinuria, myoglobinuria, Wegener's Granulomatosis, Glycogen Storage Disease Type 1, chronic kidney disease, chronic renal failure, low Glomerular Filtration Rate (GFR), nephroangiosclerosis, lupus nephritis, ANCA-positive pauci-immune crescentic glomerulonephritis, chronic allograft nephropathy, nephrotoxicity, renal toxicity, kidney necrosis, kidney damage, glomerular and tubular injury, kidney dysfunction, nephritic syndrome, acute renal failure, chronic renal failure, proximal tubal dysfunction, acute kidney transplant rejection, chronic kidney transplant rejection, non-IgA mesangioproliferative glomerulonephritis, postinfectious glomerulonephritis, vasculitides with renal involvement of any kind, any hereditary renal disease, any interstitial nephritis, renal transplant failure, kidney cancer, kidney disease associated with other conditions (e.g., hypertension, diabetes, and autoimmune disease), Dent's disease, nephrocytinosis, Heymann nephritis, a primary kidney disease, a collapsing glomerulopathy, a dense deposit disease, a cryoglobulinemia-associated glomerulonephritis, an Henoch-Schonlein disease, a postinfectious glomerulonephritis, a bacterial endocarditis, a microscopic polyangitis, a Churg-Strauss syndrome, an anti-GBM-antibody mediated glomerulonephritis, amyloidosis, a monoclonal immunoglobulin deposition disease, a fibrillary glomerulonephritis, an immunotactoid glomerulopathy, ischemic tubular injury, a medication-induced tubulo-interstitial nephritis, a toxic tubulo-interstitial nephritis, an infectious tubulo-interstitial nephritis, a bacterial pyelonephritis, a viral infectious tubulo-interstitial nephritis which results from a polyomavirus infection or an HIV infection, a metabolic-induced tubulo-interstitial disease, a mixed connective disease, a cast nephropathy, a crystal nephropathy which may results from urate or oxalate or drug-induced crystal deposition, an acute cellular tubulo-interstitial allograft rejection, a tumoral infiltrative disease which results from a lymphoma or a post-transplant lymphoproliferative disease, an obstructive disease of the kidney, vascular disease, a thrombotic microangiopathy, a nephroangiosclerosis, an atheroembolic disease, a mixed connective tissue disease, a polyarteritis *nodosa*, a calcineurin-inhibitor induced-vascular disease, an acute cellular vascular allograft rejection, an acute humoral allograft rejection, early renal function decline (ERFD), end stage renal disease (ESRD), renal vein thrombosis, acute tubular necrosis, renal occlusion, acute interstitial nephritis, established chronic kidney disease, renal artery stenosis, ischemic nephropathy, uremia, drug and toxin-induced chronic tubulointerstitial nephritis, reflux nephropathy, kidney stones, Goodpasture's syndrome, normocytic normochromic anemia, renal anemia, diabetic chronic kidney disease, IgG4-related disease, von Hippel-Lindau syndrome, tuberous sclerosis, nephronophthisis, medullary cystic kidney disease, renal cell carcinoma, adenocarcinoma, nephroblastoma, lymphoma, leukemia, hyposialylation disorder, chronic cyclosporine nephropathy, renal reperfusion injury, renal dysplasia, azotemia, bilateral arterial occlusion, acute uric acid nephropathy, hypovolemia, acute bilateral obstructive uropathy, hypercalcemic nephropathy, hemolytic uremic syndrome, acute urinary retention, malignant nephrosclerosis, postpartum glomerulosclerosis, scleroderma, non-Goodpasture's anti-GBM disease, microscopic polyarteritis *nodosa*, allergic granulomatosis, acute radiation nephritis, post-streptococcal glomerulonephritis, Waldenstrom's macroglobulinemia, analgesic nephropathy, arteriovenous fistula, arteriovenous graft, dialysis, ectopic kidney, medullary sponge kidney, renal osteodystrophy, solitary kidney, hydronephrosis, microalbuminuria, uremia, haematuria, hyperlipidemia, hypoalbuminaemia, lipiduria, acidosis, and hyperkalemia. In some embodiments, the disclosure further provides methods and ALK4:ActRIIB antagonists for use in delaying or preventing progression from: stage 1 to stage 2 kidney disease, stage 2 to stage 3 kidney disease, stage 3 to stage 4 kidney disease, or stage 4 to stage 5 kidney disease. In some embodiments, the disclosure further provides methods and ALK4:ActRIIB antagonists for use in preventing or reducing kidney inflammation. In some embodiments, the disclosure further provides methods and ALK4:ActRIIB antagonists for use in preventing or reducing kidney damage. In some embodiments, the disclosure further provides methods and ALK4:ActRIIB antagonists for use in preventing or reducing kidney fibrosis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A depicts a heterodimeric protein complex comprising one type I receptor fusion polypeptide and one type II receptor fusion polypeptide, which can be assembled covalently or noncovalently via a multimerization domain contained within each polypeptide chain. Two assembled multimerization domains constitute an interaction pair, which can be either guided or unguided. FIG. 1B depicts a heterotetrameric protein complex comprising two heterodimeric complexes as depicted in FIG. 1A. Complexes of higher order can be envisioned.

FIG. 3 shows an alignment of extracellular domains of human ActRIIA (SEQ ID NO: 49) and human ActRIIB (SEQ ID NO: 2) with the residues that are deduced herein, based on composite analysis of multiple ActRIIB and ActRIIA crystal structures, to directly contact ligand indicated with boxes.

FIG. 5 shows multiple sequence alignment of Fc domains from human IgG isotypes using Clustal 2.1. Hinge regions are indicated by dotted underline. Double underline indicates examples of positions engineered in IgG1 Fc to promote asymmetric chain pairing and the corresponding positions with respect to other isotypes IgG2, IgG3 and IgG4. FIG. 5 discloses SEQ ID NOS 31, 35, 32 and 33, respectively, in order of appearance.

FIG. 7 shows a multiple sequence alignment of ALK4 extracellular domains derived from various vertebrate species (SEQ ID NOs: 59-65).

Figure 8A:
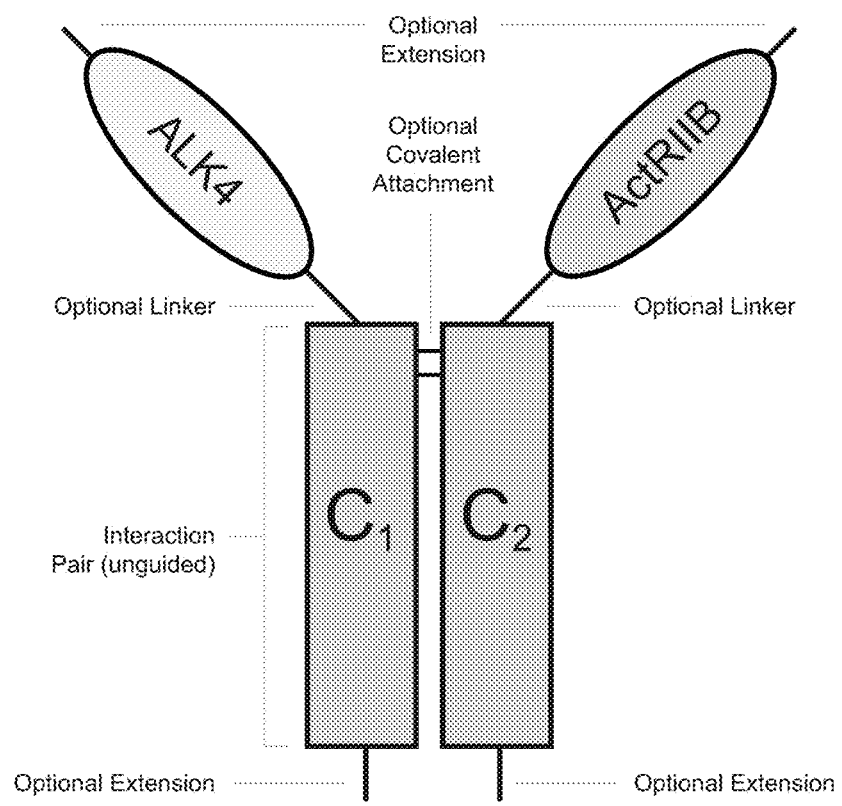
FIGS. 8A-8D show schematic examples of heteromeric protein complexes comprising an ALK4 polypeptide (e.g. a polypeptide that is at least 70%, 75%, 80%, 85%, 90%, 91%, 92%, 93%, 94%, 95%, 97%, 98%, 99% or 100% identical to an extracellular domain of an ALK4 protein from humans or other species such as those described herein, e.g., SEQ ID Nos: 9, 10, 19, 20, 42, 44, 47, and 48) and an ActRIIB polypeptide (e.g. a polypeptide that is at least 70%, 75%, 80%, 85%, 90%, 91%, 92%, 93%, 94%, 95%, 97%, 98%, 99% or 100% identical to an extracellular domain of an ActRIIB protein from humans or other species such as those described herein, e.g., SEQ ID Nos: 1, 2, 3, 4, 5, 6, 39, 41, 45, and 46).
Figure 8B:
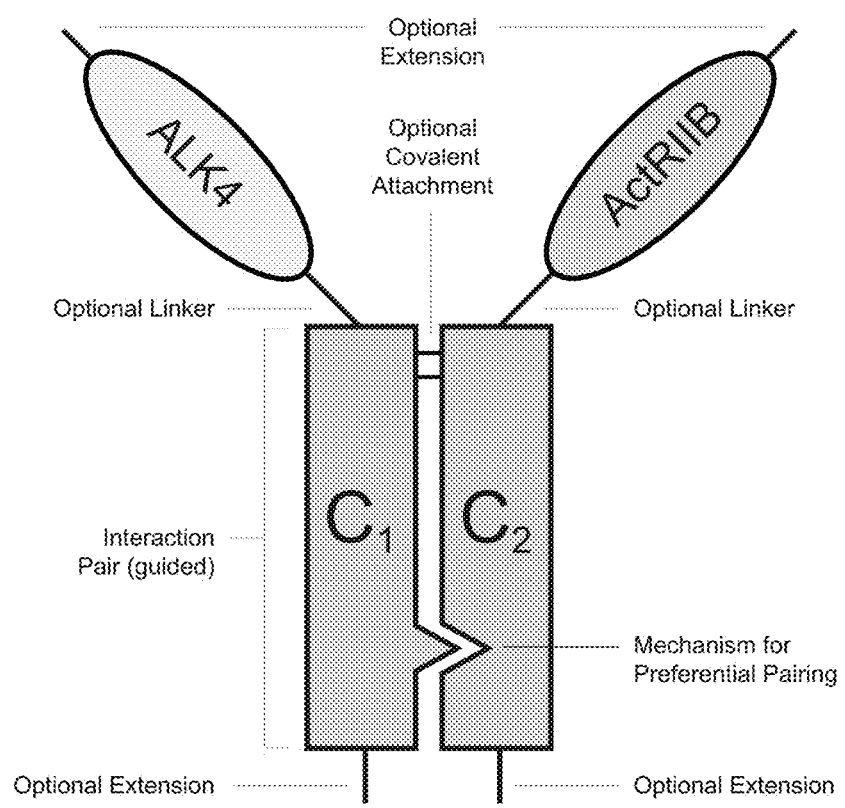
Figure 8C:
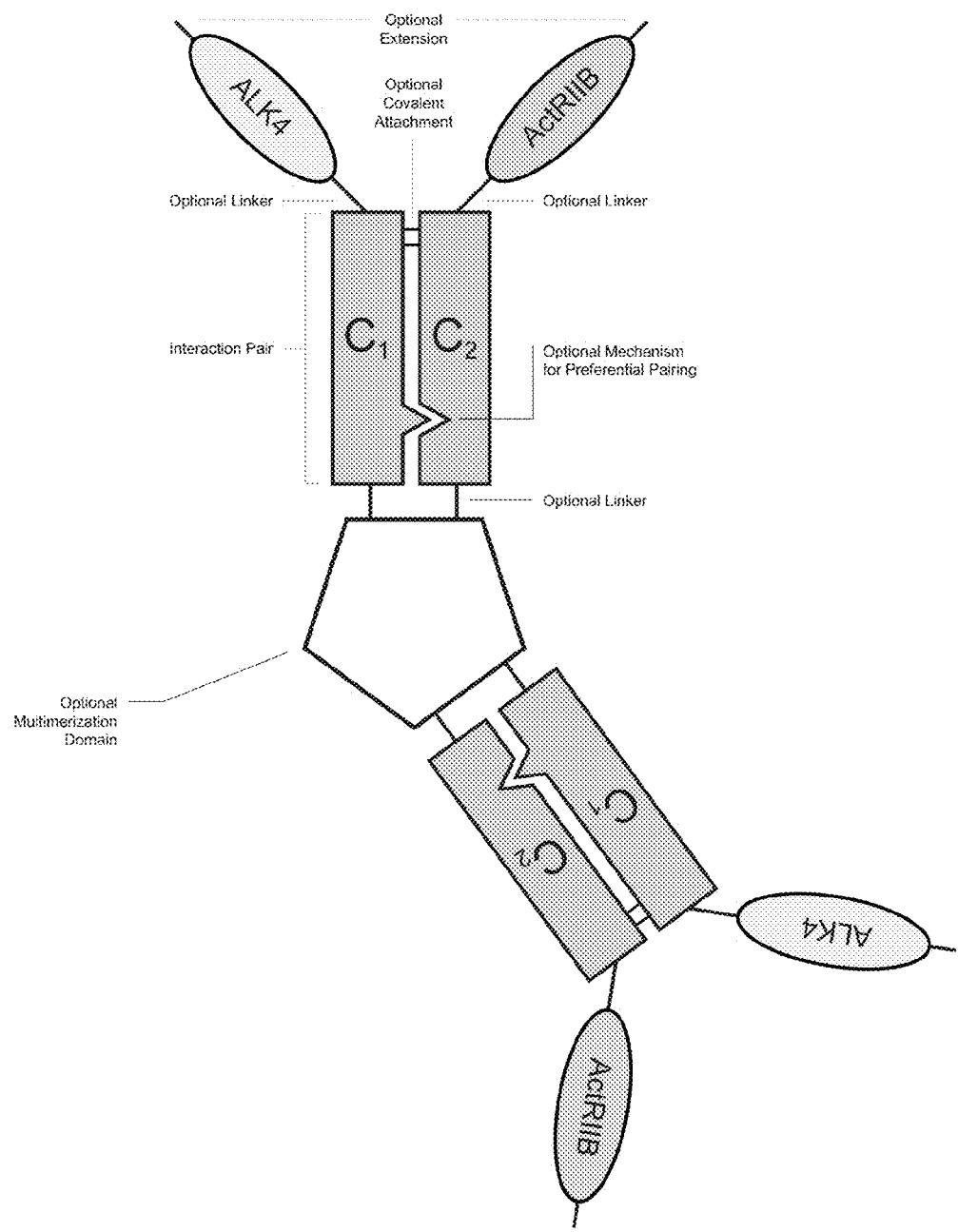
Figure 8D:
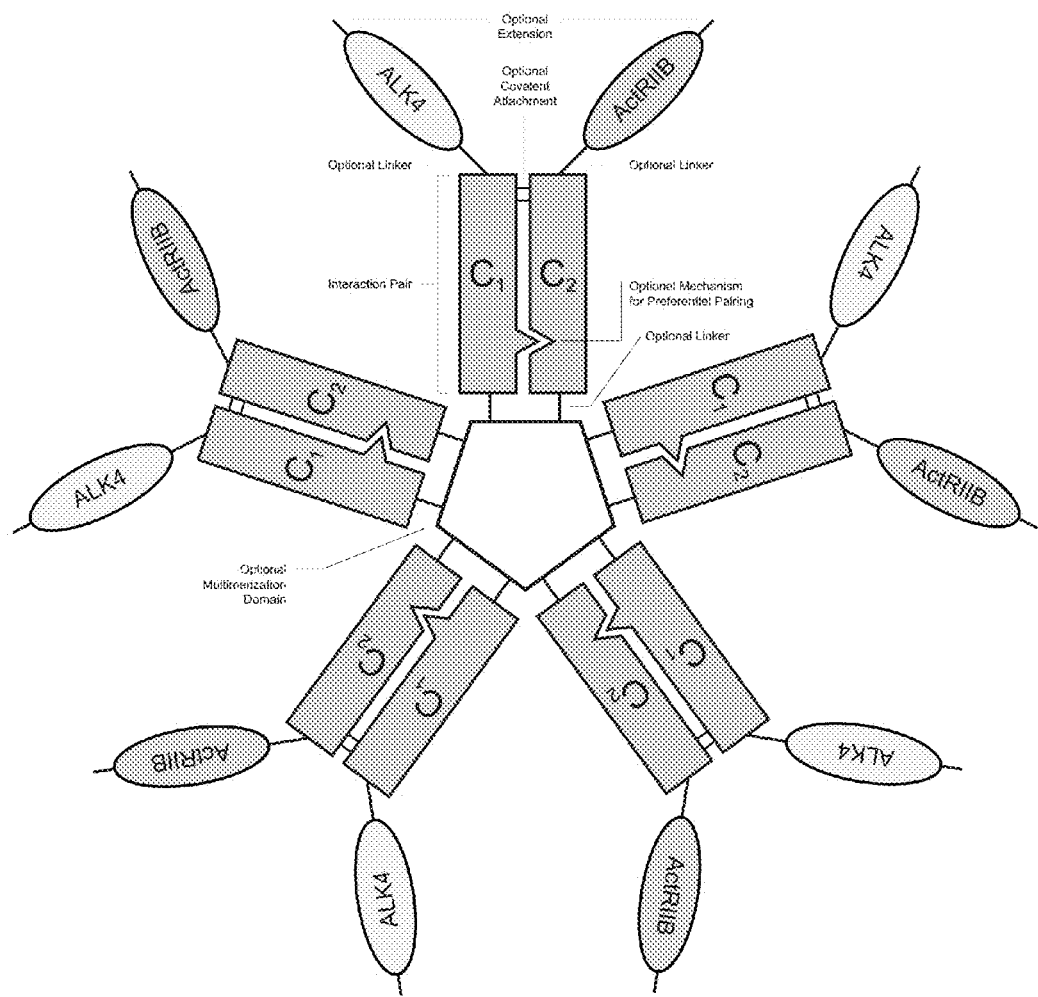

In the illustrated embodiments, the ALK4 polypeptide (from left to right) is part of a fusion polypeptide that comprises a first member of an interaction pair ("$C_1$"), and the ActRIIB polypeptide is part of a fusion polypeptide that comprises a second member of an interaction pair ("$C_2$"). Suitable interaction pairs included, for example, heavy chain and/or light chain immunoglobulin interaction pairs, truncations, and variants thereof such as those described herein [e.g., Spiess et al (2015) Molecular Immunology 67(2A): 95-106]. In each fusion polypeptide, a linker may be positioned between the ALK4 or ActRIIB polypeptide and the corresponding member of the interaction pair. The first and second members of the interaction pair may be unguided, meaning that the members of the pair may associate with each other or self-associate without substantial preference, and they may have the same or different amino acid sequences. See FIG. 8A. Alternatively, the interaction pair may be a guided (asymmetric) pair, meaning that the members of the pair associate preferentially with each other rather than self-associate. See FIG. 8B. Complexes of higher order can be envisioned. See FIGS. 8C and 8D.

FIGS. 9A-9G show schematic examples of heteromeric protein complexes comprising two ALK4 polypeptides (e.g. polypeptide that are independently at least 70%, 75%, 80%, 85%, 90%, 91%, 92%, 93%, 94%, 95%, 97%, 98%, 99% or 100% identical to an extracellular domain of an ALK4 protein from humans or other species such as those described herein, e.g., SEQ ID Nos: 9, 10, 19, 20, 42, 44, 47, and 48) and two ActRIIB polypeptides (e.g. two polypeptides that are independently at least 70%, 75%, 80%, 85%, 90%, 91%, 92%, 93%, 94%, 95%, 97%, 98%, 99% or 100% identical to an extracellular domain of an ActRIIB protein from humans or other species such as those described herein, e.g., SEQ ID Nos: 1, 2, 3, 4, 5, 6, 39, 41, 45, and 46).

Figure 9A:
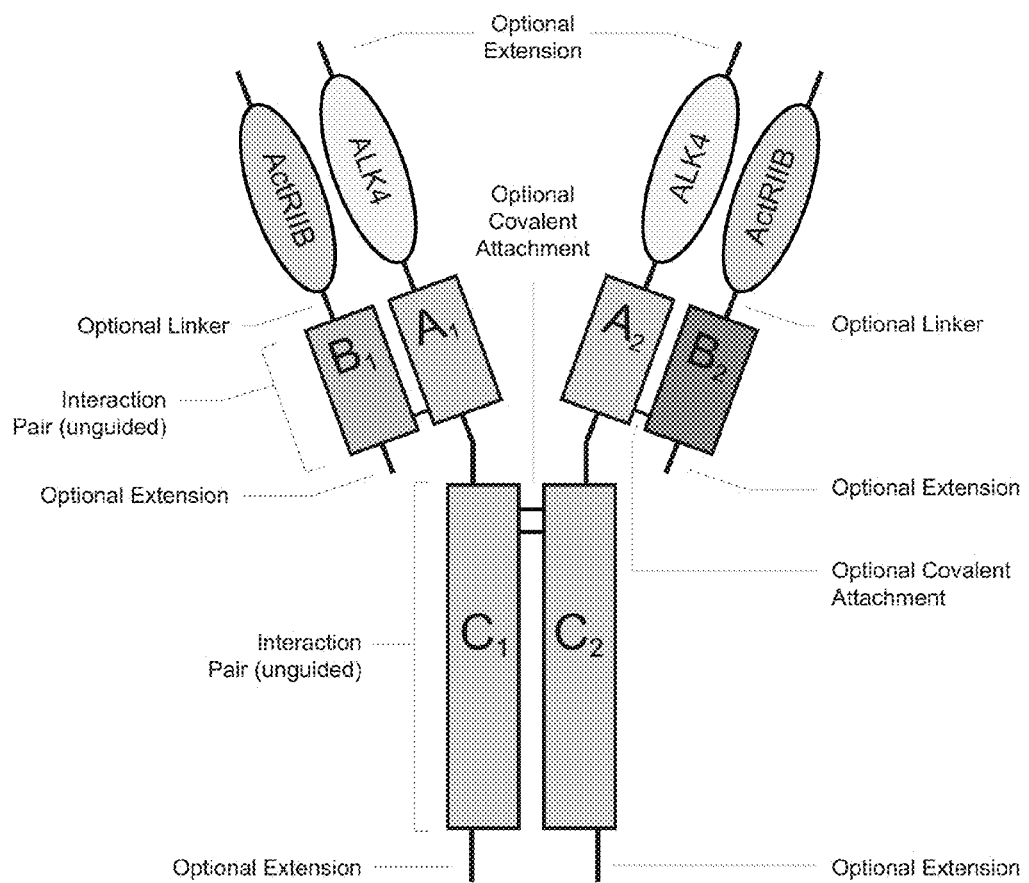

In the illustrated embodiment FIG. 9A, the first ALK4 polypeptide (from left to right) is part of a fusion polypeptide that comprises a first member of an interaction pair ("$C_1$") and further comprises an additional first member of an interaction pair ("$A_1$"); and the second ALK4 polypeptide is part of a fusion polypeptide that comprises a second member of an interaction pair ("$C_2$") and further comprises an first member of an interaction pair ("$A_2$"). The first ActRIIB polypeptide (from left to right) is part of a fusion polypeptide that comprises a second member of an interaction pair ("$B_1$"); and the second ActRIIB polypeptide is part of a fusion polypeptide that comprises a second member of an interaction pair ("$B_2$"). $A_1$ and $A_2$ may be the same or different; $B_1$ and $B_2$ may be the same or different, and $C_1$ and $C_2$ may be the same or different. In each fusion polypeptide, a linker may be positioned between the ALK4 or ActRIIB polypeptide and the corresponding member of the interaction pair as well as between interaction pairs. FIG. 9A is an example of an association of unguided interaction pairs, meaning that the members of the pair may associate with each other or self-associate without substantial preference and may have the same or different amino acid sequences.

Figure 9B:
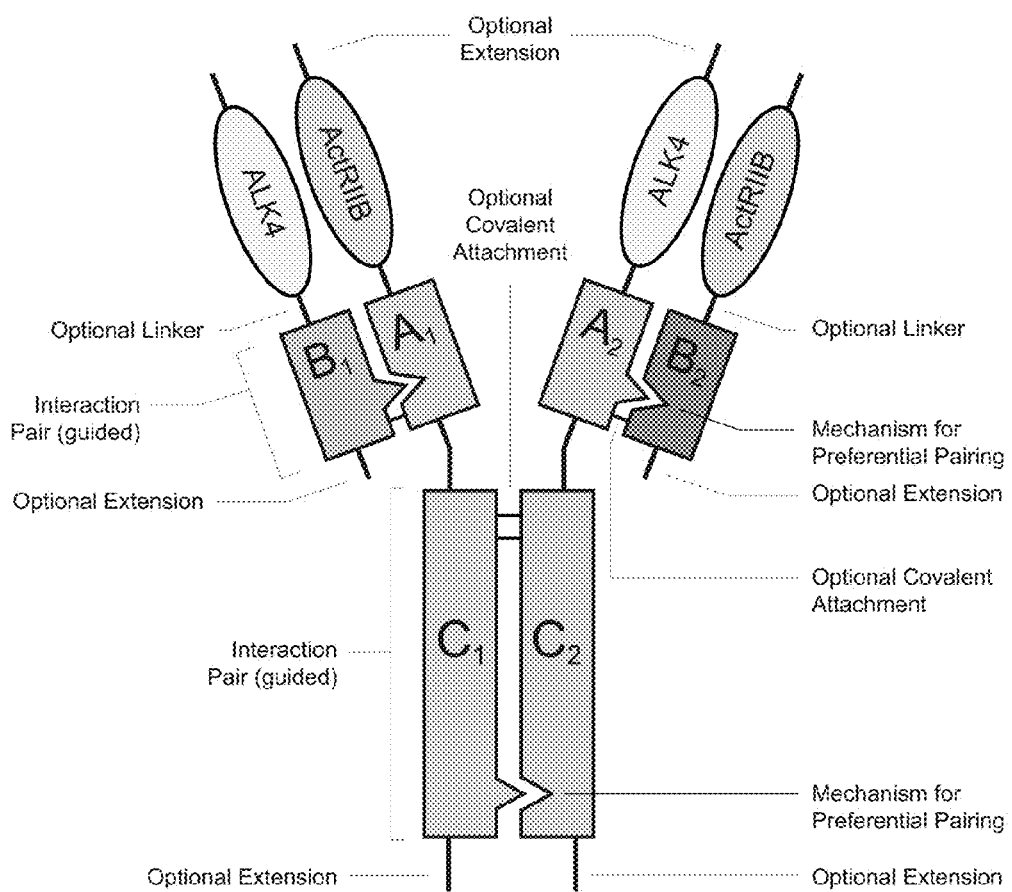
Figure 9C:
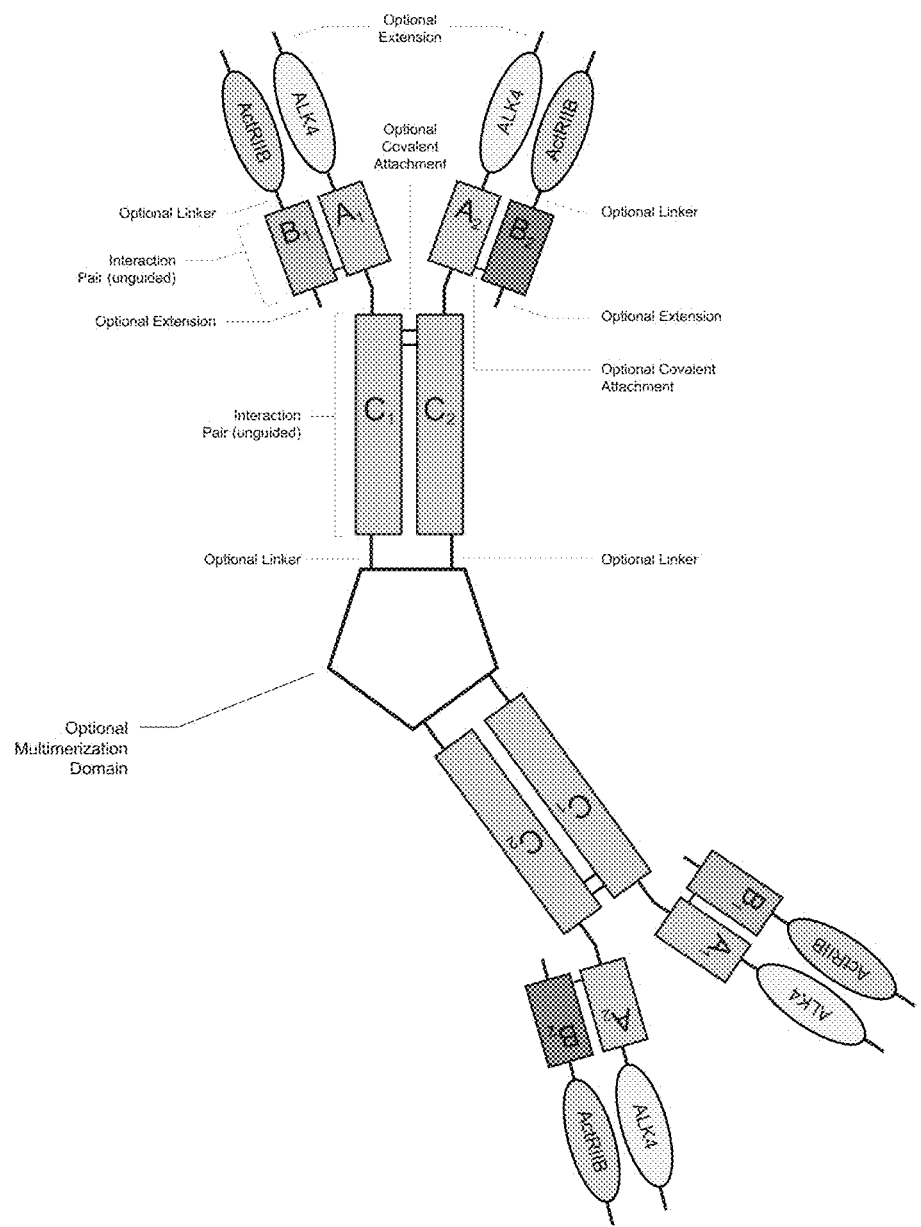
Figure 9D:
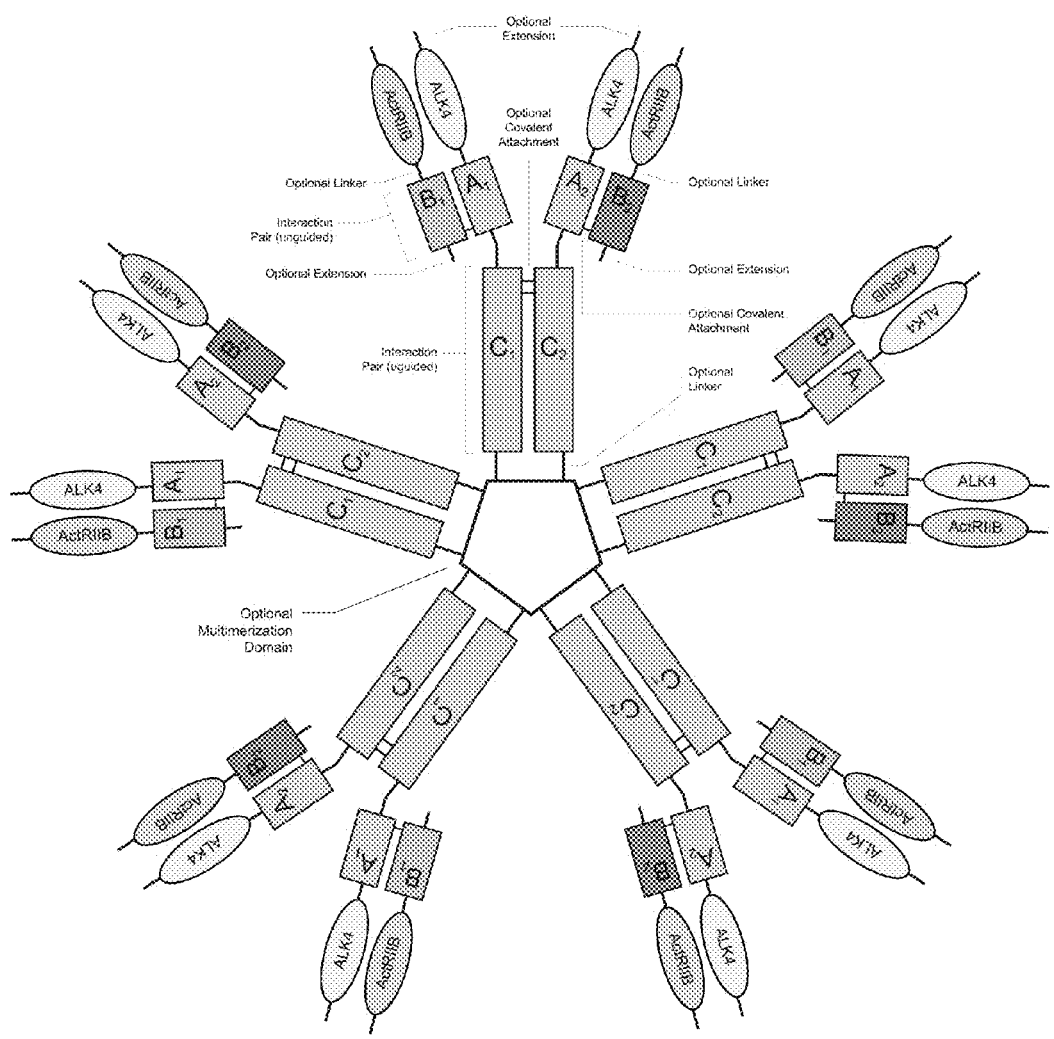
Figure 9E:
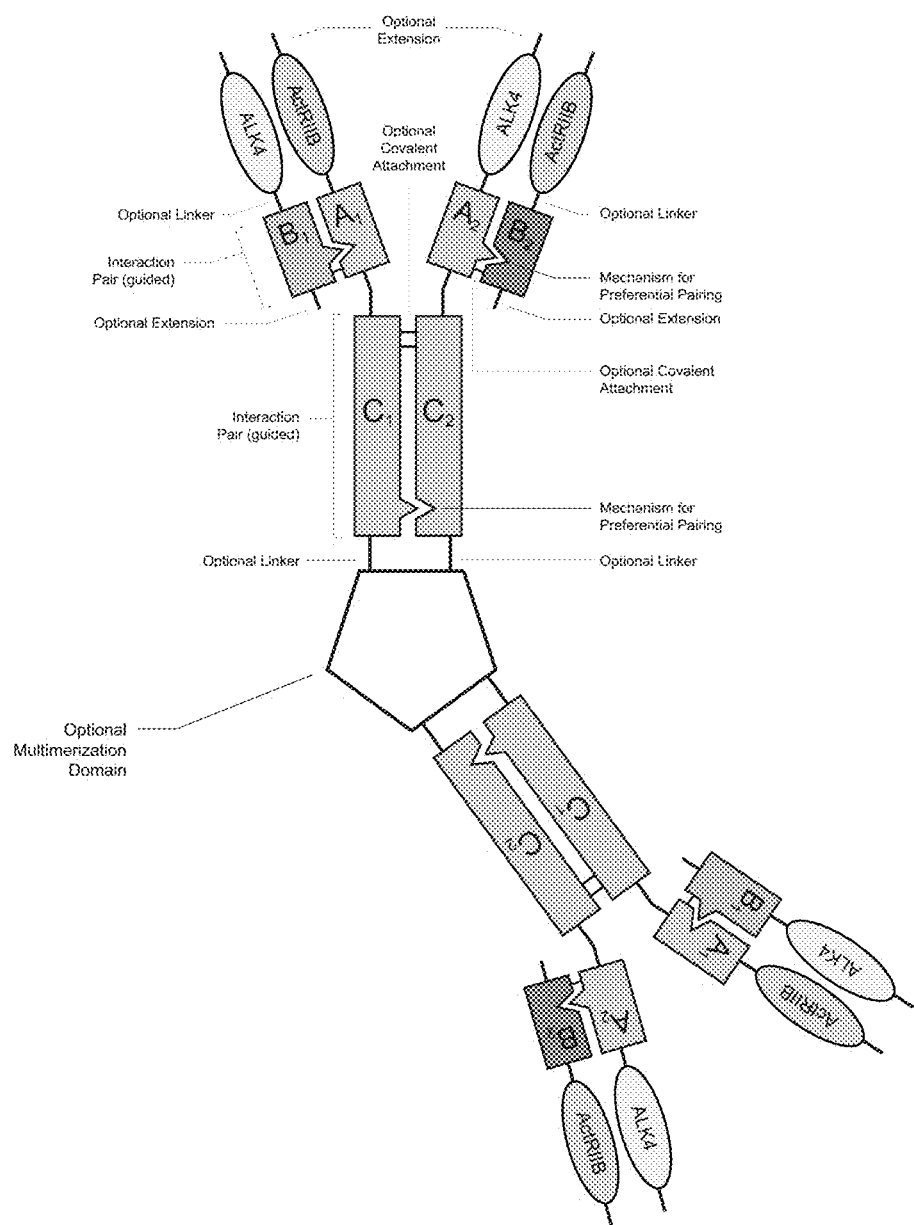
Figure 9F:
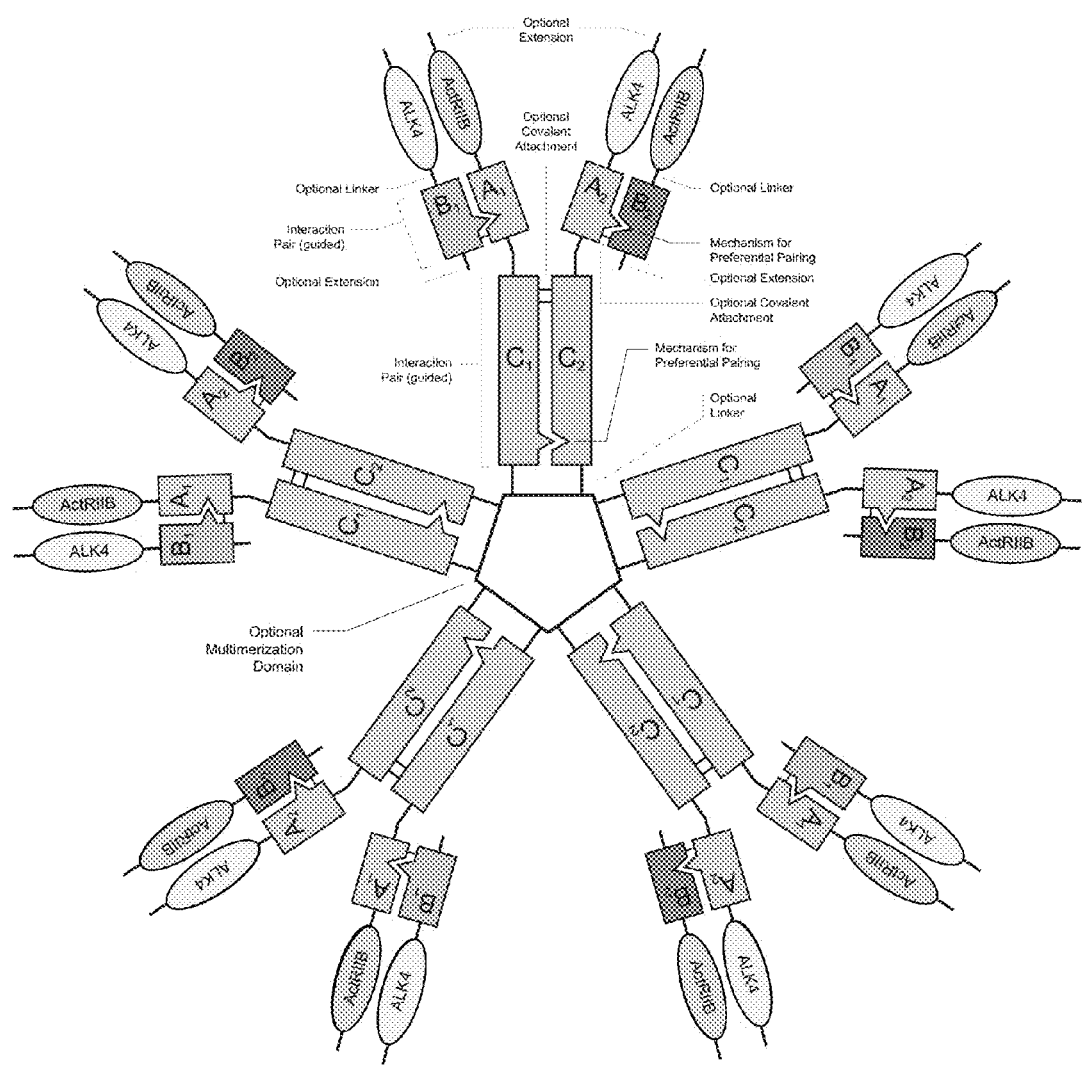
Figure 9G:
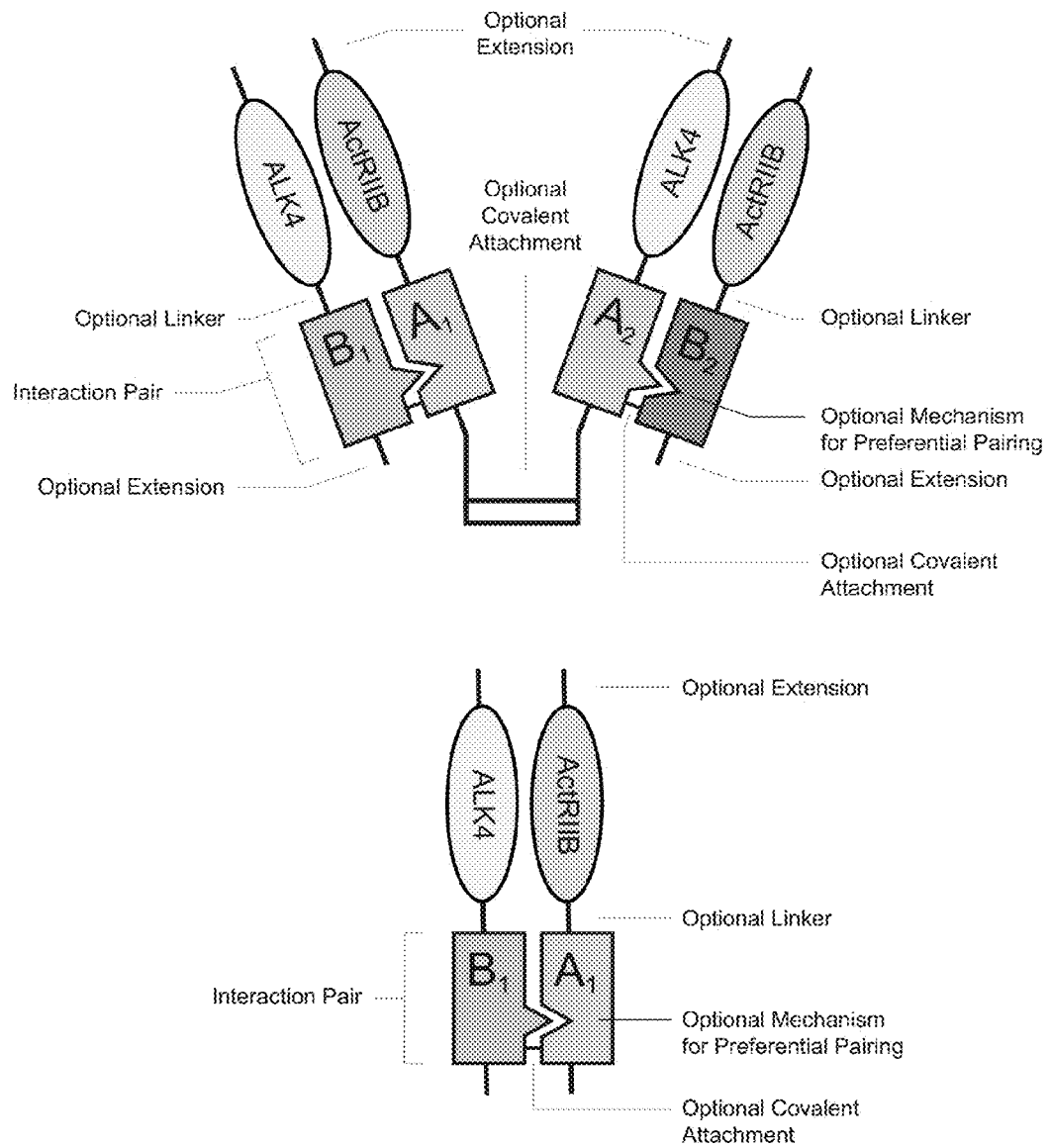

In the illustrated embodiment FIG. 9B, the first ActRIIB polypeptide (from left to right) is part of a fusion polypeptide that comprises a first member of an interaction pair ("$C_1$") and further comprises an additional first member of an interaction pair ("$A_1$"); and the second ActRIIB polypeptide is part of a fusion polypeptide that comprises a second member of an interaction pair ("$B_2$"). The first ALK4 polypeptide (from left to right) is part of a fusion polypeptide that comprises a second member of an interaction pair ("$B_1$"); and the second ALK4 polypeptide is part of a fusion polypeptide that comprises a second member of an interaction pair ("$C_2$") and further comprises a first member of an interaction pair ("$A_2$"). In each fusion polypeptide, a linker may be positioned between the ALK4 or ActRIIB polypeptide and the corresponding member of the interaction pair as well as between interaction pairs. FIG. 9B is an example of an association of guided (asymmetric) interaction pairs, meaning that the members of the pair associate preferentially with each other rather than self-associate.

Suitable interaction pairs included, for example, heavy chain and/or light chain immunoglobulin interaction pairs, truncations, and variants thereof as described herein [e.g., Spiess et al (2015) Molecular Immunology 67(2A): 95-106]. Complexes of higher order can be envisioned. See FIGS. 9C-9F. Using similar methods (particularly those that employ light and/or heavy chain immunoglobulins, truncations, or variants thereof), interaction pairs may be used to produce ALK4:ActRIIB heterodimers that resemble antibody Fab and F(ab')$_2$ complexes [e.g., Spiess et al (2015) Molecular Immunology 67(2A): 95-106]. See FIG. 9G.

Figure 10A:
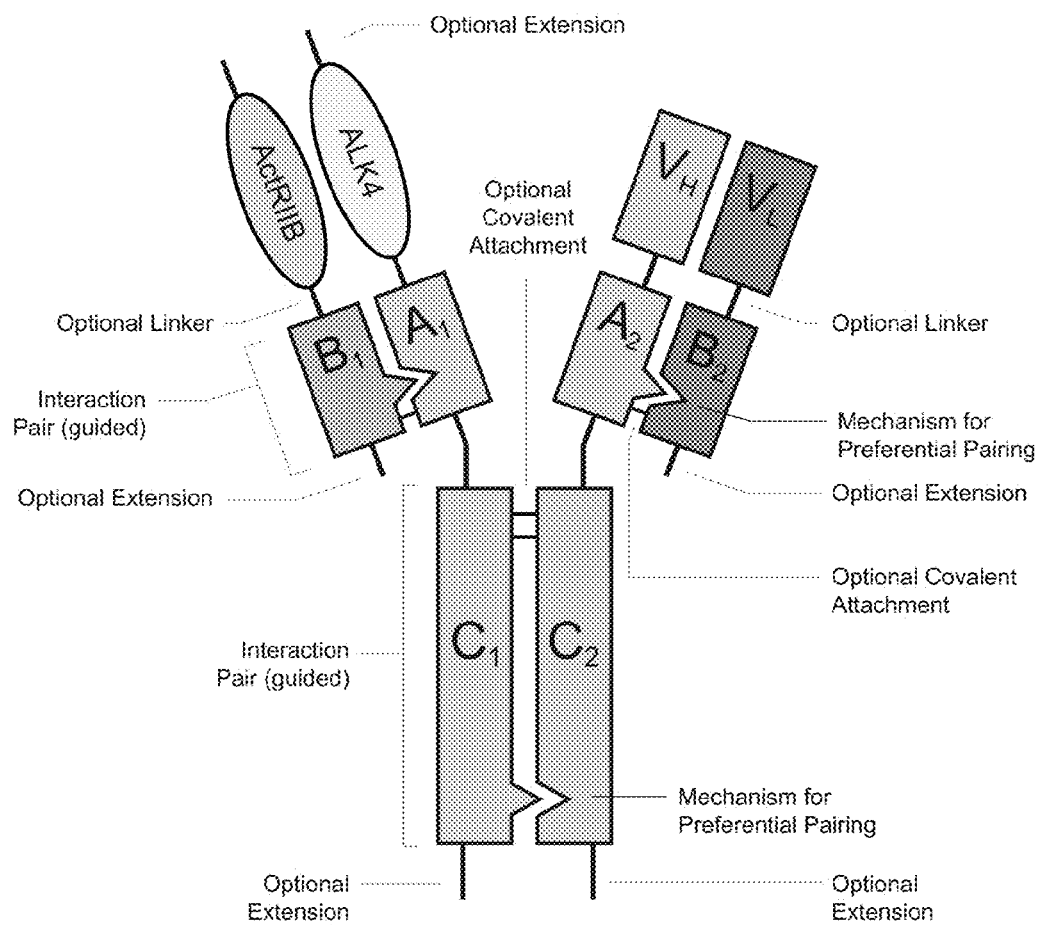
Figure 10B:
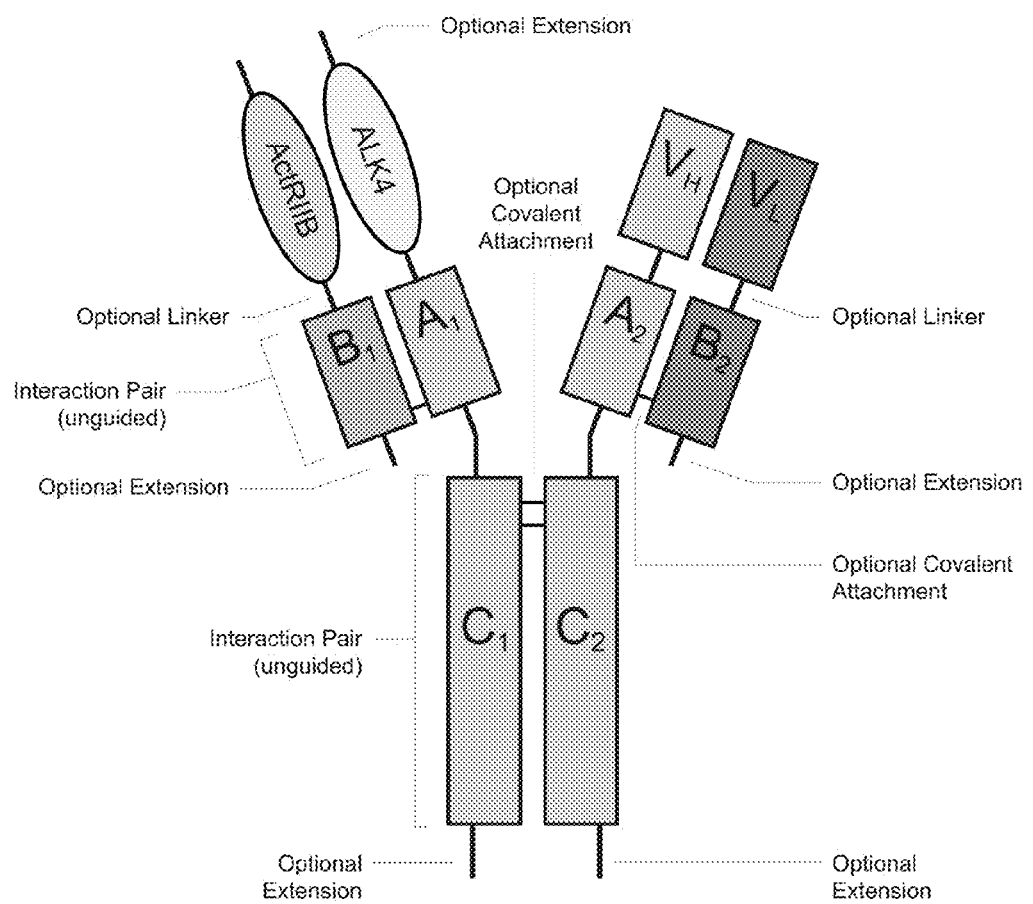

FIGS. 10A and 10B show schematic examples of a heteromeric protein complex comprising an ALK4 polypeptide (e.g. a polypeptide that is at least 70%, 75%, 80%, 85%, 90%, 91%, 92%, 93%, 94%, 95%, 97%, 98%, 99% or 100% identical to an extracellular domain of an ALK4 protein from humans or other species as described herein, e.g., SEQ ID Nos: 9, 10, 19, 20, 42, 44, 47, and 48), an ActRIIB polypeptide (e.g. a polypeptide that is at least 70%, 75%, 80%, 85%, 90%, 91%, 92%, 93%, 94%, 95%, 97%, 98%, 99% or 100% identical to an extracellular domain of an ActRIIB protein from humans or other species as such as those described herein, e.g., SEQ ID Nos: 1, 2, 3, 4, 5, 6, 39, 41, 45, and 46), and a ligand-binding domain of an antibody (e.g., a ligand-binding domain derived from an antibody that binds to one or more ALK4:ActRIIB-binding ligands). In the illustrated embodiments, the ALK4 polypeptide is part of a fusion polypeptide that comprises a first member of an interaction pair ("$C_1$"), and further comprises an additional first member of an interaction pair ("$A_1$"). The ActRIIB polypeptide is part of a fusion polypeptide that comprises a second member of an interaction pair ("$B_1$"). The variable heavy chain ($V_H$) polypeptide is part of a fusion polypeptide that comprises a second member of an interaction pair ("$C_2$"), and further comprises a first member of an interaction pair ("$A_2$"). The variable heavy chain ($V_L$) polypeptide is part of a fusion polypeptide that comprises a second member of an interaction pair ("$B_2$"). In each fusion polypeptide, a linker may be positioned between the ALK4 or ActRIIB polypeptide and the corresponding member of the interaction pair, between interaction pairs, and between the $V_H$ and $V_L$ polypeptides and a member of the interaction pair. $A_1$ and $A_2$ may be the same or different; $B_1$ and $B_2$ may be the same or different, and $C_1$ and $C_2$ may be the same or different. Suitable interaction pairs included, for example, constant heavy chain and/or light chain immunoglobulin interaction pairs, truncations, and variants thereof as described herein [e.g., Spiess et al (2015) Molecular Immunology 67(2A): 95-106]. FIG. 10A is an example of an association of guided (asymmetric) interaction pairs, meaning that the members of the pair associate preferentially with each other rather than self-associate. FIG. 10B is an example of an association of unguided interaction pairs, meaning that the members of the pair may associate with each other or self-associate without substantial preference and may have the same or different amino acid sequences.

Such antibody-ALK4:ActRIIB complexes may be useful in situations where it is desirable to further bind/antagonize an agent that is not an ALK4:ActRIIB ligand. Alternatively, such antibody-ALK4:ActRIIB complexes may be useful in situations where it is desirable to further enhance ALK4:ActRIIB ligand binding/antagonism. For example, as demonstrated by the examples herein, activin B, activin A, GDF11, and GDF8 all bind with strong affinity to an ALK4:ActRIIB heterodimer. In addition, BMP6 binds to ALK4:ActRIIB heterodimers but with weaker affinity. In certain situations where it is desirable to antagonize BMP6 activity, in addition to one or more of the high affinity-binding ligands (e.g., activin B, activin A, GDF11, and GDF8), BMP6 may be outcompeted for binding to the ALK4:ActRIIB heterodimer. In such situations, addition of BMP6-binding domain of an antibody to the ALK4:ActRIIB heteromultimer complex would improve the capacity of such protein complexes to antagonize BMP6 in addition to one or more of activin B, activin A, GDF11, and GDF8.

Figure 11:
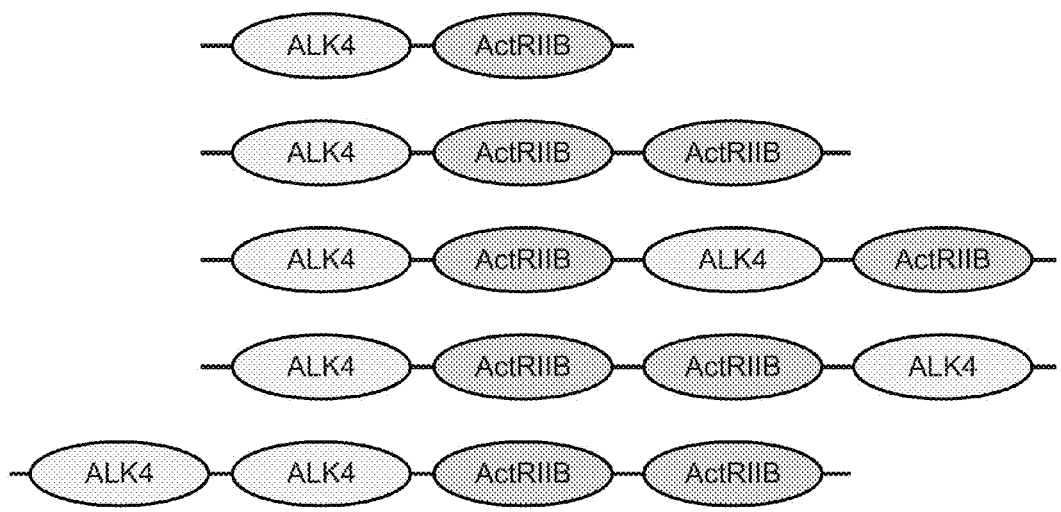

FIG. 11 shows schematic examples of ALK4:ActRIIB single-trap polypeptides. ALK4:ActRIIB single-trap polypeptides may contain multiple ALK4 domains (e.g., 1, 2, 3, 4, 5, 6, 7, 9, 10 or more domains), having the same or different sequences, and multiple ActRIIB domains (e.g., 1, 2, 3, 4, 5, 6, 7, 9, 10 or more domains), having the same or different sequences. These ALK4 and ActRIIB domains may be arranged in any order and may comprise one or more linker domains positions between one or more of the ALK4 and ActRIIB domains. Such ligand traps may be used as therapeutic agents to treat or prevent diseases or conditions described herein.

Figure 12A:
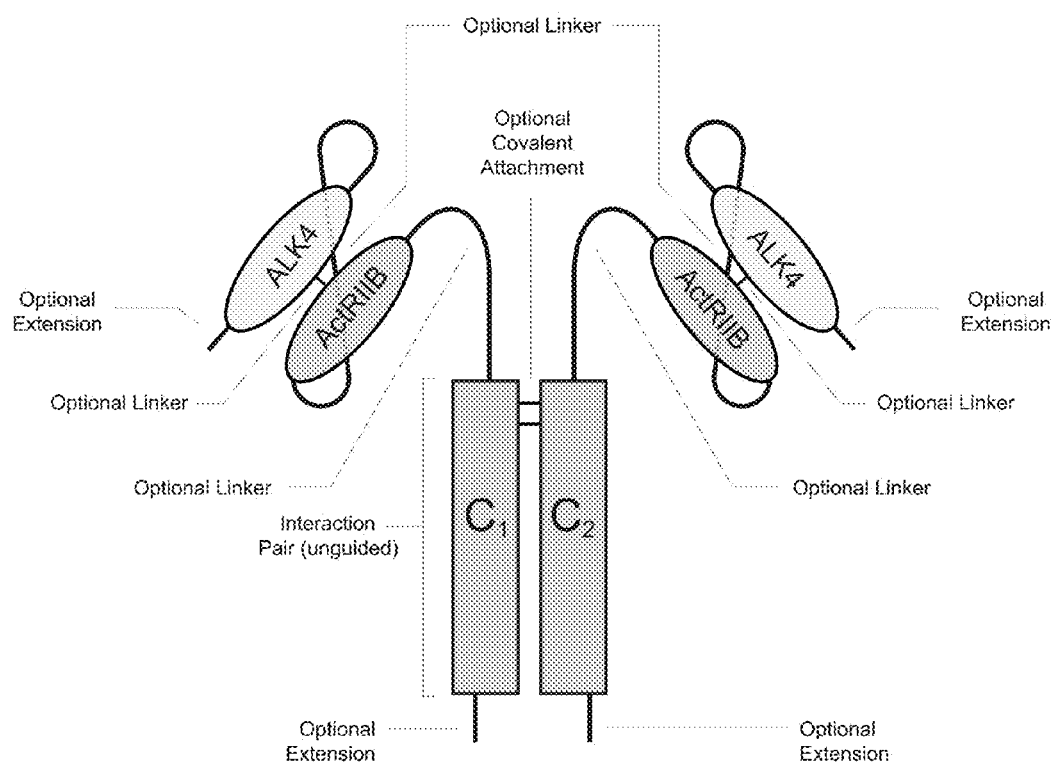
Figure 12B:
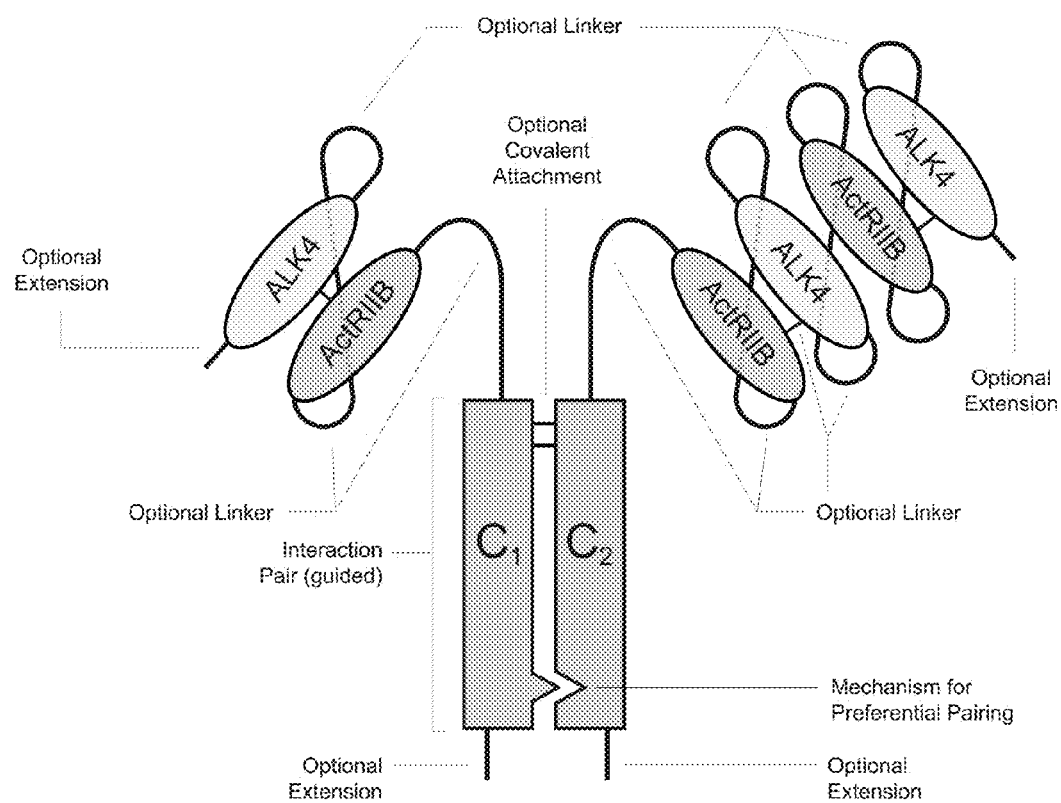
Figure 12C:
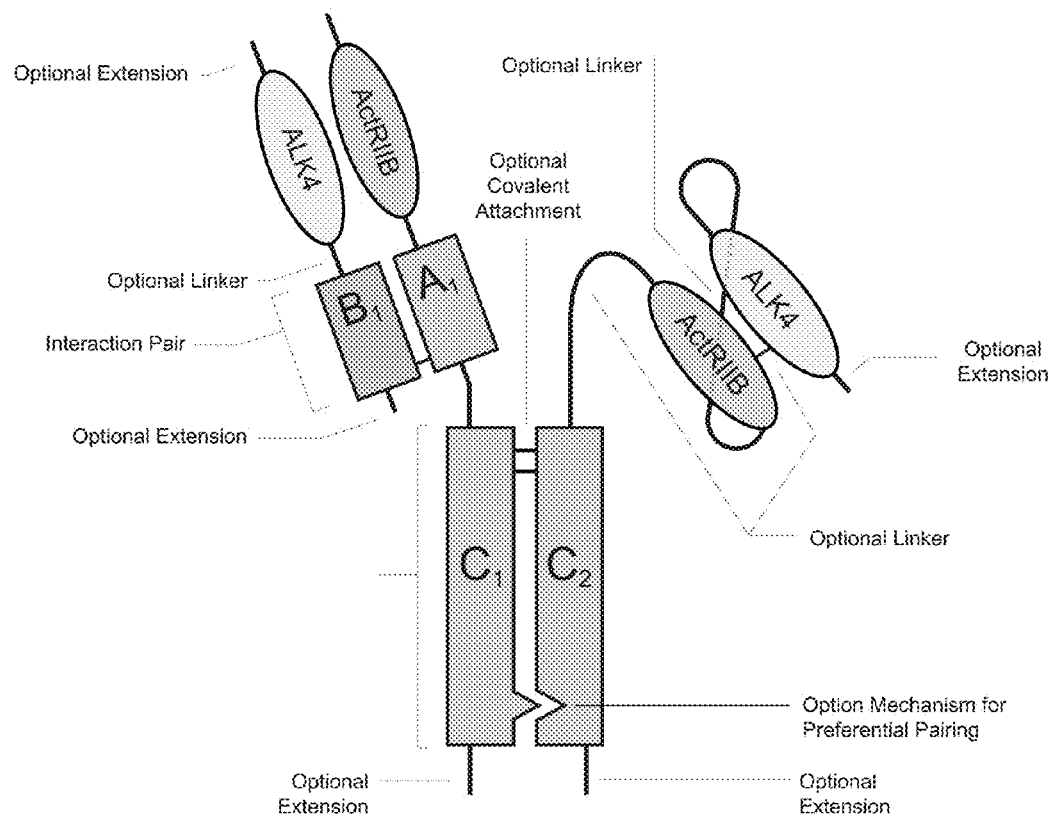
Figure 12D:
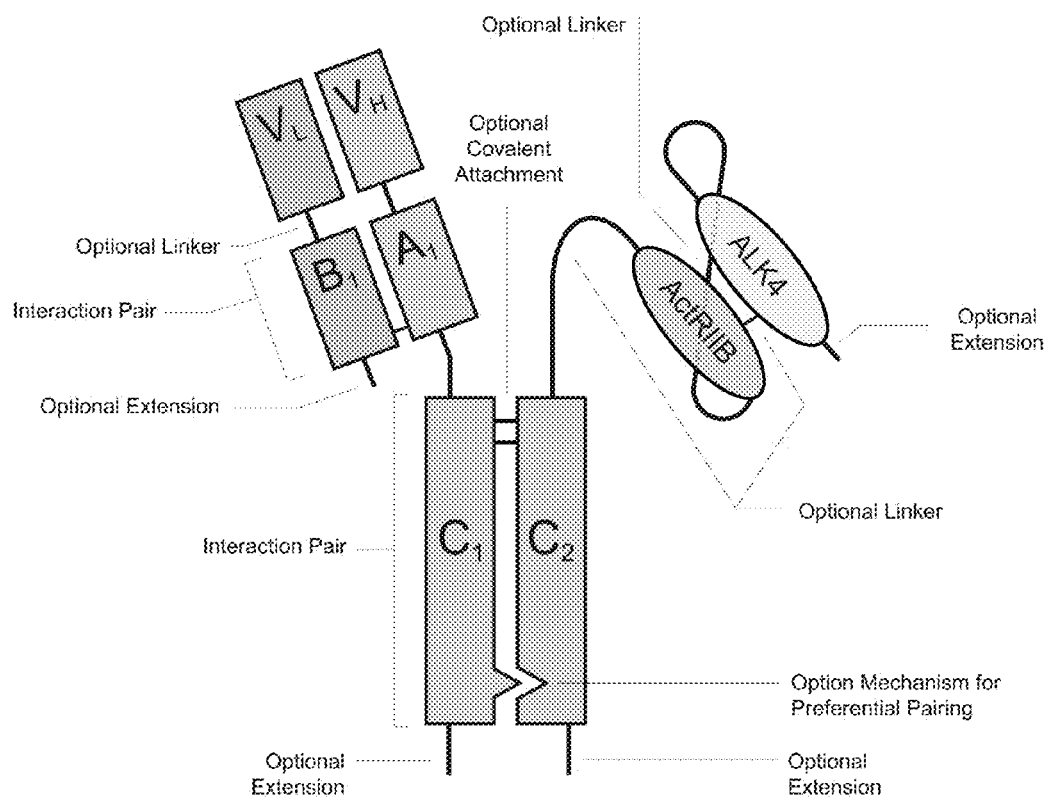

FIG. 12A-12D show schematic examples of multimeric protein complex comprising at least one ALK4:ActRIIB single-chain trap polypeptides. In the illustrated embodiments 12A and 12B, a first ALK4:ActRIIB single-chain trap polypeptide (from left to right) is part of a fusion polypeptide that comprises a first member of an interaction pair ("$C_1$"); and a second ALK4:ActRIIB single-chain trap polypeptide is part of a fusion polypeptide that comprises a second member of an interaction pair ("$C_2$"). $C_1$ and $C_2$ may be the same or different. The first and second ALK4:ActRIIB single-chain trap polypeptides may be the same or different. In each fusion polypeptide, a linker may be positioned between the ALK4:ActRIIB single-chain trap polypeptide and the corresponding member of the interaction pair. Suitable interaction pairs included, for example, heavy chain and/or light chain immunoglobulin interaction pairs, truncations, and variants thereof as described herein [e.g., Spiess et al (2015) Molecular Immunology 67(2A): 95-106]. FIG. 12A is an example of an association of unguided interaction pairs, meaning that the members of the pair may associate with each other or self-associate without substantial preference and may have the same or different amino acid sequences. FIG. 12B is an example of an association of guided (asymmetric) interaction pairs, meaning that the members of the pair associate preferentially with each other rather than self-associate. Complexes of higher order can be envisioned. In addition, such ALK4:ActRIIB single-chain trap polypeptides may be similarly be associated, covalently or non-covalently, with one or more ALK4 polypeptides and/or one or more ActRIIB polypeptides. See FIG. 12C. Also, such ALK4:ActRIIB single-chain trap polypeptides may be similarly be associated, covalently or non-covalently, with one or more ligand-binding domain of an antibody (e.g., a ligand-biding domain of an antibody that binds to one or more ALK4:ActRIIB binding ligands). See FIG. 12D.

Figure 13:
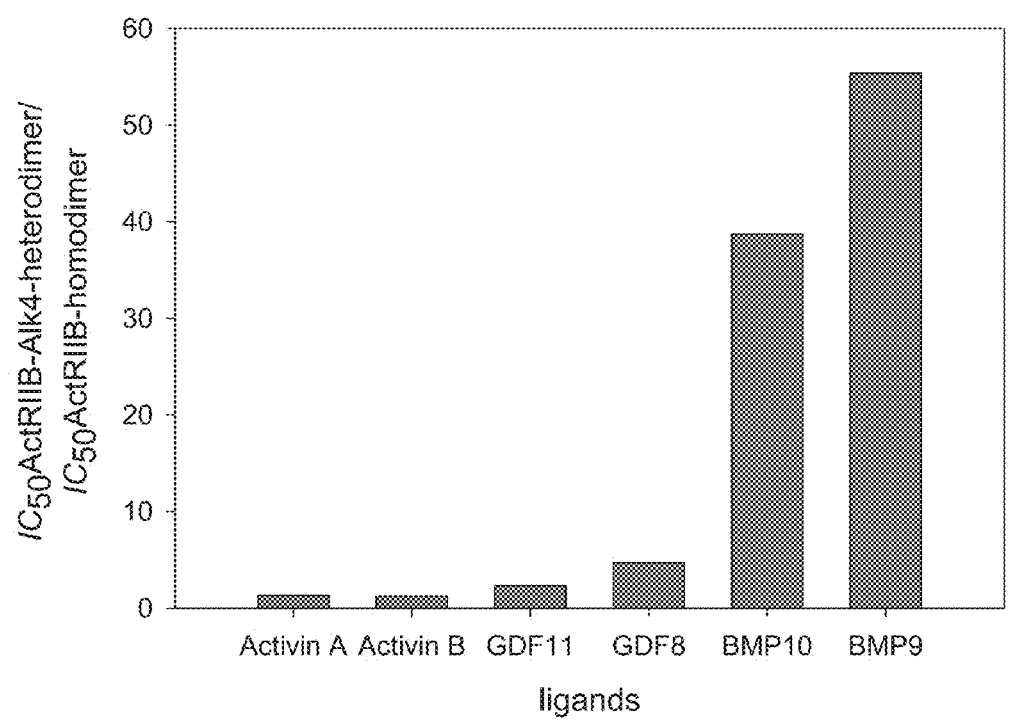

FIG. 13 shows comparative ALK4-Fc:ActRIIB-Fc heterodimer/ActRIIB-Fc:ActRIIB-Fc homodimer $IC_{50}$ data as determined by an A-204 Reporter Gene Assay as described herein. ALK4-Fc:ActRIIB-Fc heterodimer inhibits activin A, activin B, GDF8, and GDF11 signaling pathways similarly to the ActRIIB-Fc:ActRIIB-Fc homodimer. However, ALK4-Fc:ActRIIB-Fc heterodimer inhibition of BMP9 and BMP10 signaling pathways is significantly reduced compared to the ActRIIB-Fc:ActRIIB-Fc homodimer. These data demonstrate that ALK4:ActRIIB heterodimers are more selective antagonists of activin A, activin B, GDF8, and GDF11 compared to corresponding ActRIIB:ActRIIB homodimers.

Figure 14A:
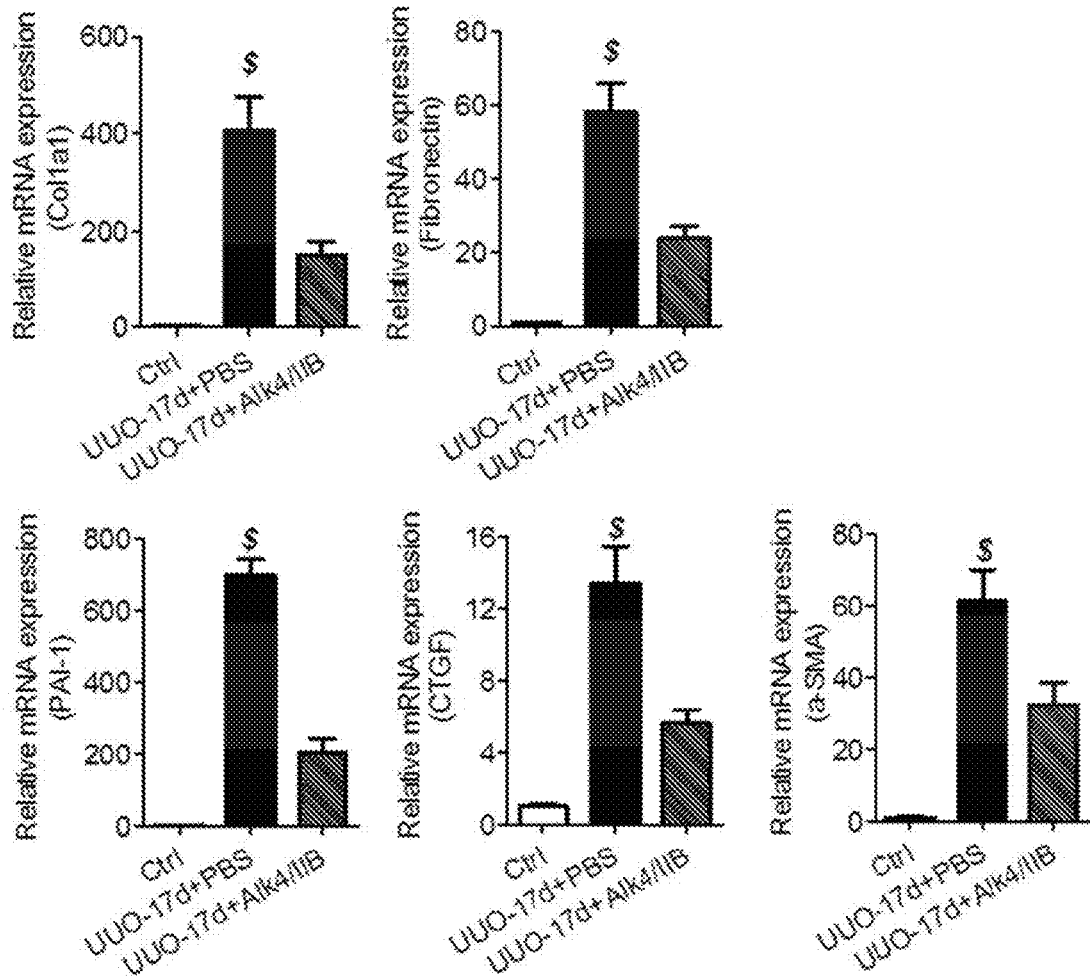
Figure 14B:
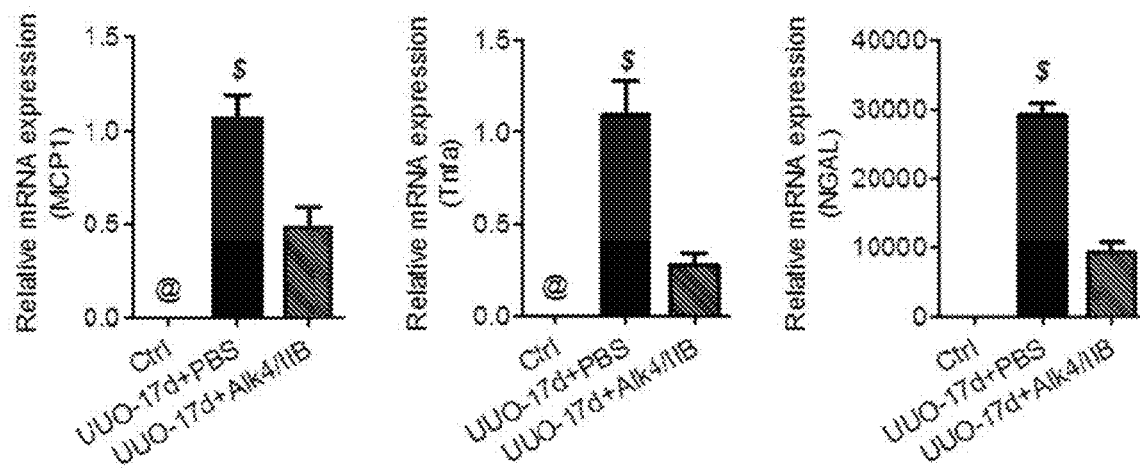
Figure 14C:
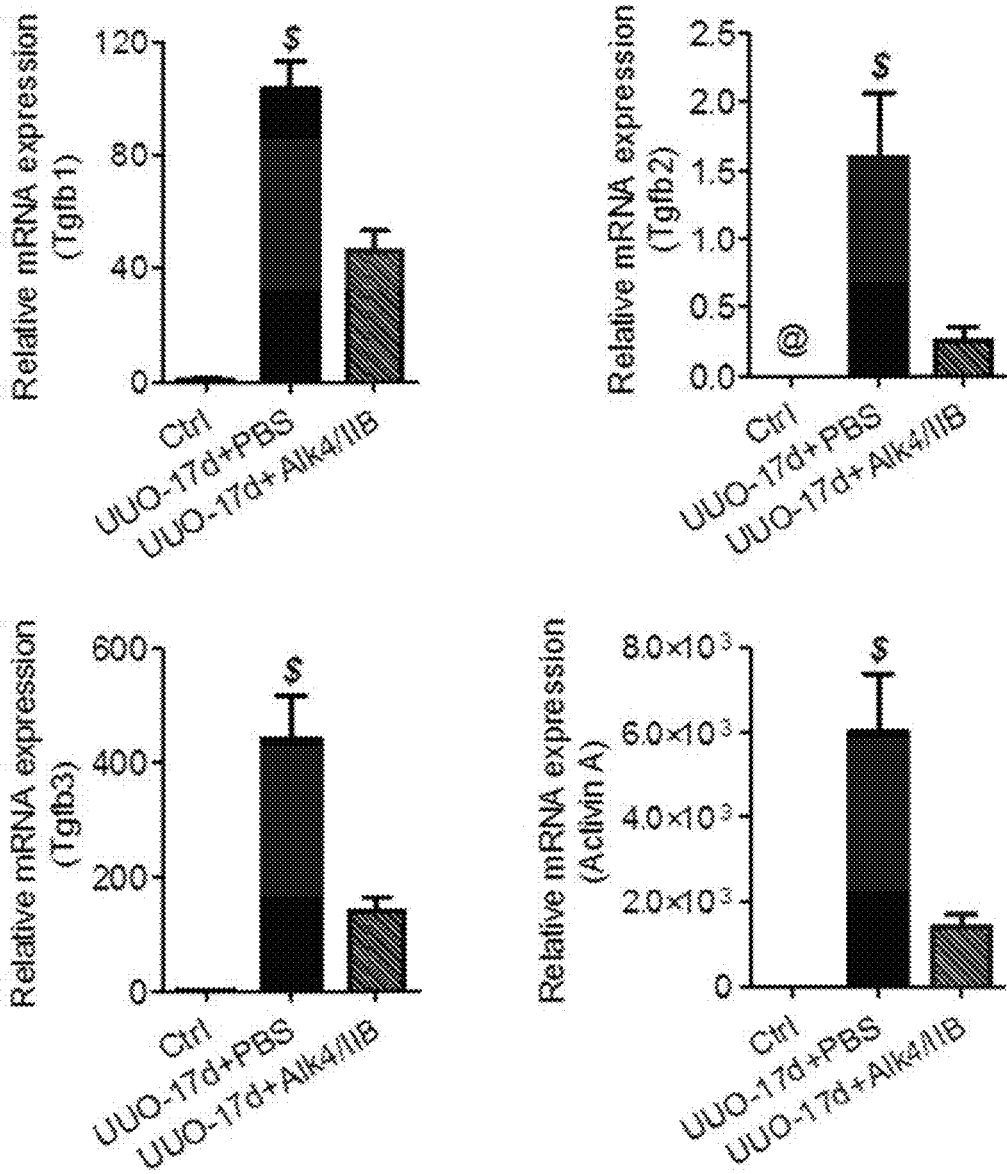

FIGS. 14A-14C shows gene expression profiles of fibrotic genes (Col1a1, Fibronectin, PAI-1, CTGF, and a-SMA), inflammatory genes (TNF-alpha, and MCP1), cytokine genes (TGF-beta 1, GF-beta 2, TGF-beta 3, and activin A), kidney injury gene (NGAL), Hypoxia-inducible factor 1-alpha (HIF1a), and activin A receptor (Acvr2A) from mouse kidneys subjected to unilateral ureteral obstruction (UUO). Samples from the contralateral, non-surgery kidney were used as a control (Ctrl). Gene expression profiles were obtained at 17 days post-surgery. Mice were administered either PBS or an ALK4-Fc:ActRIIB-Fc homodimer at days 3, 7, 10, and 14 post-surgery. ($) denotes a statistical difference between UUO kidneys at 17 days in mice administered only PBS compared UUO kidneys at 17 days in mice administered the ALK7-Fc:ActRIIB-Fc homodimer. (@) denotes that no transcript was detected.

DETAILED DESCRIPTION OF THE INVENTION

1. Overview

Figure 1A:
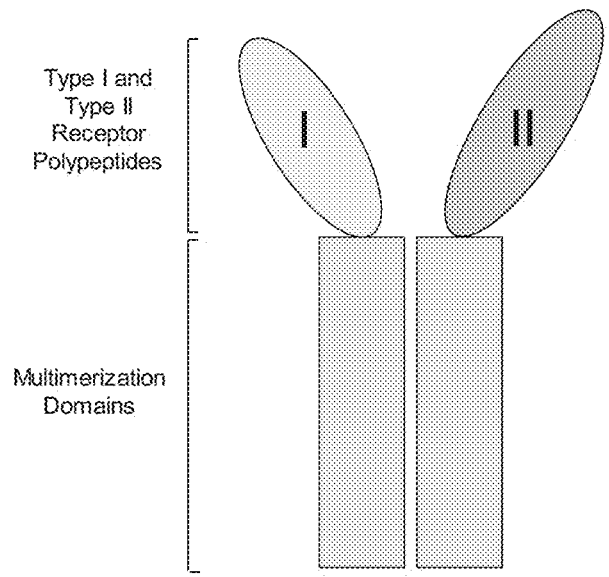
FIGS. 1A and 1B show two schematic examples of heteromeric protein complexes comprising type I receptor and type II receptor polypeptides.
Figure 1B:
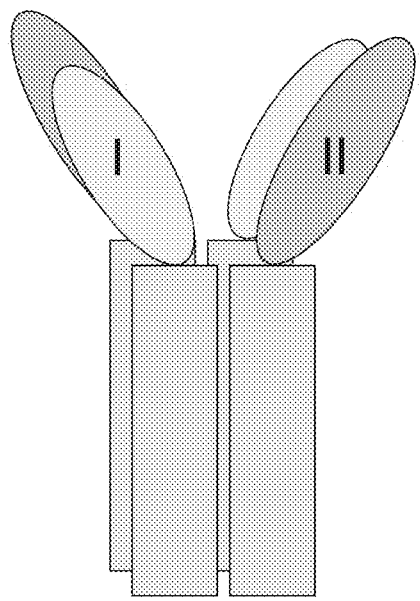
Figure 2:
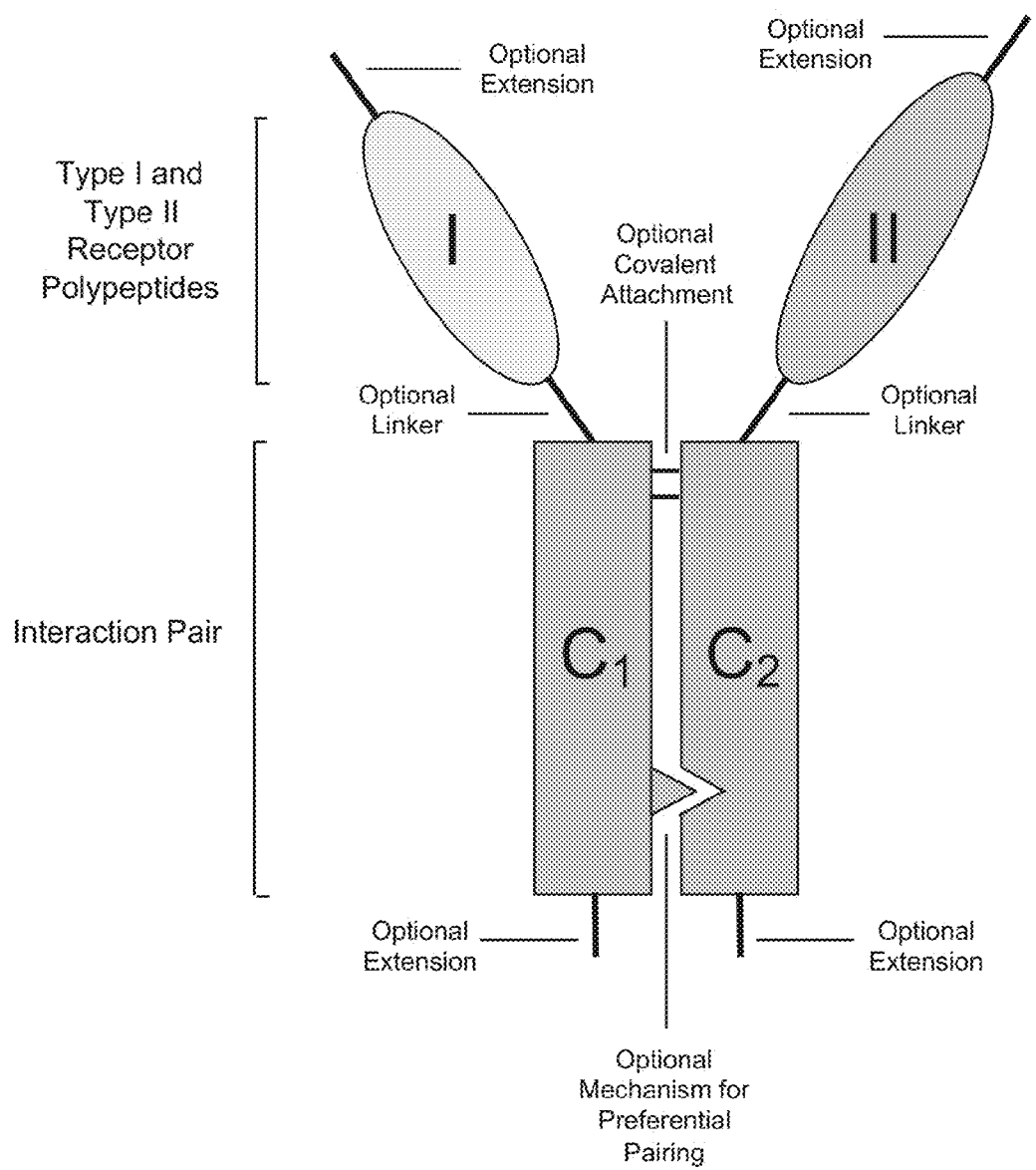
FIG. 2 show a schematic example of a heteromeric protein complex comprising a type I receptor polypeptide (indicated as "I") (e.g. a polypeptide that is at least 70%, 75%, 80%, 85%, 90%, 91%, 92%, 93%, 94%, 95%, 97%, 98%, 99% or 100% identical to an extracellular domain of an ALK4 protein from humans or other species such as those described herein, e.g., SEQ ID Nos: 9, 10, 19, 20, 42, 44, 47, and 48) and a type II receptor polypeptide (indicated as "II") (e.g. a polypeptide that is at least 70%, 75%, 80%, 85%, 90%, 91%, 92%, 93%, 94%, 95%, 97%, 98%, 99% or 100% identical to an extracellular domain of an ActRIIB protein from humans or other species as such as those described herein, e.g., SEQ ID Nos: 1, 2, 3, 4, 5, 6, 39, 41, 45, and 46). In the illustrated embodiments, the type I receptor polypeptide is part of a fusion polypeptide that comprises a first member of an interaction pair ("$C_1$"), and the type II receptor polypeptide is part of a fusion polypeptide that comprises a second member of an interaction pair ("$C_2$"). In each fusion polypeptide, a linker may be positioned between the type I or type II receptor polypeptide and the corresponding member of the interaction pair. The first and second members of the interaction pair may be a guided (asymmetric) pair, meaning that the members of the pair associate preferentially with each other rather than self-associate, or the interaction pair may be unguided, meaning that the members of the pair may associate with each other or self-associate without substantial preference and may have the same or different amino acid sequences. Traditional Fc fusion proteins and antibodies are examples of unguided interaction pairs, whereas a variety of engineered Fc domains have been designed as guided (asymmetric) interaction pairs [e.g., Spiess et al (2015) Molecular Immunology 67(2A): 95-106].

In part, the present disclosure relates to heteromultimers comprising a TGFβ superfamily type I receptor polypeptide and a TGFβ superfamily type II receptor polypeptide, uses thereof, and methods of making such heteromultimers. See, e.g., FIGS. 1 and 2. In certain preferred embodiments, heteromultimers comprise an extracellular domain of a TGFβ superfamily type I receptor polypeptide and an extracellular domain of a TGFβ superfamily type II receptor polypeptide. In particular, the disclosure provides heteromultimers that comprise an ALK4 polypeptide and an ActRIIB polypeptide. Preferably such ALK4 polypeptides comprise a ligand-binding domain of an ALK4 receptor and such ActRIIB polypeptides comprise a ligand-binding domain of an ActRIIB receptor. In certain preferred embodiments, ALK4:ActRIIB heteromultimers of the disclosure have an altered TGFβ superfamily ligand binding profile/specificity compared to a corresponding sample of a homomultimer (e.g., an ALK4:ActRIIB heterodimer compared to an ActRIIB:ActRIIB homodimer or an ALK4:ALK4 homodimer).

The TGF-β superfamily is comprised of over 30 secreted factors including TGF-betas, activins, nodals, bone morphogenetic proteins (BMPs), growth and differentiation factors (GDFs), and anti-Mullerian hormone (AMH) [Weiss et al. (2013) Developmental Biology, 2(1): 47-63]. Members of the superfamily, which are found in both vertebrates and invertebrates, are ubiquitously expressed in diverse tissues and function during the earliest stages of development throughout the lifetime of an animal. Indeed, TGF-β superfamily proteins are key mediators of stem cell self-renewal, gastrulation, differentiation, organ morphogenesis, and adult tissue homeostasis. Consistent with this ubiquitous activity, aberrant TGF-beta superfamily signaling is associated with a wide range of human pathologies including, for example, autoimmune disease, cardiovascular disease, fibrotic disease, and cancer.

Ligands of the TGF-beta superfamily share the same dimeric structure in which the central 3½ turn helix of one monomer packs against the concave surface formed by the beta-strands of the other monomer. The majority of TGF-beta family members are further stabilized by an intermolecular disulfide bond. This disulfide bonds traverses through a ring formed by two other disulfide bonds generating what has been termed a 'cysteine knot' motif [Lin et al. (2006) Reproduction 132: 179-190; and Hinck et al. (2012) FEBS Letters 586: 1860-1870].

TGF-beta superfamily signaling is mediated by heteromeric complexes of type I and type II serine/threonine kinase receptors, which phosphorylate and activate downstream SMAD proteins (e.g., SMAD proteins 1, 2, 3, 5, and 8) upon ligand stimulation [Massagué (2000) Nat. Rev. Mol. Cell Biol. 1:169-178]. These type I and type II receptors are transmembrane proteins, composed of a ligand-binding extracellular domain with cysteine-rich region, a transmembrane domain, and a cytoplasmic domain with predicted serine/threonine kinase specificity. In general, type I receptors mediate intracellular signaling while the type II receptors are required for binding TGF-beta superfamily ligands. Type I and II receptors form a stable complex after ligand binding, resulting in phosphorylation of type I receptors by type II receptors.

The TGF-beta family can be divided into two phylogenetic branches based on the type I receptors they bind and the Smad proteins they activate. One is the more recently evolved branch, which includes, e.g., the TGF-betas, activins, GDF8, GDF9, GDF11, BMP3 and nodal, which signal through type I receptors that activate Smads 2 and 3 [Hinck (2012) FEBS Letters 586:1860-1870]. The other branch comprises the more distantly related proteins of the superfamily and includes, e.g., BMP2, BMP4, BMP5, BMP6, BMP7, BMP8a, BMP8b, BMP9, BMP10, GDF1, GDF5, GDF6, and GDF7, which signal through Smads 1, 5, and 8.

TGF-beta isoforms are the founding members of the TGF-beta superfamily, of which there are 3 known isoforms in mammals designated as TGF-beta1, TGF-beta2 and TGF-beta3. Mature bioactive TGF-beta ligands function as homodimers and predominantly signal through the type I receptor ALK5, but have also been found to additionally signal through ALK1 in endothelial cells [Goumans et al. (2003) Mol Cell 12(4): 817-828]. TGF-beta1 is the most abundant and ubiquitously expressed isoform. TGF-beta1 is known to have an important role in wound healing, and mice expressing a constitutively active TGF-beta1 transgene develop fibrosis [Clouthier et al. (1997) J Clin. Invest. 100(11): 2697-2713]. TGF-beta1 is also involved in T cell activation and maintenance of T regulatory cells [Li et al. (2006) Immunity 25(3): 455-471]. TGF-beta2 expression was first described in human glioblastoma cells, and is occurs in neurons and astroglial cells of the embryonic nervous system. TGF-beta2 is known to suppress interleukin-2-dependent growth of T lymphocytes. TGF-beta3 was initially isolated from a human rhabdomyosarcoma cell line and since has been found in lung adenocarcinoma and kidney carcinoma cell lines. TGF-beta3 is known to be important for palate and lung morphogenesis [Kubiczkova et al. (2012) Journal of Translational Medicine 10:183].

Activins are members of the TGF-beta superfamily and were initially discovered as regulators of secretion of follicle-stimulating hormone, but subsequently various reproductive and non-reproductive roles have been characterized. There are three principal activin forms (A, B, and AB) that are homo/heterodimers of two closely related β subunits ($\beta_A\beta_A$, $\beta_B\beta_B$, and $\beta_A\beta_B$, respectively). The human genome also encodes an activin C and an activin E, which are primarily expressed in the liver, and heterodimeric forms containing $\beta_C$ or $\beta_E$ are also known. In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos [DePaolo et al. (1991) Proc Soc Ep Biol Med. 198:500-512; Dyson et al. (1997) Curr Biol. 7:81-84; and Woodruff (1998) Biochem Pharmacol. 55:953-963]. In several tissues, activin signaling is antagonized by its related heterodimer, inhibin. For example, in the regulation of follicle-stimulating hormone (FSH) secretion from the pituitary, activin promotes FSH synthesis and secretion, while inhibin reduces FSH synthesis and secretion. Other proteins that may regulate activin bioactivity and/or bind to activin include follistatin (FS), follistatin-related protein (FSRP, also known as FLRG or FSTL3), and $\alpha_2$-macroglobulin.

As described herein, agents that bind to "activin A" are agents that specifically bind to the $\beta_A$ subunit, whether in the context of an isolated $\beta_A$ subunit or as a dimeric complex (e.g., a $\beta_A\beta_A$ homodimer or a $\beta_A\beta_B$ heterodimer). In the case of a heterodimer complex (e.g., a $\beta_A\beta_B$ heterodimer), agents that bind to "activin A" are specific for epitopes present within the $\beta_A$ subunit, but do not bind to epitopes present within the non-$\beta_A$ subunit of the complex (e.g., the $\beta_B$ subunit of the complex). Similarly, agents disclosed herein that antagonize (inhibit) "activin A" are agents that inhibit one or more activities as mediated by a $\beta_A$ subunit, whether in the context of an isolated $\beta_A$ subunit or as a dimeric complex (e.g., a $\beta_A\beta_A$ homodimer or a $\beta_A\beta_B$ heterodimer). In the case of $\beta_A\beta_B$ heterodimers, agents that inhibit "activin A" are agents that specifically inhibit one or more activities of the $\beta_A$ subunit, but do not inhibit the activity of the non-$\beta_A$ subunit of the complex (e.g., the $\beta_B$ subunit of the complex). This principle applies also to agents that bind to and/or inhibit "activin B", "activin C", and "activin E". Agents disclosed herein that antagonize "activin AB" are agents that inhibit one or more activities as mediated by the $\beta_A$ subunit and one or more activities as mediated by the $\beta_B$ subunit. The same principle also applies to agent that bind to and/or inhibit "activin AC", "activin BC", "activin AE", and "activin BE".

Nodal proteins have functions in mesoderm and endoderm induction and formation, as well as subsequent organization of axial structures such as heart and stomach in early embryogenesis. It has been demonstrated that dorsal tissue in a developing vertebrate embryo contributes predominantly to the axial structures of the notochord and pre-chordal plate while it recruits surrounding cells to form non-axial embryonic structures. Nodal appears to signal through both type I and type II receptors and intracellular effectors known as SMAD proteins. Studies support the idea that ActRIIA and ActRIIB serve as type II receptors for Nodal [Sakuma et al. (2002) Genes Cells. 2002, 7:401-12]. It is suggested that Nodal ligands interact with their cofactors (e.g., Crypto or Cryptic) to activate activin type I and type II receptors, which phosphorylate SMAD2. Nodal proteins are implicated in many events critical to the early vertebrate embryo, including mesoderm formation, anterior patterning, and left-right axis specification. Experimental evidence has demonstrated that nodal signaling activates pAR3-Lux, a luciferase reporter previously shown to respond specifically to activin and TGF-beta. However, nodal is unable to induce pT1×2-Lux, a reporter specifically responsive to bone morphogenetic proteins. Recent results provide direct biochemical evidence that Nodal signaling is mediated by SMAD2 and SMAD3, which also mediate signaling by TGF-betas and activins. Further evidence has shown that the extracellular protein Cripto or Cryptic is required for nodal signaling, making it distinct from activin or TGF-beta signaling.

The BMPs and GDFs together form a family of cysteine-knot cytokines sharing the characteristic fold of the TGF-beta superfamily [Rider et al. (2010) Biochem J., 429(1):1-

12]. This family includes, for example, BMP2, BMP4, BMP6, BMP7, BMP2a, BMP3, BMP3b (also known as GDF10), BMP4, BMP5, BMP6, BMP7, BMP8, BMP8a, BMP8b, BMP9 (also known as GDF2), BMP10, BMP11 (also known as GDF11), BMP12 (also known as GDF7), BMP13 (also known as GDF6), BMP14 (also known as GDF5), BMP15, GDF1, GDF3 (also known as VGR2), GDF8 (also known as myostatin), GDF9, GDF15, and decapentaplegic. Besides the ability to induce bone formation, which gave the BMPs their name, the BMP/GDFs display morphogenetic activities in the development of a wide range of tissues. BMP/GDF homo- and hetero-dimers interact with combinations of type I and type II receptor dimers to produce multiple possible signaling complexes, leading to the activation of one of two competing sets of SMAD transcription factors. BMP/GDFs have highly specific and localized functions. These are regulated in a number of ways, including the developmental restriction of BMP/GDF expression and through the secretion of several specific BMP antagonist proteins that bind with high affinity to the cytokines. Curiously, a number of these antagonists resemble TGF-beta superfamily ligands.

Growth and differentiation factor-8 (GDF8) is also known as myostatin. GDF8 is a negative regulator of skeletal muscle mass and is highly expressed in developing and adult skeletal muscle. The GDF8 null mutation in transgenic mice is characterized by a marked hypertrophy and hyperplasia of skeletal muscle [McPherron et al. Nature (1997) 387:83-90]. Similar increases in skeletal muscle mass are evident in naturally occurring mutations of GDF8 in cattle and, strikingly, in humans [Ashmore et al. (1974) Growth, 38:501-507; Swatland and Kieffer, J. Anim. Sci. (1994) 38:752-757; McPherron and Lee, Proc. Natl. Acad. Sci. USA (1997) 94:12457-12461; Kambadur et al. Genome Res. (1997) 7:910-915; and Schuelke et al. (2004) N Engl J Med, 350:2682-8]. Studies have also shown that muscle wasting associated with HIV-infection in humans is accompanied by increases in GDF8 protein expression [Gonzalez-Cadavid et al., PNAS (1998) 95:14938-43]. In addition, GDF8 can modulate the production of muscle-specific enzymes (e.g., creatine kinase) and modulate myoblast cell proliferation [International Patent Application Publication No. WO 00/43781]. The GDF8 propeptide can noncovalently bind to the mature GDF8 domain dimer, inactivating its biological activity [Miyazono et al. (1988) J. Biol. Chem., 263: 6407-6415; Wakefield et al. (1988) J. Biol. Chem., 263; 7646-7654; and Brown et al. (1990) Growth Factors, 3: 35-43]. Other proteins which bind to GDF8 or structurally related proteins and inhibit their biological activity include follistatin, and potentially, follistatin-related proteins [Gamer et al. (1999) Dev. Biol., 208: 222-232].

GDF11, also known as BMP11, is a secreted protein that is expressed in the tail bud, limb bud, maxillary and mandibular arches, and dorsal root ganglia during mouse development [McPherron et al. (1999) Nat. Genet., 22: 260-264; and Nakashima et al. (1999) Mech. Dev., 80: 185-189]. GDF11 plays a unique role in patterning both mesodermal and neural tissues [Gamer et al. (1999) Dev Biol., 208:222-32]. GDF11 was shown to be a negative regulator of chondrogenesis and myogenesis in developing chick limb [Gamer et al. (2001) Dev Biol., 229:407-20]. The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium [Wu et al. (2003) Neuron., 37:197-207]. Hence, inhibitors GDF11 may have in vitro and in vivo applications in the treatment of diseases such as muscle diseases and neurodegenerative diseases (e.g., amyotrophic lateral sclerosis).

BMP7, also called osteogenic protein-1 (OP-1), is well known to induce cartilage and bone formation. In addition, BMP7 regulates a wide array of physiological processes. For example, BMP7 may be the osteoinductive factor responsible for the phenomenon of epithelial osteogenesis. It is also found that BMP7 plays a role in calcium regulation and bone homeostasis. Like activin, BMP7 binds to type II receptors, ActRIIA and ActRIIB However, BMP7 and activin recruit distinct type I receptors into heteromeric receptor complexes. The major BMP7 type I receptor observed was ALK2, while activin bound exclusively to ALK4 (ActRIIB) BMP7 and activin elicited distinct biological responses and activated different SMAD pathways [Macias-Silva et al. (1998) J Biol Chem. 273:25628-36].

As described herein, comparative binding data demonstrated that an ALK4:ActRIIB heterodimer has an altered binding profile (ligand selectivity) compared to either corresponding ActRIIB or ALK4 homodimers. In particular, the ALK4:ActRIIB heterodimer displays enhanced binding to activin B compared with either homodimer, and retains strong binding to activin A, GDF8, and GDF11 as observed with the ActRIIB homodimer. However, the ALK4:ActRIIB heterodimer exhibits substantially reduced binding to BMP9, BMP10, and GDF3 compared to the ActRIIB homodimer. In particular, BMP9 displays low or no observable affinity for the ALK4:ActRIIB heterodimer, whereas this ligand binds strongly to ActRIIB homodimer.

These results therefore demonstrate that ALK4:ActRIIB heterodimers are more selective antagonists of activin A, activin B, GDF8, and GDF11 compared to ActRIIB homodimers. Accordingly, an ALK4:ActRIIB heterodimer will be more useful than an ActRIIB homodimer in certain applications where such selective antagonism is advantageous. Examples include therapeutic applications where it is desirable to retain antagonism of one or more of activin (e.g., activin A, activin B, activin AC, activin AB), GDF8, and GDF11 but minimize antagonism of one or more of BMP9, BMP10, and BMP6.

Moreover, ALK4:ActRIIB heterodimers, as described herein, exert beneficial anabolic effects on skeletal muscle and bone as well as catabolic effects on adipose tissue, very similar to those of an ActRIIB homodimer. However, unlike ActRIIB homodimer, an ActRIIB:ALK4 heterodimer exhibits only low-affinity or transient binding to BMP9 and BMP10 and so will have little to no concurrent inhibition on processes mediated by those ligands, such as angiogenesis. This novel selectivity will be useful, for example, in treating patients in need of stimulatory effects on, e.g., muscle and bone, and inhibitory effects on fat, but not in need of altered angiogenesis.

The terms used in this specification generally have their ordinary meanings in the art, within the context of this disclosure and in the specific context where each term is used. Certain terms are discussed below or elsewhere in the specification to provide additional guidance to the practitioner in describing the compositions and methods of the disclosure and how to make and use them. The scope or meaning of any use of a term will be apparent from the specific context in which it is used.

The terms "heteromer" or "heteromultimer" is a complex comprising at least a first polypeptide chain and a second polypeptide chain, wherein the second polypeptide chain differs in amino acid sequence from the first polypeptide chain by at least one amino acid residue. The heteromer can comprise a "heterodimer" formed by the first and second polypeptide chains or can form higher order structures where one or more polypeptide chains in addition to the first and second polypeptide chains are present. Exemplary structures for the heteromultimer include heterodimers, heterotrimers, heterotetramers and further oligomeric structures. Heterodimers are designated herein as X:Y or equivalently as X-Y, where X represents a first polypeptide chain and Y represents a second polypeptide chain. Higher-order heteromers and oligomeric structures are designated herein in a corresponding manner. In certain embodiments a heteromultimer is recombinant (e.g., one or more polypeptide components may be a recombinant protein), isolated and/or purified.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. However, in common usage and in the instant application, the term "homologous," when modified with an adverb such as "highly," may refer to sequence similarity and may or may not relate to a common evolutionary origin.

The term "sequence similarity," in all its grammatical forms, refers to the degree of identity or correspondence between nucleic acid or amino acid sequences that may or may not share a common evolutionary origin.

"Percent (%) sequence identity" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

As used herein, unless otherwise stated, "does not substantially bind to X" is intended to mean that an agent has a $K_D$ that is greater than about $10^{-7}$, $10^{-6}$, $10^{-5}$, $10^{-4}$ or greater (e.g., no detectable binding by the assay used to determine the $K_D$) for "X", wherein "X" is a specified agent such as a protein or nucleic acid.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity.

The terms "about" and "approximately" as used in connection with a numerical value throughout the specification and the claims denotes an interval of accuracy, familiar and acceptable to a person skilled in the art. In general, such interval of accuracy is ±10%. Alternatively, and particularly in biological systems, the terms "about" and "approximately" may mean values that are within an order of magnitude, preferably ≤5-fold and more preferably ≤2-fold of a given value.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Throughout this specification, the word "comprise" or variations such as "comprises" or "comprising" will be understood to imply the inclusion of a stated integer or groups of integers but not the exclusion of any other integer or group of integers.

2. ALK4:ActRIIB Antagonists

Figure 6:
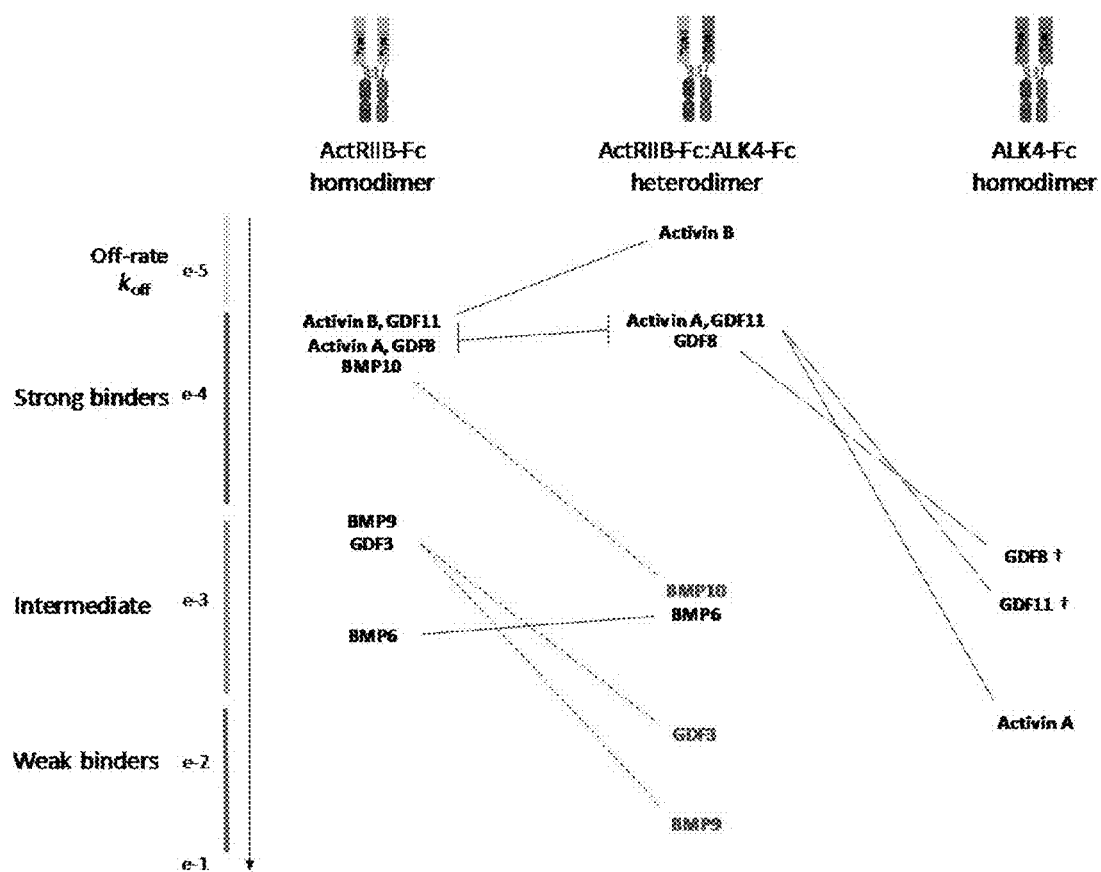
FIG. 6 shows comparative ligand binding data for an ALK4-Fc:ActRIIB-Fc heterodimeric protein complex compared to ActRIIB-Fc homodimer and ALK4-Fc homodimer. For each protein complex, ligands are ranked by $k_{off}$, a kinetic constant that correlates well with ligand signaling inhibition, and listed in descending order of binding affinity (ligands bound most tightly are listed at the top). At left, yellow, red, green, and blue lines indicate magnitude of the off-rate constant. Solid black lines indicate ligands whose binding to heterodimer is enhanced or unchanged compared with homodimer, whereas dashed red lines indicate substantially reduced binding compared with homodimer. As shown, the ALK4-Fc:ActRIIB-Fc heterodimer displays enhanced binding to activin B compared with either homodimer, retains strong binding to activin A, GDF8, and GDF11 as observed with ActRIIB-Fc homodimer, and exhibits substantially reduced binding to BMP9, BMP10, and GDF3. Like ActRIIB-Fc homodimer, the heterodimer retains intermediate-level binding to BMP6.

As described herein, it has been discovered that an ALK4:ActRIIB heterodimers are unique antagonists of ligands of the TGF-beta superfamily, exhibiting a different ligand-binding profile/selectivity compared to corresponding ActRIIB and ALK4 homodimers. In particular, an exemplary ALK4:ActRIIB heterodimer displays enhanced binding to activin B compared to either homodimer, retains strong binding to activin A, GDF8, and GDF11 as observed with ActRIIB homodimer, but exhibits substantially reduced binding to BMP9, BMP10, and GDF3. In fact, the ALK4:ActRIIB heterodimer displays low to no observable affinity for BMP9, whereas this ligand binds strongly to ActRIIB homodimer. See FIG. 6. These results therefore demonstrate that ALK4:ActRIIB heterodimers are a more selective antagonists (inhibitors) of certain ligands of the TGF-beta superfamily compared to ActRIIB homodimers. Accordingly, an ALK4:ActRIIB heterodimer will be more useful than an ActRIIB homodimer in certain applications where such selective antagonism is advantageous. Examples include therapeutic applications where it is desirable to antagonize one or more of activin (e.g., activin A, activin B, activin AB, activin AC), GDF8, and GDF11 with decreased antagonism of one or more of BMP9, BMP10, and GDF3.

Moreover, ALK4:ActRIIB heterodimer produced certain biological effects strikingly similar to those of an ActRIIB homodimer despite differential ligand selectivity of the two complexes. For example, ALK4:ActRIIB heterodimer exerts beneficial anabolic effects on skeletal muscle and bone as well as catabolic effects on adipose tissue, very similar to those of an ActRIIB-Fc homodimer. However, unlike ActRIIB homodimer, ActRIIB:ALK4 heterodimer exhibits only low-affinity or transient binding to BMP9 and BMP10 and so should have little to no concurrent inhibition on processes mediated by those ligands, such as angiogenesis. This novel selectivity may be useful, for example, in treating patients in need of stimulatory effects on muscle and bone, and/or inhibitory effects on fat, but not in need of altered angiogenesis. Therefore, while not wishing to be bound to a particular mechanisms of action, it is expected that ALK4:ActRIIB heteromultimers, as well as variants thereof, that bind to/inhibit at least one or more of ALK4:ActRIIB-binding ligands will be useful agents for promoting beneficial anabolic effects on skeletal muscle and bone and catabolic effects on adipose tissue. Furthermore, it is expected that other antagonists (inhibitors), or combinations of antagonists, that mimic the binding/inhibitory properties of the ALK4:ActRIIB heterodimers described herein as well as agents that directly or indirectly antagonize ALK4 and/or ActRIIB receptors, agents that directly or indirectly antagonize ALK4- and/or ActRIIB-binding ligands, agents that directly or indirectly antagonize downstream signaling mediators (e.g., Smads), and/or agents that directly or indirectly antagonize TGF-beta superfamily co-receptors will have similar biological effects including, for example, stimulatory effects on muscle and bone and inhibitory effects on fat. These antagonistic mimetic are collectively referred to herein as "ALK4:ActRIIB antagonists" or "ALK4:ActRIIB inhibitors".

A. ALK4:ActRIIB Heteromultimers

In certain aspects, the present disclosure relates to heteromultimers comprising one or more ALK4 receptor polypeptides (e.g., SEQ ID NOs: 9, 10, 19, 20, 42, 44, 47 and 48) and one or more ActRIIB receptor polypeptides (e.g., SEQ ID NOs: 1, 2, 3, 4, 5, 6, 39, 41, 45, and 46), which are generally referred to herein as "ALK4:ActRIIB heteromultimer complexes" or "ALK4:ActRIIB heteromultimers". Preferably, ALK4:ActRIIB heteromultimers of the disclosure are soluble, for example, a heteromultimer may comprises a soluble portion (domain) of an ALK4 receptor and a soluble portion (domain) of an ActRIIB receptor. In general, the extracellular domains of ALK4 and ActRIIB correspond to a soluble portion of these receptors. Therefore, in some embodiments, heteromultimers of the disclosure comprise an extracellular domain of an ALK4 receptor and an extracellular domain of an ActRIIB receptor. Example extracellular domains ALK4 and ActRIIB receptors are disclosed herein and such sequences, as well as fragments, functional variants, and modified forms thereof, may be used in accordance with the inventions of the disclosure (e.g., ALK4:ActRIIB heteromultimer compositions and uses thereof). ALK4:ActRIIB heteromultimers of the disclosure include, e.g., heterodimers, heterotrimers, heterotetramers and higher order oligomeric structures. See, e.g., FIGS. 1, 2, and 8-10. In certain preferred embodiments, heteromultimers of the disclosure are ALK4:ActRIIB heterodimers.

Preferably, ALK4:ActRIIB heteromultimers of the disclosure bind to one or more TGF-beta superfamily ligands. In some embodiments, ALK4:ActRIIB heteromultimers may bind to one or more of activin (e.g., activin A, activin B, activin C, activin E, activin AC, activin AB, activin BC, activin AE, and activin BE), GDF8, GDF11, BMP6, GDF3, and BMP10. In some embodiments, ALK4:ActRIIB heteromultimers bind to activin A. In some embodiments, ALK4:ActRIIB heteromultimers bind to activin B. In some embodiments, ALK4:ActRIIB heteromultimers bind to activin C. In some embodiments, ALK4:ActRIIB heteromultimers bind to activin E. In some embodiments, ALK4:ActRIIB heteromultimers bind to activin AB. In some embodiments, ALK4:ActRIIB heteromultimers bind to activin AC. In some embodiments, ALK4:ActRIIB heteromultimers bind to activin AE. In some embodiments, ALK4:ActRIIB heteromultimers bind to activin BC. In some embodiments, ALK4:ActRIIB heteromultimers bind to activin BE. In some embodiments, ALK4:ActRIIB heteromultimers bind to GDF11. In some embodiments, ALK4:ActRIIB heteromultimers bind to GDF8. In some embodiments, ALK4:ActRIIB heteromultimers bind to BMP6. In some embodiments, ALK4:ActRIIB heteromultimers bind to GDF3. In some embodiments, ALK4:ActRIIB heteromultimers bind to BMP10. In some embodiments, ALK4:ActRIIB heteromultimers do not bind to, or no not substantially bind to BMP9 (e.g., have indeterminate $K_a$ or $K_d$ due to the transient nature of the interaction between BMP9 and an ALK4:ActRIIB heteromultimer). In some embodiments, ALK4:ActRIIB heteromultimers binds with stronger affinity to activin B compared to a corresponding ActRIIB homomultimer. In some embodiments, ALK4:ActRIIB heteromultimers binds with weaker affinity to GDF3 compared to a corresponding ActRIIB homomultimer. In some embodiments, ALK4:ActRIIB heteromultimers binds with weaker affinity to BMP9 compared to a corresponding ActRIIB homomultimer. In some embodiments, ALK4:ActRIIB heteromultimers binds with weaker affinity to BMP10 compared to a corresponding ActRIIB homomultimer. Optionally, ALK4:ActRIIB heteromultimers may further bind to one or more of BMP2, BMP2/7, BMP3, BMP4, BMP4/7, BMP5, BMP7, BMP8a, BMP8b, GDF5, GDF6/BMP13, GDF7, GDF9b/BMP15, GDF15/MIC1, TGF-β1, TGF-β2, TGF-β3, nodal, glial cell-derived neurotrophic factor (GDNF), neurturin, artemin, persephin, MIS, and Lefty.

In some embodiments, ALK4:ActRIIB heteromultimers may be used to inhibit (antagonize) signaling (e.g., Smad 2/3 and/or Smad 1/5/8 signaling) mediated by one or more TGFβ superfamily ligands. In particular, ALK4:ActRIIB heteromultimers of the disclosure may be used to inhibit intracellular signaling by one or more TGFβ superfamily ligands in, for example, a cell-based assay such as those described herein. For example, ALK4:ActRIIB heteromultimers may inhibit signaling mediated by one or more of activin (e.g., activin A, activin B, activin C, activin E, activin AC, activin AB, activin BC, activin AE, and activin BE), GDF8, GDF11, BMP6, GDF3, and BMP10 in a cell-based assay. In some embodiments, ALK4:ActRIIB heteromultimers may inhibit activin A signaling in a cell-based assay. In some embodiments, ALK4:ActRIIB heteromultimers may inhibit activin B signaling in a cell-based assay. In some embodiments, ALK4:ActRIIB heteromultimers may inhibit activin C signaling in a cell-based assay. In some embodiments, ALK4:ActRIIB heteromultimers may inhibit activin D signaling in a cell-based assay. In some embodiments, ALK4:ActRIIB heteromultimers may inhibit activin E signaling in a cell-based assay. In some embodiments, ALK4:ActRIIB heteromultimers may inhibit activin AB signaling in a cell-based assay. In some embodiments, ALK4:ActRIIB heteromultimers may inhibit activin AC signaling in a cell-based assay. In some embodiments, ALK4:ActRIIB heteromultimers may inhibit activin BC signaling in a cell-based assay. In some embodiments, ALK4:ActRIIB heteromultimers may inhibit activin AE signaling in a cell-based assay. In some embodiments, ALK4:ActRIIB heteromultimers may inhibit activin BE signaling in a cell-based assay. In some embodiments, ALK4:ActRIIB heteromultimers may inhibit GDF11 signaling in a cell-based assay. In some embodiments, ALK4:ActRIIB heteromultimers may inhibit GDF8 signaling in a cell-based assay. In some embodiments, ALK4:ActRIIB heteromultimers may inhibit BMP6 signaling in a cell-based assay. In some embodiments, ALK4:ActRIIB heteromultimers may inhibit GDF3 signaling in a cell-based assay. In some embodiments, ALK4:ActRIIB heteromultimers may inhibit BMP9 signaling in a cell-based assay. In some embodiments, ALK4: ActRIIB heteromultimers do not inhibit, or do not substantially inhibit BMP9 signaling in a cell-based assay. In some embodiments, ALK4:ActRIIB heteromultimers are stronger inhibitors of activin B signaling in a cell-based assay compared to a corresponding ActRIIB homomultimer. In some embodiments, ALK4:ActRIIB heteromultimers are weaker inhibitors of BMP10 signaling in a cell-based assay compared to a corresponding ActRIIB homomultimer. In some embodiments, ALK4:ActRIIB heteromultimers are stronger inhibitors of GDF3 signaling in a cell-based assay compared to a corresponding ActRIIB homomultimer. In some embodiments, ALK4:ActRIIB heteromultimers are stronger inhibitors of BMP9 signaling in a cell-based assay compared to a corresponding ActRIIB homomultimer. Optionally, ALK4:ActRIIB heteromultimers may further inhibit intracellular signaling by one or more of BMP2, BMP2/7, BMP3, BMP4, BMP4/7, BMP5, BMP7, BMP8a, BMP8b, GDF5, GDF6/BMP13, GDF7, GDF9b/BMP15, GDF15/MIC1, TGF-β1, TGF-β2, TGF-β3, nodal, glial cell-derived neurotrophic factor (GDNF), neurturin, artemin, persephin, MIS, and Lefty in a cell-based assay.

As used herein, the term "ActRIIB" refers to a family of activin receptor type IIB (ActRIIB) proteins from any species and variants derived from such ActRIIB proteins by mutagenesis or other modification. Reference to ActRIIB herein is understood to be a reference to any one of the currently identified forms. Members of the ActRIIB family are generally transmembrane proteins, composed of a ligand-binding extracellular domain comprising a cysteine-rich region, a transmembrane domain, and a cytoplasmic domain with predicted serine/threonine kinase activity.

The term "ActRIIB polypeptide" includes polypeptides comprising any naturally occurring polypeptide of an ActRIIB family member as well as any variants thereof (including mutants, fragments, fusions, and peptidomimetic forms) that retain a useful activity. Examples of such variant ActRIIB polypeptides are provided throughout the present disclosure as well as in International Patent Application Publication Nos. WO 2006/012627, WO 2008/097541, and WO 2010/151426, which are incorporated herein by reference in their entirety. Numbering of amino acids for all ActRIIB-related polypeptides described herein is based on the numbering of the human ActRIIB precursor protein sequence provided below (SEQ ID NO: 1), unless specifically designated otherwise.

The human ActRIIB precursor protein sequence is as follows:

```
                                                              (SEQ ID NO: 1)
  1 MTAPWVALAL LWGSLCAGSG RGEAETRECI YYNANWELER TNQSGLERCE

51 GEQDKRLHCY ASWRNSSGTI ELVKKGCWLD DFNCYDRQEC VATEENPQVY

101 FCCCEGNFCN ERFTHLPEAG GPEVTYEPPP TAPTLLTVLA YSLLPIGGLS

151 LIVLLAFWMY RHRKPPYGHV DIHEDPGPPP PSPLVGLKPL QLLEIKARGR

201 FGCVWKAQLM NDFVAVKIFP LQDKQSWQSE REIFSTPGMK HENLLQFIAA

251 EKRGSNLEVE LWLITAFHDK GSLTDYLKGN IITWNELCHV AETMSRGLSY

301 LHEDVPWCRG EGHKPSIAHR DFKSKNVLLK SDLTAVLADF GLAVRFEPGK

351 PPGDTHGQVG TRRYMAPEVL EGAINFQRDA FLRIDMYAMG LVLWELVSRC

401 KAADGPVDEY MLPFEEEIGQ HPSLEELQEV VVHKKMRPTI KDHWLKHPGL

451 AQLCVTIEEC WDHDAEARLS AGCVEERVSL IRRSVNGTTS DCLVSLVTSV

501 TNVDLPPKES SI
```

The signal peptide is indicated with a single underline; the extracellular domain is indicated in bold font; and the potential, endogenous N-linked glycosylation sites are indicated with a double underline.

The processed (mature) extracellular ActRIIB polypeptide sequence is as follows:

```
                                                     (SEQ ID NO: 2)
GRGEAETRECIYYNANWELERTNQSGLERCEGEQDKRLHCYASWRNSS

GTIELVKKGCWLDDFNCYDRQECVATEENPQVYFCCCEGNFCNERFTH

LPEAGGPEVTYEPPPTAPT
```

In some embodiments, the protein may be produced with an "SGR . . . " sequence at the N-terminus. The C-terminal "tail" of the extracellular domain is indicated by a single underline. The sequence with the "tail" deleted (a Δ15 sequence) is as follows:

```
                                                     (SEQ ID NO: 3)
GRGEAETRECIYYNANWELERTNQSGLERCEGEQDKRLHCYASWRNSS

GTIELVKKGCWLDDFNCYDRQECVATEENPQVYFCCCEGNFCNERFTH

LPEA
```

A form of ActRIIB with an alanine at position 64 of SEQ ID NO: 1 (A64) is also reported in the literature See, e.g., Hilden et al. (1994) Blood, 83(8): 2163-2170. Applicants have ascertained that an ActRIIB-Fc fusion protein comprising an extracellular domain of ActRIIB with the A64 substitution has a relatively low affinity for activin and GDF11. By contrast, the same ActRIIB-Fc fusion protein with an arginine at position 64 (R64) has an affinity for activin and GDF11 in the low nanomolar to high picomolar range. Therefore, sequences with an R64 are used as the "wild-type" reference sequence for human ActRIIB in this disclosure.

The form of ActRIIB with an alanine at position 64 is as follows:

(SEQ ID NO: 4)
```
  1 MTAPWVALAL LWGSLCAGSG RGEAETRECI YYNANWELER TNQSGLERCE
 51 GEQDKRLHCY ASWANSSGTI ELVKKGCWLD DFNCYDRQEC VATEENPQVY
101 FCCCEGNFCN ERFTHLPEAG GPEVTYEPPP TAPTLLTVLA YSLLPIGGLS
151 LIVLLAFWMY RHRKPPYGHV DIHEDPGPPP PSPLVGLKPL QLLEIKARGR
201 FGCVWKAQLM NDFVAVKIFP LQDKQSWQSE REIFSTPGMK HENLLQFIAA
251 EKRGSNLEVE LWLITAFHDK GSLTDYLKGN IITWNELCHV AETMSRGLSY
301 LHEDVPWCRG EGHKPSIAHR DFKSKNVLLK SDLTAVLADF GLAVRFEPGK
351 PPGDTHGQVG TRRYMAPEVL EGAINFQRDA FLRIDMYAMG LVLWELVSRC
401 KAADGPVDEY MLPFEEEIGQ HPSLEELQEV VVHKKMRPTI KDHWLKHPGL
451 AQLCVTIEEC WDHDAEARLS AGCVEERVSL IRRSVNGTTS DCLVSLVTSV
501 TNVDLPPKES SI
```

The signal peptide is indicated by single underline and the extracellular domain is indicated by bold font.

The processed (mature) extracellular ActRIIB polypeptide sequence of the alternative A64 form is as follows:

(SEQ ID NO: 5)
```
GRGEAETRECIYYNANWELERTNQSGLERCEGEQDKRLHCYASWANSS
GTIELVKKGCWLDDFNCYDRQECVATEENPQVYFCCCEGNFCNERFTH
LPEAGGPEVTYEPPPTAPT
```

In some embodiments, the protein may be produced with an "SGR . . . " sequence at the N-terminus. The C-terminal "tail" of the extracellular domain is indicated by single underline. The sequence with the "tail" deleted (a Δ15 sequence) is as follows:

(SEQ ID NO: 6)
```
GRGEAETRECIYYNANWELERTNQSGLERCEGEQDKRLHCYASWANSS
GTIELVKKGCWLDDFNCYDRQECVATEENPQVYFCCCEGNFCNERFTH
LPEA
```

A nucleic acid sequence encoding the human ActRIIB precursor protein is shown below (SEQ ID NO: 7), representing nucleotides 25-1560 of Genbank Reference Sequence NM_001106.3, which encode amino acids 1-513 of the ActRIIB precursor. The sequence as shown provides an arginine at position 64 and may be modified to provide an alanine instead. The signal sequence is underlined.

(SEQ ID NO: 7)
```
  1 ATGACGGCGC CTGGGTGGC CCTCGCCCTC CTCTGGGGAT CGCTGTGCGC
 51 CGGCTCTGGG CGTGGGGAGG CTGAGACACG GGAGTGCATC TACTACAACG
101 CCAACTGGGA GCTGGAGCGC ACCAACCAGA GCGGCCTGGA GCGCTGCGAA
151 GGCGAGCAGG ACAAGCGGCT GCACTGCTAC GCCTCCTGGC GCAACAGCTC
```

-continued

```
201 TGGCACCATC GAGCTCGTGA AGAAGGGCTG CTGGCTAGAT GACTTCAACT
251 GCTACGATAG CAGGAGTGT GTGGCCACTG AGGAGAACCC CCAGGTGTAC
301 TTCTGCTGCT GTGAAGGCAA CTTCTGCAAC GAACGCTTCA CTCATTTGCC
351 AGAGGCTGGG GGCCCGGAAG TCACGTACGA GCCACCCCG ACAGCCCCCA
401 CCCTGCTCAC GGTGCTGGCC TACTCACTGC TGCCCATCGG GGGCCTTTCC
451 CTCATCGTCC TGCTGGCCTT TTGGATGTAC CGGCATCGCA AGCCCCCCTA
501 CGGTCATGTG GACATCCATG AGGACCCTGG GCCTCCACCA CCATCCCCTC
551 TGGTGGGCCT GAAGCCACTG CAGCTGCTGG AGATCAAGGC TCGGGGGCGC
601 TTTGGCTGTG TCTGGAAGGC CCAGCTCATG AATGACTTTG TAGCTGTCAA
651 GATCTTCCCA CTCCAGGACA AGCAGTCGTG GCAGAGTGAA CGGGAGATCT
701 TCAGCACACC TGGCATGAAG CACGAGAACC TGCTACAGTT CATTGCTGCC
751 GAGAAGCGAG GCTCCAACCT CGAAGTAGAG CTGTGGCTCA TCACGGCCTT
801 CCATGACAAG GGCTCCCTCA CGGATTACCT CAAGGGGAAC ATCATCACAT
851 GGAACGAACT GTGTCATGTA GCAGAGACGA TGTCACGAGG CCTCTCATAC
901 CTGCATGAGG ATGTGCCCTG GTGCCGTGGC GAGGGCCACA AGCCGTCTAT
951 TGCCCACAGG GACTTTAAAA GTAAGAATGT ATTGCTGAAG AGCGACCTCA
1001 CAGCCGTGCT GGCTGACTTT GGCTTGGCTG TTCGATTTGA GCCAGGGAAA
1051 CCTCCAGGGG ACACCCACGG ACAGGTAGGC ACGAGACGGT ACATGGCTCC
1101 TGAGGTGCTC GAGGGAGCCA TCAACTTCCA GAGAGATGCC TTCCTGCGCA
1151 TTGACATGTA TGCCATGGGG TTGGTGCTGT GGGAGCTTGT GTCTCGCTGC
1201 AAGGCTGCAG ACGGACCCGT GGATGAGTAC ATGCTGCCCT TTGAGGAAGA
1251 GATTGGCCAG CACCCTTCGT TGGAGGAGCT GCAGGAGGTG GTGGTGCACA
1301 AGAAGATGAG GCCCACCATT AAAGATCACT GGTTGAAACA CCCGGGCCTG
1351 GCCCAGCTTT GTGTGACCAT CGAGGAGTGC TGGGACCATG ATGCAGAGGC
1401 TCGCTTGTCC GCGGGCTGTG TGGAGGAGCG GGTGTCCCTG ATTCGGAGGT
1451 CGGTCAACGG CACTACCTCG GACTGTCTCG TTTCCCTGGT GACCTCTGTC
1501 ACCAATGTGG ACCTGCCCCC TAAAGAGTCA AGCATC
```

A nucleic acid sequence encoding processed extracellular human ActRIIB polypeptide is as follows (SEQ ID NO: 8). The sequence as shown provides an arginine at position 64, and may be modified to provide an alanine instead.

(SEQ ID NO: 8)
```
  1 GGGCGTGGGG AGGCTGAGAC ACGGGAGTGC ATCTACTACA ACGCCAACTG

51 GGAGCTGGAG CGAGCCACCC AGAGCGGCCT GGAGCGCTGC GAAGGCGAGC

101 AGGACAAGCG GCTGCACTGC TACGCCTCCT GGCGCAACAG CTCTGGCACC

151 ATCGAGCTCG TGAAGAAGGG CTGCTGGCTA GATGACTTCA ACTGCTACGA

201 TAGGCAGGAG TGTGTGGCCA CTGAGGAGAA CCCCCAGGTG TACTTCTGCT

251 GCTGTGAAGG CAACTTCTGC AACGAACGCT TCACTCATTT GCCAGAGGCT

301 GGGGGCCCGG AAGTCACGTA CGAGCCACCC CGACAGCCCC CACC
```

An alignment of the amino acid sequences of human ActRIIB extracellular domain and human ActRIIA extracellular domain are illustrated in FIG. 3. This alignment indicates amino acid residues within both receptors that are believed to directly contact ActRII ligands. For example, the composite ActRII structures indicated that the ActRIIB-ligand binding pocket is defined, in part, by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated.

Figure 4:
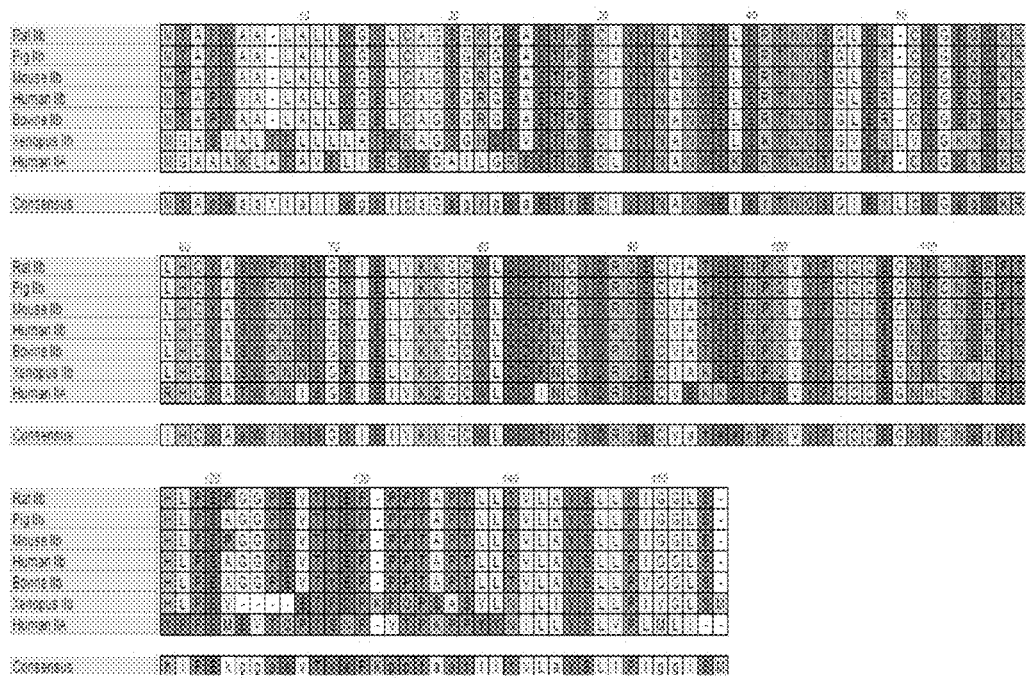
FIG. 4 shows a multiple sequence alignment of various vertebrate ActRIIB precursor proteins without their intracellular domains (SEQ ID NOs: 50-55, respectively) human ActRIIA precursor protein without its intracellular domain (SEQ ID NO: 56), and a consensus ActRII precursor protein (SEQ ID NO: 57).

In addition, ActRIIB is well-conserved among vertebrates, with large stretches of the extracellular domain completely conserved. For example, FIG. 4 depicts a multi-sequence alignment of a human ActRIIB extracellular domain compared to various ActRIIB orthologs. Many of the ligands that bind to ActRIIB are also highly conserved. Accordingly, from these alignments, it is possible to predict key amino acid positions within the ligand-binding domain that are important for normal ActRIIB-ligand binding activities as well as to predict amino acid positions that are likely to be tolerant of substitution without significantly altering normal ActRIIB-ligand binding activities. Therefore, an active, human ActRIIB variant polypeptide useful in accordance with the presently disclosed methods may include one or more amino acids at corresponding positions from the sequence of another vertebrate ActRIIB, or may include a residue that is similar to that in the human or other vertebrate sequences. Without meaning to be limiting, the following examples illustrate this approach to defining an active ActRIIB variant. L46 in the human extracellular domain (SEQ ID NO: 53) is a valine in *Xenopus* ActRIIB (SEQ ID NO: 55), and so this position may be altered, and optionally may be altered to another hydrophobic residue, such as V, I or F, or a non-polar residue such as A. E52 in the human extracellular domain is a K in *Xenopus*, indicating that this site may be tolerant of a wide variety of changes, including polar residues, such as E, D, K, R, H, S, T, P, G, Y and probably A. T93 in the human extracellular domain is a K in *Xenopus*, indicating that a wide structural variation is tolerated at this position, with polar residues favored, such as S, K, R, E, D, H, G, P, G and Y. F108 in the human extracellular domain is a Y in *Xenopus*, and therefore Y or other hydrophobic group, such as I, V or L should be tolerated. E111 in the human extracellular domain is K in *Xenopus*, indicating that charged residues will be tolerated at this position, including D, R, K and H, as well as Q and N. R112 in the human extracellular domain is K in *Xenopus*, indicating that basic residues are tolerated at this position, including R and H. A at position 119 in the human extracellular domain is relatively poorly conserved, and appears as P in rodents and V in *Xenopus*, thus essentially any amino acid should be tolerated at this position.

Moreover, ActRII proteins have been characterized in the art in terms of structural and functional characteristics, particularly with respect to ligand binding [Attisano et al. (1992) Cell 68(1):97-108; Greenwald et al. (1999) Nature Structural Biology 6(1): 18-22; Allendorph et al. (2006) PNAS 103(20: 7643-7648; Thompson et al. (2003) The EMBO Journal 22(7): 1555-1566; as well as U.S. Pat. Nos. 7,709,605, 7,612,041, and 7,842,663]. In addition to the teachings herein, these references provide amply guidance for how to generate ActRIIB variants that retain one or more normal activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. Accordingly, the core ligand-binding domains of human ActRIIB, as demarcated by the outermost of these conserved cysteines, corresponds to positions 29-109 of SEQ ID NO: 1 (ActRIIB precursor). Thus, the structurally less-ordered amino acids flanking these cysteine-demarcated core sequences can be truncated by about 1, 2, 3, 4, 5, 6, 7, 8, 9, 10, 11, 12, 13, 14, 15, 16, 17, 18, 19, 20, 21, 22, 23, 24, 25, 26, 27, or 28 residues at the N-terminus and/or by about 1, 2, 3, 4, 5, 6, 7, 8, 9, 10, 11, 12, 13, 14, 15, 16, 17, 18, 19, 20, 21, 22, 23, 24, or 25 residues at the C-terminus without necessarily altering ligand binding. Exemplary ActRIIB extracellular domains for N-terminal and/or C-terminal truncation include SEQ ID NOs: 2, 3, 5, and 6.

Attisano et al. showed that a deletion of the proline knot at the C-terminus of the extracellular domain of ActRIIB reduced the affinity of the receptor for activin. An ActRIIB-Fc fusion protein containing amino acids 20-119 of present SEQ ID NO: 1, "ActRIIB(20-119)-Fc", has reduced binding to GDF11 and activin relative to an ActRIIB(20-134)-Fc, which includes the proline knot region and the complete juxtamembrane domain (see, e.g., U.S. Pat. No. 7,842,663). However, an ActRIIB(20-129)-Fc protein retains similar, but somewhat reduced activity, relative to the wild-type, even though the proline knot region is disrupted.

Thus, ActRIIB extracellular domains that stop at amino acid 134, 133, 132, 131, 130 and 129 (with respect to SEQ ID NO: 1) are all expected to be active, but constructs stopping at 134 or 133 may be most active. Similarly, mutations at any of residues 129-134 (with respect to SEQ ID NO: 1) are not expected to alter ligand-binding affinity by large margins. In support of this, it is known in the art that mutations of P129 and P130 (with respect to SEQ ID NO: 1) do not substantially decrease ligand binding. Therefore, an ActRIIB polypeptide of the present disclosure may end as early as amino acid 109 (the final cysteine), however, forms ending at or between 109 and 119 (e.g., 109, 110, 111, 112, 113, 114, 115, 116, 117, 118, or 119) are expected to have reduced ligand binding. Amino acid 119 (with respect to present SEQ ID NO:1) is poorly conserved and so is readily altered or truncated. ActRIIB polypeptides ending at 128 (with respect to SEQ ID NO: 1) or later should retain ligand-binding activity. ActRIIB polypeptides ending at or between 119 and 127 (e.g., 119, 120, 121, 122, 123, 124, 125, 126, or 127), with respect to SEQ ID NO: 1, will have an intermediate binding ability. Any of these forms may be desirable to use, depending on the clinical or experimental setting.

At the N-terminus of ActRIIB, it is expected that a protein beginning at amino acid 29 or before (with respect to SEQ ID NO: 1) will retain ligand-binding activity. Amino acid 29 represents the initial cysteine. An alanine-to-asparagine mutation at position 24 (with respect to SEQ ID NO: 1) introduces an N-linked glycosylation sequence without substantially affecting ligand binding [U.S. Pat. No. 7,842,663]. This confirms that mutations in the region between the signal cleavage peptide and the cysteine cross-linked region, corresponding to amino acids 20-29, are well tolerated. In particular, ActRIIB polypeptides beginning at position 20, 21, 22, 23, and 24 (with respect to SEQ ID NO: 1) should retain general ligand-biding activity, and ActRIIB polypeptides beginning at positions 25, 26, 27, 28, and 29 (with respect to SEQ ID NO: 1) are also expected to retain ligand-biding activity. It has been demonstrated, e.g., U.S.

Pat. No. 7,842,663, that, surprisingly, an ActRIIB construct beginning at 22, 23, 24, or 25 will have the most activity.

Taken together, a general formula for an active portion (e.g., ligand-binding portion) of ActRIIB comprises amino acids 29-109 of SEQ ID NO: 1. Therefore ActRIIB polypeptides may, for example, comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to any one of amino acids 20-29 (e.g., beginning at any one of amino acids 20, 21, 22, 23, 24, 25, 26, 27, 28, or 29) of SEQ ID NO: 1 and ending at a position corresponding to any one amino acids 109-134 (e.g., ending at any one of amino acids 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. Other examples include polypeptides that begin at a position from 20-29 (e.g., any one of positions 20, 21, 22, 23, 24, 25, 26, 27, 28, or 29) or 21-29 (e.g., any one of positions 21, 22, 23, 24, 25, 26, 27, 28, or 29) of SEQ ID NO: 1 and end at a position from 119-134 (e.g., any one of positions 119, 120, 121, 122, 123, 124, 125, 126, 127, 128, 129, 130, 131, 132, 133, or 134), 119-133 (e.g., any one of positions 119, 120, 121, 122, 123, 124, 125, 126, 127, 128, 129, 130, 131, 132, or 133), 129-134 (e.g., any one of positions 129, 130, 131, 132, 133, or 134), or 129-133 (e.g., any one of positions 129, 130, 131, 132, or 133) of SEQ ID NO: 1. Other examples include constructs that begin at a position from 20-24 (e.g., any one of positions 20, 21, 22, 23, or 24), 21-24 (e.g., any one of positions 21, 22, 23, or 24), or 22-25 (e.g., any one of positions 22, 22, 23, or 25) of SEQ ID NO: 1 and end at a position from 109-134 (e.g., any one of positions 109, 110, 111, 112, 113, 114, 115, 116, 117, 118, 119, 120, 121, 122, 123, 124, 125, 126, 127, 128, 129, 130, 131, 132, 133, or 134), 119-134 (e.g., any one of positions 119, 120, 121, 122, 123, 124, 125, 126, 127, 128, 129, 130, 131, 132, 133, or 134) or 129-134 (e.g., any one of positions 129, 130, 131, 132, 133, or 134) of SEQ ID NO: 1. Variants within these ranges are also contemplated, particularly those having at least 70%, 75%, 80%, 85%, 86%, 87%, 88%, 89%, 90%, 91%, 92%, 93%, 94%, 95%, 96%, 97%, 98%, 99%, or 100% identity to the corresponding portion of SEQ ID NO: 1.

The variations described herein may be combined in various ways. In some embodiments, ActRIIB variants comprise no more than 1, 2, 5, 6, 7, 8, 9, 10 or 15 conservative amino acid changes in the ligand-binding pocket, and zero, one, or more non-conservative alterations at positions 40, 53, 55, 74, 79 and/or 82 in the ligand-binding pocket. Sites outside the binding pocket, at which variability may be particularly well tolerated, include the amino and carboxy termini of the extracellular domain (as noted above), and positions 42-46 and 65-73 (with respect to SEQ ID NO: 1). An asparagine-to-alanine alteration at position 65 (N65A) actually improves ligand binding in the A64 background, and is thus expected to have no detrimental effect on ligand binding in the R64 background [U.S. Pat. No. 7,842,663]. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64 [U.S. Pat. No. 7,842,663]. Additionally, the results of the mutagenesis program described in the art indicate that there are amino acid positions in ActRIIB that are often beneficial to conserve. With respect to SEQ ID NO: 1, these include position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus, the disclosure provides a framework of amino acids that may be conserved in ActRIIB polypeptides. Other positions that may be desirable to conserve are as follows: position 52 (acidic amino acid), position 55 (basic amino acid), position 81 (acidic), 98 (polar or charged, particularly E, D, R or K), all with respect to SEQ ID NO: 1.

In certain embodiments, the disclosure relates to heteromultimers that comprise at least one ActRIIB polypeptide, which includes fragments, functional variants, and modified forms thereof. Preferably, ActRIIB polypeptides for use in accordance with inventions of the disclosure are soluble (e.g., an extracellular domain of ActRIIB) In other preferred embodiments, ActRIIB polypeptides for use in accordance with the disclosure bind to one or more TGF-beta superfamily ligands. Therefore, in some embodiments, ActRIIB polypeptides for use in accordance with the disclosure inhibit (antagonize) activity (e.g., inhibition of Smad signaling) of one or more TGF-beta superfamily ligands. In some embodiments, heteromultimers of the disclosure comprise at least one ActRIIB polypeptide that comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to amino acids 20-29 (e.g., beginning at any one of amino acids 20, 21, 22, 23, 24, 25, 26, 27, 28, or 29) of SEQ ID NO: 1 and ending at a position corresponding to amino acids 109-134 (e.g., ending at any one of amino acids 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. In certain preferred embodiments, heteromultimers of the disclosure comprise at least one ActRIIB polypeptide that comprises, consists, or consists essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 29-109 of SEQ ID NO: 1. In other preferred embodiments, heteromultimer complexes of the disclosure comprise at least one ActRIIB polypeptide that comprises, consists of, or consists essentially of an an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 25-131 of SEQ ID NO: 1. In some embodiments, heteromultimers of the disclosure comprise at least one ActRIIB polypeptide that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 1, 2, 3, 4, 5, 6, 39, 41, 45, or 46. In certain preferred embodiments, heteromultimers of the disclosure comprise do not comprise an ActRIIB polypeptide wherein the position corresponding to L79 of SEQ ID NO: 1 is an acidic amino acid (i.e., is not a naturally occurring D or E amino acid residue or artificial acidic amino acid).

In certain aspects, the present disclosure relates to protein complexes that comprise an ALK4 polypeptide. As used herein, the term "ALK4" refers to a family of activin receptor-like kinase-4 proteins from any species and variants derived from such ALK4 proteins by mutagenesis or other modification. Reference to ALK4 herein is understood to be a reference to any one of the currently identified forms. Members of the ALK4 family are generally transmembrane proteins, composed of a ligand-binding extracellular domain with a cysteine-rich region, a transmembrane domain, and a cytoplasmic domain with predicted serine/threonine kinase activity.

The term "ALK4 polypeptide" includes polypeptides comprising any naturally occurring polypeptide of an ALK4 family member as well as any variants thereof (including mutants, fragments, fusions, and peptidomimetic forms) that retain a useful activity. Numbering of amino acids for all ALK4-related polypeptides described herein is based on the numbering of the human ALK4 precursor protein sequence below (SEQ ID NO: 9), unless specifically designated otherwise.

The canonical human ALK4 precursor protein sequence (NCBI Ref Seq NP_004293) is as follows:

```
                                                         (SEQ ID NO: 9)
  1 MAESAGASSF FPLVVLLLAG SGGSGPRGVQ ALLCACTSCL QANYTCETDG ACMVSIFNLD

61 GMEHHVRTCI PKVELVPAGK PFYCLSSEDL RNTHCCYTDY CNRIDLRVPS GHLKEPEHPS

121 MWGPVELVGI IAGPVFLLFL IIIIVFLVIN YHQRVYHNRQ RLDMEDPSCE MCLSKDKTLQ

181 DLVYDLSTSG SGSGLPLFVQ RTVARTIVLQ EIIGKGRFGE VWRGRWRGGD VAVKIFSSRE

241 ERSWFREAEI YQTVMLRHEN ILGFIAADNK DNGTWTQLWL VSDYHEHGSL FDYLNRYTVT

301 IEGMIKLALS AASGLAHLHM EIVGTQGKPG IAHRDLKSKN ILVKKNGMCA IADLGLAVRH

361 DAVTDTIDIA PNQRVGTKRY MAPEVLDETI NMKHFDSFKC ADIYALGLVY WEIARRCNSG

421 GVHEEYQLPY YDLVPSDPSI EEMRKVVCDQ KLRPNIPNWW QSYEALRVMG KMMRECWYAN

481 GAARLTALRI KKTLSQLSVQ EDVKI
```

The signal peptide is indicated by a single underline and the extracellular domain is indicated in bold font.

The processed (mature) extracellular human ALK4 polypeptide sequence is as follows:

```
                                               (SEQ ID NO: 10)
SGPRGVQALLCACTSCLQANYTCETDGACMVSIFNLDGMEHHVRTCIP

KVELVPAGKPFYCLSSEDLRNTHCCYTDYCNRIDLRVPSGHLKEPEHP

SMWGPVE
```

A nucleic acid sequence encoding the ALK4 precursor protein is shown below (SEQ ID NO: 11), corresponding to nucleotides 78-1592 of Genbank Reference Sequence NM_004302.4. The signal sequence is underlined and the extracellular domain is indicated in bold font.

```
                                               (SEQ ID NO: 11)
ATGGCGGAGTCGGCCGGAGCCTCCTCCTTCTTCCCCCTTGTTGTCCTCCT

GCTCGCCGGCAGCGGCGGGTCCGGGCCCCGGGGGGTCCAGGCTCTGCTGT

GTGCGTGCACCAGCTGCCTCCAGGCCAACTACACGTGTGAGACAGATGGG

GCCTGCATGGTTTCCATTTTCAATCTGGATGGGATGGAGCACCATGTGCG

CACCTGCATCCCCAAAGTGGAGCTGGTCCCTGCCGGGAAGCCCTTCTACT

GCCTGAGCTCGGAGGACCTGCGCAACACCCACTGCTGCTACACTGACTAC

TGCAACAGGATCGACTTGAGGGTGCCCAGTGGTCACCTCAAGGAGCCTGA

GCACCCGTCCATGTGGGGCCCGGTGGAGCTGGTAGGCATCATCGCCGGCC

CGGTGTTCCTCCTGTTCCTCATCATCATCATTGTTTTCCTTGTCATTAAC

TATCATCAGCGTGTCTATCACAACCGCCAGAGACTGGACATGGAAGATCC
```

```
CTCATGTGAGATGTGTCTCTCCAAAGACAAGACGCTCCAGGATCTTGTCT

ACGATCTCTCCACCTCAGGGTCTGGCTCAGGGTTACCCCTCTTTGTCCAG

CGCACAGTGGCCCGAACCATCGTTTTACAAGAGATTATTGGCAAGGGTCG

GTTTGGGGAAGTATGGCGGGGCCGCTGGAGGGGTGGTGATGTGGCTGTGA

AAATATTCTCTTCTCGTGAAGAACGGTCTTGGTTCAGGGAAGCAGAGATA

TACCAGACGGTCATGCTGCGCCATGAAAACATCCTTGGATTTATTGCTGC

TGACAATAAAGATAATGGCACCTGGACACAGCTGTGGCTTGTTTCTGACT

ATCATGAGCACGGGTCCCTGTTTGATTATCTGAACCGGTACACAGTGACA

ATTGAGGGGATGATTAAGCTGGCCTTGTCTGCTGCTAGTGGGCTGGCACA

CCTGCACATGGAGATCGTGGGCACCCAAGGGAAGCCTGGAATTGCTCATC

GAGACTTAAAGTCAAAGAACATTCTGGTGAAGAAAAATGGCATGTGTGCC

ATAGCAGACCTGGGCCTGGCTGTCCGTCATGATGCAGTCACTGACACCAT

TGACATTGCCCCGAATCAGAGGGTGGGGACCAAACGATACATGGCCCCTG

AAGTACTTGATGAAACCATTAATATGAAACACTTTGACTCCTTTAAATGT

GCTGATATTTATGCCCTCGGGCTTGTATATTGGGAGATTGCTCGAAGATG

CAATTCTGGAGGAGTCCATGAAGAATATCAGCTGCCATATTACGACTTAG

TGCCCTCTGACCCTTCCATTGAGGAAATGCGAAAGGTTGTATGTGATCAG

AAGCTGCGTCCCAACATCCCCAACTGGTGGCAGAGTTATGAGGCACTGCG

GGTGATGGGGAAGATGATGCGAGAGTGTTGGTATGCCAACGGCGCAGCCC

GCCTGACGGCCCTGCGCATCAAGAAGACCCTCTCCCAGCTCAGCGTGCAG

GAAGACGTGAAGATC
```

A nucleic acid sequence encoding the extracellular ALK4 polypeptide is as follows:

```
                                               (SEQ ID NO: 12)
TCCGGGCCCCGGGGGGTCCAGGCTCTGCTGTGTGCGTGCACCAGCTGCCT

CCAGGCCAACTACACGTGTGAGACAGATGGGGCCTGCATGGTTTCCATTT

TCAATCTGGATGGGATGGAGCACCATGTGCGCACCTGCATCCCCAAAGTG

GAGCTGGTCCCTGCCGGGAAGCCCTTCTACTGCCTGAGCTCGGAGGACCT
```

-continued

```
GCGCAACACCCACTGCTGCTACACTGACTACTGCAACAGGATCGACTTGA

GGGTGCCCAGTGGTCACCTCAAGGAGCCTGAGCACCCGTCCATGTGGGGC

CCGGTGGAG
```

An alternative isoform of human ALK4 precursor protein sequence, isoform C (NCBI Ref Seq NP_064733.3), is as follows:

(SEQ ID NO: 19)
```
  1 MAESAGASSF FPLVVLLLAG SGGSGPRGVQ ALLCACTSCL QANYTCETDG ACMVSIFNLD

61 GMEHHVRTCI PKVELVPAGK PFYCLSSEDL RNTHCCYTDY CNRIDLRVPS GHLKEPEHPS

121 MWGPVELVGI IAGPVFLLFL IIIIVFLVIN YHQRVYHNRQ RLDMEDPSCE MCLSKDKTLQ

181 DLVYDLSTSG SGSGLPLFVQ RTVARTIVLQ EIIGKGRFGE VWRGRWRGGD VAVKIFSSRE

241 ERSWFREAEI YQTVMLRHEN ILGFIAADNK ADCSFLTLPW EVVMVSAAPK LRSLRLQYKG

301 GRGRARFLFP LNNGTWTQLW LVSDYHEHGS LFDYLNRYTV TIEGMIKLAL SAASGLAHLH

361 MEIVGTQGKP GIAHRDLKSK NILVKKNGMC AIADLGLAVR HDAVTDTIDI APNQRVGTKR

421 YMAPEVLDET INMKHFDSFK CADIYALGLV YWEIARRCNS GGVHEEYQLP YYDLVPSDPS

481 IEEMRKVVCD QKLRPNIPNW WQSYEALRVM GKMMRECWYA NGAARLTALR IKKTLSQLSV

541 QEDVKI
```

The signal peptide is indicated by a single underline and the extracellular domain is indicated in bold font.

The processed (mature) extracellular ALK4 polypeptide sequence (isoform C) is as follows:

(SEQ ID NO: 20)
```
SGPRGVQALLCACTSCLQANYTCETDGACMVSIFNLDGMEHHVRTCIPKV
ELVPAGKPFYCLSSEDLRNTHCCYTDYCNRIDLRVPSGHLKEPEHPSMWG
PVE
```

A nucleic acid sequence encoding the ALK4 precursor protein (isoform C) is shown below (SEQ ID NO: 21), corresponding to nucleotides 78-1715 of Genbank Reference Sequence NM_020328.3. The signal sequence is underlined and the extracellular domain is indicated in bold font.

(SEQ ID NO: 21)
```
ATGGCGGAGTCGGCCGGAGCCTCCTCCTTCTTCCCCCTTGTTGTCCTCCT

GCTCGCCGGCAGCGGCGGGTCCGGGCCCCGGGGGGTCCAGGCTCTGCTGT

GTGCGTGCACCAGCTGCCTCCAGGCCAACTACACGTGTGAGACAGATGGG

GCCTGCATGGTTTCCATTTTCAATCTGGATGGGATGGAGCACCATGTGCG

CACCTGCATCCCCAAAGTGGAGCTGGTCCCTGCCGGGAAGCCCTTCTACT

GCCTGAGCTCGGAGGACCTGCGCAACACCCACTGCTGCTACACTGACTAC

TGCAACAGGATCGACTTGAGGGTGCCCAGTGGTCACCTCAAGGAGCCTGA

GCACCCGTCCATGTGGGGCCCGGTGGAGCTGGTAGGCATCATCGCCGGCC

CGGTGTTCCTCCTGTTCCTCATCATCATCATTGTTTTCCTTGTCATTAAC

TATCATCAGCGTGTCTATCACAACCGCCAGAGACTGGACATGGAAGATCC

CTCATGTGAGATGTGTCTCCAAAGACAAGACGCTCCAGGATCTTGTCT

ACGATCTCTCCACCTCAGGGTCTGGCTCAGGGTTACCCCTCTTTGTCCAG
```

```
CGCACAGTGGCCCGAACCATCGTTTTACAAGAGATTATTGGCAAGGGTCG

GTTTGGGGAAGTATGGCGGGGCCGCTGGAGGGGTGGTGATGTGGCTGTGA

AAATATTCTCTTCTCGTGAAGAACGGTCTTGGTTCAGGGAAGCAGAGATA

TACCAGACGGTCATGCTGCGCCATGAAAACATCCTTGGATTTATTGCTGC

TGACAATAAAGCAGACTGCTCATTCCTCACATTGCCATGGGAAGTTGTAA

TGGTCTCTGCTGCCCCCAAGCTGAGGAGCCTTAGACTCCAATACAAGGGA

GGAAGGGGAAGAGCAAGATTTTTATTCCCACTGAATAATGGCACCTGGAC

ACAGCTGTGGCTTGTTTCTGACTATCATGAGCACGGGTCCCTGTTTGATT

ATCTGAACCGGTACACAGTGACAATTGAGGGGATGATTAAGCTGGCCTTG

TCTGCTGCTAGTGGGCTGGCACACCTGCACATGGAGATCGTGGGCACCCA

AGGGAAGCCTGGAATTGCTCATCGAGACTTAAAGTCAAAGAACATTCTGG

TGAAGAAAAATGGCATGTGTGCCATAGCAGACCTGGGCCTGGCTGTCCGT

CATGATGCAGTCACTGACACCATTGACATTGCCCCGAATCAGAGGGTGGG

GACCAAACGATACATGGCCCCTGAAGTACTTGATGAAACCATTAATATGA

AACACTTTGACTCCTTTAAATGTGCTGATATTTATGCCCTCGGGCTTGTA

TATTGGGAGATTGCTCGAAGATGCAATTCTGGAGGAGTCCATGAAGAATA

TCAGCTGCCATATTACGACTTAGTGCCCTCTGACCCTTCCATTGAGGAAA

TGCGAAAGGTTGTATGTGATCAGAAGCTGCGTCCCAACATCCCCAACTGG

TGGCAGAGTTATGAGGCACTGCGGGTGATGGGAAGATGATGCGAGAGTG

TTGGTATGCCAACGGCGCAGCCCGCCTGACGGCCCTGCGCATCAAGAAGA

CCCTCTCCCAGCTCAGCGTGCAGGAAGACGTGAAGATC
```

A nucleic acid sequence encoding the extracellular ALK4 polypeptide (isoform C) is as follows:

(SEQ ID NO: 22)
```
TCCGGGCCCCGGGGGGTCCAGGCTCTGCTGTGTGCGTGCACCAGCTGCCT

CCAGGCCAACTACACGTGTGAGACAGATGGGGCCTGCATGGTTTCCATTT

TCAATCTGGATGGGATGGAGCACCATGTGCGCACCTGCATCCCCAAAGTG
```

```
GAGCTGGTCCCTGCCGGGAAGCCCTTCTACTGCCTGAGCTCGGAGGACCT

GCGCAACACCCACTGCTGCTACACTGACTACTGCAACAGGATCGACTTGA

GGGTGCCCAGTGGTCACCTCAAGGAGCCTGAGCACCCGTCCATGTGGGGC

CCGGTGGAG
```

In certain embodiments, the disclosure relates to heteromultimers that comprise at least one ALK4 polypeptide, which includes fragments, functional variants, and modified forms thereof. Preferably, ALK4 polypeptides for use in accordance with inventions of the disclosure (e.g., heteromultimers comprising an ALK4 polypeptide and uses thereof) are soluble (e.g., an extracellular domain of ALK4). In other preferred embodiments, ALK4 polypeptides for use in accordance with the inventions of the disclosure bind to and/or inhibit (antagonize) activity (e.g., Smad signaling) of one or more TGF-beta superfamily ligands. In some embodiments, heteromultimers of the disclosure comprise at least one ALK4 polypeptide that is at least 70%, 75%, 80%, 85%, 86%, 87%, 88%, 89%, 90%, 91%, 92%, 93%, 94%, 95%, 97%, 98%, or 99% identical to the amino acid sequence of SEQ ID NO: 9, 10, 19, 20, 42, 44, 47, or 48. In some embodiments, heteromultimer complexes of the disclosure consist or consist essentially of at least one ALK4 polypeptide that is at least 70%, 75%, 80%, 85%, 86%, 87%, 88%, 89%, 90%, 91%, 92%, 93%, 94%, 95%, 97%, 98%, or 99% identical to the amino acid sequence of SEQ ID NO: 9, 10, 19, 20, 42, 44, 47, or 48.

Figure 7:
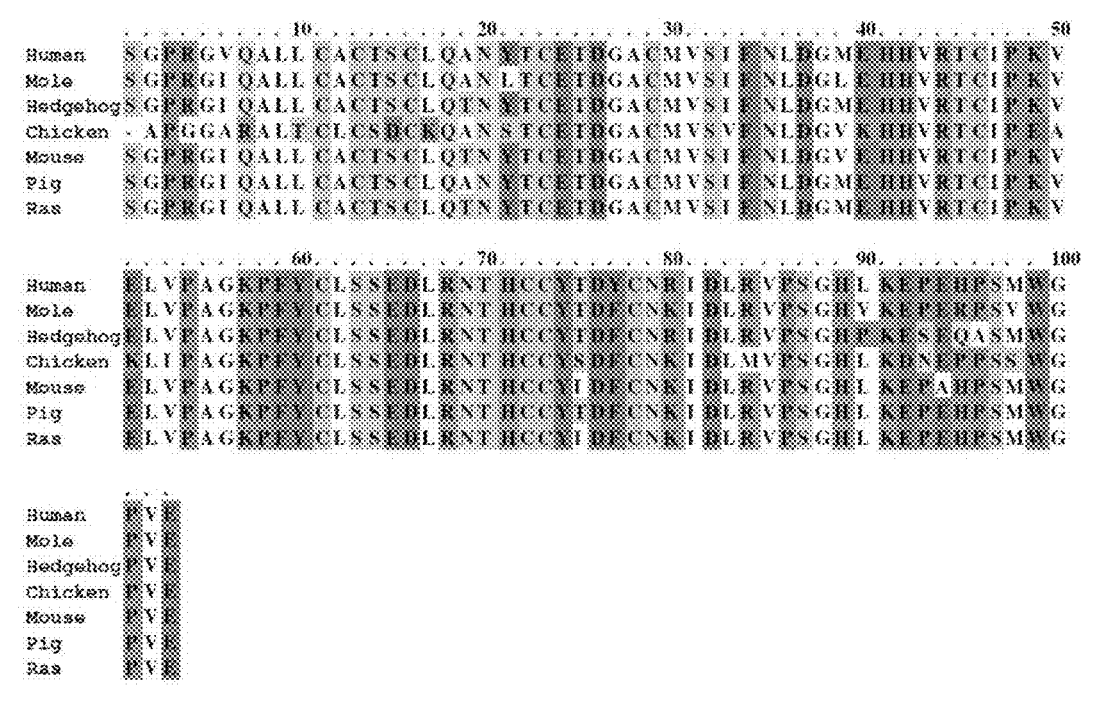

ALK4 is well-conserved among vertebrates, with large stretches of the extracellular domain completely conserved. For example, FIG. 7 depicts a multi-sequence alignment of a human ALK4 extracellular domain compared to various ALK4 orthologs. Many of the ligands that bind to ALK4 are also highly conserved. Accordingly, from these alignments, it is possible to predict key amino acid positions within the ligand-binding domain that are important for normal ALK4-ligand binding activities as well as to predict amino acid positions that are likely to be tolerant to substitution without significantly altering normal ALK4-ligand binding activities. Therefore, an active, human ALK4 variant polypeptide useful in accordance with the presently disclosed methods may include one or more amino acids at corresponding positions from the sequence of another vertebrate ALK4, or may include a residue that is similar to that in the human or other vertebrate sequences. Without meaning to be limiting, the following examples illustrate this approach to defining an active ALK4 variant. V6 in the human ALK4 extracellular domain (SEQ ID NO: 59) is isoleucine in *Mus muculus* ALK4 (SEQ ID NO: 63), and so the position may be altered, and optionally may be altered to another hydrophobic residue such as L, I, or F, or a non-polar residue such as A, as is observed in *Gallus gallus* ALK4 (SEQ ID NO: 62). E40 in the human extracellular domain is K in *Gallus gallus* ALK4, indicating that this site may be tolerant of a wide variety of changes, including polar residues, such as E, D, K, R, H, S, T, P, G, Y, and probably a non-polar residue such as A. S15 in the human extracellular domain is D in *Gallus gallus* ALK4, indicating that a wide structural variation is tolerated at this position, with polar residues favored, such as S, T, R, E, K, H, G, P, G and Y. E40 in the human extracellular domain is K in *Gallus gallus* ALK4, indicating that charged residues will be tolerated at this position, including D, R, K, H, as well as Q and N. R80 in the human extracellular domain is K in *Condylura cristata* ALK4 (SEQ ID NO: 60), indicating that basic residues are tolerated at this position, including R, K, and H. Y77 in the human extracellular domain is F in *Sus scrofa* ALK4 (SEQ ID NO: 64), indicating that aromatic residues are tolerated at this position, including F, W, and Y. P93 in the human extracellular domain is relatively poorly conserved, appearing as S in *Erinaceus europaeus* ALK4 (SEQ ID NO: 61) and N in *Gallus gallus* ALK4, thus essentially any amino acid should be tolerated at this position.

Moreover, ALK4 proteins have been characterized in the art in terms of structural and functional characteristics, particularly with respect to ligand binding [e.g., Harrison et al. (2003) J Biol Chem 278(23):21129-21135; Romano et al. (2012) J Mol Model 18(8):3617-3625; and Calvanese et al. (2009) 15(3):175-183]. In addition to the teachings herein, these references provide amply guidance for how to generate ALK4 variants that retain one or more normal activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. Accordingly, the core ligand-binding domains of human ALK4, as demarcated by the outermost of these conserved cysteines, corresponds to positions 34-101 of SEQ ID NO: 9 (ALK4 precursor). Thus, the structurally less-ordered amino acids flanking these cysteine-demarcated core sequences can be truncated by 1, 2, 3, 4, 5, 6, 7, 8, 9, or 10, residues at the N-terminus or 1, 2, 3, 4, 5, 6, 7, 8, 9, 10, 11, 12, 13, 14, 15, 16, 17, 18, 19, 20, 21, 22, 23, 24, 25, or 26 residues at the C-terminus without necessarily altering ligand binding. Exemplary ALK4 extracellular domains for N-terminal and/or C-terminal truncation include SEQ ID NOs: 10 and 20.

Accordingly, a general formula for an active portion (e.g., a ligand-binding portion) of ALK4 comprises amino acids 34-101. Therefore ALK4 polypeptides may, for example, comprise, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ALK4 beginning at a residue corresponding to any one of amino acids 24-34 (e.g., beginning at any one of amino acids 24, 25, 26, 27, 28, 29, 30, 31, 32, 33, or 34) of SEQ ID NO: 1 and ending at a position corresponding to any one amino acids 101-126 (e.g., ending at any one of amino acids 101, 102, 103, 104, 105, 106, 107, 108, 109, 110, 111, 112, 113, 114, 115, 116, 117, 118, 119, 120, 121, 122, 123, 124, 125, or 126) of SEQ ID NO: 9. Other examples include constructs that begin at a position from 24-34 (e.g., any one of positions 24, 25, 26, 27, 28, 29, 30, 31, 32, 33, or 34), 25-34 (e.g., any one of positions 25, 26, 27, 28, 29, 30, 31, 32, 33, or 34), or 26-34 (e.g., any one of positions 26, 27, 28, 29, 30, 31, 32, 33, or 34) of SEQ ID NO: 9 and end at a position from 101-126 (e.g., any one of positions 101, 102, 103, 104, 105, 106, 107, 108, 109, 110, 111, 112, 113, 114, 115, 116, 117, 118, 119, 120, 121, 122, 123, 124, 125, or 126), 102-126 (e.g., any one of positions 102, 103, 104, 105, 106, 107, 108, 109, 110, 111, 112, 113, 114, 115, 116, 117, 118, 119, 120, 121, 122, 123, 124, 125, or 126), 101-125 (e.g., any one of positions 101, 102, 103, 104, 105, 106, 107, 108, 109, 110, 111, 112, 113, 114, 115, 116, 117, 118, 119, 120, 121, 122, 123, 124, or 125), 101-124 (e.g., any one of positions 101, 102, 103, 104, 105, 106, 107, 108, 109, 110, 111, 112, 113, 114, 115, 116, 117, 118, 119, 120, 121, 122, 123, or 124), 101-121 (e.g., any one of positions 101, 102, 103, 104, 105, 106, 107, 108, 109, 110, 111, 112, 113, 114, 115, 116, 117, 118, 119, 120, or 121), 111-126 (e.g., any one of positions 111, 112, 113, 114, 115, 116, 117, 118, 119, 120, 121, 122, 123, 124, 125, or 126), 111-125 (e.g., any one of positions 111, 112, 113, 114, 115, 116, 117, 118, 119, 120, 121, 122, 123, 124, or 125), 111-124 (e.g., any one of positions 111, 112, 113, 114, 115, 116, 117, 118, 119, 120, 121, 122, 123, or 124), 121-126 (e.g., any one of positions 121, 122, 123, 124, 125, or 126), 121-125 (e.g., any one of positions 121, 122, 123, 124, or 125), 121-124 (e.g., any one of positions 121, 122, 123, or 124), or 124-126 (e.g., any one of positions 124, 125, or 126) of SEQ ID NO: 9. Variants within these ranges are also contemplated, particularly those having at least 70%, 75%, 80%, 85%, 86%, 87%, 88%, 89%, 90%, 91%, 92%, 93%, 94%, 95%, 96%, 97%, 98%, 99%, or 100% identity to the corresponding portion of SEQ ID NO: 9.

The variations described herein may be combined in various ways. In some embodiments, ALK4 variants comprise no more than 1, 2, 5, 6, 7, 8, 9, 10 or 15 conservative amino acid changes in the ligand-binding pocket. Sites outside the binding pocket, at which variability may be particularly well tolerated, include the amino and carboxy termini of the extracellular domain (as noted above), In certain aspects, the present disclosure relates to heteromultimers comprising one or more ALK4 receptor polypeptides (e.g., SEQ ID Nos: 9, 10, 19, 20, 42, 44, 47 and 48) and one or more ActRIIB receptor polypeptides (e.g., SEQ ID NOs: 1, 2, 3, 4, 5, 6, 39, 41, 45, and 46), which are generally referred to herein as "ALK4:ActRIIB heteromultimer complexes" or "ALK4:ActRIIB heteromultimers". Preferably, ALK4:ActRIIB heteromultimers of the disclosure are soluble, e.g., a heteromultimers comprises a soluble portion (domain) of an ALK4 receptor and a soluble portion (domain) of an ActRIIB receptor. In general, the extracellular domains of ALK4 and ActRIIB correspond to soluble portion of these receptors. Therefore, in some embodiments, heteromultimers of the disclosure comprise an extracellular domain of an ALK4, receptor and an extracellular domain of an ActRIIB receptor. Exemplary extracellular domains ALK4 and ActRIIB receptors are disclosed herein and such sequences, as well as fragments, functional variants, and modified forms thereof, may be used in accordance with the inventions of the disclosure (e.g., ALK4:ActRIIB heteromultimer compositions and uses thereof). In some embodiments, ALK4:ActRIIB heteromultimers of the disclosure comprise at least one ALK4 polypeptide that comprises, consists essentially of, or consists a sequence that is at least 70%, 75%, 80%, 85%, 86%, 87%, 88%, 89%, 90%, 91%, 92%, 93%, 94% 95%, 97%, 98%, 99%, or 100% identical to the amino acid sequence of SEQ ID NO: 9, 10, 19, 20, 42, 44, 47, and 48. In some embodiments, ALK4:ActRIIB heteromultimers of the disclosure comprise at least one ALK4 polypeptide that comprises, consists essentially of, consists of a sequence that is at least 70%, 75%, 80%, 85%, 86%, 87%, 88%, 89%, 90%, 91%, 92%, 93%, 94% 95%, 97%, 98%, 99%, or 100% identical to a portion of ALK4 beginning at a residue corresponding to any one of amino acids 24-34, 25-34, or 26-34 and ending at a position from 101-126, 102-126, 101-125, 101-124, 101-121, 111-126, 111-125, 111-124, 121-126, 121-125, 121-124, or 124-126 of SEQ ID NO: 9. In some embodiments, ALK4-ActRIIB heteromultimers of the disclosure comprise at least one ActRIIB polypeptide that comprises, consists essentially of, consists of a sequence that is at least 70%, 75%, 80%, 85%, 86%, 87%, 88%, 89%, 90%, 91%, 92%, 93%, 94% 95%, 97%, 98%, 99%, or 100% identical to the amino acid sequence of any one of SEQ ID NOs: 1, 2, 3, 4, 5, 6, 39, 41, 45, and 46. In some embodiments, ALK4:ActRIIB heteromultimers of the disclosure comprise at least one ActRIIB polypeptide that comprises, consists essentially of, consists of a sequence that is at least 70%, 75%, 80%, 85%, 86%, 87%, 88%, 89%, 90%, 91%, 92%, 93%, 94% 95%, 97%, 98%, 99%, or 100% identical to a portion of ActRIIB beginning at a residue corresponding to any one of amino acids 20-29, 20-24, 21-24, 22-25, or 21-29 and end at a position from 109-134, 119-134, 119-133, 129-134, or 129-133 of SEQ ID NO: 1. In certain preferred embodiments, ALK4:ActRIIB heteromultimers of the disclosure comprise at least one ActRIIB polypeptide wherein the position corresponding to L79 of SEQ ID NO: 1 is not an acidic amino acid (i.e., not a naturally occurring D or E amino acid residue or an artificially acidic amino acid). ALK4:ActRIIB heteromultimers of the disclosure include, e.g., heterodimers, heterotrimers, heterotetramers and higher order oligomeric structures. See, e.g., FIGS. 1, 2, and 8-10. In certain preferred embodiments, heteromultimer complexes of the disclosure are ALK4:ActRIIB heterodimers.

In some embodiments, the present disclosure contemplates making functional variants by modifying the structure of an ALK4 polypeptide and/or an ActRIIB polypeptide. Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide of the disclosure results in a functional homolog can be readily determined by assessing the ability of the variant polypeptide to produce a response in cells in a fashion similar to the wild-type polypeptide, or to bind to one or more TGF-beta superfamily ligands including, for example, BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin BC, activin AE, activin BE, nodal, glial cell-derived neurotrophic factor (GDNF), neurturin, artemin, persephin, MIS, and Lefty.

In some embodiments, the present disclosure contemplates making functional variants by modifying the structure of an ALK4 and/or ActRIIB polypeptide for such purposes as enhancing therapeutic efficacy or stability (e.g., increase shelf-life and/or resistance to proteolytic degradation).

In some embodiments, the present disclosure contemplates specific mutations of an ALK4 polypeptide and/or an ActRIIB polypeptide so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on a polypeptide may be accomplished chemically and/or enzymatically. Chemical deglycosylation may involve, for example, exposure of a polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on polypeptides can be achieved by the use of a variety of endo- and exo-glycosidases as described by Thotakura et al. [Meth. Enzymol. (1987) 138:350]. The sequence of a polypeptide may be adjusted, as appropriate, depending on the type of expression system used, as mammalian, yeast, insect, and plant cells may all introduce differing glycosylation patterns that can be affected by the amino acid sequence of the peptide. In general, heteromeric complexes of the present disclosure for use in humans may be expressed in a mammalian cell line that provides proper glycosylation, such as HEK293 or CHO cell lines, although other mammalian expression cell lines are expected to be useful as well.

The present disclosure further contemplates a method of generating mutants, particularly sets of combinatorial mutants of an ALK4 and/or an ActRIIB polypeptide as well as truncation mutants. Pools of combinatorial mutants are especially useful for identifying functionally active (e.g., TGF-beta superfamily ligand binding) ALK4 and/or ActRIIB sequences. The purpose of screening such combinatorial libraries may be to generate, for example, polypeptides variants which have altered properties, such as altered pharmacokinetic or altered ligand binding. A variety of screening assays are provided below, and such assays may be used to evaluate variants. For example, ALK4:ActRIIB complex variants may be screened for ability to bind to one or more TGF-beta superfamily ligands to prevent binding of a TGF-beta superfamily ligand to a TGF-beta superfamily receptor, and/or to interfere with signaling caused by an TGF-beta superfamily ligand.

The activity of a ALK4:ActRIIB heteromultimer may be tested, for example, in a cell-based or in vivo assay. For example, the effect of an ALK4:ActRIIB heteromultimer on the expression of genes or activity of proteins involved in muscle production in a muscle cell may be assessed. This may, as needed, be performed in the presence of one or more TGF-beta superfamily ligands, and cells may be transfected so as to produce an ALK4:ActRIIB heteromultimer, and optionally, a TGF-beta superfamily ligand. Likewise, an ALK4:ActRIIB heteromultimer may be administered to a mouse or other animal, and one or more measurements, such as muscle formation and strength may be assessed using art-recognized methods. Similarly, the activity of an ALK4:ActRIIB heteromultimer, or variants thereof, may be tested, for example, in osteoblasts, adipocytes, and/or neuronal cells for any effect on growth of these cells, for example, by the assays as described herein and those of common knowledge in the art. A SMAD-responsive reporter gene may be used in such cell lines to monitor effects on downstream signaling.

Combinatorial-derived variants can be generated which have increased selectivity or generally increased potency relative to a reference ALK4:ActRIIB heteromultimer. Such variants, when expressed from recombinant DNA constructs, can be used in gene therapy protocols. Likewise, mutagenesis can give rise to variants which have intracellular half-lives dramatically different than the corresponding unmodified ALK4:ActRIIB heteromultimer. For example, the altered protein can be rendered either more stable or less stable to proteolytic degradation or other cellular processes which result in destruction, or otherwise inactivation, of an unmodified polypeptide. Such variants, and the genes which encode them, can be utilized to alter polypeptide complex levels by modulating the half-life of the polypeptide. For instance, a short half-life can give rise to more transient biological effects and, when part of an inducible expression system, can allow tighter control of recombinant polypeptide complex levels within the cell. In an Fc fusion protein, mutations may be made in the linker (if any) and/or the Fc portion to alter one or more activities of the ALK4:ActRIIB heteromultimer including, for example, immunogenicity, half-life, and solubility.

A combinatorial library may be produced by way of a degenerate library of genes encoding a library of polypeptides which each include at least a portion of potential ALK4 and/or ActRIIB sequences. For instance, a mixture of synthetic oligonucleotides can be enzymatically ligated into gene sequences such that the degenerate set of potential ALK4 and/or ActRIIB encoding nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art [Narang, S A (1983) Tetrahedron 39:3; Itakura et al. (1981) Recombinant DNA, Proc. 3rd Cleveland Sympos. Macromolecules, ed. AG Walton, Amsterdam: Elsevier pp 273-289; Itakura et al. (1984) Annu. Rev. Biochem. 53:323; Itakura et al. (1984) Science 198:1056; and Ike et al. (1983) Nucleic Acid Res. 11:477]. Such techniques have been employed in the directed evolution of other proteins [Scott et al., (1990) Science 249:386-390; Roberts et al. (1992) PNAS USA 89:2429-2433; Devlin et al. (1990) Science 249: 404-406; Cwirla et al., (1990) PNAS USA 87: 6378-6382; as well as U.S. Pat. Nos. 5,223,409, 5,198,346, and 5,096,815].

Alternatively, other forms of mutagenesis can be utilized to generate a combinatorial library. For example, ALK4:ActRIIB heteromultimers can be generated and isolated from a library by screening using, for example, alanine scanning mutagenesis [Ruf et al. (1994) Biochemistry 33:1565-1572; Wang et al. (1994) J. Biol. Chem. 269:3095-3099; Balint et al. (1993) Gene 137:109-118; Grodberg et al. (1993) Eur. J. Biochem. 218:597-601; Nagashima et al. (1993) J. Biol. Chem. 268:2888-2892; Lowman et al. (1991) Biochemistry 30:10832-10838; and Cunningham et al. (1989) Science 244:1081-1085], by linker scanning mutagenesis [Gustin et al. (1993) Virology 193:653-660; and Brown et al. (1992) Mol. Cell Biol. 12:2644-2652; McKnight et al. (1982) Science 232:316], by saturation mutagenesis [Meyers et al., (1986) Science 232:613]; by PCR mutagenesis [Leung et al. (1989) Method Cell Mol Biol 1:11-19]; or by random mutagenesis, including chemical mutagenesis [Miller et al. (1992) A Short Course in Bacterial Genetics, CSHL Press, Cold Spring Harbor, N.Y.; and Greener et al. (1994) Strategies in Mol Biol 7:32-34]. Linker scanning mutagenesis, particularly in a combinatorial setting, is an attractive method for identifying truncated (bioactive) forms of ALK4 and/or ActRIIB polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ALK4:ActRIIB heteromultimers. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include TGF-beta superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin BC, activin AE, activin BE, nodal, glial cell-derived neurotrophic factor (GDNF), neurturin, artemin, persephin, MIS, and Lefty) binding assays and/or TGF-beta ligand-mediated cell signaling assays.

In certain embodiments, ALK4:ActRIIB heteromultimers may further comprise post-translational modifications in addition to any that are naturally present in the ALK4 and/or ActRIIB polypeptide. Such modifications include, but are not limited to, acetylation, carboxylation, glycosylation, phosphorylation, lipidation, and acylation. As a result, ALK4:ActRIIB heteromultimers may comprise non-amino acid elements, such as polyethylene glycols, lipids, polysaccharide or monosaccharide, and phosphates. Effects of such non-amino acid elements on the functionality of a heteromultimer complex may be tested as described herein for other heteromultimer variants. When a polypeptide of the disclosure is produced in cells by cleaving a nascent form of the polypeptide, post-translational processing may also be important for correct folding and/or function of the protein. Different cells (e.g., CHO, HeLa, MDCK, 293, WI38, NIH-3T3 or HEK293) have specific cellular machinery and characteristic mechanisms for such post-translational activities and may be chosen to ensure the correct modification and processing of the ALK4 and/or ActRIIB polypeptide as well as heteromultimers comprising the same.

In certain preferred embodiments, heteromultimers described herein comprise at least one ALK4 polypeptide associated, covalently or non-covalently, with at least one ActRIIB polypeptide. Preferably, polypeptides disclosed herein form heterodimeric complexes, although higher order heteromultimeric complexes are also included such as, but not limited to, heterotrimers, heterotetramers, and further oligomeric structures (see, e.g., FIGS. 1, 2, and 8-10). In some embodiments, ALK4 and/or ActRIIB polypeptides comprise at least one multimerization domain. As disclosed herein, the term "multimerization domain" refers to an amino acid or sequence of amino acids that promote covalent or non-covalent interaction between at least a first polypeptide and at least a second polypeptide. Polypeptides disclosed herein may be joined covalently or non-covalently to a multimerization domain. Preferably, a multimerization domain promotes interaction between a first polypeptide (e.g., an ALK4 polypeptide) and a second polypeptide (e.g., an ActRIIB polypeptide) to promote heteromultimer formation (e.g., heterodimer formation), and optionally hinders or otherwise disfavors homomultimer formation (e.g., homodimer formation), thereby increasing the yield of desired heteromultimer (see, e.g., FIG. 2).

Many methods known in the art can be used to generate ALK4:ActRIIB heteromultimers. For example, non-naturally occurring disulfide bonds may be constructed by replacing on a first polypeptide (e.g., an ALK4 polypeptide) a naturally occurring amino acid with a free thiol-containing residue, such as cysteine, such that the free thiol interacts with another free thiol-containing residue on a second polypeptide (e.g., an ActRIIB polypeptide) such that a disulfide bond is formed between the first and second polypeptides. Additional examples of interactions to promote heteromultimer formation include, but are not limited to, ionic interactions such as described in Kjaergaard et al., WO2007147901; electrostatic steering effects such as described in Kannan et al., U.S. Pat. No. 8,592,562; coiled-coil interactions such as described in Christensen et al., U.S. 20120302737; leucine zippers such as described in Pack & Plueckthun, (1992) Biochemistry 31: 1579-1584; and helix-turn-helix motifs such as described in Pack et al., (1993) Bio/Technology 11: 1271-1277. Linkage of the various segments may be obtained via, e.g., covalent binding such as by chemical cross-linking, peptide linkers, disulfide bridges, etc., or affinity interactions such as by avidin-biotin or leucine zipper technology.

In certain aspects, a multimerization domain may comprise one component of an interaction pair. In some embodiments, the polypeptides disclosed herein may form protein complexes comprising a first polypeptide covalently or non-covalently associated with a second polypeptide, wherein the first polypeptide comprises the amino acid sequence of an ALK4 polypeptide and the amino acid sequence of a first member of an interaction pair; and the second polypeptide comprises the amino acid sequence of an ActRIIB polypeptide and the amino acid sequence of a second member of an interaction pair. The interaction pair may be any two polypeptide sequences that interact to form a complex, particularly a heterodimeric complex although operative embodiments may also employ an interaction pair that can form a homodimeric complex. One member of the interaction pair may be fused to an ALK4 or ActRIIB polypeptide as described herein, including for example, a polypeptide sequence comprising, consisting essentially of, or consisting of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the sequence of any one of SEQ ID NOs: 2, 3, 5, 6, 10, and 20. An interaction pair may be selected to confer an improved property/activity such as increased serum half-life, or to act as an adaptor on to which another moiety is attached to provide an improved property/activity. For example, a polyethylene glycol moiety may be attached to one or both components of an interaction pair to provide an improved property/activity such as improved serum half-life.

The first and second members of the interaction pair may be an asymmetric pair, meaning that the members of the pair preferentially associate with each other rather than self-associate. Accordingly, first and second members of an asymmetric interaction pair may associate to form a heterodimeric complex (see, e.g., FIG. 2). Alternatively, the interaction pair may be unguided, meaning that the members of the pair may associate with each other or self-associate without substantial preference and thus may have the same or different amino acid sequences. Accordingly, first and second members of an unguided interaction pair may associate to form a homodimer complex or a heterodimeric complex. Optionally, the first member of the interaction pair (e.g., an asymmetric pair or an unguided interaction pair) associates covalently with the second member of the interaction pair. Optionally, the first member of the interaction pair (e.g., an asymmetric pair or an unguided interaction pair) associates non-covalently with the second member of the interaction pair.

As specific examples, the present disclosure provides fusion proteins comprising ALK4 or ActRIIB fused to a polypeptide comprising a constant domain of an immunoglobulin, such as a CH1, CH2, or CH3 domain of an immunoglobulin or an Fc domain. Fc domains derived from human IgG1, IgG2, IgG3, and IgG4 are provided herein. Other mutations are known that decrease either CDC or ADCC activity, and collectively, any of these variants are included in the disclosure and may be used as advantageous components of a heteromultimeric complex of the disclosure. Optionally, the IgG1 Fc domain of SEQ ID NO: 31 has one or more mutations at residues such as Asp-265, Lys-322, and Asn-434 (numbered in accordance with the corresponding full-length IgG1). In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

An example of a native amino acid sequence that may be used for the Fc portion of human IgG1 (G1Fc) is shown below (SEQ ID NO: 31). Dotted underline indicates the hinge region, and solid underline indicates positions with naturally occurring variants. In part, the disclosure provides polypeptides comprising, consisting essentially of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 31. Naturally occurring variants in G1Fc would include E134D and M136L according to the numbering system used in SEQ ID NO: 31 (see Uniprot P01857).

```
                                                             (SEQ ID NO: 31)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGK
```

An example of a native amino acid sequence that may be used for the Fc portion of human IgG2 (G2Fc) is shown below (SEQ ID NO: 32). Dotted underline indicates the hinge region and double underline indicates positions where there are data base conflicts in the sequence (according to UniProt P01859). In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 32.

```
                                                             (SEQ ID NO: 32)
  1 VECPPCPAPP VAGPSVFLFP PKPKDTLMIS RTPEVTCVVV DVSHEDPEVQ

51 FNWYVDGVEV HNAKTKPREE QFNSTFRVVS VLTVVHQDWL NGKEYKCKVS

101 NKGLPAPIEK TISKTKGQPR EPQVYTLPPS REEMTKNQVS LTCLVKGFYP

151 SDIAVEWESN GQPENNYKTT PPMLDSDGSF FLYSKLTVDK SRWQQGNVFS

201 CSVMHEALHN HYTQKSLSLS PGK
```

Two examples of amino acid sequences that may be used for the Fc portion of human IgG3 (G3Fc) are shown below. The hinge region in G3Fc can be up to four times as long as in other Fc chains and contains three identical 15-residue segments preceded by a similar 17-residue segment. The first G3Fc sequence shown below (SEQ ID NO: 33) contains a short hinge region consisting of a single 15-residue segment, whereas the second G3Fc sequence (SEQ ID NO: 34) contains a full-length hinge region. In each case, dotted underline indicates the hinge region, and solid underline indicates positions with naturally occurring variants according to UniProt P01859. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NOs: 33 and 34.

```
                                              (SEQ ID NO: 33)
  1 EPKSCDTPPP CPRCPAPELL GGPSVFLFPP KPKDTLMISR

TPEVTCVVVD

51 VSHEDPEVQF KWYVDGVEVH NAKTKPREEQ YNSTFRVVSV

LTVLHQDWLN

101 GKEYKCKVSN KALPAPIEKT ISKTKGQPRE PQVYTLPPSR

EEMTKNQVSL

151 TCLVKGFYPS DIAVEWESSG OPENNYNTTP PMLDSDGSFF

LYSKLTVDKS
```

```
                   -continued
201 RWQQGNIFSC SVMHEALHNR FTQKSLSLSP GK (SEQ ID NO: 34)
  1 ELKTPLGDTT HTCPRCPEPK SCDTPPPCPR CPEPKSCDTP

PPCPRCPEPK

51 SCDTPPPCPR CPAPELLGGP SVFLFPPKPK DTLMISRTPE

VTCVVVDVSH

101 EDPEVQFKWY VDGVEVHNAK TKPREEQYNS TFRVVSVLTV

LHQDWLNGKE

151 YKCKVSNKAL PAPIEKTISK TKGQPREPQV YTLPPSREEM

TKNQVSLTCL

201 VKGFYPSDIA VEWESSGQPE NNYNTTPPML DSDGSFFLYS

KLTVDKSRWQ

251 QGNIFSCSVM HEALHNRFTQ KSLSLSPGK
```

Naturally occurring variants in G3Fc (for example, see Uniprot P01860) include E68Q, P76L, E79Q, Y81F, D97N, N100D, T124A, S169N, S169del, F221Y when converted to the numbering system used in SEQ ID NO: 33, and the present disclosure provides fusion proteins comprising G3Fc domains containing one or more of these variations. In addition, the human immunoglobulin IgG3 gene (IGHG3) shows a structural polymorphism characterized by different hinge lengths [see Uniprot P01859]. Specifically, variant WIS is lacking most of the V region and all of the CH1 region. It has an extra interchain disulfide bond at position 7 in addition to the 11 normally present in the hinge region. Variant ZUC lacks most of the V region, all of the CH1 region, and part of the hinge. Variant OMM may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 35). Dotted underline indicates the hinge region. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 35.

```
                                              (SEQ ID NO: 35)
  1 ESKYGPPCPS CPAPEFLGGP SVFLFPPKPK DTLMISRTPE VTCVVVDVSQ

51 EDPEVQFNWY VDGVEVHNAK TKPREEQFNS TYRVVSVLTV LHQDWLNGKE

101 YKCKVSNKGL PSSIEKTISK AKGQPREPQV YTLPPSQEEM TKNQVSLTCL

151 VKGFYPSDIA VEWESNGQPE NNYKTTPPVL DSDGSFFLYS RLTVDKSRWQ

201 EGNVFSCSVM HEALHNHYTQ KSLSLSLGK
```

A variety of engineered mutations in the Fc domain are presented herein with respect to the G1Fc sequence (SEQ ID NO: 31), and analogous mutations in G2Fc, G3Fc, and G4Fc can be derived from their alignment with G1Fc in FIG. 5. Due to unequal hinge lengths, analogous Fc positions based on isotype alignment (FIG. 5) possess different amino acid numbers in SEQ ID NOs: 31, 32, 33, 34, and 35. It can also be appreciated that a given amino acid position in an immunoglobulin sequence consisting of hinge, $C_H2$, and $C_H3$ regions (e.g., SEQ ID NOs: 31, 32, 33, 34, and 35) will be identified by a different number than the same position when numbering encompasses the entire IgG1 heavy-chain constant domain (consisting of the $C_H1$, hinge, $C_H2$, and $C_H3$ regions) as in the Uniprot database. For example, correspondence between selected $C_H3$ positions in a human G1Fc sequence (SEQ ID NO: 31), the human IgG1 heavy chain constant domain (Uniprot P01857), and the human IgG1 heavy chain is as follows.

| Correspondence of $C_H3$ Positions in Different Numbering Systems | | |
| --- | --- | --- |
| G1Fc (Numbering begins at first threonine in hinge region) | IgG1 heavy chain constant domain (Numbering begins at $C_H1$) | IgG1 heavy chain (EU numbering scheme of Kabat et al., 1991*) |
| Y127 | Y232 | Y349 |
| S132 | S237 | S354 |
| E134 | E239 | E356 |
| T144 | T249 | T366 |

-continued

Correspondence of C$_H$3 Positions in Different Numbering Systems

| G1Fc (Numbering begins at first threonine in hinge region) | IgG1 heavy chain constant domain (Numbering begins at C$_H$1) | IgG1 heavy chain (EU numbering scheme of Kabat et al., 1991*) |
| --- | --- | --- |
| L146 | L251 | L368 |
| K170 | K275 | K392 |
| D177 | D282 | D399 |
| Y185 | Y290 | Y407 |
| K187 | K292 | K409 |

*Kabat et al. (eds) 1991; pp. 688-696 in Sequences of Proteins of Immunological Interest, 5$^{th}$ ed., Vol. 1, NIH, Bethesda, MD.

A problem that arises in large-scale production of asymmetric immunoglobulin-based proteins from a single cell line is known as the "chain association issue". As confronted prominently in the production of bispecific antibodies, the chain association issue concerns the challenge of efficiently producing a desired multichain protein from among the multiple combinations that inherently result when different heavy chains and/or light chains are produced in a single cell line [Klein et al (2012) mAbs 4:653-663]. This problem is most acute when two different heavy chains and two different light chains are produced in the same cell, in which case there are a total of 16 possible chain combinations (although some of these are identical) when only one is typically desired. Nevertheless, the same principle accounts for diminished yield of a desired multichain fusion protein that incorporates only two different (asymmetric) heavy chains.

Various methods are known in the art that increase desired pairing of Fc-containing fusion polypeptide chains in a single cell line to produce a preferred asymmetric fusion protein at acceptable yields [Klein et al (2012) mAbs 4:653-663; and Spiess et al (2015) Molecular Immunology 67(2A): 95-106]. Methods to obtain desired pairing of Fc-containing chains include, but are not limited to, charge-based pairing (electrostatic steering), "knobs-into-holes" steric pairing, SEEDbody pairing, and leucine zipper-based pairing [Ridgway et al (1996) Protein Eng 9:617-621; Merchant et al (1998) Nat Biotech 16:677-681; Davis et al (2010) Protein Eng Des Sel 23:195-202; Gunasekaran et al (2010); 285:19637-19646; Wranik et al (2012) J Biol Chem 287:43331-43339; U.S. Pat. No. 5,932,448; WO 1993/011162; WO 2009/089004, and WO 2011/034605]. As described herein, these methods may be used to generate ALK4-Fc:ActRIIB-Fc heteromultimer complexes. See FIGS. 8-10.

For example, one means by which interaction between specific polypeptides may be promoted is by engineering protuberance-into-cavity (knob-into-holes) complementary regions such as described in Arathoon et al., U.S. Pat. No. 7,183,076 and Carter et al., U.S. Pat. No. 5,731,168. "Protuberances" are constructed by replacing small amino acid side chains from the interface of the first polypeptide (e.g., a first interaction pair) with larger side chains (e.g., tyrosine or tryptophan). Complementary "cavities" of identical or similar size to the protuberances are optionally created on the interface of the second polypeptide (e.g., a second interaction pair) by replacing large amino acid side chains with smaller ones (e.g., alanine or threonine). Where a suitably positioned and dimensioned protuberance or cavity exists at the interface of either the first or second polypeptide, it is only necessary to engineer a corresponding cavity or protuberance, respectively, at the adjacent interface.

At neutral pH (7.0), aspartic acid and glutamic acid are negatively charged and lysine, arginine, and histidine are positively charged. These charged residues can be used to promote heterodimer formation and at the same time hinder homodimer formation. Attractive interactions take place between opposite charges and repulsive interactions occur between like charges. In part, protein complexes disclosed herein make use of the attractive interactions for promoting heteromultimer formation (e.g., heterodimer formation), and optionally repulsive interactions for hindering homodimer formation (e.g., homodimer formation) by carrying out site directed mutagenesis of charged interface residues.

For example, the IgG1 CH3 domain interface comprises four unique charge residue pairs involved in domain-domain interactions: Asp356-Lys439', Glu357-Lys370', Lys392-Asp399', and Asp399-Lys409' [residue numbering in the second chain is indicated by (')]. It should be noted that the numbering scheme used here to designate residues in the IgG1 CH3 domain conforms to the EU numbering scheme of Kabat. Due to the 2-fold symmetry present in the CH3-CH3 domain interactions, each unique interaction will represented twice in the structure (e.g., Asp-399-Lys409' and Lys409-Asp399'). In the wild-type sequence, K409-D399' favors both heterodimer and homodimer formation. A single mutation switching the charge polarity (e.g., K409E; positive to negative charge) in the first chain leads to unfavorable interactions for the formation of the first chain homodimer. The unfavorable interactions arise due to the repulsive interactions occurring between the same charges (negative-negative; K409E-D399' and D399-K409E'). A similar mutation switching the charge polarity (D399K'; negative to positive) in the second chain leads to unfavorable interactions (K409'-D399K' and D399K-K409') for the second chain homodimer formation. But, at the same time, these two mutations (K409E and D399K') lead to favorable interactions (K409E-D399K' and D399-K409') for the heterodimer formation.

The electrostatic steering effect on heterodimer formation and homodimer discouragement can be further enhanced by mutation of additional charge residues which may or may not be paired with an oppositely charged residue in the second chain including, for example, Arg355 and Lys360. The table below lists possible charge change mutations that can be used, alone or in combination, to enhance ALK4:ActRIIB heteromultimer formation.

Examples of Pair-Wise Charged Residue Mutations to Enhance Heterodimer Formation

| Position in first chain | Mutation in first chain | Interacting position in second chain | Corresponding mutation in second chain |
| --- | --- | --- | --- |
| Lys409 | Asp or Glu | Asp399' | Lys, Arg, or His |
| Lys392 | Asp or Glu | Asp399' | Lys, Arg, or His |
| Lys439 | Asp or Glu | Asp356' | Lys, Arg, or His |
| Lys370 | Asp or Glu | Glu357' | Lys, Arg, or His |
| Asp399 | Lys, Arg, or His | Lys409' | Asp or Glu |
| Asp399 | Lys, Arg, or His | Lys392' | Asp or Glu |
| Asp356 | Lys, Arg, or His | Lys439' | Asp or Glu |
| Glu357 | Lys, Arg, or His | Lys370' | Asp or Glu |

In some embodiments, one or more residues that make up the CH3-CH3 interface in a fusion protein of the instant application are replaced with a charged amino acid such that the interaction becomes electrostatically unfavorable. For example, a positive-charged amino acid in the interface (e.g., a lysine, arginine, or histidine) is replaced with a negatively charged amino acid (e.g., aspartic acid or glutamic acid). Alternatively, or in combination with the forgoing substitution, a negative-charged amino acid in the interface is replaced with a positive-charged amino acid. In certain embodiments, the amino acid is replaced with a non-naturally occurring amino acid having the desired charge characteristic. It should be noted that mutating negatively charged residues (Asp or Glu) to His will lead to increase in side chain volume, which may cause steric issues. Furthermore, His proton donor- and acceptor-form depends on the localized environment. These issues should be taken into consideration with the design strategy. Because the interface residues are highly conserved in human and mouse IgG subclasses, electrostatic steering effects disclosed herein can be applied to human and mouse IgG1, IgG2, IgG3, and IgG4. This strategy can also be extended to modifying uncharged residues to charged residues at the CH3 domain interface.

In part, the disclosure provides desired pairing of asymmetric Fc-containing polypeptide chains using Fc sequences engineered to be complementary on the basis of charge pairing (electrostatic steering). One of a pair of Fc sequences with electrostatic complementarity can be arbitrarily fused to the ALK4 or ActRIIB polypeptide of the construct, with or without an optional linker, to generate an ALK4:ActRIIB heteromultimer. This single chain can be coexpressed in a cell of choice along with the Fc sequence complementary to the first Fc to favor generation of the desired multichain construct (e.g., ALK4:ActRIIB heteromultimer). In this example based on electrostatic steering, SEQ ID NO: 23 [human G1Fc(E134K/D177K)] and SEQ ID NO: 24 [human G1Fc(K170D/K187D)] are examples of complementary Fc sequences in which the engineered amino acid substitutions are double underlined, and the TGF-beta superfamily type I or type II receptor polypeptide of the construct can be fused to either SEQ ID NO: 23 or SEQ ID NO: 24, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 5) will generate complementary Fc pairs which may be used instead of the complementary hG1Fc pair below (SEQ ID NOs: 23 and 24).

```
                                                         (SEQ ID NO: 23)
  1  THTCPPCPAP ELLGGPSVFL FPPKPKDTLM ISRTPEVTCV VVDVSHEDPE

51  VKFNWYVDGV EVHNAKTKPR EEQYNSTYRV VSVLTVLHQD WLNGKEYKCK

101  VSNKALPAPI EKTISKAKGQ PREPQVYTLP PSRKEMTKNQ VSLTCLVKGF

151  YPSDIAVEWE SNGQPENNYK TTPPVLKSDG SFFLYSKLTV DKSRWQQGNV

201  FSCSVMHEAL HNHYTQKSLS LSPGK
```

```
                                                         (SEQ ID NO: 24)
  1  THTCPPCPAP ELLGGPSVFL FPPKPKDTLM ISRTPEVTCV VVDVSHEDPE

51  VKFNWYVDGV EVHNAKTKPR EEQYNSTYRV VSVLTVLHQD WLNGKEYKCK

101  VSNKALPAPI EKTISKAKGQ PREPQVYTLP PSREEMTKNQ VSLTCLVKGF

151  YPSDIAVEWE SNGQPENNYD TTPPVLDSDG SFFLYSDLTV DKSRWQQGNV

201  FSCSVMHEAL HNHYTQKSLS LSPGK
```

In part, the disclosure provides desired pairing of asymmetric Fc-containing polypeptide chains using Fc sequences engineered for steric complementarity. In part, the disclosure provides knobs-into-holes pairing as an example of steric complementarity. One of a pair of Fc sequences with steric complementarity can be arbitrarily fused to the ALK4 or ActRIIB polypeptide of the construct, with or without an optional linker, to generate an ALK4:ActRIIB heteromultimer. This single chain can be co-expressed in a cell of choice along with the Fc sequence complementary to the first Fc to favor generation of the desired multi-chain construct. In this example based on knobs-into-holes pairing, SEQ ID NO: 25 [human G1Fc(T144Y)] and SEQ ID NO: 26 [human G1Fc (Y185T)] are examples of complementary Fc sequences in which the engineered amino acid substitutions are double underlined, and the ALK4 or ActRIIB polypeptide of the construct can be fused to either SEQ ID NO: 25 or SEQ ID NO: 26, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 5) will generate complementary Fc pairs which may be used instead of the complementary hG1Fc pair below (SEQ ID NOs: 25 and 26).

```
                                                         (SEQ ID NO: 25)
  1  THTCPPCPAP ELLGGPSVFL FPPKPKDTLM ISRTPEVTCV VVDVSHEDPE

51  VKFNWYVDGV EVHNAKTKPR EEQYNSTYRV VSVLTVLHQD WLNGKEYKCK

101  VSNKALPAPI EKTISKAKGQ PREPQVYTLP PSREEMTKNQ VSLYCLVKGF
```

```
151  YPSDIAVEWE  SNGQPENNYK  TTPPVLDSDG  SFFLYSKLTV  DKSRWQQGNV

201  FSCSVMHEAL  HNHYTQKSLS  LSPGK
```

(SEQ ID NO: 26)
```
  1  THTCPPCPAP  ELLGGPSVFL  FPPKPKDTLM  ISRTPEVTCV  VVDVSHEDPE

51  VKFNWYVDGV  EVHNAKTKPR  EEQYNSTYRV  VSVLTVLHQD  WLNGKEYKCK

101  VSNKALPAPI  EKTISKAKGQ  PREPQVYTLP  PSREEMTKNQ  VSLTCLVKGF

151  YPSDIAVEWE  SNGQPENNYK  TTPPVLDSDG  SFFLTSKLTV  DKSRWQQGNV

201  FSCSVMHEAL  HNHYTQKSLS  LSPGK
```

An example of Fc complementarity based on knobs-into-holes pairing combined with an engineered disulfide bond is disclosed in SEQ ID NO: 27 [hG1Fc(S132C/T144W)] and SEQ ID NO: 28 [hG1Fc(Y127C/T144S/L146A/Y185V)]. The engineered amino acid substitutions in these sequences are double underlined, and the TGF-beta superfamily type I or type II polypeptide of the construct can be fused to either SEQ ID NO: 27 or SEQ ID NO: 28, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 5) will generate complementary Fc pairs which may be used instead of the complementary hG1Fc pair below (SEQ ID NOs: 27 and 28).

proteins [Davis et al. (2010) Protein Eng Design Sel 23:195-202]. One of a pair of Fc sequences with SEEDbody complementarity can be arbitrarily fused to the ALK4 or ActIIB of the construct, with or without an optional linker, to generate a ALK4 or ActRIIB fusion polypeptide. This single chain can be co-expressed in a cell of choice along with the Fc sequence complementary to the first Fc to favor generation of the desired multi-chain construct. In this example based on SEEDbody (Sb) pairing, SEQ ID NO: 29 [hG1Fc($Sb_{AG}$)] and SEQ ID NO: 30 [hG1Fc($Sb_{GA}$)] are examples of complementary IgG Fc sequences in which the engineered amino acid substitutions from IgA Fc are double underlined, and the ALK4 or ActRIIB polypeptide of the construct can be fused to either SEQ ID NO: 29 or SEQ ID NO: 30, but not both. Given the high degree of amino acid (SEQ ID NO: 27)
```
  1  THTCPPCPAP  ELLGGPSVFL  FPPKPKDTLM  ISRTPEVTCV  VVDVSHEDPE

51  VKFNWYVDGV  EVHNAKTKPR  EEQYNSTYRV  VSVLTVLHQD  WLNGKEYKCK

101  VSNKALPAPI  EKTISKAKGQ  PREPQVYTLP  PCREEMTKNQ  VSLWCLVKGF

151  YPSDIAVEWE  SNGQPENNYK  TTPPVLDSDG  SFFLYSKLTV  DKSRWQQGNV

201  FSCSVMHEAL  HNHYTQKSLS  LSPGK
```

(SEQ ID NO: 28)
```
  1  THTCPPCPAP  ELLGGPSVFL  FPPKPKDTLM  ISRTPEVTCV  VVDVSHEDPE

51  VKFNWYVDGV  EVHNAKTKPR  EEQYNSTYRV  VSVLTVLHQD  WLNGKEYKCK

101  VSNKALPAPI  EKTISKAKGQ  PREPQVCTLP  PSREEMTKNQ  VSLSCAVKGF

151  YPSDIAVEWE  SNGQPENNYK  TTPPVLDSDG  SFFLVSKLTV  DKSRWQQGNV

201  FSCSVMHEAL  HNHYTQKSLS  LSPGK
```

In part, the disclosure provides desired pairing of asymmetric Fc-containing polypeptide chains using Fc sequences engineered to generate interdigitating β-strand segments of human IgG and IgA $C_H3$ domains. Such methods include the use of strand-exchange engineered domain (SEED) $C_H3$ heterodimers allowing the formation of SEEDbody fusion sequence identity between native hG1Fc, native hG2Fc, native hG3Fc, and native hG4Fc, it can be appreciated that amino acid substitutions at corresponding positions in hG1Fc, hG2Fc, hG3Fc, or hG4Fc (see FIG. 5) will generate an Fc monomer which may be used in the complementary IgG-IgA pair below (SEQ ID NOs: 29 and 30).

(SEQ ID NO: 29)
```
  1  THTCPPCPAP  ELLGGPSVFL  FPPKPKDTLM  ISRTPEVTCV  VVDVSHEDPE

51  VKFNWYVDGV  EVHNAKTKPR  EEQYNSTYRV  VSVLTVLHQD  WLNGKEYKCK

101  VSNKALPAPI  EKTISKAKGQ  PFRPEVHLLP  PSREEMTKNQ  VSLTCLARGF

151  YPKDIAVEWE  SNGQPENNYK  TIPSRQEPSQ  GTTTFAVTSK  LTVDKSRWQQ

201  GNVFSCSVMH  EALHNHYTQK  TISLSPGK
```

```
                                                   (SEQ ID NO: 30)
  1  THTCPPCPAP ELLGGPSVFL FPPKPKDTLM ISRTPEVTCV VVDVSHEDPE

51  VKFNWYVDGV EVHNAKTKPR EEQYNSTYRV VSVLTVLHQD WLNGKEYKCK

101  VSNKALPAPI EKTISKAKGQ PREPQVYTLP PPSEELALNE LVTLTCLVKG

151  FYPSDIAVEW ESNGQELPRE KYLTWAPVLD SDGSFFLYSI LRVAAEDWKK

201  GDTFSCSVMH EALHNHYTQK SLDRSPGK
```

In part, the disclosure provides desired pairing of asymmetric Fc-containing polypeptide chains with a cleavable leucine zipper domain attached at the C-terminus of the Fc $C_H3$ domains. Attachment of a leucine zipper is sufficient to cause preferential assembly of heterodimeric antibody heavy chains [Wranik et al (2012) J Biol Chem 287:43331-43339]. As disclosed herein, one of a pair of Fc sequences attached to a leucine zipper-forming strand can be arbitrarily fused to the ALK4 or ActRIIB polypeptide of the construct, with or without an optional linker, to generate a ALK4 or ActRIIB fusion polypeptide. This single chain can be co-expressed in a cell of choice along with the Fc sequence attached to a complementary leucine zipper-forming strand to favor generation of the desired multi-chain construct. Proteolytic digestion of the construct with the bacterial endoproteinase Lys-C post purification can release the leucine zipper domain, resulting in an Fc construct whose structure is identical to that of native Fc. In this example based on leucine zipper pairing, SEQ ID NO: 36 [hG1Fc-Ap1 (acidic)] and SEQ ID NO: 37 [hG1Fc-Bp1 (basic)] are examples of complementary IgG Fc sequences in which the engineered complementary leucine zipper sequences are underlined, and the ALK4 or ActRIIB polypeptide of the construct can be fused to either SEQ ID NO: 36 or SEQ ID NO: 37, but not both. Given the high degree of amino acid sequence identity between native hG1Fc, native hG2Fc, native hG3Fc, and native hG4Fc, it can be appreciated that leucine zipper-forming sequences attached, with or without an optional linker, to hG1Fc, hG2Fc, hG3Fc, or hG4Fc (see FIG. 5) will generate an Fc monomer which may be used in the complementary leucine zipper-forming pair below (SEQ ID NOs: 36 and 37).

As described above, various methods are known in the art that increase desired pairing of Fc-containing fusion polypeptide chains in a single cell line to produce a preferred asymmetric fusion protein at acceptable yields [Klein et al (2012) mAbs 4:653-663; and Spiess et al (2015) Molecular Immunology 67(2A): 95-106]. In addition, ALK4:ActRIIB heteromultimers may be generated using a combination of heavy and light chain fusion proteins comprising either an ALK4 or ActRIIB polypeptide. For example, in some embodiments, an ALK4 polypeptide may be fused, with or without a linker domain, to an immunoglobulin heavy chain (IgG1, IgG2, IgG3, IgG4, IgM, IgA1, or IgA2) that comprises at least a portion of the $C_H1$ domain. Similarly, an ActRIIB polypeptide may be fused, with or without a linker domain, to an immunoglobulin light chain (kappa or lambda) that comprises at least a portion of the light chain constant domain ($C_L$). In alternative embodiments, an ActRIIB polypeptide may be fused, with or without a linker domain, to an immunoglobulin heavy chain (IgG1, IgG2, IgG3, IgG4, IgM, IgA1, or IgA2) that comprises at least a portion of the $C_H1$ domain, and an ALK4 polypeptide may be fused, with or without a linker domain, to an immunoglobulin light chain (kappa or lambda) that comprises at least a portion of the light chain constant domain ($C_L$). This design takes advantage of the natural ability of the heavy chains to heterodimerize with light chains. In particular, heterodimerization of a heavy and light chain occurs between the $C_H1$ with the $C_L$, which is generally stabilized by covalent linking of the two domains via a disulfide bridge. Constructs employing the full-length heavy chain, or at least a portion of the heavy chain comprising the hinge region, could give rise to antibody-like molecules compris-

```
                                                   (SEQ ID NO: 36)
  1  THTCPPCPAP ELLGGPSVFL FPPKPKDTLM ISRTPEVTCV VVDVSHEDPE

51  VKFNWYVDGV EVHNAKTKPR EEQYNSTYRV VSVLTVLHQD WLNGKEYKCK

101  VSNKALPAPI EKTISKAKGQ PREPQVYTLP PSREEMTKNQ VSLTCLVKGF

151  YPSDIAVEWE SNGQPENNYK TTPPVLDSDG SFFLYSKLTV DKSRWQQGNV

201  FSCSVMHEAL HNHYTQKSLS LSPGKGGSAQ LEKELQALEK ENAQLEWELQ

251  ALEKELAQGA T (SEQ ID NO: 37)
  1  THTCPPCPAP ELLGGPSVFL FPPKPKDTLM ISRTPEVTCV VVDVSHEDPE

51  VKFNWYVDGV EVHNAKTKPR EEQYNSTYRV VSVLTVLHQD WLNGKEYKCK

101  VSNKALPAPI EKTISKAKGQ PREPQVYTLP PSREEMTKNQ VSLTCLVKGF

151  YPSDIAVEWE SNGQPENNYK TTPPVLDSDG SFFLYSKLTV DKSRWQQGNV

201  FSCSVMHEAL HNHYTQKSLS LSPGKGGSAQ LKKKLQALKK KNAQLKWKLQ

251  ALKKKLAQGA T
``` ing two "light chains" and two "heavy chains". See FIG. 9. A potential advantage of this design is that it may more closely mimic the naturally occurring ALK4-ligand-ActRIIB complex and may display higher affinity for the ligand than comparable single heterodimers. In some embodiments, this design may be modified by incorporating various heavy chain truncations including, for example, truncations that comprise the $C_H1$ domain and some or all of the hinge domain (giving rise to F(ab')$_2$-like molecules) as well as truncations that only comprise the $C_H1$ domain or a fragment thereof (giving rise to Fab-like molecules). See FIG. 9G. Various methods for designing such heteromultimer constructs are described in US 2009/0010879, Klein et al [(2012) mAbs 4:653-663], and Spiess et al [(2015) Molecular Immunology 67(2A): 95-106] the contents of which are incorporated in their entirety herein.

In some embodiments, it is desirable to generate antibody-like ALK4:ActRIIB heterodimers comprising at least one branch of the complex comprising an ALK4-$C_L$:ActRIIB-$C_H1$ heterodimer pair and at least a second branch comprising an ActRIIB-$C_L$:ALK4-$C_H1$ heterodimer pair. See, e.g., FIG. 9B. Such heterodimer complexes can be generated, for example, using combinations of heavy chain and light chain asymmetrical pairing technologies [Spiess et al (2015) Molecular Immunology 67(2A): 95-106]. For example, in CrossMab technology, [Schaefer et al (2011). Proc. Natl. Acad. Sci. U.S.A. 108: 11187-11192] light chain mispairing is overcome using domain crossovers and heavy chains heterodimerized using knobs-into-holes [Merchant et al (1998) Nat. Biotechnol. 16: 677-681}. For the domain crossovers either the variable domains or the constant domains are swapped between light and heavy chains to create two asymmetric Fab arms that drive cognate light chain pairing while preserving the structural and functional integrity of the variable domain [Fenn et al (2013) PLoS ONE 8: e61953]. An alternative approach for overcoming light chain mispairing is designing heavy and light chains with orthogonal Fab inter-faces [Lewis (2014) Nat. Biotechnol. 32: 191-198]. This has been accomplished by computational modeling [Das et al (2008) Annu. Rev. Biochem. 77: 363-382] in combination with X-ray crystallography to identify mutations at the $V_H/V_L$ and $C_H1/C_L$ interfaces. For the heterodimers generated using this methodology, it may be necessary to engineer mutations in both $V_H/V_L$ and $C_H1/C_L$ interfaces to minimize heavy/light chain mispairing. The designed orthogonal Fab interface may be used in conjunction with a heavy chain heterodimerization strategy to facilitate efficient IgG production in a single host cell. Electrostatic steering may also be used to generate orthogonal Fab interfaces to facilitate the construction of such heterodimers. Peptide linkers may be used to ensure cognate pairing of light and heavy chains in a format known as "LUZ-Y" [Wranik et al (2012) J. Biol. Chem. 287: 43331-43339], wherein heavy chain heterodimerization is accomplished using leucine zippers which may be subsequently removed by proteolysis in vitro.

Alternatively, ALK4:ActRIIB heteromultimers may comprise one or more single-chain ligand traps as described herein, optionally which may be covalently or non-covalently associated with one or more ALK4 or ActRIIB polypeptides as well as additional ALK4:ActRIIB single chain ligand traps [US 2011/0236309 and US2009/0010879]. See FIG. 12. As described herein, single-chain ligand traps do not require fusion to any multimerization domain such as coiled-coil Fc domains to be multivalent. In general, single-chain ligand traps of the present disclosure comprise at least one ALK4 polypeptide domain and one ActRIIB polypeptide domain. The ALK4 and ActRIIB polypeptide domains, generally referred to herein as binding domains (BD), optionally may be joined by a linker region.

For example, in one aspect, the present disclosure provides heteromultimers comprising a polypeptide having the following structure:

(<BD1>-linker1)$_k$-[<BD2>-linker2-{<BD3>-linker3}$_f$]$_n$-(<BD4>)$_m$-(linker4-BD5>$_d$)$_h$ where: n and h are independently greater than or equal to one; d, f, m, and k are independently equal to or greater than zero; BD1, BD2, BD3, BD4, and BD5 are independently ALK4 or ActRIIB polypeptide domains, wherein at least one of BD1, BD2, BD3, and BD4 is an ALK4 polypeptide domain, and wherein at least one of BD1, BD2, BD3, and BD4 is an ActRIIB polypeptide domain, and linker1, linker2, linker3, and linker 4 are independently greater than or equal to zero. In some embodiment, ALK4:ActRIIB single-chain traps comprise at least two different ALK4 polypeptides. In some embodiments, ALK4:ActRIIB single-chain traps comprise at least two different ActRIIB polypeptides. In some embodiment, ALK4:ActRIIB single-chain traps comprise at least two different linkers. Depending on the values of selected for d, f, h, k, m, and n, the heteromultimer structure may comprise a large number of repeating units in various combinations or may be a relatively simple structure.

In another aspect, the present disclosure provides heteromultimers comprising a polypeptide having the following structure:

<BD1>-linker1-<BD2>

In yet another aspect, the present disclosure provides heteromultimers comprising a polypeptide having the following structure:

<BD1>-(linker2-<BD2>)$_n$ where n is greater than or equal one.

Another aspect of the invention provides heteromultimers comprising a polypeptide having the following structure:

(<BD1>-linker1-<BD1>)$_f$-linker2-(<BD2>-linker3-<BD3>)$_g$ wherein f and g are greater than or equal to one.

In an embodiment where BD2 and BD3 are the same, and f and g are the same number, this can result in a substantially mirror symmetric structure around linker 2, subject to differences in the linkers. In instances where BD2 is different from BD3 and/or where f and g are different numbers, different structures will be produced. It is within the capacity of one of ordinary skill in the art to select suitable binding domains, linkers, and repeat frequencies in light of the disclosure herein and knowledge in the art. Specific, non-limiting examples of such single-chain ligand traps in accordance with the present disclosure are represented schematically in FIG. 11.

The linkers (1, 2, 3, and 4) may be the same or different. The linker region provides a segment that is distinct from the structured ligand-binding domains of ALK4 and ActRIIB and thus can be used for conjugation to accessory molecules (e.g., molecules useful in increasing stability such as PEGylation moieties) without having to chemically modify the binding domains. The linker may include an unstructured amino acid sequence that may be either the same as or derived from conservative modifications to the sequence of a natural unstructured region in the extracellular portion of the receptor for the ligand of interest or another receptor in the TGF-β superfamily. In other instances, such linkers may be entirely artificial in composition and origin but will contain amino acids selected to provide an unstructured flexible linker with a low likelihood of encountering electrostatic or steric hindrance complications when brought into close proximity to the ligand of interest. Linker length will be considered acceptable when it permits binding domains located on each of the N- and C-termini of the linker to bind their natural binding sites on their natural ligand such that, with both binding domains so bound, the ligand is bound with a higher affinity than it would be bound by binding of only one of the binding domains. In some instances, the number of amino acid residues in the linker of either natural or artificial origin is selected to be equal to or greater than the minimum required distance for simultaneous (bridged) binding to two binding sites on the ALK4 and/or ActRIIB ligand. For example, and without wishing to be limiting in any manner, the linker length may be between 1-10 amino acids, 10-20 amino acids, about 18-80 amino acids, 25-60 amino acids, 35-45 amino acids, or any other suitable length.

Linkers may be designed to facilitate purification of the polypeptide. The exact purification scheme chosen will determine what modifications are needed, for example and without wishing to be limiting, additions of purification "tags" such as His tags is contemplated; in other examples, the linker may include regions to facilitate the addition of cargo or accessory molecules. When such additions affect the unstructured nature of the linker or introduce potential electrostatic or steric concerns, appropriate increases to the linker length will be made to ensure that the two binding domains are able to bind their respective sites on the ligand. In light of the methods and teachings herein, such determinations could be made routinely by one skilled in the art.

In addition, the present design permits linkage of other cargo molecules (for example imaging agents like fluorescent molecules), toxins, etc. For example, and without wishing to be limiting in any manner, single-chain polypeptides can be modified to add one or more cargo and/or accessory molecules (referred to collectively herein by R1, R2, R3, R4, etc.):

$$R1-(<BD1>\text{-linker1})_k-[<BD2>\text{-linker2-}\{<BD3>\text{-linker3}\}_j]_n-(<BD4>)_m-(\text{linker4-}BD5>_d)_h-R2$$

with R3, R4, R5, R6, R7, R8, R9 as substituents.

Without limiting the generality of R substituents available, R1, R2, R3, R4, R5, R6, R7, R8, R9, may or may not be present; when present, they may be the same or different, and may independently be one or more of: a fusion protein for targeting, for example, but not limited to such as an antibody fragment (e.g. single chain Fv) and/or a single domain antibody (sdAb); a radiotherapy and/or imaging agent, for example, but not limited to a radionuceotide (e.g. $^{123}$I, $^{111}$In, $^{18}$F, $^{64}$C, $^{68}$Y, $^{124}$I, $^{131}$I, $^{90}$Y, $^{177}$Lu, $^{57}$Cu, $^{213}$Bi, $^{211}$At), a fluorescent dye (e.g. Alexa Fluor, Cy dye) and/or a fluorescent protein tag (e.g. GFP, DsRed); a cytotoxic agent for chemotherapy, for example, but not limited to doxorubicin, calicheamicin, a maytansinoid derivatives (e.g. DM1, DM4), a toxin (eg. truncated *Pseudomonas* endotoxin A, diphteria toxin); a nanoparticle-based carrier, for example, but not limited to polyethylene glycol (PEG), a polymer-conjugated to drug, nanocarrier or imaging agent (e.g. of a polymer N-(2-hydorxylpropyl) methacrylamide (HPMA), glutamic acid, PEG, dextran); a drug (for example, but not limited to doxorubicin, camptothecin, paclitaxel, palatinate); a nanocarrier, for example, but not limited to a nanoshell or liposome; an imaging agent, for example, but not limited to Supermagnetic Iron Oxide (SPIO); a dendrimer; and/or a solid support for use in ligand purification, concentration or sequestration (e.g. nanoparticles, inert resins, suitable silica supports).

In general, it will not be preferable to have cargo or accessory molecules in all possible positions, as this may cause steric or electrostatic complications. However, the effects of adding a cargo or accessory molecule to any given position or positions on the structure can be determined routinely in light of the disclosure herein by modeling the linker between the binding domains and carrying out molecular dynamics simulations to substantially minimize molecular mechanics energy and reduce steric and electrostatic incompatibility between the linker and the ALK4 and ActRIIB polypeptides as taught herein.

It may be preferable to add the cargo or accessory molecule to the linker portion of the agent, rather to the binding domain, to reduce the likelihood of interference in binding function. However, addition to the binding domain is possible and could be desirable in some instances and the effect of such an addition can be determined routinely in advance by modeling the binding agent and the linker with the proposed addition as described herein.

Conjugation methodologies can be performed using commercial kits that enable conjugation via common reactive groups such as primary amines, succinimidyl (NHS) esters and sulfhydral-reactive groups. Some non-limiting examples are: Alexa Fluor 488 protein labeling kit (Molecular Probes, Invitrogen detection technologies) and PEGylation kits (Pierce Biotechnology Inc.).

In certain aspects, ALK4:ActRIIB single-chain traps may be covalently or non-covalently associated with one or more ALK4 or ActRIIB polypeptides as well as additional ALK4: ActRIIB single chain ligand traps to form higher order heteromultimers, which may be used in accordance with the methods described herein. See, e.g., FIG. 12. For example, an ALK4:ActRIIB single chain ligand trap may further comprise a multimerization domain as described herein. In some embodiments, ALK4:ActRIIB single chain ligand traps comprise a constant domain of an Ig immunoglobulin. Such immunoglobulins constant domains may be selected to promote symmetrical or asymmetrical complexes comprising at least one single-chain ALK4:ActRIIB trap.

In certain aspects, an ALK4:ActRIIB single-chain trap, or combinations of such traps, may be used as ALK4:ActRIIB antagonists to treat or prevent an ALK4:ActRIIB disorder or disease as described herein.

It is understood that different elements of the fusion proteins (e.g., immunoglobulin Fc fusion proteins) may be arranged in any manner that is consistent with desired functionality. For example, an ALK4 and/or ActRIIB polypeptide domain may be placed C-terminal to a heterologous domain, or alternatively, a heterologous domain may be placed C-terminal to an ALK4 and/or ActRIIB polypeptide domain. The ALK4 and/or ActRIIB polypeptide domain and the heterologous domain need not be adjacent in a fusion protein, and additional domains or amino acid sequences may be included C- or N-terminal to either domain or between the domains.

For example, an ALK4 and/or ActRIIB receptor fusion protein may comprise an amino acid sequence as set forth in the formula A-B-C. The B portion corresponds to an ALK4 or ActRIIB polypeptide domain. The A and C portions may be independently zero, one, or more than one amino acid, and both the A and C portions when present are heterologous to B. The A and/or C portions may be attached to the B portion via a linker sequence. A linker may be rich in glycine (e.g., 2-10, 2-5, 2-4, 2-3 glycine residues) or glycine and proline residues and may, for example, contain a single sequence of threonine/serine and glycines or repeating sequences of threonine/serine and/or glycines, e.g., GGG (SEQ ID NO: 13), GGGG (SEQ ID NO: 14), TGGGG(SEQ ID NO: 15), SGGGG(SEQ ID NO: 16), TGGG(SEQ ID NO: 17), SGGG(SEQ ID NO: 18), or GGGGS (SEQ ID NO: 58) singlets, or repeats. In certain embodiments, an ALK4 and/or ActRIIB fusion protein comprises an amino acid sequence as set forth in the formula A-B-C, wherein A is a leader (signal) sequence, B consists of an ALK4 and/or ActRIIB polypeptide domain, and C is a polypeptide portion that enhances one or more of in vivo stability, in vivo half-life, uptake/administration, tissue localization or distribution, formation of protein complexes, and/or purification. In certain embodiments, an ALK4 and/or ActRIIB fusion protein comprises an amino acid sequence as set forth in the formula A-B-C, wherein A is a TPA leader sequence, B consists of a ALK4 or ActRIIB receptor polypeptide domain, and C is an immunoglobulin Fc domain. Preferred fusion proteins comprise the amino acid sequence set forth in any one of SEQ ID NOs: 39, 41, 42, 44, 45, 46, 47, and 48.

In some embodiments, ALK4:ActRIIB heteromultimers further comprise one or more heterologous portions (domains) so as to confer a desired property. For example, some fusion domains are particularly useful for isolation of the fusion proteins by affinity chromatography. Well-known examples of such fusion domains include, but are not limited to, polyhistidine, Glu-Glu, glutathione S-transferase (GST), thioredoxin, protein A, protein G, an immunoglobulin heavy-chain constant region (Fc), maltose binding protein (MBP), or human serum albumin. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) fusion partners ("HIS$_6$" disclosed as SEQ ID NO: 96). As another example, a fusion domain may be selected so as to facilitate detection of the ligand trap polypeptides. Examples of such detection domains include the various fluorescent proteins (e.g., GFP) as well as "epitope tags," which are usually short peptide sequences for which a specific antibody is available. Well-known epitope tags for which specific monoclonal antibodies are readily available include FLAG, influenza virus haemagglutinin (HA), and c-myc tags. In some cases, the fusion domains have a protease cleavage site, such as for factor Xa or thrombin, which allows the relevant protease to partially digest the fusion proteins and thereby liberate the recombinant proteins therefrom. The liberated proteins can then be isolated from the fusion domain by subsequent chromatographic separation.

In certain embodiments, ALK4 and/or ActRIIB polypeptides may contain one or more modifications that are capable of stabilizing the polypeptides. For example, such modifications enhance the in vitro half-life of the polypeptides, enhance circulatory half-life of the polypeptides, and/or reduce proteolytic degradation of the polypeptides. Such stabilizing modifications include, but are not limited to, fusion proteins (including, for example, fusion proteins comprising an ALK4 and/or ActRIIB polypeptide domain and a stabilizer domain), modifications of a glycosylation site (including, for example, addition of a glycosylation site to a polypeptide of the disclosure), and modifications of carbohydrate moiety (including, for example, removal of carbohydrate moieties from a polypeptide of the disclosure). As used herein, the term "stabilizer domain" not only refers to a fusion domain (e.g., an immunoglobulin Fc domain) as in the case of fusion proteins, but also includes nonproteinaceous modifications such as a carbohydrate moiety, or nonproteinaceous moiety, such as polyethylene glycol.

In preferred embodiments, ALK4:ActRIIB heteromultimers to be used in accordance with the methods described herein are isolated complexes. As used herein, an isolated protein (or protein complex) or polypeptide (or polypeptide complex) is one which has been separated from a component of its natural environment. In some embodiments, a heteromultimer of the disclosure is purified to greater than 95%, 96%, 97%, 98%, or 99% purity as determined by, for example, electrophoretic (e.g., SDS-PAGE, isoelectric focusing (IEF), capillary electrophoresis) or chromatographic (e.g., ion exchange or reverse phase HPLC). Methods for assessment of antibody purity are well known in the art [Flatman et al., (2007) J. Chromatogr. B 848:79-87]. In some embodiments, ALK4:ActRIIB heteromultimer preparations are substantially free of ALK4 and/or ActRIIB homomultimers. For example, in some embodiments, ALK4:ActRIIB heteromultimer preparations comprise less than about 10%, 9%, 8%, 7%, 6%, 5%, 4%, 3%, 2%, or less than 1% ALK4 homomultimers. In some embodiments, ALK4:ActRIIB heteromultimer preparations comprise less than about 10%, 9%, 8%, 7%, 6%, 5%, 4%, 3%, 2%, or less than 1% ActRIIB homomultimers. In some embodiments, ALK4:ActRIIB heteromultimer preparations comprise less than about 10%, 9%, 8%, 7%, 6%, 5%, 4%, 3%, 2%, or less than 1% ALK4 homomultimers and less than about 10%, 9%, 8%, 7%, 6%, 5%, 4%, 3%, 2%, or less than 1% ActRIIB homomultimers.

In certain embodiments, ALK4 and/or ActRIIB polypeptides, as well as heteromultimers comprising the same, of the disclosure can be produced by a variety of art-known techniques. For example, polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (Advanced ChemTech Model 396; Milligen/Biosearch 9600). Alternatively, the polypeptides, including fragments or variants thereof, may be recombinantly produced using various expression systems [E. coli, Chinese Hamster Ovary (CHO) cells, COS cells, baculovirus] as is well known in the art. In a further embodiment, the modified or unmodified polypeptides may be produced by digestion of recombinantly produced full-length ALK4 and/or ActRIIB polypeptides by using, for example, a protease, e.g., trypsin, thermolysin, chymotrypsin, pepsin, or paired basic amino acid converting enzyme (PACE). Computer analysis (using commercially available software, e.g., MacVector, Omega, PCGene, Molecular Simulation, Inc.) can be used to identify proteolytic cleavage sites.

B. Nucleic Acids Encoding ALK4 and/or ActRIIB Polypeptides

In certain embodiments, the present disclosure provides isolated and/or recombinant nucleic acids encoding ALK4 and/or ActRIIB receptors (including fragments, functional variants, and fusion proteins thereof) disclosed herein. For example, SEQ ID NO: 11 encodes a naturally occurring human ALK4 precursor polypeptide, while SEQ ID NO: 12 encodes the mature extracellular domain of ALK4. The subject nucleic acids may be single-stranded or double stranded. Such nucleic acids may be DNA or RNA molecules. These nucleic acids may be used, for example, in methods for making ALK4:ActRIIB heteromultimers as described herein.

As used herein, isolated nucleic acid(s) refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

In certain embodiments, nucleic acids encoding ALK4 and/or ActRIIB polypeptides of the present disclosure are understood to include any one of SEQ ID NOs: 7, 8, 11, 12, 21, 22, 40, or 43, as well as variants thereof. Variant nucleotide sequences include sequences that differ by one or more nucleotide substitutions, additions, or deletions including allelic variants, and therefore, will include coding sequences that differ from the nucleotide sequence designated in any one of SEQ ID NOs: 7, 8, 11, 12, 21, 22, 40, 43.

In certain embodiments, TGFβ superfamily ALK4 and/or ActRIIB polypeptides of the present disclosure are encoded by isolated or recombinant nucleic acid sequences that comprise, consist essentially of, or consists of a sequence that is least 70%, 75%, 80%, 85%, 86%, 87%, 88%, 89%, 90%, 91%, 92%, 93%, 94%, 95%, 96%, 97%, 98%, 99% or 100% identical to SEQ ID NOs: 7, 8, 11, 12, 21, 22, 40, or 43. One of ordinary skill in the art will appreciate that nucleic acid sequences that comprise, consist essentially of, or consists of a sequence complementary to a sequence that is least 70%, 75%, 80%, 85%, 86%, 87%, 88%, 89%, 90%, 91%, 92%, 93%, 94%, 95%, 96%, 97%, 98%, 99% or 100% identical to SEQ ID NOs: 7, 8, 11, 12, 21, 22, 40, or 43 also within the scope of the present disclosure. In further embodiments, the nucleic acid sequences of the disclosure can be isolated, recombinant, and/or fused with a heterologous nucleotide sequence or in a DNA library.

In other embodiments, nucleic acids of the present disclosure also include nucleotide sequences that hybridize under stringent conditions to the nucleotide sequence designated in SEQ ID NOs: 7, 8, 11, 12, 21, 22, 40, or 43, the complement sequence of SEQ ID NOs: 7, 8, 11, 12, 21, 22, 40, or 43, or fragments thereof. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 7, 8, 11, 12, 21, 22, 40, or 43 to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and will vary with the host cell used.

In certain aspects, the subject nucleic acid is provided in an expression vector comprising a nucleotide sequence encoding an ALK4 and/or ActRIIB polypeptide and operably linked to at least one regulatory sequence. Regulatory sequences are art-recognized and are selected to direct expression of ALK4 and/or ActRIIB polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a ALK4 and/or ActRIIB polypeptides. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant ALK4 and/or ActRIIB polypeptides include plasmids and other vectors. For instance, suitable vectors include plasmids of the following types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures [Molecular Cloning A Laboratory Manual, 3rd Ed., ed. by Sambrook, Fritsch and Maniatis Cold Spring Harbor Laboratory Press, 2001]. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ALK4 and/or ActRIIB polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ALK4 and/or ActRIIB polypeptide in cells propagated in culture, e.g., to produce proteins, including fusion proteins or variant proteins, for purification.

This disclosure also pertains to a host cell transfected with a recombinant gene including a coding sequence for one or more of the subject ALK4 and/or ActRIIB polypeptides. The host cell may be any prokaryotic or eukaryotic cell. For example, an ALK4 and/or ActRIIB polypeptide may be expressed in bacterial cells such as E. coli, insect cells (e.g., using a baculovirus expression system), yeast, or mammalian cells [e.g. a Chinese hamster ovary (CHO) cell line]. Other suitable host cells are known to those skilled in the art.

Accordingly, the present disclosure further pertains to methods of producing the subject ALK4 and/or ActRIIB polypeptides. For example, a host cell transfected with an expression vector encoding an ALK4 and/or ActRIIB polypeptide can be cultured under appropriate conditions to allow expression of the ALK4 and/or ActRIIB polypeptide to occur. The polypeptide may be secreted and isolated from a mixture of cells and medium containing the polypeptide. Alternatively, ALK4 and/or ActRIIB polypeptide may be isolated from a cytoplasmic or membrane fraction obtained from harvested and lysed cells. A cell culture includes host cells, media and other byproducts. Suitable media for cell culture are well known in the art. The subject polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of ALK4 and/or ActRIIB polypeptides and affinity purification with an agent that binds to a domain fused to ALK4 and/or ActRIIB polypeptide (e.g., a protein A column may be used to purify ALK4-Fc and/or ActRIIB-Fc fusion proteins). In some embodiments, the ALK4 and/or ActRIIB polypeptide is a fusion protein containing a domain which facilitates its purification.

In some embodiments, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. An ALK4 and/or ActRIIB polypeptides, as well as fusion proteins thereof, may be purified to a purity of >90%, >95%, >96%, >98%, or >99% as determined by size exclusion chromatography and >90%, >95%, >96%, >98%, or >99% as determined by SDS PAGE. The target level of purity should be one that is sufficient to achieve desirable results in mammalian systems, particularly non-human primates, rodents (mice), and humans.

In another embodiment, a fusion gene coding for a purification leader sequence, such as a poly-(His)/enterokinase cleavage site sequence at the N-terminus of the desired portion of the recombinant ALK4 and/or ActRIIB polypeptide, can allow purification of the expressed fusion protein by affinity chromatography using a $Ni^{2+}$ metal resin. The purification leader sequence can then be subsequently removed by treatment with enterokinase to provide the purified ALK4 and/or ActRIIB polypeptide, as well as heteromultimers thereof [Hochuli et al. (1987) J. Chromatography 411:177; and Janknecht et al. (1991) PNAS USA 88:8972].

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence. See, e.g., Current Protocols in Molecular Biology, eds. Ausubel et al., John Wiley & Sons: 1992.

C. Antibody Antagonists

In certain aspects, an ALK4:ActRIIB antagonist is an antibody (ALK4:ActRIIB antagonist antibody), or combination of antibodies. An ALK4:ActRIIB antagonist antibody, or combination of antibodies, may bind to, for example, one or more ALK4 ligands, ActRIIB ligands, ALK4:ActRIIB-binding ligands, an ALK4 receptor, an ActRIIB receptor, and/or one or more TGF-beta superfamily co-receptors. As described herein, ALK4:ActRIIB antagonist antibodies may be used alone, or in combination with one or more supportive therapies or active agents, to treat a in need thereof (e.g., a subject with a bone-related disease or condition, a muscle related disease or condition, or a disease or condition associated with excess or unwanted fat)

In certain aspects, an ALK4:ActRIIB antagonist antibody, or combination of antibodies, is an antibody that inhibits one or more of the ligands bound or likely bound by an ALK4:ActRIIB heteromultimer, such as activin B, GDF11, activin A, GDF8, BMP10, BMP6, and GDF3. Therefore, in some embodiments, an ALK4:ActRIIB antagonist antibody, or combination of antibodies, binds to at least one of such ligands. As an example, as used herein, an activin B antibody (or anti-activin B antibody) generally refers to an antibody that can bind to activin B with sufficient affinity such that the antibody is useful as a diagnostic and/or therapeutic agent in targeting activin B. In certain embodiments, the extent of binding of a activin B antibody to an unrelated, non-activin B protein is less than about 10%, 9%, 8%, 7%, 6%, 5%, 4%, 3%, 2%, or less than about 1% of the binding of the antibody to activin B as measured, for example, by a radioimmunoassay (RIA), Biacore, or other protein interaction or binding affinity assay. In certain embodiments, an activin B antibody binds to an epitope of activin B that is conserved among activin B from different species. In certain preferred embodiments, an anti-activin B antibody binds to human activin B. In some embodiments, an activin B antibody may inhibit activin B from binding to a type I and/or type II receptor (e.g., ActRIIB and/or ALK4) and thus inhibit activin B-mediated signaling (e.g., Smad signaling). In some embodiments, an activin B antibody may inhibit activin B from binding to a co-receptor and thus inhibit activin B-mediated signaling (e.g., Smad signaling). It should be noted that activin B shares some sequence homology to activin A, C and E and therefore antibodies that bind to activin B, in some instances, may also bind to and/or inhibit another activin. In some embodiments, the disclosure relates to a multispecific antibody (e.g., bi-specific antibody), and uses thereof, that binds to, for example, activin B and further binds to, for example, one or more additional TGF-β superfamily ligands that bind to ALK4:ActRIIB heteromultimer [e.g., activin (e.g., activin A, activin AB, and activin B), GDF11, GDF8, BMP10, BMP6, and GDF3], one or more type I receptor and/or type II receptors (e.g., ActRIIB and/or ALK4), and/or one or more co-receptors. In some embodiments, a multispecific antibody that binds to activin B does not bind or does not substantially bind to BMP9 (e.g., binds to BMP9 with a $K_D$ of greater than $1 \times 10^{-7}$ M or has relatively modest binding, e.g., about $1 \times 10^{-8}$ M or about $1 \times 10^{-9}$ M). In some embodiments, the disclosure relates to combinations of antibodies, and uses thereof, wherein the combination of antibodies comprises a combination of antibodies that bind to, for example, two or more TGF-β superfamily ligand that bind to ALK4:ActRIIB heteromultimer [e.g., activin (e.g., activin A, activin B, and activin AB), GDF11, GDF8, BMP10, BMP6, and GDF] one or more type I receptor and/or type II receptors (e.g., ActRIIB and/or ALK4), and/or one or more co-receptors. In some embodiments, a combination of antibodies does not comprise a BMP9 antibody.

In certain aspects, an ALK4:ActRIIB antagonist antibody, or combination of antibodies, is an antibody that inhibits at least GDF8. Therefore, in some embodiments, an ALK4:ActRIIB antagonist antibody, or combination of antibodies, binds to at least GDF8. As used herein, a GDF8 antibody (or anti-GDF8 antibody) generally refers to an antibody that binds to GDF8 with sufficient affinity such that the antibody is useful as a diagnostic and/or therapeutic agent in targeting GDF8. In certain embodiments, the extent of binding of a GDF8 antibody to an unrelated, non-GDF8 protein is less than about 10%, 9%, 8%, 7%, 6%, 5%, 4%, 3%, 2%, or less than about 1% of the binding of the antibody to GDF8 as measured, for example, by a radioimmunoassay (RIA), Biacore, or other protein interaction or binding affinity assay. In certain embodiments, a GDF8 antibody binds to an epitope of GDF8 that is conserved among GDF8 from different species. In certain preferred embodiments, an anti-GDF8 antibody binds to human GDF8. In some embodiments, a GDF8 antibody may inhibit GDF8 from binding to a type I and/or type II receptor (e.g., ActRIIB and/or ALK4) and thus inhibit GDF8-mediated signaling (e.g., Smad signaling). In some embodiments, a GDF8 antibody may inhibit GDF8 from binding to a co-receptor and thus inhibit GDF8-mediated signaling (e.g., Smad signaling). It should be noted that GDF8 has high sequence homology to GDF11 and therefore antibodies that bind to GDF8, in some instances, may also bind to and/or inhibit GDF11. In some embodiments, the disclosure relates to a multispecific antibody (e.g., bi-specific antibody), and uses thereof, that binds to GDF8 and further binds to, for example, one or more additional TGF-β superfamily ligands that bind to ALK4:ActRIIB heteromultimer [e.g., activin (e.g., activin A, activin B, and activin AB), GDF11, BMP10, BMP6, and GDF3], one or more type I receptor and/or type II receptors (e.g., ActRIIB and/or ALK4), and/or one or more co-receptors. In some embodiments, a multispecific antibody that binds to GDF8 does not bind or does not substantially bind to BMP9 (e.g., binds to BMP9 with a $K_D$ of greater than $1 \times 10^{-7}$M or has relatively modest binding, e.g., about $1 \times 10^{-8}$M or about $1 \times 10^{-9}$M). In some embodiments, the disclosure relates to combinations of antibodies, and uses thereof, wherein the combination of antibodies comprises a GDF8 antibody and one or more additional antibodies that bind to, for example, one or more additional TGF-β superfamily ligands that bind to ALK4:ActRIIB heteromultimer [e.g., activin (e.g., activin A, activin B, and activin AB), GDF11, GDF3, BMP6, and BMP10], one or more type I receptor and/or type II receptors (e.g., ActRIIB and/or ALK4), and/or one or more co-receptors. In some embodiments, a combination of antibodies that comprises a GDF8 antibody does not comprise a BMP9 antibody.

In certain aspects, an ALK4:ActRIIB antagonist antibody, or combination of antibodies, is an antibody that inhibits at least GDF11. Therefore, in some embodiments, an ALK4:ActRIIB antagonist antibody, or combination of antibodies, binds to at least GDF11. As used herein, a GDF11 antibody (or anti-GDF11 antibody) generally refers to an antibody that binds to GDF11 with sufficient affinity such that the antibody is useful as a diagnostic and/or therapeutic agent in targeting GDF11. In certain embodiments, the extent of binding of a GDF11 antibody to an unrelated, non-GDF11 protein is less than about 10%, 9%, 8%, 7%, 6%, 5%, 4%, 3%, 2%, or less than about 1% of the binding of the antibody to GDF11 as measured, for example, by a radioimmunoassay (RIA), Biacore, or other protein interaction or binding affinity assay. In certain embodiments, a GDF11 antibody binds to an epitope of GDF11 that is conserved among GDF11 from different species. In certain preferred embodiments, an anti-GDF11 antibody binds to human GDF11. In some embodiments, a GDF11 antibody may inhibit GDF11 from binding to a type I and/or type II receptor (e.g., ActRIIB and/or ALK4) and thus inhibit GDF11-mediated signaling (e.g., Smad signaling). In some embodiments, a GDF11 antibody may inhibit GDF11 from binding to a co-receptor and thus inhibit GDF11-mediated signaling (e.g., Smad signaling). It should be noted that GDF11 has high sequence homology to GDF8 and therefore antibodies that bind to GDF11, in some instances, may also bind to and/or inhibit GDF8. In some embodiments, the disclosure relates to a multispecific antibody (e.g., bi-specific antibody), and uses thereof, that binds to GDF11 and further binds to, for example, one or more additional TGF-β superfamily ligands that bind to ALK4:ActRIIB heteromultimer [e.g., activin (e.g., activin A, activin B, and activin AB), GDF8, BMP10, BMP6, and GDF3], one or more type I receptor and/or type II receptors (e.g., ActRIIB and/or ALK4), and/or one or more co-receptors. In some embodiments, a multispecific antibody that binds to GDF11 does not bind or does not substantially bind to BMP9 (e.g., binds to BMP9 with a $K_D$ of greater than $1\times10^{-7}$M or has relatively modest binding, e.g., about $1\times10^{-8}$M or about $1\times10^{-9}$M). In some embodiments, the disclosure relates to combinations of antibodies, and uses thereof, wherein the combination of antibodies comprises a GDF11 antibody and one or more additional antibodies that bind to, for example, one or more additional TGF-β superfamily ligands that bind to ALK4:ActRIIB heteromultimer [e.g., activin (e.g., activin A, activin B, and activin AB), GDF8, GDF3, BMP6, and BMP10], one or more type I receptor and/or type II receptors (e.g., ActRIIB and/or ALK4), and/or one or more co-receptors. In some embodiments, a combination of antibodies that comprises a GDF11 antibody does not comprise a BMP9 antibody.

In certain aspects, an ALK4:ActRIIB antagonist antibody, or combination of antibodies, is an antibody that inhibits at least GDF3. Therefore, in some embodiments, an ALK4:ActRIIB antagonist antibody, or combination of antibodies, binds to at least GDF3. As used herein, a GDF3 antibody (or anti-GDF3 antibody) generally refers to an antibody that binds to GDF3 with sufficient affinity such that the antibody is useful as a diagnostic and/or therapeutic agent in targeting GDF3. In certain embodiments, the extent of binding of a GDF3 antibody to an unrelated, non-GDF3 protein is less than about 10%, 9%, 8%, 7%, 6%, 5%, 4%, 3%, 2%, or less than about 1% of the binding of the antibody to GDF3 as measured, for example, by a radioimmunoassay (RIA), Biacore, or other protein interaction or binding affinity assay. In certain embodiments, a GDF3 antibody binds to an epitope of GDF3 that is conserved among GDF3 from different species. In certain preferred embodiments, an anti-GDF3 antibody binds to human GDF3. In some embodiments, a GDF3 antibody may inhibit GDF3 from binding to a type I and/or type II receptor (e.g., ActRIIB and/or ALK4) and thus inhibit GDF3-mediated signaling (e.g., Smad signaling). In some embodiments, a GDF3 antibody may inhibit GDF3 from binding to a co-receptor and thus inhibit GDF3-mediated signaling (e.g., Smad signaling). In some embodiments, the disclosure relates to a multispecific antibody (e.g., bi-specific antibody), and uses thereof, that binds to GDF3 and further binds to, for example, one or more additional TGF-β superfamily ligands that bind to ALK4:ActRIIB heteromultimer [e.g., activin (e.g., activin A, activin B, and activin AB), GDF8, BMP10, BMP6, and GDF11], one or more type I receptor and/or type II receptors (e.g., ActRIIB and/or ALK4), and/or one or more co-receptors. In some embodiments, a multispecific antibody that binds to GDF3 does not bind or does not substantially bind to BMP9 (e.g., binds to BMP9 with a $K_D$ of greater than $1\times10^{-7}$M or has relatively modest binding, e.g., about $1\times10^{-8}$ M or about $1\times10^{-9}$ M). In some embodiments, the disclosure relates to combinations of antibodies, and uses thereof, wherein the combination of antibodies comprises a GDF3 antibody and one or more additional antibodies that bind to, for example, one or more additional TGF-β superfamily ligands that bind to ALK4:ActRIIB heteromultimer [e.g., activin (e.g., activin A, activin B, and activin AB), GDF8, GDF11, BMP6, and BMP10], one or more type I receptor and/or type II receptors (e.g., ActRIIB and/or ALK4), and/or one or more co-receptors. In some embodiments, a combination of antibodies that comprises a GDF3 antibody does not comprise a BMP9 antibody.

In certain aspects, an ALK4:ActRIIB antagonist antibody, or combination of antibodies, is an antibody that inhibits at least BMP6. Therefore, in some embodiments, an ALK4:ActRIIB antagonist antibody, or combination of antibodies, binds to at least BMP6. As used herein, a BMP6 antibody (or anti-BMP6 antibody) generally refers to an antibody that binds to BMP6 with sufficient affinity such that the antibody is useful as a diagnostic and/or therapeutic agent in targeting BMP6. In certain embodiments, the extent of binding of a BMP6 antibody to an unrelated, non-BMP6 protein is less than about 10%, 9%, 8%, 7%, 6%, 5%, 4%, 3%, 2%, or less than about 1% of the binding of the antibody to BMP6 as measured, for example, by a radioimmunoassay (RIA), Biacore, or other protein interaction or binding affinity assay. In certain embodiments, a BMP6 antibody binds to an epitope of BMP6 that is conserved among BMP6 from different species. In certain preferred embodiments, an anti-BMP6 antibody binds to human BMP6. In some embodiments, a BMP6 antibody may inhibit BMP6 from binding to a type I and/or type II receptor (e.g., ActRIIB and/or ALK4) and thus inhibit BMP6-mediated signaling (e.g., Smad signaling). In some embodiments, a BMP6 antibody may inhibit BMP6 from binding to a co-receptor and thus inhibit BMP6-mediated signaling (e.g., Smad signaling). In some embodiments, the disclosure relates to a multispecific antibody (e.g., bi-specific antibody), and uses thereof, that binds to BMP6 and further binds to, for example, one or more additional TGF-β superfamily ligands that bind to ALK4:ActRIIB heteromultimer [e.g., activin (e.g., activin A, activin B, and activin AB), GDF8, BMP10, GDF3, and GDF11], one or more type I receptor and/or type II receptors (e.g., ActRIIB and/or ALK4), and/or one or more co-receptors. In some embodiments, a multispecific antibody that binds to BMP6 does not bind or does not substantially bind to BMP9 (e.g., binds to BMP9 with a $K_D$ of greater than $1\times10^{-7}$M or has relatively modest binding, e.g., about $1\times10^{-8}$ M or about $1\times10^{-9}$ M). In some embodiments, the disclosure relates to combinations of antibodies, and uses thereof, wherein the combination of antibodies comprises a BMP6 antibody and one or more additional antibodies that bind to, for example, one or more additional TGF-β superfamily ligands that bind to ALK4:ActRIIB heteromultimer [e.g., activin (e.g., activin A, activin B, and activin AB), GDF8, GDF11, GDF3, and BMP10], one or more type I receptor and/or type II receptors (e.g., ActRIIB and/or ALK4), and/or one or more co-receptors. In some embodiments, a combination of antibodies that comprises a BMP6 antibody does not comprise a BMP9 antibody.

In certain aspects, an ALK4:ActRIIB antagonist antibody, or combination of antibodies, is an antibody that inhibits at least BMP10. Therefore, in some embodiments, an ALK4:ActRIIB antagonist antibody, or combination of antibodies, binds to at least BMP10. As used herein, a BMP10 antibody (or anti-BMP10 antibody) generally refers to an antibody that binds to BMP10 with sufficient affinity such that the antibody is useful as a diagnostic and/or therapeutic agent in targeting BMP10. In certain embodiments, the extent of binding of a BMP10 antibody to an unrelated, non-BMP10 protein is less than about 10%, 9%, 8%, 7%, 6%, 5%, 4%, 3%, 2%, or less than about 1% of the binding of the antibody to BMP10 as measured, for example, by a radioimmunoassay (RIA), Biacore, or other protein interaction or binding affinity assay. In certain embodiments, a BMP10 antibody binds to an epitope of BMP10 that is conserved among BMP10 from different species. In certain preferred embodiments, an anti-BMP10 antibody binds to human BMP10. In some embodiments, a BMP10 antibody may inhibit BMP10 from binding to a type I and/or type II receptor (e.g., ActRIIB and/or ALK4) and thus inhibit BMP10-mediated signaling (e.g., Smad signaling). In some embodiments, a BMP10 antibody may inhibit BMP10 from binding to a co-receptor and thus inhibit BMP10-mediated signaling (e.g., Smad signaling). In some embodiments, the disclosure relates to a multispecific antibody (e.g., bi-specific antibody), and uses thereof, that binds to BMP10 and further binds to, for example, one or more additional TGF-β superfamily ligands that bind to ALK4:ActRIIB heteromultimer [e.g., activin (e.g., activin A, activin B, and activin AB), GDF8, BMP6, GDF3, and GDF11], one or more type I receptor and/or type II receptors (e.g., ActRIIB and/or ALK4), and/or one or more co-receptors. In some embodiments, a multispecific antibody that binds to BMP10 does not bind or does not substantially bind to BMP9 (e.g., binds to BMP9 with a $K_D$ of greater than $1 \times 10^{-7}$ M or has relatively modest binding, e.g., about $1 \times 10^{-8}$ M or about $1 \times 10^{-9}$ M). In some embodiments, the disclosure relates to combinations of antibodies, and uses thereof, wherein the combination of antibodies comprises a BMP10 antibody and one or more additional antibodies that bind to, for example, one or more additional TGF-β superfamily ligands that bind to ALK4:ActRIIB heteromultimer [e.g., activin (e.g., activin A, activin B, and activin AB), GDF8, GDF11, GDF3, and BMP6], one or more type I receptor and/or type II receptors (e.g., ActRIIB and/or ALK4), and/or one or more co-receptors. In some embodiments, a combination of antibodies that comprises a BMP10 antibody does not comprise a BMP9 antibody.

In certain aspects, an ALK4:ActRIIB antagonist antibody, or combination of antibodies, is an antibody that inhibits at least activin (activin A, activin B, activin C, activin E, activin AB, activin AC, activin AE, activin BC and/or activin BE). Therefore, in some embodiments, an ALK4:ActRIIB antagonist antibody, or combination of antibodies, binds to at least activin (activin A, activin B, activin C, activin E, activin AB, activin AC, activin AE, activin BC and/or activin BE). As used herein, an activin antibody (or anti-activin antibody) generally refers to an antibody that can bind to a form of activin with sufficient affinity such that the antibody is useful as a diagnostic and/or therapeutic agent in targeting that form of activin. In certain embodiments, the extent of binding of an activin antibody to an unrelated, non-activin protein is less than about 10%, 9%, 8%, 7%, 6%, 5%, 4%, 3%, 2%, or less than about 1% of the binding of the antibody to activin as measured, for example, by a radioimmunoassay (RIA), Biacore, or other protein interaction or binding affinity assay. In certain embodiments, an activin antibody binds to an epitope of activin that is conserved among activin from different species. In certain preferred embodiments, an anti-activin antibody binds to human activin. In other preferred embodiments, a activin antibody may inhibit activin from binding to a type I and/or type II receptor (e.g., ActRIIB and/or ALK4) and thus inhibit activin-mediated signaling (e.g., Smad signaling). In some embodiments, an activin antibody binds to activin B. In some embodiments, an activin antibody binds to activin A. In some embodiments, an activin antibody binds to activin A and activin B. In some embodiments, an activin antibody binds to activin AB. In some embodiments, an activin antibody binds to activin C. In some embodiments, an activin antibody binds to activin E. In some embodiments, an activin antibody binds to activin A and activin C. In some embodiments, an activin antibody binds to activin AC. In some embodiments, an activin antibody binds to activin A and activin E. In some embodiments, an activin antibody binds to activin AE. In some embodiments, an activin antibody binds to activin B and activin C. In some embodiments, an activin antibody binds to activin BC. In some embodiments, an activin antibody binds to activin B and activin E. In some embodiments, an activin antibody binds to activin BE. In some embodiments, an activin antibody binds to activin A, activin B, and activin C. In some embodiments, an activin antibody binds to activin A, activin B, and activin E. Optionally, an activin antibody that binds to one or more of activin A, activin B, and activin C may further bind to activin E. In some embodiments, the disclosure relates to a multispecific antibody (e.g., bi-specific antibody), and uses thereof, that binds to activin and further binds to, for example, one or more additional TGF-β superfamily ligands that bind to an ALK4:ActRIIB heteromultimer [e.g., GDF11, GDF8, BMP10, BMP6, and GDF3], one or more type I receptor and/or type II receptors (e.g., ActRIIB and/or ALK4), and/or one or more co-receptors. In some embodiments, a multispecific antibody that binds to activin does not bind or does not substantially bind to BMP9 (e.g., binds to BMP9 with a $K_D$ of greater than $1 \times 10^{-7}$ M or has relatively modest binding, e.g., about $1 \times 10^{-8}$ M or about $1 \times 10^{-9}$ M. In some embodiments, the disclosure relates to combinations of antibodies, and uses thereof, wherein the combination of antibodies comprises an activin antibody and one or more additional antibodies that bind to, for example, one or more additional TGF-β superfamily ligand that bind to an ALK4:ActRIIB heteromultimer [e.g., GDF11, GDF8 GDF3, BMP6, and BMP10], one or more type I receptor and/or type II receptors (e.g., ActRIIB and/or ALK4), and/or one or more co-receptors. In some embodiments, a combination of antibodies that comprises an activin antibody does not comprise a BMP9 antibody.

With respect to antibodies that bind to and antagonize ligands that bind to ALK4:ActRIIB, [e.g., activin (e.g., activin A, activin B, and activin AB), GDF8, GDF3, BMP6, GDF11, and BMP10], it is contemplated that an antibody may be designed as a bispecific antibody comprising a first portion that binds to an epitope of such ligand, such that the first portion of the antibody competes for binding with a type I receptor and comprising a second portion that binds to an epitope of such ligand, such that the second portion of the antibody competes for binding with a type II receptor. In this manner, a bispecific antibody targeting a single ligand can be designed to mimic the dual type I-type II receptor binding blockade that may be conferred by an ALK4:ActRIIB heteromultimer. Similarly it is contemplated that the same effect could be achieved using a combination of two or more antibodies wherein at least a first antibody binds to an epitope of such ligand, such that the first antibody competes for binding with a type I receptor and at least a second antibody binds to an epitope of such ligand, such that the second antibody competes for binding with a type II receptor.

In certain aspects, an ALK4:ActRIIB antagonist antibody, or combination of antibodies, is an antibody that inhibits at least ActRIIB Therefore, in some embodiments, an ALK4:ActRIIB antagonist antibody, or combination of antibodies, binds to at least ActRIIB As used herein, an ActRIIB antibody (anti-ActRIIB antibody) generally refers to an antibody that binds to ActRIIB with sufficient affinity such that the antibody is useful as a diagnostic and/or therapeutic agent in targeting ActRIIB In certain embodiments, the extent of binding of an anti-ActRIIB antibody to an unrelated, non-ActRIIB protein is less than about 10%, 9%, 8%, 7%, 6%, 5%, 4%, 3%, 2%, or less than about 1% of the binding of the antibody to ActRIIB as measured, for example, by a radioimmunoassay (RIA), Biacore, or other protein-protein interaction or binding affinity assay. In certain embodiments, an anti-ActRIIB antibody binds to an epitope of ActRIIB that is conserved among ActRIIB from different species. In certain preferred embodiments, an anti-ActRIIB antibody binds to human ActRIIB In some embodiments, an anti-ActRIIB antibody may inhibit one or more TGF-β superfamily ligands that bind to ALK4:ActRIIB heteromultimers [e.g., GDF8, activin (e.g., activin A, activin B, and activin AB) GDF3, BMP6, and BMP10] from binding to ActRIIB and/or ALK4. In some embodiments, an anti-ActRIIB antibody is a multispecific antibody (e.g., bi-specific antibody) that binds to ActRIIB and one or more TGF-β superfamily ligands that bind to ALK4:ActRIIB heteromultimers [e.g., GDF11, GDF8, activin (e.g., activin A, activin B, and, activin AB) GDF3, BMP6, and BMP10], type I receptor (e.g., ALK4), co-receptor, and/or an additional type II receptor. In some embodiments, the disclosure relates to combinations of antibodies, and uses thereof, wherein the combination of antibodies comprises an anti-ActRIIB antibody and one or more additional antibodies that bind to, for example, one or more TGF-β superfamily ligands that bind to ALK4:ActRIIB heteromultimers [e.g., GDF11, GDF8, activin (e.g., activin A, activin B, and activin AB) GDF3, BMP6, BMP10, nodal, and BMP9], co-receptors, type I receptors (e.g., ALK4), and/or additional type II receptors. It should be noted that ActRIIB has sequence similarity to ActRIIA and therefore antibodies that bind to ActRIIB, in some instances, may also bind to and/or inhibit ActRIIA.

In certain aspects, an ALK4:ActRIIB antagonist antibody, or combination of antibodies, is an antibody that inhibits at least ALK4. Therefore, in some embodiments, an ALK4:ActRIIB antagonist antibody, or combination of antibodies, binds to at least ALK4. As used herein, an ALK4 antibody (anti-ALK4 antibody) generally refers to an antibody that binds to ALK4 with sufficient affinity such that the antibody is useful as a diagnostic and/or therapeutic agent in targeting ALK4. In certain embodiments, the extent of binding of an anti-ALK4 antibody to an unrelated, non-ALK4 protein is less than about 10%, 9%, 8%, 7%, 6%, 5%, 4%, 3%, 2%, or less than about 1% of the binding of the antibody to ALK4 as measured, for example, by a radioimmunoassay (RIA), Biacore, or other protein-protein interaction or binding affinity assay. In certain embodiments, an anti-ALK4 antibody binds to an epitope of ALK4 that is conserved among ALK4 from different species. In certain preferred embodiments, an anti-ALK4 antibody binds to human ALK4. In some embodiments, an anti-ALK4 antibody may inhibit one or more TGF-β superfamily ligands that bind to ALK4:ActRIIB heteromultimers [e.g., GDF11, GDF8, activin (e.g., activin A, activin B, and activin AB) GDF3, BMP6, and BMP10] from binding to a type I receptor (e.g., ALK4), type II receptor (e.g., ActRIIB), or co-receptor. In some embodiments, an anti-ALK4 antibody is a multispecific antibody (e.g., bi-specific antibody) that binds to ALK4 and one or more TGF-β superfamily ligands that bind to ALK4:ActRIIB heteromultimers [e.g., activin (e.g., activin A, activin B, and activin AB), GDF11, GDF8, BMP10, BMP6, and GDF3], type II receptors (e.g., ActRIIB), co-receptors, and/or an additional type I receptor. In some embodiments, the disclosure relates to combinations of antibodies, and uses thereof, wherein the combination of antibodies comprises an anti-ALK4 antibody and one or more additional antibodies that bind to, for example, one or more TGF-β superfamily ligands that bind to ALK4:ActRIIB heteromultimers [e.g., activin (e.g., activin A, activin B, and activin AB), GDF11, GDF8, BMP10, BMP6, and GDF3], co-receptors, an additional type I receptor, and/or type II receptors (e.g., ActRIIB).

As described herein, there are a variety of methods for generating heteromultimers. Such methods may be used to generate heteromultimers comprising an antibody-binding domain (e.g., a complex of $V_L$ and $V_H$ chains) and one or more polypeptides selected from an ALK4 polypeptide, an ActRIIB polypeptide, an ALK4:ActRIIB heteromer, or an ALK4:ActRIIB single trap polypeptide. See FIGS. 10 and 12D. For example, in some embodiments, the present disclosure provides protein complexes comprising a ligand-binding domain of an antibody that binds to an ALK4:ActRIIB-binding ligand [e.g., activin (e.g., activin A, activin B, and activin AB), GDF11, GDF8, BMP10, BMP6, and GDF3] which is covalently or non-covalently associated with an ALK4 polypeptide. In some embodiments, the disclosure provides protein complexes comprising a ligand-binding domain of an antibody that binds to an ALK4:ActRIIB-binding ligand [e.g., activin (e.g., activin A, activin B, and activin AB), GDF11, GDF8, BMP10, BMP6, and GDF3] which is covalently or non-covalently associated with an ActRIIB polypeptide. In some embodiments, the present disclosure provides protein complexes comprising a ligand-binding domain of an antibody that binds to an ALK4:ActRIIB-binding ligand [e.g., activin (e.g., activin A, activin B, and activin AB), GDF11, GDF8, BMP10, BMP6, and GDF3] which is covalently or non-covalently associated with a ALK4:ActRIIB single-chain ligand trap. In some embodiments, the present disclosure provides protein complexes comprising a ligand-binding domain of an antibody that binds to an ALK4:ActRIIB-binding ligand covalently or non-covalently associated with a ALK4:ActRIIB heteromultimer.

The term antibody is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody fragment refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$_2$; diabodies; linear antibodies; single-chain antibody molecules (e.g., scFv); and multispecific antibodies formed from antibody fragments [see, e.g., Hudson et al. (2003) Nat. Med. 9:129-134; Plückthun, in The Pharmacology of Monoclonal Antibodies, vol. 113, Rosenburg and Moore eds., (Springer-Verlag, New York), pp. 269-315 (1994); WO 93/16185; and U.S. Pat. Nos. 5,571,894; 5,587,458; and 5,869,046]. Diabodies are antibody fragments with two antigen-binding sites that may be bivalent or bispecific [see, e.g., EP 404,097; WO 1993/01161; Hudson et al. (2003) Nat. Med. 9:129-134 (2003); and Hollinger et al. (1993) Proc. Natl. Acad. Sci. USA 90: 6444-6448]. Triabodies and tetrabodies are also described in Hudson et al. (2003) Nat. Med. 9:129-134. Single-domain antibodies are antibody fragments comprising all or a portion of the heavy-chain variable domain or all or a portion of the light-chain variable domain of an antibody. In certain embodiments, a single-domain antibody is a human single-domain antibody [see, e.g., U.S. Pat. No. 6,248,516]. Antibodies disclosed herein may be polyclonal antibodies or monoclonal antibodies. In certain embodiments, the antibodies of the present disclosure comprise a label attached thereto and able to be detected (e.g., the label can be a radioisotope, fluorescent compound, enzyme, or enzyme co-factor). In certain preferred embodiments, the antibodies of the present disclosure are isolated antibodies. In certain preferred embodiments, the antibodies of the present disclosure are recombinant antibodies.

The antibodies herein may be of any class. The class of an antibody refers to the type of constant domain or constant region possessed by its heavy chain. There are five major classes of antibodies: IgA, IgD, IgE, IgG, and IgM, and several of these may be further divided into subclasses (isotypes), for example, IgG$_1$, IgG$_2$, IgG$_3$, IgG$_4$, IgA$_1$, and IgA$_2$. The heavy chain constant domains that correspond to the different classes of immunoglobulins are called alpha, delta, epsilon, gamma, and mu.

In general, an antibody for use in the methods disclosed herein specifically binds to its target antigen, preferably with high binding affinity. Affinity may be expressed as a $K_D$ value and reflects the intrinsic binding affinity (e.g., with minimized avidity effects). Typically, binding affinity is measured in vitro, whether in a cell-free or cell-associated setting. Any of a number of assays known in the art, including those disclosed herein, can be used to obtain binding affinity measurements including, for example, Biacore, radiolabeled antigen-binding assay (RIA), and ELISA. In some embodiments, antibodies of the present disclosure bind to their target antigens (e.g. ALK4, ActRIIB, activin A, activin B, activin AB, GDF11, GDF8, BMP10, BMP6, and GDF3) with at least a $K_D$ of $1\times10^{-7}$ or stronger, $1\times10^{-8}$ or stronger, $1\times10^{-9}$ or stronger, $1\times10^{-10}$ or stronger, $1\times10^{-11}$ or stronger, $1\times10^{-12}$ or stronger, $1\times10^{-13}$ or stronger, or $1\times10^{-14}$ or stronger.

In certain embodiments, $K_D$ is measured by RIA performed with the Fab version of an antibody of interest and its target antigen as described by the following assay. Solution binding affinity of Fabs for the antigen is measured by equilibrating Fab with a minimal concentration of radiolabeled antigen (e.g., $^{125}$I-labeled) in the presence of a titration series of unlabeled antigen, then capturing bound antigen with an anti-Fab antibody-coated plate [see, e.g., Chen et al. (1999) J. Mol. Biol. 293:865-881]. To establish conditions for the assay, multi-well plates (e.g., MICROTI-TER® from Thermo Scientific) are coated (e.g., overnight) with a capturing anti-Fab antibody (e.g., from Cappel Labs) and subsequently blocked with bovine serum albumin, preferably at room temperature (approximately 23° C.). In a non-adsorbent plate, radiolabeled antigen are mixed with serial dilutions of a Fab of interest [e.g., consistent with assessment of the anti-VEGF antibody, Fab-12, in Presta et al., (1997) Cancer Res. 57:4593-4599]. The Fab of interest is then incubated, preferably overnight but the incubation may continue for a longer period (e.g., about 65 hours) to ensure that equilibrium is reached. Thereafter, the mixtures are transferred to the capture plate for incubation, preferably at room temperature for about one hour. The solution is then removed and the plate is washed times several times, preferably with polysorbate 20 and PBS mixture. When the plates have dried, scintillant (e.g., MICROSCINT® from Packard) is added, and the plates are counted on a gamma counter (e.g., TOPCOUNT® from Packard).

According to another embodiment, $K_D$ is measured using surface plasmon resonance assays using, for example a BIACORE® 2000 or a BIACORE® 3000 (BIAcore, Inc., Piscataway, N.J.) with immobilized antigen CM5 chips at about 10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. For example, an antigen can be diluted with 10 mM sodium acetate, pH 4.8, to 5 µg/ml (about 0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20®) surfactant (PBST) at at a flow rate of approximately 25 µl/min. Association rates ($k_{on}$) and dissociation rates ($k_{off}$) are calculated using, for example, a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$ [see, e.g., Chen et al., (1999) J. Mol. Biol. 293:865-881]. If the on-rate exceeds, for example, $10^6 M^{-1} s^{-1}$ by the surface plasmon resonance assay above, then the on-rate can be determined by using a fluorescent quenching technique that measures the increase or decrease in fluorescence emission intensity (e.g., excitation=295 nm; emission=340 nm, 16 nm band-pass) of a 20 nM anti-antigen antibody (Fab form) in PBS in the presence of increasing concentrations of antigen as measured in a spectrometer, such as a stop-flow equipped spectrophometer (Aviv Instruments) or a 8000-series SLM-AMINCO® spectrophotometer (ThermoSpectronic) with a stirred cuvette.

Antibody fragments can be made by various techniques, including but not limited to proteolytic digestion of an intact antibody as well as production by recombinant host cells (e.g., E. coli or phage), as described herein. The nucleic acid and amino acid sequences of human GDF11, activin A, activin B, activin C, activin E, GDF8, BMP6, ActRIIB, ALK4, GDF3, and BMP9 are well known in the art. In addition, numerous methods for generating antibodies are well known in the art, some of which are described herein. Therefore antibody antagonists for use in accordance with this disclosure may be routinely made by the skilled person in the art based on the knowledge in the art and teachings provided herein.

In certain embodiments, an antibody provided herein is a chimeric antibody. A chimeric antibody refers to an antibody in which a portion of the heavy and/or light chain is derived from a particular source or species, while the remainder of the heavy and/or light chain is derived from a different source or species. Certain chimeric antibodies are described, for example, in U.S. Pat. No. 4,816,567; and Morrison et al., (1984) Proc. Natl. Acad. Sci. USA, 81:6851-6855. In some embodiments, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched" antibody in which the class or subclass has been changed from that of the parent antibody. In general, chimeric antibodies include antigen-binding fragments thereof.

In certain embodiments, a chimeric antibody provided herein is a humanized antibody. A humanized antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Humanized antibodies and methods of making them are reviewed, for example, in Almagro and Fransson (2008) Front. Biosci. 13:1619-1633 and are further described, for example, in Riechmann et al., (1988) Nature 332:323-329; Queen et al. (1989) Proc. Nat'l Acad. Sci. USA 86:10029-10033; U.S. Pat. Nos. 5,821,337; 7,527,791; 6,982,321; and U.S. Pat. No. 7,087,409; Kashmiri et al., (2005) Methods 36:25-34 [describing SDR (a-CDR) grafting]; Padlan, Mol. Immunol. (1991) 28:489-498 (describing "resurfacing"); Dall'Acqua et al. (2005) Methods 36:43-60 (describing "FR shuffling"); Osbourn et al. (2005) Methods 36:61-68; and Klimka et al. Br. J. Cancer (2000) 83:252-260 (describing the "guided selection" approach to FR shuffling). Human framework regions that may be used for humanization include but are not limited to: framework regions selected using the "best-fit" method [see, e.g., Sims et al. (1993) J. Immunol. 151:2296]; framework regions derived from the consensus sequence of human antibodies of a particular subgroup of light or heavy chain variable regions [see, e.g., Carter et al. (1992) Proc. Natl. Acad. Sci. USA, 89:4285; and Presta et al. (1993) J. Immunol., 151:2623]; human mature (somatically mutated) framework regions or human germline framework regions [see, e.g., Almagro and Fransson (2008) Front. Biosci. 13:1619-1633]; and framework regions derived from screening FR libraries [see, e.g., Baca et al., (1997) J. Biol. Chem. 272:10678-10684; and Rosok et al., (1996) J. Biol. Chem. 271:22611-22618].

In certain embodiments, an antibody provided herein is a human antibody. Human antibodies can be produced using various techniques known in the art. Human antibodies are described generally in van Dijk and van de Winkel (2008) Curr. Opin. Pharmacol. 5: 368-74 (2001) and Lonberg, Curr. Opin. Immunol. 20:450-459. For example, human antibodies may be prepared by administering an immunogen (e.g., a GDF11 polypeptide, an activin B polypeptide, an ActRIIA polypeptide, or an ActRIIB polypeptide) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. For a review of methods for obtaining human antibodies from transgenic animals see, for example, Lonberg (2005) Nat. Biotech. 23:1117-1125; U.S. Pat. Nos. 6,075,181 and 6,150,584 (describing XENOMOUSE™ technology); U.S. Pat. No. 5,770,429 (describing HuMab® technology); U.S. Pat. No. 7,041,870 (describing K-M MOUSE® technology); and U.S. Patent Application Publication No. 2007/0061900 (describing VelociMouse® technology). Human variable regions from intact antibodies generated by such animals may be further modified, for example, by combining with a different human constant region.

Human antibodies provided herein can also be made by hybridoma-based methods. Human myeloma and mouse-human heteromyeloma cell lines for the production of human monoclonal antibodies have been described [see, e.g., Kozbor J. Immunol., (1984) 133: 3001; Brodeur et al. (1987) Monoclonal Antibody Production Techniques and Applications, pp. 51-63, Marcel Dekker, Inc., New York; and Boerner et al. (1991) J. Immunol., 147: 86]. Human antibodies generated via human B-cell hybridoma technology are also described in Li et al., (2006) Proc. Natl. Acad. Sci. USA, 103:3557-3562. Additional methods include those described, for example, in U.S. Pat. No. 7,189,826 (describing production of monoclonal human IgM antibodies from hybridoma cell lines) and Ni, Xiandai Mianyixue (2006) 26(4):265-268 (2006) (describing human-human hybridomas). Human hybridoma technology (Trioma technology) is also described in Vollmers and Brandlein (2005) Histol. Histopathol., 20(3):927-937 (2005) and Vollmers and Brandlein (2005) Methods Find Exp. Clin. Pharmacol., 27(3):185-91. Human antibodies provided herein may also be generated by isolating Fv clone variable-domain sequences selected from human-derived phage display libraries. Such variable-domain sequences may then be combined with a desired human constant domain. Techniques for selecting human antibodies from antibody libraries are known in the art and described herein.

For example, antibodies of the present disclosure may be isolated by screening combinatorial libraries for antibodies with the desired activity or activities. A variety of methods are known in the art for generating phage display libraries and screening such libraries for antibodies possessing the desired binding characteristics. Such methods are reviewed, for example, in Hoogenboom et al. (2001) in Methods in Molecular Biology 178:1-37, O'Brien et al., ed., Human Press, Totowa, N.J. and further described, for example, in the McCafferty et al. (1991) Nature 348:552-554; Clackson et al., (1991) Nature 352: 624-628; Marks et al. (1992) J. Mol. Biol. 222:581-597; Marks and Bradbury (2003) in Methods in Molecular Biology 248:161-175, Lo, ed., Human Press, Totowa, N.J.; Sidhu et al. (2004) J. Mol. Biol. 338(2):299-310; Lee et al. (2004) J. Mol. Biol. 340(5):1073-1093; Fellouse (2004) Proc. Natl. Acad. Sci. USA 101(34): 12467-12472; and Lee et al. (2004) J. Immunol. Methods 284(1-2): 119-132.

In certain phage display methods, repertoires of VH and VL genes are separately cloned by polymerase chain reaction (PCR) and recombined randomly in phage libraries, which can then be screened for antigen-binding phage as described in Winter et al. (1994) Ann. Rev. Immunol., 12: 433-455. Phage typically display antibody fragments, either as single-chain Fv (scFv) fragments or as Fab fragments. Libraries from immunized sources provide high-affinity antibodies to the immunogen (e.g., GDF11, activin B, ALK4, or ActRIIB) without the requirement of constructing hybridomas. Alternatively, the naive repertoire can be cloned (e.g., from human) to provide a single source of antibodies to a wide range of non-self and also self-antigens without any immunization as described by Griffiths et al. (1993) EMBO J, 12: 725-734. Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter (1992) J. Mol. Biol., 227: 381-388. Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

In certain embodiments, an antibody provided herein is a multispecific antibody, for example, a bispecific antibody. Multispecific antibodies (typically monoclonal antibodies) that have binding specificities for at least two different epitopes (e.g., two, three, four, five, or six or more) on one or more (e.g., two, three, four, five, six or more) antigens.

Techniques for making multispecific antibodies include, but are not limited to, recombinant co-expression of two immunoglobulin heavy-chain/light-chain pairs having different specificities [see, e.g., Milstein and Cuello (1983) Nature 305: 537; International patent publication no. WO 93/08829; and Traunecker et al. (1991) EMBO J. 10: 3655, and U.S. Pat. No. 5,731,168 ("knob-in-hole" engineering)]. Multispecific antibodies may also be made by engineering electrostatic steering effects for making antibody Fc-heterodimeric molecules (see, e.g., WO 2009/089004A1); cross-linking two or more antibodies or fragments [see, e.g., U.S. Pat. No. 4,676,980; and Brennan et al. (1985) Science, 229: 81]; using leucine zippers to produce bispecific antibodies [see, e.g., Kostelny et al. (1992) J. Immunol., 148 (5):1547-1553]; using "diabody" technology for making bispecific antibody fragments [see, e.g., Hollinger et al. (1993) Proc. Natl. Acad. Sci. USA, 90:6444-6448]; using single-chain Fv (sFv) dimers [see, e.g., Gruber et al. (1994) J. Immunol., 152:5368]; and preparing trispecific antibodies (see, e.g., Tutt et al. (1991) J. Immunol. 147: 60. Multispecific antibodies can be prepared as full-length antibodies or antibody fragments. Engineered antibodies with three or more functional antigen-binding sites, including "Octopus antibodies," are also included herein [see, e.g., US 2006/0025576A1].

In certain embodiments, an antibody disclosed herein is a monoclonal antibody. Monoclonal antibody refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present methods may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

For example, by using immunogens derived from GDF11, anti-protein/anti-peptide antisera or monoclonal antibodies can be made by standard protocols [see, e.g., Antibodies: A Laboratory Manual ed. by Harlow and Lane (1988) Cold Spring Harbor Press: 1988]. A mammal, such as a mouse, hamster, or rabbit, can be immunized with an immunogenic form of the GDF11 polypeptide, an antigenic fragment which is capable of eliciting an antibody response, or a fusion protein. Techniques for conferring immunogenicity on a protein or peptide include conjugation to carriers or other techniques well known in the art. An immunogenic portion of a GDF11 polypeptide can be administered in the presence of adjuvant. The progress of immunization can be monitored by detection of antibody titers in plasma or serum. Standard ELISA or other immunoassays can be used with the immunogen as antigen to assess the levels of antibody production and/or level of binding affinity.

Following immunization of an animal with an antigenic preparation of GDF11, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique [see, e.g., Kohler and Milstein (1975) Nature, 256: 495-497], the human B cell hybridoma technique [see, e.g., Kozbar et al. (1983) Immunology Today, 4:72], and the EBV-hybridoma technique to produce human monoclonal antibodies [Cole et al. (1985) Monoclonal Antibodies and Cancer Therapy, Alan R. Liss, Inc. pp. 77-96]. Hybridoma cells can be screened immunochemically for production of antibodies specifically reactive with a GDF11 polypeptide, and monoclonal antibodies isolated from a culture comprising such hybridoma cells.

In certain embodiments, one or more amino acid modifications may be introduced into the Fc region of an antibody provided herein thereby generating an Fc region variant. The Fc region variant may comprise a human Fc region sequence (e.g., a human IgG1, IgG2, IgG3 or IgG4 Fc region) comprising an amino acid modification (e.g., a substitution, deletion, and/or addition) at one or more amino acid positions.

For example, the present disclosure contemplates an antibody variant that possesses some but not all effector functions, which make it a desirable candidate for applications in which the half-life of the antibody in vivo is important yet certain effector functions [e.g., complement-dependent cytotoxicity (CDC) and antibody-dependent cellular cytotoxicity (ADCC)] are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in, for example, Ravetch and Kinet (1991) Annu. Rev. Immunol. 9:457-492. Non-limiting examples of in vitro assays to assess ADCC activity of a molecule of interest are described in U.S. Pat. No. 5,500,362; Hellstrom, I. et al. (1986) Proc. Natl. Acad. Sci. USA 83:7059-7063]; Hellstrom, I et al. (1985) Proc. Natl. Acad. Sci. USA 82:1499-1502; U.S. Pat. No. 5,821,337; Bruggemann, M. et al. (1987) J. Exp. Med. 166:1351-1361. Alternatively, non-radioactive assays methods may be employed (e.g., ACTI™, non-radioactive cytotoxicity assay for flow cytometry; CellTechnology, Inc. Mountain View, Calif.; and CytoTox 96® non-radioactive cytotoxicity assay, Promega, Madison, Wis.). Useful effector cells for such assays include peripheral blood mononuclear cells (PBMC) and natural killer (NK) cells. Alternatively, or additionally, ADCC activity of the molecule of interest may be assessed in vivo, for example, in an animal model such as that disclosed in Clynes et al. (1998) Proc. Natl. Acad. Sci. USA 95:652-656. C1q binding assays may also be carried out to confirm that the antibody is unable to bind C1q and hence lacks CDC activity [see, e.g., C1q and C3c binding ELISA in WO 2006/029879 and WO 2005/100402]. To assess complement activation, a CDC assay may be performed [see, e.g, Gazzano-Santoro et al. (1996) J. Immunol. Methods 202:163; Cragg, M. S. et al. (2003) Blood 101:1045-1052; and Cragg, M. S, and M. J. Glennie (2004) Blood 103:2738-2743]. FcRn binding and in vivo clearance/half-life determinations can also be performed using methods known in the art [see, e.g., Petkova, S. B. et al. (2006) Intl. Immunol. 18(12):1759-1769]. Antibodies of the present disclosure with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, for example, in U.S. Pat. No. 7,521,541.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interactions between antibodies and antigens to identify particularly desirable antibodies. Such techniques include ELISAs, surface plasmon resonance binding assays (e.g., the Biacore binding assay, Biacore AB, Uppsala, Sweden), sandwich assays (e.g., the paramagnetic bead system of IGEN International, Inc., Gaithersburg, Md.), western blots, immunoprecipitation assays, and immunohistochemistry.

In certain embodiments, amino acid sequence variants of the antibodies and/or the binding polypeptides provided herein are contemplated. For example, it may be desirable to improve the binding affinity and/or other biological properties of the antibody and/or binding polypeptide. Amino acid sequence variants of an antibody and/or binding polypeptides may be prepared by introducing appropriate modifications into the nucleotide sequence encoding the antibody and/or binding polypeptide, or by peptide synthesis. Such modifications include, for example, deletions from, and/or insertions into and/or substitutions of residues within the amino acid sequences of the antibody and/or binding polypeptide. Any combination of deletion, insertion, and substitution can be made to arrive at the final construct, provided that the final construct possesses the desired characteristics, e.g., target-binding (GDF11 and/or activin B binding).

Alterations (e.g., substitutions) may be made in HVRs, for example, to improve antibody affinity. Such alterations may be made in HVR "hotspots," i.e., residues encoded by codons that undergo mutation at high frequency during the somatic maturation process [see, e.g., Chowdhury (2008) Methods Mol. Biol. 207:179-196 (2008)], and/or SDRs (a-CDRs), with the resulting variant VH or VL being tested for binding affinity. Affinity maturation by constructing and reselecting from secondary libraries has been described in the art [see, e.g., Hoogenboom et al., in Methods in Molecular Biology 178:1-37, O'Brien et al., ed., Human Press, Totowa, N.J., (2001). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind to the antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of the antibody and/or the binding polypeptide that may be targeted for mutagenesis is called "alanine scanning mutagenesis" as described by Cunningham and Wells (1989) Science, 244:1081-1085. In this method, a residue or group of target residues (e.g., charged residues such as Asp, Arg, His, Lys, and Glu) are identified and replaced by a neutral or negatively charged amino acid (e.g., alanine or polyalanine) to determine whether the interaction of the antibody-antigen is affected. Further substitutions may be introduced at the amino acid locations demonstrating functional sensitivity to the initial substitutions. Alternatively, or additionally, a crystal structure of an antigen-antibody complex is determined to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion of the N- or C-terminus of the antibody to an enzyme (e.g., for ADEPT) or a polypeptide which increases the serum half-life of the antibody.

In certain embodiments, an antibody and/or binding polypeptide provided herein may be further modified to contain additional nonproteinaceous moieties that are known in the art and readily available. The moieties suitable for derivatization of the antibody and/or binding polypeptide include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody and/or binding polypeptide may vary, and if more than one polymer are attached, they can be the same or different molecules. In general, the number and/or type of polymers used for derivatization can be determined based on considerations including, but not limited to, the particular properties or functions of the antibody and/or binding polypeptide to be improved, whether the antibody derivative and/or binding polypeptide derivative will be used in a therapy under defined conditions.

D. Small Molecule Antagonists

In other aspects, an ALK4:ActRIIB antagonist is a small molecule (ALK4:ActRIIB small molecule antagonist), or combination of small molecule antagonists. An ALK4:ActRIIB small molecule antagonist, or combination of small molecule antagonists, may inhibit, for example, one or more ALK4:ActRIIB-binding ligands, a type I receptor (e.g., ALK4), a type II receptor (e.g., ActRIIB), and/or co-receptor. In some embodiments, ALK4:ActRIIB small molecule antagonist, or combination of small molecule antagonists, inhibits signaling mediated by one or more ALK4:ActRIIB-binding ligands, for example, as determined in a cell-based assay such as those described herein. As described herein, ALK4:ActRIIB small molecule antagonists may be used, alone or in combination with one or more supportive therapies or active agents, to treat a patient in need thereof (e.g., a subject with a bone-related disease or condition, a muscle related disease or condition, or a disease or condition associated with excess or unwanted fat).

In some embodiments, an ALK4:ActRIIB small molecule antagonist, or combination of small molecule antagonists, inhibits at least GDF11. In some embodiments, an ALK4:ActRIIB small molecule antagonist, or combination of small molecule antagonists, inhibits at least GDF8. In some embodiments, an ALK4:ActRIIB small molecule antagonist, or combination of small molecule antagonists, inhibits at least activin (activin A, activin B, activin C, activin E, activin AB, activin AC, activin BC, activin AE and/or activin BE). In some embodiments, an ALK4:ActRIIB small molecule antagonist, or combination of small molecule antagonists, inhibits at least GDF11, GDF8, and activin. In some embodiments, an ALK4:ActRIIB small molecule antagonist, or combination of small molecule antagonists, inhibits at least ALK4. In some embodiments, an ALK4:ActRIIB small molecule antagonist, or combination of small molecule antagonists, inhibits at least ActRIIB In some embodiments, an ALK4:ActRIIB small molecule antagonist, or combination of small molecule antagonists, inhibits at least BMP6. In some embodiments, an ALK4:ActRIIB small molecule antagonist, or combination of small molecule antagonists, inhibits at least GDF3. In some embodiments, an ALK4:ActRIIB small molecule antagonist, or combination of small molecule antagonists, inhibits at least BMP10. In some embodiments, an ALK4:ActRIIB small molecule antagonist, or combination of small molecule antagonists, as disclosed herein does not inhibit or does not substantially inhibit BMP9.

ALK4:ActRIIB small molecule antagonists can be direct or indirect inhibitors. For example, an indirect small molecule antagonist, or combination of small molecule antagonists, may inhibit the expression (e.g., transcription, translation, cellular secretion, or combinations thereof) of at least one or more TGF-β superfamily ligands that bind to an ALK4:ActRIIB heteromultimer [e.g., activin (e.g., activin A, activin B, and activin AB), GDF8, GDF11, BMP10, BMP6, and GDF3], type I receptor (e.g., ALK4), type II receptors (e.g., ActRIIB), and/or one or more downstream signaling components (e.g., Smads). Alternatively, a direct small molecule antagonist, or combination of small molecule antagonists, may directly bind to and inhibit, for example, one or more TGF-β superfamily ligands that bind to an ALK4:ActRIIB heteromultimer [e.g., activin (e.g., activin A, activin B, and activin AB), GDF11, GDF8, BMP10, BMP6, and GDF3], type I receptors (e.g., ALK4), type II receptors (e.g., ActRIIB), co-receptors (e.g., Cripto or Cryptic), and/or downstream signaling components (e.g., Smads). Combinations of one or more indirect and one or more direct ALK4:ActRIIB small molecule antagonists may be used in accordance with the methods disclosed herein.

Binding small-molecule antagonists of the present disclosure may be identified and chemically synthesized using known methodology (see, e.g., PCT Publication Nos. WO 00/00823 and WO 00/39585). In general, small-molecule antagonists of the disclosure are usually less than about 2000 daltons in size, alternatively less than about 1500, 750, 500, 250 or 200 daltons in size, wherein such organic small molecules that are capable of binding, preferably specifically, to a polypeptide as described herein. These small molecule antagonists may be identified without undue experimentation using well-known techniques. In this regard, it is noted that techniques for screening organic small-molecule libraries for molecules that are capable of binding to a polypeptide target are well known in the art (see, e.g., international patent publication Nos. WO00/00823 and WO00/39585).

Binding organic small molecules of the present disclosure may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, and acid chlorides.

E. Polynucleotide Antagonists

In other aspects, an ALK4:ActRIIB antagonist is a polynucleotide (ALK4:ActRIIB polynucleotide antagonist), or combination of polynucleotides. An ALK4:ActRIIB polynucleotide antagonist, or combination of polynucleotide antagonists, may inhibit, for example, one or more ALK4:ActRIIB-binding ligands [e.g., activin (e.g., activin A, activin B, and activin AB), GDF8, GDF11, BMP10, BMP6, and GDF3], type I receptors (e.g., ALK4), type II receptors (e.g., ActRIIB), co-receptor, and/or downstream signaling component (e.g., Smads). In some embodiments, ALK4:ActRIIB polynucleotide antagonist, or combination of polynucleotide antagonists, inhibits signaling mediated by one or more ALK4:ActRIIB-binding ligands, for example, as determined in a cell-based assay such as those described herein. As described herein, ALK4:ActRIIB polynucleotide antagonists may be used, alone or in combination with one or more supportive therapies or active agents, to treat a patient in need thereof (e.g., a subject with a bone-related disease or condition, a muscle related disease or condition, or a disease or condition associated with excess or unwanted fat).

In some embodiments, an ALK4:ActRIIB polynucleotide antagonists, or combination of polynucleotide antagonists, inhibits at least GDF11. In some embodiments, an ALK4:ActRIIB polynucleotide antagonist, or combination of polynucleotide antagonists, inhibits at least GDF8. In some embodiments, an ALK4:ActRIIB polynucleotide antagonist, or combination of polynucleotide antagonists, inhibits at least activin (activin A, activin B, activin C, activin E, activin AB, activin AC, activin AE, activin BC and/or activin BE). In some embodiments, an ALK4:ActRIIB polynucleotide antagonist, or combination of polynucleotide antagonists, inhibits at least GDF11, GDF8, and activin. In some embodiments, an ALK4:ActRIIB polynucleotide antagonist, or combination of polynucleotide antagonists, inhibits at least ALK4. In some embodiments, an ALK4:ActRIIB polynucleotide antagonist, or combination of polynucleotide antagonists, inhibits at least ActRIIB In some embodiments, an ALK4:ActIIB polynucleotide antagonist, or combination of polynucleotide antagonists, inhibits at least BMP6. In some embodiments, an ALK4:ActRIIB polynucleotide antagonist, or combination of polynucleotide antagonists, inhibits at least GDF3. In some embodiments, an ALK4:ActRIIB polynucleotide antagonist, or combination of polynucleotide antagonists, inhibits at least BMP10. In some embodiments, an ALK4:ActRIIB polynucleotide antagonist, or combination of polynucleotide antagonists, as disclosed herein does not inhibit or does not substantially inhibit BMP9.

In some embodiments, the polynucleotide antagonists of the disclosure may be an antisense nucleic acid, an RNAi molecule [e.g., small interfering RNA (siRNA), small-hairpin RNA (shRNA), microRNA (miRNA)], an aptamer and/or a ribozyme. The nucleic acid and amino acid sequences of human GDF11, activin B, GDF8, activin A, BMP6, GDF3, ALK4, ActRIIB, and BMP10 are known in the art. In addition, many different methods of generating polynucleotide antagonists are well known in the art. Therefore polynucleotide antagonists for use in accordance with this disclosure may be routinely made by the skilled person in the art based on the knowledge in the art and teachings provided herein.

Antisense technology can be used to control gene expression through antisense DNA or RNA, or through triple-helix formation. Antisense techniques are discussed, for example, in Okano (1991) J. Neurochem. 56:560; Oligodeoxynucleotides as Antisense Inhibitors of Gene Expression, CRC Press, Boca Raton, Fla. (1988). Triple-helix formation is discussed in, for instance, Cooney et al. (1988) Science 241:456; and Dervan et al., (1991) Science 251:1300. The methods are based on binding of a polynucleotide to a complementary DNA or RNA. In some embodiments, the antisense nucleic acids comprise a single-stranded RNA or DNA sequence that is complementary to at least a portion of an RNA transcript of a gene disclosed herein. However, absolute complementarity, although preferred, is not required.

A sequence "complementary to at least a portion of an RNA," referred to herein, means a sequence having sufficient complementarity to be able to hybridize with the RNA, forming a stable duplex; in the case of double-stranded antisense nucleic acids of a gene disclosed herein, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with an RNA it may contain and still form a stable duplex (or triplex as the case may be). One skilled in the art can ascertain a tolerable degree of mismatch by use of standard procedures to determine the melting point of the hybridized complex.

Polynucleotides that are complementary to the 5' end of the message, for example, the 5'-untranslated sequence up to and including the AUG initiation codon, should work most efficiently at inhibiting translation. However, sequences complementary to the 3'-untranslated sequences of mRNAs have been shown to be effective at inhibiting translation of mRNAs as well [see, e.g., Wagner, R., (1994) Nature 372:333-335]. Thus, oligonucleotides complementary to either the 5'- or 3'-non-translated, non-coding regions of a gene of the disclosure, could be used in an antisense approach to inhibit translation of an endogenous mRNA. Polynucleotides complementary to the 5'-untranslated region of the mRNA should include the complement of the AUG start codon. Antisense polynucleotides complementary to mRNA coding regions are less efficient inhibitors of translation but could be used in accordance with the methods of the present disclosure. Whether designed to hybridize to the 5'-, 3'- or coding region of an mRNA of the disclosure, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

In one embodiment, the antisense nucleic acid of the present disclosure is produced intracellularly by transcription from an exogenous sequence. For example, a vector or a portion thereof is transcribed, producing an antisense nucleic acid (RNA) of a gene of the disclosure. Such a vector would contain a sequence encoding the desired antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding desired genes of the instant disclosure, or fragments thereof, can be by any promoter known in the art to act in vertebrate, preferably human cells. Such promoters can be inducible or constitutive. Such promoters include, but are not limited to, the SV40 early promoter region [see, e.g., Benoist and Chambon (1981) Nature 290:304-310], the promoter contained in the 3' long-terminal repeat of Rous sarcoma virus [see, e.g., Yamamoto et al. (1980) Cell 22:787-797], the herpes thymidine promoter [see, e.g., Wagner et al. (1981) Proc. Natl. Acad. Sci. U.S.A. 78:1441-1445], and the regulatory sequences of the metallothionein gene [see, e.g., Brinster, et al. (1982) Nature 296:39-42].

In some embodiments, the polynucleotide antagonists are interfering RNA (RNAi) molecules that target the expression of one or more of: GDF11, activin B, GDF8, activin A, BMP6, GDF3, BMP10, ALK4, and ActRIIB RNAi refers to the expression of an RNA which interferes with the expression of the targeted mRNA. Specifically, RNAi silences a targeted gene via interacting with the specific mRNA through a siRNA (small interfering RNA). The ds RNA complex is then targeted for degradation by the cell. An siRNA molecule is a double-stranded RNA duplex of 10 to 50 nucleotides in length, which interferes with the expression of a target gene which is sufficiently complementary (e.g. at least 80% identity to the gene). In some embodiments, the siRNA molecule comprises a nucleotide sequence that is at least 85, 90, 95, 96, 97, 98, 99, or 100% identical to the nucleotide sequence of the target gene.

Additional RNAi molecules include short-hairpin RNA (shRNA); also short-interfering hairpin and microRNA (miRNA). The shRNA molecule contains sense and antisense sequences from a target gene connected by a loop. The shRNA is transported from the nucleus into the cytoplasm, and it is degraded along with the mRNA. Pol III or U6 promoters can be used to express RNAs for RNAi. Paddison et al. [Genes & Dev. (2002) 16:948-958, 2002] have used small RNA molecules folded into hairpins as a means to affect RNAi. Accordingly, such short-hairpin RNA (shRNA) molecules are also advantageously used in the methods described herein. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the double-stranded RNA (dsRNA) products of the DICER RNase and, in any event, have the same capacity for inhibiting expression of a specific gene. The shRNA can be expressed from a lentiviral vector. An miRNA is a single-stranded RNA of about 10 to 70 nucleotides in length that are initially transcribed as pre-miRNA characterized by a "stem-loop" structure, which are subsequently processed into mature miRNA after further processing through the RISC.

Molecules that mediate RNAi, including without limitation siRNA, can be produced in vitro by chemical synthesis (Hohjoh, FEBS Lett 521:195-199, 2002), hydrolysis of dsRNA (Yang et al., Proc Natl Acad Sci USA 99:9942-9947, 2002), by in vitro transcription with T7 RNA polymerase (Donzeet et al., Nucleic Acids Res 30:e46, 2002; Yu et al., Proc Natl Acad Sci USA 99:6047-6052, 2002), and by hydrolysis of double-stranded RNA using a nuclease such as E. coli RNase III (Yang et al., Proc Natl Acad Sci USA 99:9942-9947, 2002).

According to another aspect, the disclosure provides polynucleotide antagonists including but not limited to, a decoy DNA, a double-stranded DNA, a single-stranded DNA, a complexed DNA, an encapsulated DNA, a viral DNA, a plasmid DNA, a naked RNA, an encapsulated RNA, a viral RNA, a double-stranded RNA, a molecule capable of generating RNA interference, or combinations thereof.

In some embodiments, the polynucleotide antagonists of the disclosure are aptamers. Aptamers are nucleic acid molecules, including double-stranded DNA and single-stranded RNA molecules, which bind to and form tertiary structures that specifically bind to a target molecule. The generation and therapeutic use of aptamers are well established in the art (see, e.g., U.S. Pat. No. 5,475,096). Additional information on aptamers can be found in U.S. Patent Application Publication No. 20060148748. Nucleic acid aptamers are selected using methods known in the art, for example via the Systematic Evolution of Ligands by Exponential Enrichment (SELEX) process. SELEX is a method for the in vitro evolution of nucleic acid molecules with highly specific binding to target molecules as described in, e.g., U.S. Pat. Nos. 5,475,096; 5,580,737; 5,567,588; 5,707, 796; 5,763,177; 6,011,577; and 6,699,843. Another screening method to identify aptamers is described in U.S. Pat. No. 5,270,163. The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets. The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, which can comprise a segment of randomized sequence, the SELEX method includes steps of contacting the mixture with the target under conditions favorable for binding; partitioning unbound nucleic acids from those nucleic acids which have bound specifically to target molecules; dissociating the nucleic acid-target complexes; amplifying the nucleic acids dissociated from the nucleic acid-target complexes to yield a ligand enriched mixture of nucleic acids. The steps of binding, partitioning, dissociating and amplifying are repeated through as many cycles as desired to yield nucleic acid ligands which bind with high affinity and specificity to the target molecule.

Typically, such binding molecules are separately administered to the animal [see, e.g., O'Connor (1991) J. Neurochem. 56:560], but such binding molecules can also be expressed in vivo from polynucleotides taken up by a host cell and expressed in vivo [see, e.g., Oligodeoxynucleotides as Antisense Inhibitors of Gene Expression, CRC Press, Boca Raton, Fla. (1988)].

F. Follistatin and FLRG Antagonists

It is known that members of the follistatin and FLRG group of proteins antagonize ligands that signal through the ALK4:ActRIIB pathway. Accordingly, in other aspects, an ALK4:ActRIIB antagonist is a follistatin or FLRG polypeptide, which may be used alone or in combination with one or more additional supportive therapies and/or active agents as disclosed herein to achieve a desired effect (e.g., treat patients having kidney disease and/or a metabolic disorder).

The term "follistatin polypeptide" includes polypeptides comprising any naturally occurring polypeptide of follistatin as well as any variants thereof (including mutants, fragments, fusions, and peptidomimetic forms) that retain a useful activity, and further includes any functional monomer or multimer of follistatin. In certain preferred embodiments, follistatin polypeptides of the disclosure bind to and/or inhibit activin and/or GDF8 activity. Variants of follistatin polypeptides that retain activin binding properties can be identified based on previous studies involving follistatin and activin interactions. For example, WO2008/030367 discloses specific follistatin domains ("FSDs") that are shown to be important for activin binding. As shown below in SEQ ID NOs: 90-94, the follistatin N-terminal domain ("FSND" SEQ ID NO: 92), FSD2 (SEQ ID NO: 94), and to a lesser extent FSD1 (SEQ ID NO: 93) represent exemplary domains within follistatin that are important for activin binding. In addition, methods for making and testing libraries of polypeptides are described above in the context of ActRII polypeptides, and such methods also pertain to making and testing variants of follistatin. Follistatin polypeptides include polypeptides derived from the sequence of any known follistatin having a sequence at least about 80% identical to the sequence of a follistatin polypeptide, and optionally at least 85%, 90%, 95%, 96%, 97%, 98%, 99% or greater identity. Examples of follistatin polypeptides include the mature follistatin polypeptide or shorter isoforms or other variants of the human follistatin precursor polypeptide (SEQ ID NO: 90) as described, for example, in WO2005/025601.

The human follistatin precursor polypeptide isoform FST344 is as follows:

```
(SEQ ID NO: 90; NCBI Reference No. NP_037541.1)
  1 MVRARHQPGG LCLLLLLLCQ FMEDRSAQAG NCWLRQAKNG RCQVLYKTEL

51 SKEECCSTGR LSTSWTEEDV NDNTLFKWMI FNGGAPNCIP CKETCENVDC

101 GPGKKCRMNK KNKPRCVCAP DCSNITWKGP VCGLDGKTYR NECALLKARC

151 KEQPELEVQY QGRCKKTCRD VFCPGSSTCV VDQTNNAYCV TCNRICPEPA

201 SSEQYLCGND GVTYSSACHL RKATCLLGRS IGLAYEGKCI KAKSCEDIQC

251 TGGKKCLWDF KVGRGRCSLC DELCPDSKSD EPVCASDNAT YASECAMKEA

301 ACSSGVLLEV KHSGSCNSIS EDTEEEEEDE DQDYSFPISS ILEW
```

The signal peptide is underlined; also underlined above are the last 27 residues which represent the C-terminal extension distinguishing this follistatin isoform from the shorter follistatin isoform FST317 shown below.

The human follistatin precursor polypeptide isoform FST317 is as follows:

```
(SEQ ID NO: 91; NCBI Reference No. NP_006341.1)
  1 MVRARHQPGG LCLLLLLLCQ FMEDRSAQAG NCWLRQAKNG RCQVLYKTEL

51 SKEECCSTGR LSTSWTEEDV NDNTLFKWMI FNGGAPNCIP CKETCENVDC

101 GPGKKCRMNK KNKPRCVCAP DCSNITWKGP VCGLDGKTYR NECALLKARC

151 KEQPELEVQY QGRCKKTCRD VFCPGSSTCV VDQTNNAYCV TCNRICPEPA

201 SSEQYLCGND GVTYSSACHL RKATCLLGRS IGLAYEGKCI KAKSCEDIQC

251 TGGKKCLWDF KVGRGRCSLC DELCPDSKSD EPVCASDNAT YASECAMKEA

301 ACSSGVLLEV KHSGSCN
```

The signal peptide is underlined.

The follistatin N-terminal domain (FSND) sequence is as follows:

```
(SEQ ID NO: 92; FSND)
GNCWLRQAKNGRCQVLYKTELSKEECCSTGRLSTSWTEEDVNDNTLF
KWMIFNGGAPNCIPCK
```

The FSD1 and FSD2 sequences are as follows:

```
(SEQ ID NO: 93; FSD1)
ETCENVDCGPGKKCRMNKKNKPRCV (SEQ ID NO: 94; FSD2)
KTCRDVFCPGSSTCVVDQTNNAYCVT
```

In other aspects, an ALK4:ActRIIB antagonist is a follistatin-like related gene (FLRG), also known as follistatin-related protein 3 (FSTL3). The term "FLRG polypeptide" includes polypeptides comprising any naturally occurring polypeptide of FLRG as well as any variants thereof (including mutants, fragments, fusions, and peptidomimetic forms) that retain a useful activity. In certain embodiments, FLRG polypeptides of the disclosure bind to and/or inhibit activin activity, particularly activin A. Variants of FLRG polypeptides that retain activin binding properties can be identified using routine methods to assay FLRG and activin interactions (see, e.g., U.S. Pat. No. 6,537,966). In addition, methods for making and testing libraries of polypeptides are described above in the context of ActRII and ALK4 polypeptides and such methods also pertain to making and testing variants of FLRG. FLRG polypeptides include polypeptides derived from the sequence of any known FLRG having a sequence at least about 80% identical to the sequence of an FLRG polypeptide, and optionally at least 85%, 90%, 95%, 97%, 99% or greater identity.

The human FLRG precursor (follistatin-related protein 3 precursor) polypeptide is as follows:

```
(SEQ ID NO: 95; NCBI Reference No. NP_005851.1)
  1 MRPGAPGPLW PLPWGALAWA VGFVSSMGSG NPAPGGVCWL QQGQEATCSL

51 VLQTDVTRAE CCASGNIDTA WSNLTHPGNK INLLGFLGLV HCLPCKDSCD

101 GVECGPGKAC RMLGGRPRCE CAPDCSGLPA RLQVCGSDGA TYRDECELRA

151 ARCRGHPDLS VMYRGRCRKS CEHVVCPRPQ SCVVDQTGSA HCVVCRAAPC

201 PVPSSPGQEL CGNNNVTYIS SCHMRQATCF LGRSIGVRHA GSCAGTPEEP

251 PGGESAEEEE NFV
```

The signal peptide is underlined.

In certain embodiments, functional variants or modified forms of the follistatin polypeptides and FLRG polypeptides include fusion proteins having at least a portion of the follistatin polypeptide or FLRG polypeptide and one or more fusion domains, such as, for example, domains that facilitate isolation, detection, stabilization or multimerization of the polypeptide. Suitable fusion domains are discussed in detail above with reference to the ActRII polypeptides. In some embodiment, an antagonist agent of the disclosure is a fusion protein comprising an activin-binding portion of a follistatin polypeptide fused to an Fc domain. In another embodiment, an antagonist agent of the disclosure is a fusion protein comprising an activin binding portion of an FLRG polypeptide fused to an Fc domain.

5. Screening Assays

In certain aspects, the present disclosure relates to the use of ALK4:ActRIIB heteromultimers to identify compounds (agents) which are agonists or antagonists of TGFβ superfamily receptors. Compounds identified through this screening can be tested to assess their ability to modulate tissues such as bone, cartilage, muscle, fat, and/or neurons, to assess their ability to modulate tissue growth in vivo or in vitro. These compounds can be tested, for example, in animal models.

There are numerous approaches to screening for therapeutic agents for modulating tissue growth by targeting TGFβ superfamily ligand signaling (e.g., SMAD 2/3 and/or SMAD 1/5/8 signaling). In certain embodiments, high-throughput screening of compounds can be carried out to identify agents that perturb TGFβ superfamily receptor-mediated effects on a selected cell line. In certain embodiments, the assay is carried out to screen and identify compounds that specifically inhibit or reduce binding of an ALK4:ActRIIB heteromultimer to its binding partner, such as a TGFβ superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin AB, activin AC, nodal, glial cell-derived neurotrophic factor (GDNF), neurturin, artemin, persephin, MIS, and Lefty). Alternatively, the assay can be used to identify compounds that enhance binding of an ALK4:ActRIIB heteromultimer to its binding partner such as an TGFβ superfamily ligand. In a further embodiment, the compounds can be identified by their ability to interact with an ALK4:ActRIIB heteromultimers.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In certain embodiments, the test agent is a small organic molecule having a molecular weight of less than about 2,000 Daltons.

The test compounds of the disclosure can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S-transferase (GST), photoactivatible crosslinkers or any combinations thereof.

In many drug-screening programs which test libraries of compounds and natural extracts, high-throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ALK4:ActRIIB heteromultimers and its binding partner (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, glial cell-derived neurotrophic factor (GDNF), neurturin, artemin, persephin, MIS, and Lefty).

Merely to illustrate, in an exemplary screening assay of the present disclosure, the compound of interest is contacted with an isolated and purified ALK4:ActRIIB heteromultimers which is ordinarily capable of binding to a TGF-beta superfamily ligand, as appropriate for the intention of the assay. To the mixture of the compound and ALK4:ActRIIB heteromultimer is then added to a composition containing the appropriate TGF-beta superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, nodal, glial cell-derived neurotrophic factor (GDNF), neurturin, artemin, persephin, MIS, and Lefty). Detection and quantification of heteromultimer-superfamily ligand complexes provides a means for determining the compound's efficacy at inhibiting (or potentiating) complex formation between the ALK4:ActRIIB heteromultimer and its binding protein. The efficacy of the compound can be assessed by generating dose-response curves from data obtained using various concentrations of the test compound. Moreover, a control assay can also be performed to provide a baseline for comparison. For example, in a control assay, isolated and purified TGF-beta superfamily ligand is added to a composition containing the ALK4:ActRIIB heteromultimer, and the formation of heteromultimer-ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Binding of a ALK4:ActRIIB heteromultimer to another protein may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ALK4:ActRIIB heteromeric and/or its binding protein, by immunoassay, or by chromatographic detection.

In certain embodiments, the present disclosure contemplates the use of fluorescence polarization assays and fluorescence resonance energy transfer (FRET) assays in measuring, either directly or indirectly, the degree of interaction between an ALK4:ActRIIB heteromultimer and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the disclosure.

Moreover, the present disclosure contemplates the use of an interaction trap assay, also known as the "two-hybrid assay," for identifying agents that disrupt or potentiate interaction between an ALK4:ActRIIB heteromultimer and its binding partner. See, e.g., U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present disclosure contemplates the use of reverse two-hybrid systems to identify compounds (e.g., small molecules or peptides) that dissociate interactions between an ALK4:ActRIIB heteromultimer and its binding protein [Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368].

In certain embodiments, the subject compounds are identified by their ability to interact with an ALK4:ActRIIB heteromultimer of the disclosure. The interaction between the compound and the ALK4:ActRIIB heteromultimer may be covalent or non-covalent. For example, such interaction can be identified at the protein level using in vitro biochemical methods, including photo-crosslinking, radiolabeled ligand binding, and affinity chromatography [Jakoby W B et al. (1974) Methods in Enzymology 46:1]. In certain cases, the compounds may be screened in a mechanism-based assay, such as an assay to detect compounds which bind to an ALK4:ActRIIB heteromultime. This may include a solid-phase or fluid-phase binding event. Alternatively, the gene encoding an ALK4:ActRIIB heteromultimer can be transfected with a reporter system (e.g., β-galactosidase, luciferase, or green fluorescent protein) into a cell and screened against the library preferably by high-throughput screening or with individual members of the library. Other mechanism-based binding assays may be used; for example, binding assays which detect changes in free energy. Binding assays can be performed with the target fixed to a well, bead or chip or captured by an immobilized antibody or resolved by capillary electrophoresis. The bound compounds may be detected usually using colorimetric endpoints or fluorescence or surface plasmon resonance.

6. Exemplary Therapeutic Uses

In certain embodiments, an ALK4:ActRIIB antagonist, or combinations of ALK4:ActRIIB antagonists, of the present disclosure can be used to treat or prevent a disease or condition that is associated with abnormal activity of an ALK4:ActRIIB-binding ligand. These diseases, disorders, or conditions are generally referred to herein as "ALK4:ActRIIB-associated conditions" or "ALK4:ActRIIB-associated disorders." In certain embodiments, the present disclosure provides methods of treating or preventing an ALK4:ActRIIB-associated condition in an individual by administering to an individual in need thereof a therapeutically effective amount of an ALK4:ActRIIB antagonist (e.g., an ALK4:ActRIIB heteromultimer such as an ALK4:ActRIIB heterodimer), or combinations of such antagonists, as described herein. The terms "subject," an "individual," or a "patient" are interchangeable throughout the specification. Any of the ALK4:ActRIIB antagonists of the disclosure can potentially be employed individually or in combination for therapeutic uses disclosed herein. These methods are particularly aimed at therapeutic and prophylactic treatments of mammals including, for example, rodents, primates, and humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes amelioration or elimination of the condition once it has been established. In either case, prevention or treatment may be discerned in the diagnosis provided by a physician or other health care provider and the intended result of administration of the therapeutic agent.

In general, treatment or prevention of a disease or condition as described in the present disclosure is achieved by administering an ALK4:ActRIIB antagonist, or combinations of such antagonists, of the present disclosure in an "effective amount". An effective amount of an agent refers to an amount effective, at dosages and for periods of time necessary, to achieve the desired therapeutic or prophylactic result. A "therapeutically effective amount" of an agent of the present disclosure may vary according to factors such as the disease state, age, sex, and weight of the individual, and the ability of the agent to elicit a desired response in the individual. A "prophylactically effective amount" refers to an amount effective, at dosages and for periods of time necessary, to achieve the desired prophylactic result.

Naturally occurring ALK4 and ActRIIB receptor-ligand complexes play essential roles in tissue growth as well as early developmental processes such as the correct formation of various structures or in one or more post-developmental capacities including sexual development, pituitary hormone production, and creation of bone and cartilage. Thus, ALK4:ActRIIB-associated conditions include, but are not limited to, abnormal tissue growth and developmental defects. In addition, ALK4:ActRIIB-associated conditions include, but are not limited to, disorders of cell growth and differentiation such as inflammation, allergy, autoimmune diseases, and tumors.

For example, ALK4:ActRIIB-associated conditions include neuromuscular disorders (e.g., muscular dystrophy and muscle atrophy), congestive obstructive pulmonary disease (and muscle wasting associated with COPD), muscle wasting syndrome, sarcopenia, cachexia, adipose tissue disorders (e.g., obesity), type 2 diabetes (NIDDM, adult-onset diabetes), and bone degenerative disease (e.g., osteoporosis). Other exemplary ALK4:ActRIIB-associated conditions include musculodegenerative and neuromuscular disorders, tissue repair (e.g., wound healing), neurodegenerative diseases (e.g., amyotrophic lateral sclerosis), and immunologic disorders (e.g., disorders related to abnormal proliferation or function of lymphocytes).

In certain embodiments, an ALK4:ActRIIB antagonist (e.g., an ALK4:ActRIIB heterodimer), or combinations of such antagonists, of the disclosure may be used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject TGF-beta superfamily heteromultimer complexes include: Duchenne muscular dystrophy (DMD), Becker muscular dystrophy (BMD), Emery-Dreifuss muscular dystrophy (EDMD), limb-girdle muscular dystrophy (LGMD), facioscapulohumeral muscular dystrophy (FSH or FSHD) (also known as Landouzy-Dejerine), myotonic dystrophy (MMD; also known as Steinert's Disease), oculopharyngeal muscular dystrophy (OPMD), distal muscular dystrophy (DD), congenital muscular dystrophy (CMD).

Duchenne muscular dystrophy (DMD) was first described by the French neurologist Guillaume Benjamin Amand Duchenne in the 1860s. Becker muscular dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is defective. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

BMD results from different mutations in the dystrophin gene. BMD patients have some dystrophin, but it is either of insufficient quantity or poor quality. The presence of some dystrophin protects the muscles of patients with BMD from degenerating as severely or as quickly as those of patients with DMD.

Studies in animals indicate that inhibition of the GDF8 signaling pathway may effectively treat various aspects of disease in DMD and BMD patients (Bogdanovich et al., 2002, Nature 420:418-421; Pistilli et al., 2011, Am J Pathol 178:1287-1297). Thus, ALK4:ActRIIB antagonists of the disclosure may act as GDF8 inhibitors (antagonists), and constitute an alternative means of blocking signaling by GDF8 and/or related TGFβ superfamily ligands in vivo in DMD and BMD patients.

Similarly, ALK4:ActRIIB antagonists of the disclosure may provide an effective means to increase muscle mass in other disease conditions that are in need of muscle growth. For example, amyotrophic lateral sclerosis (ALS), also called Lou Gehrig's disease or motor neuron disease, is a chronic, progressive, and incurable CNS disorder that attacks motor neurons, which are components of the central nervous system required for initiation of skeletal muscle contraction. In ALS, motor neurons deteriorate and eventually die, and though a person's brain normally remains fully functioning and alert, initiation of muscle contraction is blocked at the spinal level. Individuals who develop ALS are typically between 40 and 70 years old, and the first motor neurons to degenerate are those innervating the arms or legs. Patients with ALS may have trouble walking, may drop things, fall, slur their speech, and laugh or cry uncontrollably. As the disease progresses, muscles in the limbs begin to atrophy from disuse. Muscle weakness becomes debilitating, and patients eventually require a wheel chair or become confined to bed. Most ALS patients die from respiratory failure or from complications of ventilator assistance like pneumonia 3-5 years from disease onset.

Promotion of increased muscle mass by ALK4:ActRIIB antagonists might also benefit those suffering from muscle wasting diseases. Gonzalez-Cadavid et al. (supra) reported that GDF8 expression correlates inversely with fat-free mass in humans and that increased expression of the GDF8 gene is associated with weight loss in men with AIDS wasting syndrome. By inhibiting the function of GDF8 in AIDS patients, at least certain symptoms of AIDS may be alleviated, if not completely eliminated, thus significantly improving quality of life in AIDS patients.

Since loss of GDF8 function is also associated with fat loss without diminution of nutrient intake (Zimmers et al., supra; McPherron and Lee, supra), the subject ALK4:ActRIIB antagonists may further be used as a therapeutic agent for slowing or preventing the development of obesity and type 2 diabetes.

Cancer anorexia-cachexia syndrome is among the most debilitating and life-threatening aspects of cancer. This syndrome is a common feature of many types of cancer—present in approximately 80% of cancer patients at death—and is responsible not only for a poor quality of life and poor response to chemotherapy but also a shorter survival time than is found in patients with comparable tumors but without weight loss. Cachexia is typically suspected in patients with cancer if an involuntary weight loss of greater than five percent of premorbid weight occurs within a six-month period. Associated with anorexia, wasting of fat and muscle tissue, and psychological distress, cachexia arises from a complex interaction between the cancer and the host. Cancer cachexia affects cytokine production, release of lipid-mobilizing and proteolysis-inducing factors, and alterations in intermediary metabolism. Although anorexia is common, a decreased food intake alone is unable to account for the changes in body composition seen in cancer patients, and increasing nutrient intake is unable to reverse the wasting syndrome. Currently, there is no treatment to control or reverse the cachexic process. Since systemic overexpression of GDF8 in adult mice was found to induce profound muscle and fat loss analogous to that seen in human cachexia syndromes (Zimmers et al., supra), the subject ALK4:ActRIIB antagonists may be beneficially used to prevent, treat, or alleviate the symptoms of the cachexia syndrome, where muscle growth is desired. An example of a heteromeric complex useful for preventing, treating, or alleviating muscle loss as described above is an ALK4:ActRIIB heterodimer.

In certain embodiments, an ALK4:ActRIIB antagonist (e.g., an ALK4:ActrIIB heterodimer), or combinations of such antagonists, of the present disclosure may be used in methods of inducing bone and/or cartilage formation, preventing bone loss, increasing bone mineralization, preventing the demineralization of bone, and/or increasing bone density. ALK4:ActRIIB antagonists may be useful in patients who are diagnosed with subclinical low bone density, as a protective measure against the development of osteoporosis.

In some embodiments, an ALK4:ActRIIB antagonist (e.g., an ALK4:ActRIIB heterodimer), or combinations of such antagonists, of the present disclosure may find medical utility in the healing of bone fractures and cartilage defects in humans and other animals. The subject methods and compositions may also have prophylactic use in closed as well as open fracture reduction and also in the improved fixation of artificial joints. De novo bone formation induced by an osteogenic agent is useful for repair of craniofacial defects that are congenital, trauma-induced, or caused by oncologic resection, and is also useful in cosmetic plastic surgery. Further, methods and compositions of the invention may be used in the treatment of periodontal disease and in other tooth repair processes. In certain cases, an ALK4:ActRIIB antagonist (e.g., an ALK4:ActRIIB heterodimer), or combinations of such antagonists, may provide an environment to attract bone-forming cells, stimulate growth of bone-forming cells, or induce differentiation of progenitors of bone-forming cells. An ALK4:ActRIIB antagonist (e.g., an ALK4:ActRIIB heterodimer), or combinations of such antagonists, of the disclosure may also be useful in the treatment of osteoporosis. Further, ALK4:ActRIIB antagonists may be used in repair of cartilage defects and prevention/reversal of osteoarthritis. Examples of heteromeric complexes useful for inducing bone formation, preventing bone loss, increasing bone mineralization, preventing the demineralization of bone, and/or increasing bone density as described herein are ALK4:ActRIIB heterodimers.

Rosen et al. (ed) Primer on the Metabolic Bone Diseases and Disorders of Mineral Metabolism, 7$^{th}$ ed. American Society for Bone and Mineral Research, Washington D.C. (incorporated herein by reference) provides an extensive discussion of bone disorders that may be subject to treatment with an ALK4:ActRIIB antagonist, or with combinations of such antagonists. A partial listing is provided herein. Methods and compositions of the invention can be applied to conditions characterized by or causing bone loss, such as osteoporosis (including secondary osteoporosis), hyperparathyroidism, chronic kidney disease mineral bone disorder, sex hormone deprivation or ablation (e.g. androgen and/or estrogen), glucocorticoid treatment, rheumatoid arthritis, severe burns, hyperparathyroidism, hypercalcemia, hypocalcemia, hypophosphatemia, osteomalacia (including tumor-induced osteomalacia), hyperphosphatemia, vitamin D deficiency, hyperparathyroidism (including familial hyperparathyroidism) and pseudohypoparathyroidism, tumor metastases to bone, bone loss as a consequence of a tumor or chemotherapy, tumors of the bone and bone marrow (e.g., multiple myeloma), ischemic bone disorders, periodontal disease and oral bone loss, Cushing's disease, Paget's disease, thyrotoxicosis, chronic diarrheal state or malabsorption, renal tubular acidosis, or anorexia nervosa. Methods and compositions of the invention may also be applied to conditions characterized by a failure of bone formation or healing, including non-union fractures, fractures that are otherwise slow to heal, fetal and neonatal bone dysplasias (e.g., hypocalcemia, hypercalcemia, calcium receptor defects and vitamin D deficiency), osteonecrosis (including osteonecrosis of the jaw) and osteogenesis imperfecta. Additionally, the anabolic effects will cause such antagonists to diminish bone pain associated with bone damage or erosion. As a consequence of the anti-resorptive effects, such antagonists may be useful to treat disorders of abnormal bone formation, such as osteoblastic tumor metastases (e.g., associated with primary prostate or breast cancer), osteogenic osteosarcoma, osteopetrosis, progressive diaphyseal dysplasia, endosteal hyperostosis, osteopoikilosis, and melorheostosis. Other disorders that may be treated include fibrous dysplasia and chondrodysplasias.

In another specific embodiment, the disclosure provides a therapeutic method and composition for repairing fractures and other conditions related to cartilage and/or bone defects or periodontal diseases. The invention further provides therapeutic methods and compositions for wound healing and tissue repair. The types of wounds include, but are not limited to, burns, incisions and ulcers. See, e.g., PCT Publication No. WO 84/01106. Such compositions comprise a therapeutically effective amount of at least one of the ALK4:ActRIIB antagonists of the disclosure in admixture with a pharmaceutically acceptable vehicle, carrier, or matrix.

In some embodiments, an ALK4:ActRIIB antagonist (e.g., an ALK4:ActRIIB heterodimer), or combinations of such antagonists, of the disclosure can be applied to conditions causing bone loss such as osteoporosis, hyperparathyroidism, Cushing's disease, thyrotoxicosis, chronic diarrheal state or malabsorption, renal tubular acidosis, or anorexia nervosa. It is commonly appreciated that being female, having a low body weight, and leading a sedentary lifestyle are risk factors for osteoporosis (loss of bone mineral density, leading to fracture risk). However, osteoporosis can also result from the long-term use of certain medications. Osteoporosis resulting from drugs or another medical condition is known as secondary osteoporosis. In Cushing's disease, the excess amount of cortisol produced by the body results in osteoporosis and fractures. The most common medications associated with secondary osteoporosis are the corticosteroids, a class of drugs that act like cortisol, a hormone produced naturally by the adrenal glands. Although adequate levels of thyroid hormones are needed for the development of the skeleton, excess thyroid hormone can decrease bone mass over time. Antacids that contain aluminum can lead to bone loss when taken in high doses by people with kidney problems, particularly those undergoing dialysis. Other medications that can cause secondary osteoporosis include phenytoin (Dilantin) and barbiturates that are used to prevent seizures; methotrexate (Rheumatrex, Immunex, Folex PFS), a drug for some forms of arthritis, cancer, and immune disorders; cyclosporine (Sandimmune, Neoral), a drug used to treat some autoimmune diseases and to suppress the immune system in organ transplant patients; luteinizing hormone-releasing hormone agonists (Lupron, Zoladex), used to treat prostate cancer and endometriosis; heparin (Calciparine, Liquaemin), an anticlotting medication; and cholestyramine (Questran) and colestipol (Colestid), used to treat high cholesterol. Bone loss resulting from cancer therapy is widely recognized and termed cancer therapy-induced bone loss (CTIBL). Bone metastases can create cavities in the bone that may be corrected by treatment with An ALK4:ActRIIB antagonist (e.g., an ALK4:ActRIIB heterodimer). Bone loss can also be caused by gum disease, a chronic infection in which bacteria located in gum recesses produce toxins and harmful enzymes.

In a further embodiment, the present disclosure provides methods and therapeutic agents for treating diseases or disorders associated with abnormal or unwanted bone growth. For example, patients with the congenital disorder fibrodysplasia ossificans progressiva (FOP) are afflicted by progressive ectopic bone growth in soft tissues spontaneously or in response to tissue trauma, with a major impact on quality of life. Additionally, abnormal bone growth can occur after hip replacement surgery and thus ruin the surgical outcome. This is a more common example of pathological bone growth and a situation in which the subject methods and compositions may be therapeutically useful. The same methods and compositions may also be useful for treating other forms of abnormal bone growth (e.g., pathological growth of bone following trauma, burns or spinal cord injury), and for treating or preventing the undesirable conditions associated with the abnormal bone growth seen in connection with metastatic prostate cancer or osteosarcoma.

In certain embodiments, an ALK4:ActRIIB antagonist (e.g., an ALK4:ActRIIB heterodimer), or combinations of such antagonists, of the disclosure may be used to promote bone formation in patients with cancer. Patients having certain tumors (e.g. prostate, breast, multiple myeloma or any tumor causing hyperparathyroidism) are at high risk for bone loss due to tumor-induced bone loss, bone metastases, and therapeutic agents. Such patients may be treated with a TGF-beta superfamily heteromultimer complex, or a combination of complexes, even in the absence of evidence of bone loss or bone metastases. Patients may also be monitored for evidence of bone loss or bone metastases, and may be treated with an ALK4:ActRIIB antagonist in the event that indicators suggest an increased risk. Generally, DEXA scans are employed to assess changes in bone density, while indicators of bone remodeling may be used to assess the likelihood of bone metastases. Serum markers may be monitored. Bone specific alkaline phosphatase (B SAP) is an enzyme that is present in osteoblasts. Blood levels of BSAP are increased in patients with bone metastasis and other conditions that result in increased bone remodeling. Osteocalcin and procollagen peptides are also associated with bone formation and bone metastases. Increases in BSAP have been detected in patients with bone metastasis caused by prostate cancer, and to a lesser degree, in bone metastases from breast cancer. BMP7 levels are high in prostate cancer that has metastasized to bone, but not in bone metastases due to bladder, skin, liver, or lung cancer. Type I carboxyterminal telopeptide (ICTP) is a crosslink found in collagen that is formed during to the resorption of bone. Since bone is constantly being broken down and reformed, ICTP will be found throughout the body. However, at the site of bone metastasis, the level will be significantly higher than in an area of normal bone. ICTP has been found in high levels in bone metastasis due to prostate, lung, and breast cancer. Another collagen crosslink, Type I N-terminal telopeptide (NTx), is produced along with ICTP during bone turnover. The amount of NTx is increased in bone metastasis caused by many different types of cancer including lung, prostate, and breast cancer. Also, the levels of NTx increase with the progression of the bone metastasis. Therefore, this marker can be used to both detect metastasis as well as measure the extent of the disease. Other markers of resorption include pyridinoline and deoxypyridinoline. Any increase in resorption markers or markers of bone metastases indicate the need for therapy with an ALK4:ActRIIB antagonist in a patient.

In another embodiment, an ALK4:ActRIIB antagonist (e.g., an ALK4:ActRIIB heterodimer), or combinations of such antagonists, may be used in patients with chronic kidney disease mineral bone disorder (CKD-MBD), a broad syndrome of interrelated skeletal, cardiovascular, and mineral-metabolic disorders arising from kidney disease. CKD-MBD encompasses various skeletal pathologies often referred to as renal osteodystrophy (ROD), which is a preferred embodiment for treatment with, an ALK4:ActRIIB antagonist (e.g., an ALK4:ActRIIB heterodimer), or combinations of such antagonists. Depending on the relative contribution of different pathogenic factors, ROD is manifested as diverse pathologic patterns of bone remodeling (Hruska et al., 2008, Chronic kidney disease mineral bone disorder (CKD-MBD); in Rosen et al. (ed) Primer on the Metabolic Bone Diseases and Disorders of Mineral Metabolism, 7th ed. American Society for Bone and Mineral Research, Washington D.C., pp 343-349). At one end of the spectrum is ROD with uremic osteodystrophy and low bone turnover, characterized by a low number of active remodeling sites, profoundly suppressed bone formation, and low bone resorption. At the other extreme is ROD with hyperparathyroidism, high bone turnover, and osteitis fibrosa. Given that an ALK4:ActRIIB antagonist (e.g., an ALK4:ActRIIB heterodimer), or combinations of such antagonists, may exert both anabolic and antiresorptive effects, these agents may be useful in patients across the ROD pathology spectrum.

An ALK4:ActRIIB antagonist (e.g., an ALK4:ActRIIB heterodimer), or combinations of such antagonists, of the disclosure may be conjointly administered with other bone-active pharmaceutical agents. Conjoint administration may be accomplished by administration of a single co-formulation, by simultaneous administration, or by administration at separate times. ALK4:ActRIIB antagonists may be particularly advantageous if administered with other bone-active agents. A patient may benefit from conjointly receiving an ALK4:ActRIIB antagonist complex and taking calcium supplements, vitamin D, appropriate exercise and/or, in some cases, other medication. Examples of other medications include, bisphosphonates (alendronate, ibandronate and risedronate), calcitonin, estrogens, parathyroid hormone and raloxifene. The bisphosphonates (alendronate, ibandronate and risedronate), calcitonin, estrogens and raloxifene affect the bone remodeling cycle and are classified as anti-resorptive medications. Bone remodeling consists of two distinct stages: bone resorption and bone formation.

Anti-resorptive medications slow or stop the bone-resorbing portion of the bone-remodeling cycle but do not slow the bone-forming portion of the cycle. As a result, new formation continues at a greater rate than bone resorption, and bone density may increase over time. Teriparatide, a form of parathyroid hormone, increases the rate of bone formation in the bone remodeling cycle. Alendronate is approved for both the prevention (5 mg per day or 35 mg once a week) and treatment (10 mg per day or 70 mg once a week) of postmenopausal osteoporosis. Alendronate reduces bone loss, increases bone density and reduces the risk of spine, wrist and hip fractures. Alendronate also is approved for treatment of glucocorticoid-induced osteoporosis in men and women as a result of long-term use of these medications (i.e., prednisone and cortisone) and for the treatment of osteoporosis in men. Alendronate plus vitamin D is approved for the treatment of osteoporosis in postmenopausal women (70 mg once a week plus vitamin D), and for treatment to improve bone mass in men with osteoporosis. Ibandronate is approved for the prevention and treatment of postmenopausal osteoporosis. Taken as a once-a-month pill (150 mg), ibandronate should be taken on the same day each month. Ibandronate reduces bone loss, increases bone density and reduces the risk of spine fractures. Risedronate is approved for the prevention and treatment of postmenopausal osteoporosis. Taken daily (5 mg dose) or weekly (35 mg dose or 35 mg dose with calcium), risedronate slows bone loss, increases bone density and reduces the risk of spine and non-spine fractures. Risedronate also is approved for use by men and women to prevent and/or treat glucocorticoid-induced osteoporosis that results from long-term use of these medications (i.e., prednisone or cortisone). Calcitonin is a naturally occurring hormone involved in calcium regulation and bone metabolism. In women who are more than 5 years beyond menopause, calcitonin slows bone loss, increases spinal bone density, and may relieve the pain associated with bone fractures. Calcitonin reduces the risk of spinal fractures. Calcitonin is available as an injection (50-100 IU daily) or nasal spray (200 IU daily).

A patient may also benefit from conjointly receiving an ALK4:ActRIIB antagonist, or combinations of such antagonists, and additional bone-active medications. Estrogen therapy (ET)/hormone therapy (HT) is approved for the prevention of osteoporosis. ET has been shown to reduce bone loss, increase bone density in both the spine and hip, and reduce the risk of hip and spinal fractures in postmenopausal women. ET is administered most commonly in the form of a pill or skin patch that delivers a low dose of approximately 0.3 mg daily or a standard dose of approximately 0.625 mg daily and is effective even when started after age 70. When estrogen is taken alone, it can increase a woman's risk of developing cancer of the uterine lining (endometrial cancer). To eliminate this risk, healthcare providers prescribe the hormone progestin in combination with estrogen (hormone replacement therapy or HT) for those women who have an intact uterus. ET/HT relieves menopause symptoms and has been shown to have a beneficial effect on bone health. Side effects may include vaginal bleeding, breast tenderness, mood disturbances and gallbladder disease. Raloxifene, 60 mg a day, is approved for the prevention and treatment of postmenopausal osteoporosis. It is from a class of drugs called Selective Estrogen Receptor Modulators (SERMs) that have been developed to provide the beneficial effects of estrogens without their potential disadvantages. Raloxifene increases bone mass and reduces the risk of spine fractures. Data are not yet available to demonstrate that raloxifene can reduce the risk of hip and other non-spine fractures. Teriparatide, a form of parathyroid hormone, is approved for the treatment of osteoporosis in postmenopausal women and men who are at high risk for a fracture. This medication stimulates new bone formation and significantly increases bone mineral density. In postmenopausal women, fracture reduction was noted in the spine, hip, foot, ribs and wrist. In men, fracture reduction was noted in the spine, but there were insufficient data to evaluate fracture reduction at other sites. Teriparatide is self-administered as a daily injection for up to 24 months.

In other embodiments, an ALK4:ActRIIB antagonist, or combinations of such antagonists, can be used for regulating body fat content in an animal and for treating or preventing conditions related thereto, and particularly, health-compromising conditions related thereto. According to the present invention, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). One embodiment of the present disclosure relates to regulating body weight by administering to an animal (e.g., a human) in need thereof a TGF-beta superfamily heteromultimer complex, or combinations of TGF-beta superfamily heteromultimer complexes, of the disclosure.

In some embodiments, an ALK4:ActRIIB antagonist, or combinations of such antagonists, of the present disclosure can be used for reducing body weight and/or reducing weight gain in an animal, and more particularly, for treating or ameliorating obesity in patients at risk for or suffering from obesity. In another specific embodiment, the present invention is directed to methods and compounds for treating an animal that is unable to gain or retain weight (e.g., an animal with a wasting syndrome). Such methods are effective to increase body weight and/or mass, or to reduce weight and/or mass loss, or to improve conditions associated with or caused by undesirably low (e.g., unhealthy) body weight and/or mass. In addition, disorders of high cholesterol (e.g., hypercholesterolemia or dislipidemia) may be treated with an ALK4:ActRIIB antagonist, or combinations of such antagonists, of the disclosure.

In other embodiments, an ALK4:ActRIIB antagonist (e.g., an ALK4:ActRIIB heterodimer), or combinations of such antagonists, can be used for regulating body fat content in an animal and for treating or preventing conditions related thereto, and particularly, health-compromising conditions related thereto. According to the present invention, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). One embodiment of the present disclosure relates to regulating body weight by administering to an animal (e.g., a human) in need thereof an ALK4:ActRIIB antagonist (e.g., an ALK4:ActRIIB heterodimer), or combinations of such antagonists. For example, in some embodiments, an ALK4:ActRIIB antagonist (e.g., an ALK4:ActRIIB heterodimer), or combinations of such antagonists, may be used to treat or prevent a disorder or condition selected from obesity (e.g., abdominal obesity); overweight; insulin resistance; metabolic syndrome and other metabolic diseases or conditions; a lipid disorder such as, low HDL levels, high LDL levels, hyperlipidemia, hypertriglyceridemia or dyslipidemia; lipoprotein aberrations; decreased triglycerides; inflammation (e.g., liver inflammation and/or inflammation of adipose tissue), fatty liver disease; non-alcoholic fatty liver disease; hyperglycemia; impaired glucose tolerance (IGT); hyperinsulinemia; high cholesterol (e.g., high LDL levels and hypercholesterolemia); cardiovascular disease such as, heart disease including coronary heart disease, congestive heart failure, stroke, peripheral vascular disease, atherosclerosis; arteriosclerosis, and hypertension; Syndrome X; vascular restenosis; neuropathy; retinopathy; neurodegenerative disease; endothelial dysfunction, respiratory dysfunction; pancreatitis; polycystic ovarian syndrome; elevated uric acid levels; haemochromatosis (iron overload); acanthosis *nigricans* (dark patches on the skin); or cancer (e.g., ovarian, breast, endometrial, and colon cancer); or a another disorders/conditions associated with one or more of the above diseases or conditions. In some embodiments, the disease or condition treated using an ALK4:ActRIIB antagonist (e.g., an ALK4:ActRIIB heterodimer), or combinations of such antagonists, is associated with overweight (e.g., BMI of ≥25 kg/m$^2$), or with too much body fat.

In one embodiment, the disclosure provides a method of reducing body weight comprising administering to a subject desiring to reduce body weight, or in need thereof, an effective amount of an ALK4:ActRIIB antagonist (e.g., an ALK4:ActRIIB heterodimer), or combinations of such antagonists. In some embodiments, the subject is overweight (e.g., pre-obese). In some embodiments, the subject has a body mass index (BMI) of 25 kg/m$^2$ or greater. In further embodiments, the subject has a BMI of 25 kg/m$^2$ to 29.9 kg/m$^2$, 30 kg/m$^2$ to 39.9 kg/m$^2$, 25 kg/m$^2$ to 39.9 kg/m$^2$, or 25 kg/m$^2$ to 50 kg/m$^2$. In some embodiments, the subject is obese. In some embodiments, the subject has a BMI of 30 kg/m$^2$ or greater (e.g., 30 to 39.9 kg/m$^2$ or 30 kg/m$^2$ to 50 kg/m$^2$). In some embodiments, the subject is morbidly obese. In some embodiments, the subject has a BMI of 40 kg/m$^2$ or greater. In further embodiments, the subject has a BMI of 40 kg/m$^2$ to 45 kg/m$^2$, or 40 kg/m$^2$ to 50 kg/m$^2$. In some embodiments, the subject has central obesity (e.g., excess adiposity in the abdominal region, including belly fat and/or visceral fat). In some embodiments, the subject has a waist/hip circumference ratio (WHR) of 0.85 or greater. In some embodiments, the subject has peripheral obesity (e.g., excess adiposity on the hips). In some embodiments, the subject has type 2 diabetes mellitus. The ALK4:ActRIIB antagonist, or combination of antagonists, may administered alone or as a combination therapy other type of supportive therapy. For example, in some embodiments, the supportive therapy is diet and/or exercise.

In one embodiment, the disclosure provides a method of reducing weight gain comprising administering to a subject desiring to reduce weight gain, or in need thereof, an effective amount of an ALK4:ActRIIB antagonist (e.g., an ALK4:ActRIIB heterodimer), or combination of such antagonists. In some embodiments, the subject is overweight (e.g., pre-obese). In some embodiments, the subject has a BMI of 25 kg/m$^2$ or greater. In further embodiments, the subject has a BMI of 25 kg/m$^2$ to 29.9 kg/m$^2$, 30 kg/m$^2$ to 39.9 kg/m$^2$, 25 kg/m$^2$ to 39.9 kg/m$^2$, or 25 kg/m$^2$ to 50 kg/m$^2$. In some embodiments, the subject is obese. In some embodiments, the subject has a BMI of 30 kg/m$^2$ or greater (e.g., 30 to 39.9 kg/m$^2$ or 30 kg/m$^2$ to 50 kg/m$^2$). In some embodiments, the subject is morbidly obese. In some embodiments, the subject has a BMI of 40 kg/m$^2$ or greater. In further embodiments, the subject has a BMI of 40 kg/m$^2$ to 45 kg/m$^2$, or 40 kg/m$^2$ to 50 kg/m$^2$. In some embodiments, the subject has type 2 diabetes mellitus.

Also provided is a method of treating or preventing a disease or condition associated with excess body weight, comprising administering to a subject in need of treatment or prevention, an effective amount of an ALK4:ActRIIB antagonist (e.g., an ALK4:ActRIIB heterodimer), or combination of such antagonists. In one embodiment, the treated or prevented disease or condition is obesity. In one embodiment, the treated or prevented disease or condition is insulin resistance. In one embodiment, the treated or prevented disease or condition is a member selected from the group consisting of: dyslipidemia, hyperlipidemia (total cholesterol level >240 mg/dL), hypercholesterolemia (e.g., total cholesterol level of >200 mg/dL, >220 mg/dL, >240 mg/dL, >250 mg/dL, or >275 mg/dL), low HDL serum level (e.g., <40 mg/dL, <45 mg/dL, or <50 mg/dL), high LDL serum level (e.g., ≥100 mg/dL, ≥130 mg/dL, ≥160 mg/dL, or ≥190 mg/dL), and hypertriglyceridemia (e.g., a fasting TG level of ≥150 mg/dL, ≥175 mg/dL, ≥200 mg/dL, ≥300 mg/dL, ≥400 mg/dL, or ≥499 mg/dL). In certain instances, the ALK4:ActRIIB antagonists treatment is an adjunct to diet and/or exercise.

In another embodiment the disclosure provides a method of reducing body weight in a subject who is overweight. The method includes administering to an overweight subject an effective amount of an ALK4:ActRIIB antagonist (e.g., an ALK4:ActRIIB heterodimer), or combination of such antagonists. In some embodiments, the subject has a body mass index (BMI) of 25 kg/m$^2$ or greater. In further embodiments, the subject has a BMI of 25 kg/m$^2$ to 29.9 kg/m$^2$, 30 kg/m$^2$ to 39.9 kg/m$^2$, 25 kg/m$^2$ to 39.9 kg/m$^2$, or 25 kg/m$^2$ to 50 kg/m$^2$ or 27 to 40 kg/m$^2$. In some embodiments, the subject is obese. In some embodiments, the subject has a BMI of 30 kg/m$^2$ or greater (e.g., 30 to 39.9 kg/m$^2$ or 30 kg/m$^2$ to 50 kg/m$^2$). The ALK4:ActRIIB antagonist is administered alone or as a combination therapy. In some embodiments, the ALK4:ActRIIB antagonist treatment is an adjunct to diet and/or exercise.

In one embodiment the disclosure provides a method of reducing body weight in an obese subject. The method includes administering to the subject an effective amount of an ALK4:ActRIIB antagonist (e.g., an ALK4:ActRIIB heterodimer), or combination of such antagonists. In some embodiments, the subject has a BMI of 30 kg/m$^2$ or greater (e.g., 30 to 39.9 kg/m$^2$ or 30 kg/m$^2$ to 50 kg/m$^2$. In some embodiments, the subject has a BMI of 40 kg/m$^2$ or greater. In some embodiments, the subject has central obesity (e.g., excess adiposity in the abdominal region, including belly fat and/or visceral fat). In some embodiments, the subject has a waist/hip circumference ratio (WHR) of 0.85 or greater. In some embodiments, the subject has peripheral obesity (e.g., excess adiposity on the hips). In some embodiments, the ALK4:ActRIIB antagonist treatment is an adjunct to diet and/or exercise.

In another embodiment, the disclosure provides a method of treating and/or ameliorating obesity or a disease or condition associated with obesity, comprising administering to an obese subject, an effective amount of an ALK4:ActRIIB antagonist (e.g., an ALK4:ActRIIB heterodimer), or combination of such antagonists. In some embodiments, the subject has a BMI of 30 kg/m$^2$ or greater. In further embodiments, the subject has a BMI of 30 to 39.9 kg/m$^2$ or 30 kg/m$^2$ to 50 kg/m$^2$. In some embodiments, the subject is morbidly obese. In some embodiments, the subject has a body BMI of 40 kg/m$^2$ or greater. In further embodiments, the subject has a BMI of 40 kg/m$^2$ to 45 kg/m$^2$, or 40 kg/m$^2$ to 50 kg/m$^2$ In some embodiments, the subject has type 2 diabetes mellitus. In some embodiments, the subject has a BMI of 30 kg/m² or greater (e.g., 30 to 39.9 kg/m²). In some embodiments, the subject has a BMI of at least 40 kg/m². In some embodiments, the subject has central obesity (e.g., excess adiposity in the abdominal region, including belly fat and/or visceral fat). In some embodiments, the subject has a waist/hip circumference ratio (WHR) of 0.85 or greater. In some embodiments, the subject has peripheral obesity (e.g., excess adiposity on the hips). In some embodiments, the ALK4:ActRIIB antagonist treatment is an adjunct to diet and/or exercise.

Also provided is a method of treating or preventing a disease or condition associated with obesity, comprising administering to a subject in need of treatment or prevention, an effective amount of an ALK4:ActRIIB antagonist (e.g., an ALK4:ActRIIB heterodimer), or combination of such antagonists. In one embodiment, the treated or prevented disease or condition is a member selected from the group consisting of: dyslipidemia, hyperlipidemia (total cholesterol level >240 mg/dL), hypercholesterolemia (e.g., total cholesterol level of >200 mg/dL, >220 mg/dL, >240 mg/dL, >250 mg/dL, or >275 mg/dL), low HDL serum level (e.g., <40 mg/dL, <45 mg/dL, or <50 mg/dL), high LDL serum level (e.g., ≥100 mg/dL, ≥130 mg/dL, ≥160 mg/dL, or ≥190 mg/dL), and hypertriglyceridemia (e.g., a fasting TG level of ≥150 mg/dL, ≥175 mg/dL, ≥200 mg/dL, ≥300 mg/dL, ≥400 mg/dL, or ≥499 mg/dL). In one embodiment, the treated or prevented disease or condition is cardiovascular disease. In an additional embodiment, the treated or prevented disease or condition is hypertension (high blood pressure), myocardial infarction, peripheral artery disease, vasoregulatoin dysfunction, arteriosclerosis congestive heart failure, atherosclerosis, coronary heart disease, or microvascular disease. In one embodiment, the treated or prevented disease or condition is liver disease. In one embodiment, the treated or prevented liver disease or condition is NAFLD. In one embodiment, the liver disease is fatty liver. In one embodiment, the liver disease is NASH. In another embodiment, the treated or prevented disease or condition is a member selected from the group: steatohepatitis, steatosis, fibrosis, and/or cirrhosis. In certain instances, the ALK4:ActRIIB antagonist treatment is an adjunct to diet and/or exercise.

In another embodiment, the disclosure provides a method of treating, ameliorating, and/or preventing type 2 diabetes mellitus or a disease or condition associated with diabetes comprising administering to a subject having type 2 diabetes mellitus, or at risk of developing type 2 diabetes, an effective amount of an ALK4:ActRIIB antagonist (e.g., an ALK4:ActRIIB heterodimer), or combination of such antagonists. In some embodiments, the subject has a body mass index BMI of 30 kg/m² or greater (e.g., 30 to 39.9 kg/m²). In some embodiments, the subject has a BMI of at least 40 kg/m². In some embodiments, the subject has central obesity (e.g., excess adiposity in the abdominal region, including belly fat and/or visceral fat). In some embodiments, the subject has a WHR of 0.85 or greater. In some embodiments, the subject has peripheral obesity (e.g., excess adiposity on the hips). In some embodiments, the ALK4:ActRIIB antagonist treatment is an adjunct to diet and/or exercise.

Also provided is a method of treating, ameliorating or preventing a disease or condition associated with diabetes, comprising administering to a subject having diabetes, an effective amount of an ALK4:ActRIIB antagonist (e.g., an ALK4:ActRIIB heterodimer), or combination of such antagonists. In one embodiment, the treated or prevented disease or condition is a member selected from the group consisting of: dyslipidemia, hyperlipidemia (total cholesterol level >240 mg/dL), hypercholesterolemia (e.g., total cholesterol level of >200 mg/dL, >220 mg/dL, >240 mg/dL, >250 mg/dL, or >275 mg/dL), low HDL serum level (e.g., <40 mg/dL, <45 mg/dL, or <50 mg/dL), high LDL serum level (e.g., ≥100 mg/dL, ≥130 mg/dL, ≥160 mg/dL, or ≥190 mg/dL), and hypertriglyceridemia (e.g., a fasting TG level of ≥150 mg/dL, ≥175 mg/dL, ≥200 mg/dL, ≥300 mg/dL, ≥400 mg/dL, or ≥499 mg/dL). In one embodiment, the treated or prevented disease or condition is cardiovascular disease. In an additional embodiment, the treated or prevented disease or condition is hypertension (high blood pressure), myocardial infarction, peripheral artery disease, vasoregulatoin dysfunction, or arteriosclerosis. In one embodiment, the treated or prevented disease or condition is liver disease. In another embodiment, the treated or prevented disease or condition is a member selected from the group: fatty liver disease, steatohepatitis, steatosis, and/or cirrhosis. In one embodiment, the treated or prevented disease or condition is a member selected from the group consisting of: cataracts, obstructive sleep apnea, phlebitis, gout, osteoarthritis, gallbladder disease, and high cholesterol. In certain instances, the ALK4:ActRIIB antagonist treatment is an adjunct to diet and/or exercise.

The disclosure also provides a method for improving the blood-lipid profile in a subject, comprising administering to a subject in need of such treatment an effective amount of an ALK4:ActRIIB antagonist (e.g., an ALK4:ActRIIB heterodimer), or combination of such antagonists. In some embodiments, the disclosure provides a method for reducing levels of LDL cholesterol or increasing levels of HDL-cholesterol. In one embodiment, the subject has dyslipidemia. In another embodiment, the subject has elevated serum lipids (e.g., cholesterol (hypercholesterolemia) and/or triglycerides (e.g., hypertriglyceridemia). In one embodiment the subject has an LDL-C ≥100 mg/dL, ≥130 mg/dL, or ≥160 mg/dL). In one embodiment the subject has a TG ≥150 mg/dL, ≥160 mg/dL, ≥170 mg/dL). In one embodiment, the subject has elevated plasma insulin levels (hyperinsulinemia; e.g., fasting insulin level of >20 ug/ml can exceed 100). In some embodiments, the subject has type II diabetes.

According to one embodiment, the disclosure provides a method of treating or preventing a metabolic disease or disorder or a condition associated with a metabolic disease or disorder, comprising administering an ALK4:ActRIIB antagonist (e.g., an ALK4:ActRIIB heterodimer), or combination of such antagonists, to a subject in need thereof. In one embodiment, the treated metabolic disease, disorder, or condition is hyperglycemia (e.g., >130 mg/dL in the fasting state or following glucose administration during an oral glucose tolerance test). In one embodiment, the treated metabolic disease, disorder, or condition is a lipid metabolism disease, disorder, or condition. In one embodiment, the treated metabolic disease, disorder, or condition is dislipidemia. In a further embodiment, the lipid metabolism disease, disorder, or condition is a member selected from: low HDL levels, high LDL levels, high triglyceride levels, hyperlipidemia, and a lipoprotein aberration. In one embodiment, the subject has a total cholesterol level of >200 mg/dL, >220 mg/dL, >240 mg/dL, >250 mg/dL, or >275 mg/dL. In one embodiment, the subject has a HDL serum level of <40 mg/dL, <45 mg/dL, or <50 mg/dL). In one embodiment, the subject has a LDL serum level ≥100 mg/dL, ≥130 mg/dL, ≥160 mg/dL, or ≥190 mg/dL. In one embodiment, the subject has fasting TG level of ≥150 mg/dL, ≥175 mg/dL, ≥200 mg/dL, ≥300 mg/dL, ≥400 mg/dL, or ≥499 mg/dL. In one embodiment, the treated metabolic disease, disorder, or condition is a glucose metabolism disease, disorder, or condition. In a further embodiment, the glucose metabolism disease, disorder, or condition is a member selected from: glucose intolerance, insulin resistance, impaired glucose tolerance (IGT), impaired fasting glucose (IFG). In one embodiment, the treated metabolic disease, disorder, or condition is a member selected from the group consisting of: high uric acid levels, NAFLD, fatty liver, NASH, and polycystic ovarian syndrome. In one embodiment, the treated subject has hyperinsulinemia. In one embodiment, the treated subject is obese (e.g., the subject has abdominal obesity). In another embodiment, the treated subject has type II diabetes.

Metabolic syndrome is a condition involving a set of disorders that enhances the risk of heart disease. The major components of metabolic syndrome are excess weight, the cardiovascular parameters (high blood pressure, dyslipidemia, high levels of triglycerides and/or low levels of HDL in the blood), atherosclerosis, diabetes, and/or insulin resistance. A subject having several of these components, i.e. metabolic syndrome, is highly prone to heart disease, though each component is a risk factor. The disclosure also provides a method for treating or preventing 1, 2, 3, or more of the above components of metabolic syndrome, comprising administering to a subject in need of treatment an effective amount of an ALK4:ActRIIB antagonist (e.g., an ALK4: ActRIIB heterodimer), or combination of such antagonists.

Additionally provided is a method of treating, preventing or ameliorating a cardiovascular disease or condition, comprising administering an ALK4:ActRIIB antagonist (e.g., an ALK4:ActRIIB heterodimer), or combination of such antagonists, to a subject in need thereof. In one embodiment, the treated, prevented, or ameliorated cardiovascular disease or condition is atherosclerosis. In one embodiment, the treated, prevented, or ameliorated cardiovascular disease or condition is hypertension (e.g., blood pressure >130/80 mmHg or >140/90 mmHg, in a resting state. In one embodiment, the cardiovascular disease is atherosclerosis (coronary heart disease disease).

In one embodiment, the disclosure provides a method for treating and/or ameliorating an inflammatory liver disease or condition that comprises administering an ALK4:ActRIIB antagonist (e.g., an ALK4:ActRIIB heterodimer), or combination of such antagonists, to a subject in need thereof. In one embodiment, the disease or condition is NAFLD. In a further embodiment, the disease or condition is fatty liver. In a further embodiment, the disease or condition is steatosis (e.g., nonalcoholic steatohepatitis (NASH)). In a further embodiment, the disease or condition is alcoholic fatty liver disease.

This disclosure also provides a method of improving glycemic control, comprising administering to a subject in need of treatment an effective amount of an ALK4:ActRIIB antagonist (e.g., an ALK4:ActRIIB heterodimer). In one embodiment, the subject is administered has a fasting blood sugar level of >130, >135, >140, >145, or >150 mg/dL. In one embodiment, the subject is administered has a postprandial blood sugar level of >180, >185, >190, >195, or >200 mg/dL 2 hours after eating. In certain instances, the ALK4: ActRIIB antagonist treatment is an adjunct to diet and/or exercise. The administration can also reduce body weight or treat obesity. In certain instances, the subject has type 2 diabetes mellitus. In certain instances, the subject has a BMI of 27 to 40 kg/m2. In certain instances, the subject has a BMI of 30 to 39.9 kg/m2. In certain instances, the subject has a BMI of at least 40. In certain instances, the subject is overweight. In certain instances, the subject is obese. An improvement in glycemic control can be assessed using techniques known in the art such as a mixed-meal test.

The disclosure also provides compositions and methods for treating, preventing or ameliorating hyperglycemia or a condition associated with hyperglycemia in a subject comprising administering to a subject in need of such treatment an effective amount of an ALK4:ActRIIB antagonist (e.g., an ALK4:ActRIIB heterodimer). In one embodiment, the subject is administered has a fasting blood sugar level of >130, >135, >140, >145, or >150 mg/dL. In one embodiment, the subject is administered has a postprandial blood sugar level of >180, >185, >190, >195, or >200 mg/dL 2 hours after eating. In one embodiment, the result of the treatment, prevention or amelioration is a member selected from the group consisting of: a decrease in serum levels of glucose, a decrease in serum levels of triglycerides, a decrease in serum levels of insulin, and/or a decrease in serum levels of non-esterified fatty acids, as compared to serum levels in the subject prior to treatment. In one embodiment, the result of the treatment, prevention or amelioration is an increase in body temperature of about 0.4° C. to 1° C. as compared to body temperature of the subject prior to treatment. In some embodiments, the ALK4:ActRIIB treatment also reduces body weight of the subject.

In another embodiment, the disclosure provides a method of decreasing plasma insulin levels in a subject, comprising administering an effective amount of an ALK4:ActRIIB antagonist (e.g., an ALK4:ActRIIB heterodimer), to a subject in need of such treatment. In one embodiment, the subject has a fasting blood sugar level of >130, >135, >140, >145, or >150 mg/dL. In one embodiment, the subject has a postprandial blood sugar level of >180, >185, >190, >195, or >200 mg/dL 2 hours after eating. In one embodiment, the subject is overweight. In one embodiment, the subject is obese. In another embodiment, the subject has type 2 diabetes.

The disclosure also provides compositions and methods for treating, preventing or ameliorating hyperglycemia or a condition associated with hyperglycemia in a subject comprising administering to a subject in need of such treatment an effective amount of an ALK4:ActRIIB antagonist (e.g., an ALK4:ActRIIB heterodimer). In one embodiment, the subject has a fasting blood sugar level of >130, >135, >140, >145, or >150 mg/dL. In one embodiment, the subject has a postprandial blood sugar level of >180, >185, >190, >195, or >200 mg/dL 2 hours after eating. In one embodiment, the result of the treatment, prevention or amelioration is a member selected from the group consisting of: a decrease in serum levels of glucose, a decrease in serum levels of triglycerides, a decrease in serum levels of insulin, and/or a decrease in serum levels of non-esterified fatty acids, as compared to serum levels in the subject prior to treatment. In one embodiment, the result of the treatment, prevention or amelioration is an increase in body temperature of about 0.4° C. to 1° C. as compared to body temperature of the subject prior to treatment. In some embodiments, the ALK4:ActRIIB antagonist treatment also reduces body weight of the subject.

In another embodiment, the disclosure provides a method of decreasing plasma insulin levels in a subject, comprising administering an effective amount of an ALK4:ActRIIB antagonist (e.g., an ALK4:ActRIIB heterodimer), or combination of such antagonists, to a subject in need of such treatment. In one embodiment, the subject has a fasting blood sugar level of >130, >135, >140, >145, or >150 mg/dL. In one embodiment, the has a postprandial blood sugar level of >180, >185, >190, >195, or >200 mg/dL 2 hours after eating. In one embodiment, the subject is overweight. In one embodiment, the subject is obese. In another embodiment, the subject has type 2 diabetes.

In another embodiment, the disclosure provides a method of treating, preventing, or ameliorating liver disease in a subject, comprising administering an effective amount of an ALK4:ActRIIB antagonist (e.g., an ALK4:ActRIIB heterodimer), or combination of such antagonists, to a subject having a liver disease. In one embodiment, the subject has inflammation of the liver. In one embodiment, the subject has NAFLD. In on embodiment the subject has fatty liver. In another embodiment, the subject has NASH. In on embodiment the subject has fatty liver. In another embodiment, the subject has alcoholic fatty liver disease. In one embodiment, the treated, prevented or ameliorated liver disease is fibrosis, scarring, cirrhosis, or liver failure. In another embodiment, the treated, prevented or ameliorated liver disease is liver cancer. In one embodiment, the subject is overweight. In another embodiment, the subject is obese. In another embodiment, the subject has type 2 diabetes.

Fibrosis generally refers to an excessive deposition of both collagen fibers and extracellular matrix combined with a relative decrease of cell number in an organ or tissue. While this process is an important feature of natural wound healing following injury, fibrosis can lead to pathological damage in various tissue and organs including, for example, the lungs, kidneys, liver, bone, muscle, and skin. The role TGF-beta in fibrosis has been extensively study. However, other TGF-beta superfamily ligands have also been implicated in fibrosis including, for example, activins (e.g., activin A and activin B) and GDF8 [Hedger et al (2013) Cytokine and Growth Factor Reviews 24:285-295; Hardy et al. (2015) 93: 567-574; and Cantini et al. (2008) J Sex Med 5:1607-1622]. Therefore, in some embodiments, an ALK4: ActRIIB antagonist (e.g., an ALK4:ActRIIB heterodimer), or combinations of such antagonists, of the present disclosure can be used to treat fibrosis, particularly fibrosis-associated disorders and conditions. For example, an ALK4: ActRIIB antagonist (e.g., an ALK4:ActRIIB heterodimer), or combinations of such antagonists, may be used to treat or prevent one or more of: pulmonary fibrosis, hypersensitivity pneumonitis, idiopathic fibrosis, tuberculosis, pneumonia, cystic fibrosis, asthma, chronic obstructive pulmonary disease (COPD), emphysema, renal (kidney) fibrosis, renal (kidney) failure, chronic renal (kidney) disease, bone fibrosis, myelofibrosis, rheumatoid arthritis, systemic lupus erythematosus, scleroderma, sarcoidosis, granulomatosis with polyangiitis, Peyronie's disease, liver fibrosis, Wilson's disease, glycogen storage diseases (particularly types III, IV, IX, and X), iron-overload, Gaucher disease, Zellweger syndrome, nonalcoholic and alcoholic steatohepatitis, biliary cirrhosis, sclerosing cholangitis, Budd-Chiari syndrome, surgery-associated fibrosis, Crohn's disease, Duputren's contracture, mediastinal fibrosis, nephrogeneic fibrosis, retroperitoneal fibrosis, atrial fibrosis, endomyocardial fibrosis, pancreatic fibrosis.

The kidneys maintain many features of the blood, including volume, pH balance, electrolyte concentrations, and blood pressure, as well as bearing responsibility for toxin and waste filtration. These functions depend upon the intricate structure of the kidney nephrons, constant flow of blood through the various capillaries of the kidney, and the regulation of the kidney by signals from the rest of the body, including endocrine hormones. Problems with kidney function manifest by direct mechanisms (e.g. genetic defects, infection, or toxin exposure) and by indirect mechanisms progressively proceeding from long term stressors like hypertrophy and hyperfiltration (themselves often a result of more direct insults to kidney function). Due to the central role of the kidney in blood maintenance and waste secretion, kidney-associated disease manifestations are many and varied; they can be reviewed in Harrison's Principles of Internal Medicine, $18^{th}$ edition, McGraw Hill, N.Y., Part 13, Chp 277-289.

As described herein, an ALK4:ActRIIB antagonist had various beneficial effects in a kidney disease model. In particular, treatment with an ALK4:ActRIIB heteromultimer reduced kidney tissue damage, inflammation, and fibrosis in subjects having unilateral ureteral obstruction. These data indicate that ALK4:ActRIIB antagonists may be used to treat or prevent kidney disease, particularly treating or preventing various complications (manifestations) of kidney disease including, for example, kidney tissue damage, inflammation, and/or fibrosis.

Therefore, methods of this invention can be applied to various kidney-associated diseases or conditions. As used herein, "kidney-associated disease or condition" can refer to any disease, disorder, or condition that affects the kidneys or the renal system. Examples of kidney-associated diseases or conditions include, but are not limited to, chronic kidney diseases (or failure), acute kidney diseases (or failure), primary kidney diseases, non-diabetic kidney diseases, glomerulonephritis, interstitial nephritis, diabetic kidney diseases, diabetic nephropathy, glomerulosclerosis, rapid progressive glomerulonephritis, renal fibrosis, Alport syndrome, IDDM nephritis, mesangial proliferative glomerulonephritis, membranoproliferative glomerulonephritis, crescentic glomerulonephritis, renal interstitial fibrosis, focal segmental glomerulosclerosis, membranous nephropathy, minimal change disease, pauci-immune rapid progressive glomerulonephritis, IgA nephropathy, polycystic kidney disease, Dent's disease, nephrocytinosis, Heymann nephritis, autosomal dominant (adult) polycystic kidney disease, autosomal recessive (childhood) polycystic kidney disease, acute kidney injury, nephrotic syndrome, renal ischemia, podocyte diseases or disorders, proteinuria, glomerular diseases, membranous glomerulonephritis, focal segmental glomerulonephritis, pre-eclampsia, eclampsia, kidney lesions, collagen vascular diseases, benign orthostatic (postural) proteinuria, IgM nephropathy, membranous nephropathy, sarcoidosis, diabetes mellitus, kidney damage due to drugs, Fabry's disease, aminoaciduria, Fanconi syndrome, hypertensive nephrosclerosis, interstitial nephritis, Sickle cell disease, hemoglobinuria, myoglobinuria, Wegener's Granulomatosis, Glycogen Storage Disease Type 1, chronic kidney disease, chronic renal failure, low Glomerular Filtration Rate (GFR), nephroangiosclerosis, lupus nephritis, ANCA-positive pauci-immune crescentic glomerulonephritis, chronic allograft nephropathy, nephrotoxicity, renal toxicity, kidney necrosis, kidney damage, glomerular and tubular injury, kidney dysfunction, nephritic syndrome, acute renal failure, chronic renal failure, proximal tubal dysfunction, acute kidney transplant rejection, chronic kidney transplant rejection, non-IgA mesangioproliferative glomerulonephritis, postinfectious glomerulonephritis, vasculitides with renal involvement of any kind, any hereditary renal disease, any interstitial nephritis, renal transplant failure, kidney cancer, kidney disease associated with other conditions (e.g., hypertension, diabetes, and autoimmune disease), Dent's disease, nephrocytinosis, Heymann nephritis, a primary kidney disease, a collapsing glomerulopathy, a dense deposit disease, a cryoglobulinemia-associated glomerulonephritis, an Henoch-Schonlein disease, a postinfectious glomerulonephritis, a bacterial endocarditis, a microscopic polyangitis, a Churg-Strauss syndrome, an anti-GBM-antibody mediated glomerulonephritis, amyloidosis, a monoclonal immunoglobulin deposition disease, a fibrillary glomerulonephritis, an immunotactoid glomerulopathy, ischemic tubular injury, a medication-induced tubulo-interstitial nephritis, a toxic tubulo-interstitial nephritis, an infectious tubulo-interstitial nephritis, a bacterial pyelonephritis, a viral infectious tubulo-interstitial nephritis which results from a polyomavirus infection or an HIV infection, a metabolic-induced tubulo-interstitial disease, a mixed connective disease, a cast nephropathy, a crystal nephropathy which may results from urate or oxalate or drug-induced crystal deposition, an acute cellular tubulo-interstitial allograft rejection, a tumoral infiltrative disease which results from a lymphoma or a post-transplant lymphoproliferative disease, an obstructive disease of the kidney, vascular disease, a thrombotic microangiopathy, a nephroangiosclerosis, an atheroembolic disease, a mixed connective tissue disease, a polyarteritis nodosa, a calcineurin-inhibitor induced-vascular disease, an acute cellular vascular allograft rejection, an acute humoral allograft rejection, early renal function decline (ERFD), end stage renal disease (ESRD), renal vein thrombosis, acute tubular necrosis, acute interstitial nephritis, established chronic kidney disease, renal artery stenosis, ischemic nephropathy, uremia, drug and toxin-induced chronic tubulointerstitial nephritis, reflux nephropathy, kidney stones, Goodpasture's syndrome, normocytic normochromic anemia, renal anemia, diabetic chronic kidney disease, IgG4-related disease, von Hippel-Lindau syndrome, tuberous sclerosis, nephronophthisis, medullary cystic kidney disease, renal cell carcinoma, adenocarcinoma, nephroblastoma, lymphoma, leukemia, hyposialylation disorder, chronic cyclosporine nephropathy, renal reperfusion injury, renal dysplasia, azotemia, bilateral arterial occlusion, acute uric acid nephropathy, hypovolemia, acute bilateral obstructive uropathy, hypercalcemic nephropathy, hemolytic uremic syndrome, acute urinary retention, malignant nephrosclerosis, postpartum glomerulosclerosis, scleroderma, non-Goodpasture's anti-GBM disease, microscopic polyarteritis nodosa, allergic granulomatosis, acute radiation nephritis, post-streptococcal glomerulonephritis, Waldenstrom's macroglobulinemia, analgesic nephropathy, arteriovenous fistula, arteriovenous graft, dialysis, ectopic kidney, medullary sponge kidney, renal osteodystrophy, solitary kidney, hydronephrosis, microalbuminuria, uremia, haematuria, hyperlipidemia, hypoalbuminaemia, lipiduria, acidosis, hyperkalemia, and edema.

In some embodiments, an ALK4:ActRIIB antagonist, or combinations of such antagonists, of the present disclosure (e.g., ALK4:ActRIIB heteromultimers such as an ALK4:ActRIIB heterodimer) may be used to treat or prevent chronic kidney disease, optionally in combination with one or more supportive therapies for treating chronic kidney disease. In some embodiments, an ALK4:ActRIIB antagonist, or combinations of such antagonists, of the present disclosure (e.g., ALK4:ActRIIB heteromultimers such as an ALK4:ActRIIB heterodimer) may be used to treat or prevent one or more complications (symptoms or manifestations) of chronic kidney disease, optionally in combination with one or more supportive therapies for treating chronic kidney disease. In some embodiments, an ALK4:ActRIIB antagonist, or combinations of such antagonists, of the present disclosure (e.g., ALK4:ActRIIB heteromultimers such as an ALK4:ActRIIB heterodimer) may be used to treat or prevent end-stage kidney failure, optionally in combination with one or more supportive therapies for treating end-stage kidney disease. Chronic kidney disease (CKD), also known as chronic renal disease, is a progressive loss in renal function over a period of months or years. The symptoms of worsening kidney function may include feeling generally unwell and experiencing a reduced appetite. Often, chronic kidney disease is diagnosed as a result of screening of people known to be at risk of kidney problems, such as those with high blood pressure or diabetes and those with a blood relative with CKD. This disease may also be identified when it leads to one of its recognized complications, such as cardiovascular disease, anemia, or pericarditis. Recent professional guidelines classify the severity of CKD in five stages, with stage 1 being the mildest and usually causing few symptoms and stage 5 being a severe illness with poor life expectancy if untreated. Stage 5 CKD is often called end-stage kidney disease, end-stage renal disease, or end-stage kidney failure, and is largely synonymous with the now outdated terms chronic renal failure or chronic kidney failure; and usually means the patient requires renal replacement therapy, which may involve a form of dialysis, but ideally constitutes a kidney transplant. CKD is initially without specific symptoms and is generally only detected as an increase in serum creatinine or protein in the urine. As the kidney function decreases and various symptoms may manifest as described below. Blood pressure may be increased due to fluid overload and production of vasoactive hormones created by the kidney via the renin-angiotensin system, increasing one's risk of developing hypertension and/or suffering from congestive heart failure. Urea may accumulate, leading to azotemia and ultimately uremia (symptoms ranging from lethargy to pericarditis and encephalopathy). Due to its high systemic circulation, urea is excreted in eccrine sweat at high concentrations and crystallizes on skin as the sweat evaporates ("uremic frost"). Potassium may accumulate in the blood (hyperkalemia with a range of symptoms including malaise and potentially fatal cardiac arrhythmias). Hyperkalemia usually does not develop until the glomerular filtration rate falls to less than 20-25 ml/min/1.73 m2, at which point the kidneys have decreased ability to excrete potassium. Hyperkalemia in CKD can be exacerbated by acidemia (which leads to extracellular shift of potassium) and from lack of insulin. Erythropoietin synthesis may be decreased causing anemia. Fluid volume overload symptoms may occur, ranging from mild edema to life-threatening pulmonary edema. Hyperphosphatemia, due to reduced phosphate excretion, may occur generally following the decrease in glomerular filtration. Hyperphosphatemia is associated with increased cardiovascular risk, being a direct stimulus to vascular calcification. Hypocalcemia may manifest, which is generally caused by stimulation of fibroblast growth factor-23. Osteocytes are responsible for the increased production of FGF23, which is a potent inhibitor of the enzyme 1-alpha-hydroxylase (responsible for the conversion of 25-hydroxycholecalciferol into 1,25 dihydroxyvitamin D3). Later, this progresses to secondary hyperparathyroidism, renal osteodystrophy, and vascular calcification that further impairs cardiac function. Metabolic acidosis (due to accumulation of sulfates, phosphates, uric acid etc.) may occur and cause altered enzyme activity by excess acid acting on enzymes; and also increased excitability of cardiac and neuronal membranes by the promotion of hyperkalemia due to excess acid (acidemia). Acidosis is also due to decreased capacity to generate enough ammonia from the cells of the proximal tubule. Iron deficiency anemia, which increases in prevalence as kidney function decreases, is especially prevalent in those requiring haemodialysis. It is multifactoral in cause, but includes increased inflammation, reduction in erythropoietin, and hyperuricemia leading to bone marrow suppression. People with CKD suffer from accelerated atherosclerosis and are more likely to develop cardiovascular disease than the general population. Patients afflicted with CKD and cardiovascular disease tend to have significantly worse prognoses than those suffering only from the latter.

As used herein, "in combination with", "combinations of", or "conjoint administration" refers to any form of administration such that additional therapies (e.g., second, third, fourth, etc.) are still effective in the body (e.g., multiple compounds are simultaneously effective in the patient, which may include synergistic effects of those compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapies. One or more ALK4:ActRIIB antagonists of the disclosure can be administered concurrently with, prior to, or subsequent to, one or more other additional agents or supportive therapies. In general, each therapeutic agent will be administered at a dose and/or on a time schedule determined for that particular agent. The particular combination to employ in a regimen will take into account compatibility of the antagonist of the present disclosure with the therapy and/or the desired.

7. Pharmaceutical Compositions

In certain aspects, ALK4:ActRIIB antagonists (e.g., ALK4:ActRIIB heteromultimers), or combinations of such antagonists, of the present disclosure can be administered alone or as a component of a pharmaceutical formulation (also referred to as a therapeutic composition or pharmaceutical composition). A pharmaceutical formation refers to a preparation which is in such form as to permit the biological activity of an active ingredient (e.g., an agent of the present disclosure) contained therein to be effective and which contains no additional components which are unacceptably toxic to a subject to which the formulation would be administered. The subject compounds may be formulated for administration in any convenient way for use in human or veterinary medicine. For example, one or more agents of the present disclosure may be formulated with a pharmaceutically acceptable carrier. A pharmaceutically acceptable carrier refers to an ingredient in a pharmaceutical formulation, other than an active ingredient, which is generally nontoxic to a subject. A pharmaceutically acceptable carrier includes, but is not limited to, a buffer, excipient, stabilizer, and/or preservative. In general, pharmaceutical formulations for use in the present disclosure are in a pyrogen-free, physiologically-acceptable form when administered to a subject. Therapeutically useful agents other than those described herein, which may optionally be included in the formulation as described above, may be administered in combination with the subject agents in the methods of the present disclosure.

In certain embodiments, compositions will be administered parenterally [e.g., by intravenous (I. V.) injection, intraarterial injection, intraosseous injection, intramuscular injection, intrathecal injection, subcutaneous injection, or intradermal injection]. Pharmaceutical compositions suitable for parenteral administration may comprise one or more agents of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use. Injectable solutions or dispersions may contain antioxidants, buffers, bacteriostats, suspending agents, thickening agents, or solutes which render the formulation isotonic with the blood of the intended recipient. Examples of suitable aqueous and nonaqueous carriers which may be employed in the pharmaceutical formulations of the present disclosure include water, ethanol, polyols (e.g., glycerol, propylene glycol, polyethylene glycol, etc.), vegetable oils (e.g., olive oil), injectable organic esters (e.g., ethyl oleate), and suitable mixtures thereof. Proper fluidity can be maintained, for example, by the use of coating materials (e.g., lecithin), by the maintenance of the required particle size in the case of dispersions, and by the use of surfactants.

In some embodiments, a therapeutic method of the present disclosure includes administering the pharmaceutical composition systemically, or locally, from an implant or device. Further, the pharmaceutical composition may be encapsulated or injected in a form for delivery to a target tissue site (e.g., bone marrow or muscle). In certain embodiments, compositions of the present disclosure may include a matrix capable of delivering one or more of the agents of the present disclosure to a target tissue site (e.g., bone marrow or muscle), providing a structure for the developing tissue and optimally capable of being resorbed into the body. For example, the matrix may provide slow release of one or more agents of the present disclosure. Such matrices may be formed of materials presently in use for other implanted medical applications.

The choice of matrix material may be based on one or more of: biocompatibility, biodegradability, mechanical properties, cosmetic appearance, and interface properties. The particular application of the subject compositions will define the appropriate formulation. Potential matrices for the compositions may be biodegradable and chemically defined calcium sulfate, tricalciumphosphate, hydroxyapatite, polylactic acid, and polyanhydrides. Other potential materials are biodegradable and biologically well-defined including, for example, bone or dermal collagen. Further matrices are comprised of pure proteins or extracellular matrix components. Other potential matrices are non-biodegradable and chemically defined including, for example, sintered hydroxyapatite, bioglass, aluminates, or other ceramics. Matrices may be comprised of combinations of any of the above mentioned types of material including, for example, polylactic acid and hydroxyapatite or collagen and tricalciumphosphate. The bioceramics may be altered in composition (e.g., calcium-aluminate-phosphate) and processing to alter one or more of pore size, particle size, particle shape, and biodegradability.

In certain embodiments, pharmaceutical compositions of present disclosure can be administered topically. "Topical application" or "topically" means contact of the pharmaceutical composition with body surfaces including, for example, the skin, wound sites, and mucous membranes. The topical pharmaceutical compositions can have various application forms and typically comprises a drug-containing layer, which is adapted to be placed near to or in direct contact with the tissue upon topically administering the composition. Pharmaceutical compositions suitable for topical administration may comprise one or more one or more ALK4:ActRIIB antagonists of the disclosure in combination formulated as a liquid, a gel, a cream, a lotion, an ointment, a foam, a paste, a putty, a semi-solid, or a solid. Compositions in the liquid, gel, cream, lotion, ointment, foam, paste, or putty form can be applied by spreading, spraying, smearing, dabbing or rolling the composition on the target tissue. The compositions also may be impregnated into sterile dressings, transdermal patches, plasters, and bandages. Compositions of the putty, semi-solid or solid forms may be deformable. They may be elastic or non-elastic (e.g., flexible or rigid). In certain aspects, the composition forms part of a composite and can include fibers, particulates, or multiple layers with the same or different compositions.

Topical compositions in the liquid form may include pharmaceutically acceptable solutions, emulsions, microemulsions, and suspensions. In addition to the active ingredient(s), the liquid dosage form may contain an inert diluent commonly used in the art including, for example, water or other solvent, a solubilizing agent and/or emulsifier [e.g., ethyl alcohol, isopropyl alcohol, ethyl carbonate, ethyl acetate, benzyl alcohol, benzyl benzoate, propylene glycol, or 1,3-butylene glycol, an oil (e.g., cottonseed, groundnut, corn, germ, olive, castor, and sesame oil), glycerol, tetrahydrofuryl alcohol, a polyethylene glycol, a fatty acid ester of sorbitan, and mixtures thereof].

Topical gel, cream, lotion, ointment, semi-solid or solid compositions may include one or more thickening agents, such as a polysaccharide, synthetic polymer or protein-based polymer. In one embodiment of the invention, the gelling agent herein is one that is suitably nontoxic and gives the desired viscosity. The thickening agents may include polymers, copolymers, and monomers of: vinylpyrrolidones, methacrylamides, acrylamides N-vinylimidazoles, carboxy vinyls, vinyl esters, vinyl ethers, silicones, polyethyleneoxides, polyethyleneglycols, vinylalcohols, sodium acrylates, acrylates, maleic acids, NN-dimethylacrylamides, diacetone acrylamides, acrylamides, acryloyl morpholine, pluronic, collagens, polyacrylamides, polyacrylates, polyvinyl alcohols, polyvinylenes, polyvinyl silicates, polyacrylates substituted with a sugar (e.g., sucrose, glucose, glucosamines, galactose, trehalose, mannose, or lactose), acylamidopropane sulfonic acids, tetramethoxyorthosilicates, methyltrimethoxyorthosilicates, tetraalkoxyorthosilicates, trialkoxyorthosilicates, glycols, propylene glycol, glycerine, polysaccharides, alginates, dextrans, cyclodextrin, celluloses, modified celluloses, oxidized celluloses, chitosans, chitins, guars, carrageenans, hyaluronic acids, inulin, starches, modified starches, agarose, methylcelluloses, plant gums, hylaronans, hydrogels, gelatins, glycosaminoglycans, carboxymethyl celluloses, hydroxyethyl celluloses, hydroxy propyl methyl celluloses, pectins, low-methoxy pectins, cross-linked dextrans, starch-acrylonitrile graft copolymers, starch sodium polyacrylate, hydroxyethyl methacrylates, hydroxyl ethyl acrylates, polyvinylene, polyethylvinylethers, polymethyl methacrylates, polystyrenes, polyurethanes, polyalkanoates, polylactic acids, polylactates, poly (3-hydroxybutyrate), sulfonated hydrogels, AMPS (2-acrylamido-2-methyl-1-propanesulfonic acid), SEM (sulfoethylmethacrylate), SPM (sulfopropyl methacrylate), SPA (sulfopropyl acrylate), N,N-dimethyl-N-methacryloxyethyl-N-(3-sulfopropyl)ammonium betaine, methacryllic acid amidopropyl-dimethyl ammonium sulfobetaine, SPI (itaconic acid-bis(1-propyl sulfonizacid-3) ester di-potassium salt), itaconic acids, AMBC (3-acrylamido-3-methylbutanoic acid), beta-carboxyethyl acrylate (acrylic acid dimers), and maleic anhydride-methylvinyl ether polymers, derivatives thereof, salts thereof, acids thereof, and combinations thereof. In certain embodiments, pharmaceutical compositions of present disclosure can be administered orally, for example, in the form of capsules, cachets, pills, tablets, lozenges (using a flavored basis such as sucrose and acacia or tragacanth), powders, granules, a solution or a suspension in an aqueous or non-aqueous liquid, an oil-in-water or water-in-oil liquid emulsion, or an elixir or syrup, or pastille (using an inert base, such as gelatin and glycerin, or sucrose and acacia), and/or a mouth wash, each containing a predetermined amount of a compound of the present disclosure and optionally one or more other active ingredients. A compound of the present disclosure and optionally one or more other active ingredients may also be administered as a bolus, electuary, or paste.

In solid dosage forms for oral administration (e.g., capsules, tablets, pills, dragees, powders, and granules), one or more compounds of the present disclosure may be mixed with one or more pharmaceutically acceptable carriers including, for example, sodium citrate, dicalcium phosphate, a filler or extender (e.g., a starch, lactose, sucrose, glucose, mannitol, and silicic acid), a binder (e.g. carboxymethylcellulose, an alginate, gelatin, polyvinyl pyrrolidone, sucrose, and acacia), a humectant (e.g., glycerol), a disintegrating agent (e.g., agar-agar, calcium carbonate, potato or tapioca starch, alginic acid, a silicate, and sodium carbonate), a solution retarding agent (e.g. paraffin), an absorption accelerator (e.g. a quaternary ammonium compound), a wetting agent (e.g., cetyl alcohol and glycerol monostearate), an absorbent (e.g., kaolin and bentonite clay), a lubricant (e.g., a talc, calcium stearate, magnesium stearate, solid polyethylene glycols, sodium lauryl sulfate), a coloring agent, and mixtures thereof. In the case of capsules, tablets, and pills, the pharmaceutical formulation (composition) may also comprise a buffering agent. Solid compositions of a similar type may also be employed as fillers in soft and hard-filled gelatin capsules using one or more excipients including, e.g., lactose or a milk sugar as well as a high molecular-weight polyethylene glycol.

Liquid dosage forms for oral administration of the pharmaceutical composition may include pharmaceutically acceptable emulsions, microemulsions, solutions, suspensions, syrups, and elixirs. In addition to the active ingredient (s), the liquid dosage form may contain an inert diluent commonly used in the art including, for example, water or other solvent, a solubilizing agent and/or emulsifier [e.g., ethyl alcohol, isopropyl alcohol, ethyl carbonate, ethyl acetate, benzyl alcohol, benzyl benzoate, propylene glycol, or 1,3-butylene glycol, an oil (e.g., cottonseed, groundnut, corn, germ, olive, castor, and sesame oil), glycerol, tetrahydrofuryl alcohol, a polyethylene glycol, a fatty acid ester of sorbitan, and mixtures thereof]. Besides inert diluents, the oral formulation can also include an adjuvant including, for example, a wetting agent, an emulsifying and suspending agent, a sweetening agent, a flavoring agent, a coloring agent, a perfuming agent, a preservative agent, and combinations thereof.

Suspensions, in addition to the active compounds, may contain suspending agents including, for example, an ethoxylated isostearyl alcohol, polyoxyethylene sorbitol, a sorbitan ester, microcrystalline cellulose, aluminum metahydroxide, bentonite, agar-agar, tragacanth, and combinations thereof.

Prevention of the action and/or growth of microorganisms may be ensured by the inclusion of various antibacterial and antifungal agents including, for example, paraben, chlorobutanol, and phenol sorbic acid.

In certain embodiments, it may be desirable to include an isotonic agent including, for example, a sugar or sodium chloride into the compositions. In addition, prolonged absorption of an injectable pharmaceutical form may be brought about by the inclusion of an agent that delay absorption including, for example, aluminum monostearate and gelatin.

It is understood that the dosage regimen will be determined by the attending physician considering various factors which modify the action of the one or more of the agents of the present disclosure. In the case of a ALK4:ActRIIB antagonist that promotes red blood cell formation, various factors may include, but are not limited to, the patient's red blood cell count, hemoglobin level, the desired target red blood cell count, the patient's age, the patient's sex, the patient's diet, the severity of any disease that may be contributing to a depressed red blood cell level, the time of administration, and other clinical factors. The addition of other known active agents to the final composition may also affect the dosage. Progress can be monitored by periodic assessment of one or more of red blood cell levels, hemoglobin levels, reticulocyte levels, and other indicators of the hematopoietic process.

In certain embodiments, the present disclosure also provides gene therapy for the in vivo production of one or more of the agents of the present disclosure. Such therapy would achieve its therapeutic effect by introduction of the agent sequences into cells or tissues having one or more of the disorders as listed above. Delivery of the agent sequences can be achieved, for example, by using a recombinant expression vector such as a chimeric virus or a colloidal dispersion system. Preferred therapeutic delivery of one or more of agent sequences of the disclosure is the use of targeted liposomes.

Various viral vectors which can be utilized for gene therapy as taught herein include adenovirus, herpes virus, vaccinia, or an RNA virus (e.g., a retrovirus). The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing one or more of the agents of the present disclosure.

Alternatively, tissue culture cells can be directly transfected with plasmids encoding the retroviral structural genes (gag, pol, and env), by conventional calcium phosphate transfection. These cells are then transfected with the vector plasmid containing the genes of interest. The resulting cells release the retroviral vector into the culture medium.

Another targeted delivery system for one or more of the agents of the present disclosure is a colloidal dispersion system. Colloidal dispersion systems include, for example, macromolecule complexes, nanocapsules, microspheres, beads, and lipid-based systems including oil-in-water emulsions, micelles, mixed micelles, and liposomes. In certain embodiments, the preferred colloidal system of this disclosure is a liposome. Liposomes are artificial membrane vesicles which are useful as delivery vehicles in vitro and in vivo. RNA, DNA, and intact virions can be encapsulated within the aqueous interior and be delivered to cells in a biologically active form [Fraley, et al. (1981) Trends Biochem. Sci., 6:77]. Methods for efficient gene transfer using a liposome vehicle are known in the art [Mannino, et al. (1988) Biotechniques, 6:682, 1988].

The composition of the liposome is usually a combination of phospholipids, which may include a steroid (e.g. cholesterol). The physical characteristics of liposomes depend on pH, ionic strength, and the presence of divalent cations. Other phospholipids or other lipids may also be used including, for example a phosphatidyl compound (e.g., phosphatidylglycerol, phosphatidylcholine, phosphatidylserine, phosphatidylethanolamine, a sphingolipid, a cerebroside, and a ganglioside), egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

EXEMPLIFICATION

The invention now being generally described, it will be more readily understood by reference to the following examples, which are included merely for purposes of illustration of certain embodiments and embodiments of the present invention, and are not intended to limit the invention.

Example 1. Generation of an ALK4:ActRIIB Heterodimer

Applicants constructed a soluble ALK4-Fc:ActRIIB-Fc heteromeric complex comprising the extracellular domains of human ActRIIB and human ALK4, which are each separately fused to an Fc domain with a linker positioned between the extracellular domain and the Fc domain. The individual constructs are referred to as ActRIIB-Fc fusion polypeptide and ALK4-Fc fusion polypeptide, respectively, and the sequences for each are provided below.

A methodology for promoting formation of ALK4-Fc:ActRIIB-Fc heteromeric complexes, as opposed to ActRIIB-Fc or ALK4-Fc homodimeric complexes, is to introduce alterations in the amino acid sequence of the Fc domains to guide the formation of asymmetric heteromeric complexes. Many different approaches to making asymmetric interaction pairs using Fc domains are described in this disclosure.

In one approach, illustrated in the ActRIIB-Fc and ALK4-Fc polypeptide sequences of SEQ ID NOs: 39-41 and 42-44, respectively, one Fc domain is altered to introduce cationic amino acids at the interaction face, while the other Fc domain is altered to introduce anionic amino acids at the interaction face. ActRIIB-Fc fusion polypeptide and ALK4-Fc fusion polypeptide each employ the tissue plasminogen activator (TPA) leader: MDAMKRGLCCVLLLC-GAVFVSP (SEQ ID NO: 38).

The ActRIIB-Fc polypeptide sequence (SEQ ID NO: 39) is shown below:

```
                                                          (SEQ ID NO: 39)
  1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPSRKEMT KNQVSLTCLV KGFYPSDIAV

301 EWESNGQPEN NYKTTPPVLK SDGSFFLYSK LTVDKSRWQQ GNVFSCSVMH

351 EALHNHYTQK SLSLSPGK
```

The leader (signal) sequence and linker are underlined. To promote formation of ALK4-Fc:ActRIIB-Fc heterodimer rather than either of the possible homodimeric complexes, two amino acid substitutions (replacing acidic amino acids with lysine) can be introduced into the Fc domain of the ActRIIB fusion protein as indicated by double underline above. The amino acid sequence of SEQ ID NO: 39 may optionally be provided with lysine (K) removed from the C-terminus.

This ActRIIB-Fc fusion protein is encoded by the following nucleic acid sequence (SEQ ID NO: 40):

```
                                                          (SEQ ID NO: 40)
   1 ATGGATGCAA TGAAGAGAGG GCTCTGCTGT GTGCTGCTGC TGTGTGGAGC

51 AGTCTTCGTT TCGCCCGGCG CCTCTGGGCG TGGGGAGGCT GAGACACGGG

101 AGTGCATCTA CTACAACGCC AACTGGGAGC TGGAGCGCAC CAACCAGAGC

151 GGCCTGGAGC GCTGCGAAGG CGAGCAGGAC AAGCGGCTGC ACTGCTACGC

201 CTCCTGGCGC AACAGCTCTG GCACCATCGA GCTCGTGAAG AAGGGCTGCT

251 GGCTAGATGA CTTCAACTGC TACGATAGGC AGGAGTGTGT GGCCACTGAG

301 GAGAACCCCC AGGTGTACTT CTGCTGCTGT GAAGGCAACT TCTGCAACGA

351 GCGCTTCACT CATTTGCCAG AGGCTGGGGG CCCGGAAGTC ACGTACGAGC

401 CACCCCCGAC AGCCCCCACC GGTGGTGGAA CTCACACATG CCCACCGTGC

451 CCAGCACCTG AACTCCTGGG GGGACCGTCA GTCTTCCTCT TCCCCCCAAA

501 ACCCAAGGAC ACCCTCATGA TCTCCCGGAC CCCTGAGGTC ACATGCGTGG

551 TGGTGGACGT GAGCCACGAA GACCCTGAGG TCAAGTTCAA CTGGTACGTG

601 GACGGCGTGG AGGTGCATAA TGCCAAGACA AAGCCGCGGG AGGAGCAGTA

651 CAACAGCACG TACCGTGTGG TCAGCGTCCT CACCGTCCTG CACCAGGACT

701 GGCTGAATGG CAAGGAGTAC AAGTGCAAGG TCTCCAACAA AGCCCTCCCA

751 GCCCCCATCG AGAAAACCAT CTCCAAAGCC AAAGGGCAGC CCGAGAACC

801 ACAGGTGTAC ACCCTGCCCC CATCCCGGAA GGAGATGACC AAGAACCAGG

851 TCAGCCTGAC CTGCCTGGTC AAAGGCTTCT ATCCCAGCGA CATCGCCGTG

901 GAGTGGGAGA GCAATGGGCA GCCGGAGAAC AACTACAAGA CCACGCCTCC

951 CGTGCTGAAG TCCGACGGCT CCTTCTTCCT CTATAGCAAG CTCACCGTGG

1001 ACAAGAGCAG GTGGCAGCAG GGGAACGTCT TCTCATGCTC CGTGATGCAT

1051 GAGGCTCTGC ACAACCACTA CACGCAGAAG AGCCTCTCCC TGTCTCCGGG

1101 TAAA
```

The mature ActRIIB-Fc fusion polypeptide (SEQ ID NO: 41) is as follows, and may optionally be provided with lysine (K) removed from the C-terminus.

```
                                                     (SEQ ID NO: 41)
  1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPS

251 RKEMTKNQVS LTCLVKGFYP SDIAVEWESN GQPENNYKTT PPVLKSDGSF

301 FLYSKLTVDK SRWQQGNVFS CSVMHEALHN HYTQKSLSLS PGK
```

The complementary form of ALK4-Fc fusion polypeptide (SEQ ID NO: 42) is as follows:

```
                                                     (SEQ ID NO: 42)
  1 MDAMKRGLCC VLLLCGAVFV SPGASGPRGV QALLCACTSC LQANYTCETD

51 GACMVSIFNL DGMEHHVRTC IPKVELVPAG KPFYCLSSED LRNTHCCYTD

101 YCNRIDLRVP SGHLKEPEHP SMWGPVETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVYTL PPSREEMTKN QVSLTCLVKG FYPSDIAVEW ESNGQPENNY

301 DTTPPVLDSD GSFFLYSDLT VDKSRWQQGN VFSCSVMHEA LHNHYTQKSL

351 SLSPG
```

The leader sequence and linker are underlined. To guide heterodimer formation with the ActRIIB-Fc fusion polypeptide of SEQ ID NOs: 39 and 41 above, two amino acid substitutions (replacing lysines with aspartic acids) can be introduced into the Fc domain of the ALK4-Fc fusion polypeptide as indicated by double underline above. The amino acid sequence of SEQ ID NO: 42 may optionally be provided with lysine (K) added at the C-terminus.

This ALK4-Fc fusion protein is encoded by the following nucleic acid (SEQ ID NO: 43):

```
                                                     (SEQ ID NO: 43)
  1 ATGGATGCAA TGAAGAGAGG GCTCTGCTGT GTGCTGCTGC TGTGTGGAGC

51 AGTCTTCGTT TCGCCCGGCG CCTCCGGGCC CCGGGGGGTC CAGGCTCTGC

101 TGTGTGCGTG CACCAGCTGC CTCCAGGCCA ACTACACGTG TGAGACAGAT

151 GGGGCCTGCA TGGTTTCCAT TTTCAATCTG GATGGGATGG AGCACCATGT

201 GCGCACCTGC ATCCCCAAAG TGGAGCTGGT CCCTGCCGGG AAGCCCTTCT

251 ACTGCCTGAG CTCGGAGGAC CTGCGCAACA CCCACTGCTG CTACACTGAC

301 TACTGCAACA GGATCGACTT GAGGGTGCCC AGTGGTCACC TCAAGGAGCC

351 TGAGCACCCG TCCATGTGGG GCCCGGTGGA GACCGGTGGT GGAACTCACA

401 CATGCCCACC GTGCCCAGCA CCTGAACTCC TGGGGGGACC GTCAGTCTTC

451 CTCTTCCCCC CAAAACCCAA GGACACCCTC ATGATCTCCC GGACCCCTGA

501 GGTCACATGC GTGGTGGTGG ACGTGAGCCA CGAAGACCCT GAGGTCAAGT

551 TCAACTGGTA CGTGGACGGC GTGGAGGTGC ATAATGCCAA GACAAAGCCG

601 CGGGAGGAGC AGTACAACAG CACGTACCGT GTGGTCAGCG TCCTCACCGT

651 CCTGCACCAG GACTGGCTGA ATGGCAAGGA GTACAAGTGC AAGGTCTCCA

701 ACAAAGCCCT CCCAGCCCCC ATCGAGAAAA CCATCTCCAA AGCCAAAGGG
```

```
 751 CAGCCCCGAG AACCACAGGT GTACACCCTG CCCCCATCCC GGGAGGAGAT

801 GACCAAGAAC CAGGTCAGCC TGACCTGCCT GGTCACATGC TTCTATCCCA

851 GCGACATCGC CGTGGAGTGG GAGAGCAATG GGCAGCCGGA GAACAACTAC

901 GACACCACGC CTCCCGTGCT GGACTCCGAC GGCTCCTTCT TCCTCTATAG

951 CGACCTCACC GTGGACAAGA GCAGGTGGCA GCAGGGGAAC GTCTTCTCAT

1001 GCTCCGTGAT GCATGAGGCT CTGCACAACC ACTACACGCA GAAGAGCCTC

1051 TCCCTGTCTC CGGGT
```

The mature ALK4-Fc fusion protein sequence (SEQ ID NO: 44) is as follows and may optionally be provided with lysine (K) added at the C-terminus.

```
                                              (SEQ ID NO: 44)
  1 SGPRGVQALL CACTSCLQAN YTCETDGACM VSIFNLDGME HHVRTCIPKV

51 ELVPAGKPFY CLSSEDLRNT HCCYTDYCNR IDLRVPSGHL KEPEHPSMWG

101 PVETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVYTLPPSR EEMTKNQVSL

251 TCLVKGFYPS DIAVEWESNG QPENNYDTTP PVLDSDGSFF LYSDLTVDKS

301 RWQQGNVFSC SVMHEALHNH YTQKSLSLSP G
```

The ActRIIB-Fc and ALK4-Fc proteins of SEQ ID NO: 41 and SEQ ID NO: 44, respectively, may be co-expressed and purified from a CHO cell line, to give rise to a heteromeric complex comprising ALK4-Fc:ActRIIB-Fc.

In another approach to promote the formation of heteromultimer complexes using asymmetric Fc fusion proteins the Fc domains are altered to introduce complementary hydrophobic interactions and an additional intermolecular disulfide bond as illustrated in the ActRIIB-Fc and ALK4-Fc polypeptide sequences of SEQ ID NOs: 45-46 and 47-48, respectively. The ActRIIB-Fc fusion polypeptide and ALK4-Fc fusion polypeptide each employ the tissue plasminogen activator (TPA) leader: MDAMKRGLCCVLLLC-GAVFVSP (SEQ ID NO: 38).

The ActRIIB-Fc polypeptide sequence (SEQ ID NO: 45) is shown below:

```
                                              (SEQ ID NO: 45)
  1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPCREEMT KNQVSLWCLV KGFYPSDIAV

301 EWESNGQPEN NYKTTPPVLD SDGSFFLYSK LTVDKSRWQQ GNVFSCSVMH

351 EALHNHYTQK SLSLSPGK
```

The leader (signal) sequence and linker are underlined. To promote formation of the ALK4-Fc:ActRIIB-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 45 may optionally be provided with lysine (K) removed from the C-terminus.

The mature ActRIIB-Fc fusion polypeptide is as follows:

```
                                                     (SEQ ID NO: 46)
  1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPC

251 REEMTKNQVS LWCLVKGFYP SDIAVEWESN GQPENNYKTT PPVLDSDGSF

301 FLYSKLTVDK SRWQQGNVFS CSVMHEALHN HYTQKSLSLS PGK
```

The complementary form of ALK4-Fc fusion polypeptide (SEQ ID NO: 47) is as follows and may optionally be provided with lysine (K) removed from the C-terminus.

```
                                                     (SEQ ID NO: 47)
  1 MDAMKRGLCC VLLLCGAVFV SPGASGPRGV QALLCACTSC LQANYTCETD

51 GACMVSIFNL DGMEHHVRTC IPKVELVPAG KPFYCLSSED LRNTHCCYTD

101 YCNRIDLRVP SGHLKEPEHP SMWGPVETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVCTL PPSREEMTKN QVSLSCAVKG FYPSDIAVEW ESNGQPENNY

301 KTTPPVLDSD GSFFLVSKLT VDKSRWQQGN VFSCSVMHEA LHNHYTQKSL

351 SLSPGK
```

The leader sequence and the linker are underlined. To guide heterodimer formation with the ActRIIB-Fc fusion polypeptide of SEQ ID NOs: 45 and 46 above, four amino acid substitutions can be introduced into the Fc domain of the ALK4 fusion polypeptide as indicated by double underline above. The amino acid sequence of SEQ ID NO: 47 may optionally be provided with lysine (K) removed from the C-terminus.

The mature ALK4-Fc fusion protein sequence is as follows and may optionally be provided with lysine (K) removed from the C-terminus.

```
                                                     (SEQ ID NO: 48)
  1 SGPRGVQALL CACTSCLQAN YTCETDGACM VSIFNLDGME HHVRTCIPKV

51 ELVPAGKPFY CLSSEDLRNT HCCYTDYCNR IDLRVPSGHL KEPEHPSMWG

101 PVETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVCTLPPSR EEMTKNQVSL

251 SCAVKGFYPS DIAVEWESNG QPENNYKTTP PVLDSDGSFF LVSKLTVDKS

301 RWQQGNVFSC SVMHEALHNH YTQKSLSLSP GK
```

ActRIIB-Fc and ALK4-Fc proteins of SEQ ID NO: 46 and SEQ ID NO: 48, respectively, may be co-expressed and purified from a CHO cell line, to give rise to a heteromeric complex comprising ALK4-Fc:ActRIIB-Fc.

Purification of various ALK4-Fc:ActRIIB-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 2. Ligand Binding Profile of ALK4-Fc:ActRIIB-Fc Heterodimer Compared to ActRIIB-Fc Homodimer and ALK4-Fc Homodimer A Biacore™-based binding assay was used to compare ligand binding selectivity of the ALK4-Fc:ActRIIB-Fc heterodimeric complex described above with that of ActRIIB-Fc and ALK4-Fc homodimer complexes. The ALK4-Fc:ActRIIB-Fc heterodimer, ActRIIB-Fc homodimer, and ALK4-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Ligand binding profile of ALK4-Fc:ActRIIB-Fc heterodimer compared to ActRIIB-Fc homodimer and ALK4-Fc homodimer

| Ligand | ActRIIB-Fc homodimer | | | ALK4-Fc homodimer | | | ALK4-Fc:ActRIIB-Fc heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_b$ (1/s) | $K_D$ (pM) |
| Activin A | $1.2 \times 10^7$ | $\mathbf{2.3 \times 10^{-4}}$ | 19 | $5.8 \times 10^5$ | $1.2 \times 10^{-2}$ | 20000 | $1.3 \times 10^7$ | $\mathbf{1.5 \times 10^{-4}}$ | 12 |
| Activin B | $5.1 \times 10^6$ | $\mathbf{1.0 \times 10^{-4}}$ | 20 | | No binding | | $7.1 \times 10^6$ | $\mathbf{4.0 \times 10^{-5}}$ | 6 |
| BMP6 | $3.2 \times 10^7$ | $6.8 \times 10^{-3}$ | 190 | — | — | — | $2.0 \times 10^6$ | $5.5 \times 10^{-3}$ | 2700 |
| BMP9 | $1.4 \times 10^7$ | $1.1 \times 10^{-3}$ | 77 | — | — | — | Transient* | | 3400 |
| BMP10 | $2.3 \times 10^7$ | $\mathbf{2.6 \times 10^{-4}}$ | 11 | — | — | — | $5.6 \times 10^7$ | $4.1 \times 10^{-3}$ | 74 |
| GDF3 | $1.4 \times 10^6$ | $2.2 \times 10^{-3}$ | 1500 | — | — | — | $3.4 \times 10^6$ | $1.7 \times 10^{-2}$ | 4900 |
| GDF8 | $8.3 \times 10^5$ | $\mathbf{2.3 \times 10^{-4}}$ | 280 | $1.3 \times 10^5$ | $1.9 \times 10^{-3}$ | 15000† | $3.9 \times 10^5$ | $\mathbf{2.1 \times 10^{-4}}$ | 550 |
| GDF11 | $5.0 \times 10^7$ | $\mathbf{1.1 \times 10^{-4}}$ | 2 | $5.0 \times 10^6$ | $4.8 \times 10^{-3}$ | 270† | $3.8 \times 10^7$ | $\mathbf{1.1 \times 10^{-4}}$ | 3 |

*Indeterminate due to transient nature of interaction
†Very low signal
—Not tested These comparative binding data demonstrate that ALK4-Fc:ActRIIB-Fc heterodimer has an altered binding profile/selectivity relative to either ActRIIB-Fc or ALK4-Fc homodimers. ALK4-Fc:ActRIIB-Fc heterodimer displays enhanced binding to activin B compared with either homodimer, retains strong binding to activin A, GDF8, and GDF11 as observed with ActRIIB-Fc homodimer, and exhibits substantially reduced binding to BMP9, BMP10, and GDF3. In particular, BMP9 displays low or no observable affinity for ALK4-Fc:ActRIIB-Fc heterodimer, whereas this ligand binds strongly to ALK4-Fc:ActRIIB-Fc heterodimer. Like the ActRIIB-Fc homodimer, the heterodimer retains intermediate-level binding to BMP6. See FIG. 6.

In addition, an A-204 Reporter Gene Assay was used to evaluate the effects of ALK4-Fc:ActRIIB-Fc heterodimer and ActRIIB-Fc:ActRIIB-Fc homodimer on signaling by activin A, activin B, GDF11, GDF8, BMP10, and BMP9. Cell line: Human Rhabdomyosarcoma (derived from muscle). Reporter vector: pGL3(CAGA)12 (as described in Dennler et al, 1998, EMBO 17: 3091-3100). The CAGA12 motif is present in TGF-beta responsive genes (PAI-1 gene), so this vector is of general use for factors signaling through Smad2 and 3. An exemplary A-204 Reporter Gene Assay is outlined below.

Day 1: Split A-204 cells into 48-well plate.
Day 2: A-204 cells transfected with 10 ug pGL3(CAGA)12 or pGL3(CAGA)12(10 ug)+pRLCMV (1 ug) and Fugene.
Day 3: Add factors (diluted into medium+0.1% BSA). Inhibitors need to be pre-incubated with Factors for about one hr before adding to cells. About six hrs later, cells are rinsed with PBS and then lysed.

Following the above steps, applicant performed a Luciferase assay.

Both the ALK4-Fc:ActRIIB-Fc heterodimer and ActRIIB-Fc:ActRIIB-Fc homodimer were determined to be potent inhibitors of activin A, activin B, GDF11, and GDF8 in this assay. In particular, as can be seen in the comparative homodimer/heterodimer $IC_{50}$ data illustrated in FIG. 13, ALK4-Fc:ActRIIB-Fc heterodimer inhibits activin A, activin B, GDF8, and GDF11 signaling pathways similarly to the ActRIIB-Fc:ActRIIB-Fc homodimer. However, ALK4-Fc:ActRIIB-Fc heterodimer inhibition of BMP9 and BMP10 signaling pathways is significantly reduced compared to the ActRIIB-Fc:ActRIIB-Fc homodimer. This data is consistent with the above-discussed binding data in which it was observed that both the ALK4-Fc:ActRIIB-Fc heterodimer and ActRIIB-Fc:ActRIIB-Fc homodimer display strong binding to activin A, activin B, GDF8, and GDF11, but BMP10 and BMP9 have significantly reduced affinity for the ALK4-Fc:ActRIIB-Fc heterodimer compared to the ActRIIB-Fc:ActRIIB-Fc homodimer.

Together, these data therefore demonstrate that ALK4-Fc:ActRIIB-Fc heterodimer is a more selective antagonist of activin B, activin A, GDF8, and GDF11 compared to ActRIIB-Fc homodimer. Accordingly, an ALK4-Fc:ActRIIB-Fc heterodimer will be more useful than an ActRIIB-Fc homodimer in certain applications where such selective antagonism is advantageous. Examples include therapeutic applications where it is desirable to retain antagonism of one or more of activin A, activin B, activin AB, GDF8, and GDF11 but minimize antagonism of one or more of BMP9, BMP10, GDF3, and BMP6.

Example 3. Activity Profile of ALK4-Fc:ActRIIB-Fc Heterodimer in Mice Compared to ActRIIB-Fc Homodimer Homodimeric and heterodimeric complexes were tested in mice to investigate differences in their activity profiles in vivo. Wild-type C57BL/6 mice were dosed subcutaneously with ActRIIB-Fc homodimer (10 mg/kg), ALK4-Fc:ActRIIB-Fc heterodimer (3 or 10 mg/kg), or vehicle (phosphate-buffered saline, PBS) twice per week for 4 weeks beginning at approximately 10 weeks of age (n=9 mice per group). ALK4-Fc homodimer was not tested in vivo due to its inability to bind ligands with high affinity under cell-free conditions as determined by surface plasmon resonance. Study endpoints included: body weight; total lean mass and total adipose mass as determined by nuclear magnetic resonance (NMR) at baseline and study completion (4 weeks); total bone mineral density as determined by dual energy x-ray absorptiometry (DEXA) at baseline and 4 weeks; and weights of the gastrocnemius, rectus femoris, and *pectoralis* muscles determined at 4 weeks.

| Activity of ActRIIB-Fc and ALK4-Fc Complexes in Wild-Type Mice | | | | |
|---|---|---|---|---|
| Endpoint | | ActRIIB-Fc homodimer | ALK4-Fc:ActRIIB-Fc heterodimer | |
| (4 wk) | Vehicle | 10 mg/kg | 10 mg/kg | 3 mg/kg |
| Change in body weight from baseline | ↑ 15% | ↑ 38%** | ↑ 41%** | ↑ 33%** |
| Change in total lean mass from baseline | ↓ 1% | ↑ 5%** | ↑ 5%** | ↑ 5%** |
| Change in total adipose mass from baseline | ↑ 5% | ↓ 3.6%** | ↓ 3.5%** | ↓ 3.5%** |
| Change in total bone mineral density from baseline | ↑ 8% | ↑ 14%* | ↑ 12%* | ↑ 11% |
| Gastrocnemius weight † | 23 | 36** | 35** | 30** |
| Femoris weight † | 11.5 | 17** | 16** | 14** |
| Pectoralis weight † | 15 | 23** | 28** | 23** |

*$P < 0.05$ vs. vehicle
**$P < 0.01$ vs. vehicle
† Combined left and right muscle weights normalized to femur length (mg/mm) to control for body size Study results are summarized in the table above. As expected, ActRIIB-Fc homodimer caused marked changes in body composition, many consistent with known effects of GDF8 and activin inhibition. Treatment of wild-type mice with ActRIIB-Fc homodimer more than doubled body weight gain over the course of the study compared to vehicle-treated controls. Accompanying this net weight gain were significant increases in total lean mass and total bone mineral density, as well as a significant reduction in total adipose mass, compared to vehicle. It should be recognized that normalized (percentage-based) changes in lean and adipose tissues differ in their correspondence to absolute changes because lean mass (typically about 70% of body weight in a mouse) is much larger than adipose mass (typically about 10% of body weight). Individual skeletal muscles examined, including the gastrocnemius, femoris, and *pectoralis* all increased significantly in weight compared to vehicle controls over the course of treatment with ActRIIB-Fc homodimer.

The ALK4-Fc:ActRIIB-Fc heterodimer produced certain effects strikingly similar to those of the ActRIIB-Fc homodimer despite differential ligand selectivity of the two complexes. As shown in the table above, treatment of mice with the ALK4-Fc:ActRIIB-Fc heterodimer at a dose level of 10 mg/kg matched, nearly matched, or exceeded the effects of ActRIIB-Fc homodimer at the same dose level for all endpoints listed. Effects of the ALK4-Fc:ActRIIB-Fc heterodimer at 3 mg/kg were mildly attenuated for several endpoints compared to 10 mg/kg, thus providing evidence for a dose-effect relationship.

Thus, an ALK4-Fc:ActRIIB-Fc heterodimer exerts beneficial anabolic effects on skeletal muscle and bone, and catabolic effects on adipose tissue, very similar to those of ActRIIB-Fc homodimer. However, unlike ActRIIB homodimer, ALK4-Fc:ActRIIB-Fc heterodimer exhibits only low-affinity or transient binding to BMP9 and BMP10 and so should have little to no concurrent inhibition on processes mediated by those ligands, such as angiogenesis. This novel selectivity will be useful, for example, in treating patients in need of stimulatory effects on muscle and bone, and inhibitory effects on fat, but not in need of altered angiogenesis.

Example 4. ALK4:ActRIIB Heteromultimer Treatment Suppresses Kidney Fibrosis and Inflammation and Reduces Kidney Injury The effects of the ALK4-Fc:ActRIIB-Fc heterodimer described in Example 2 on kidney disease was assessed in a mouse unilateral ureteral obstruction model. See, e.g., Klahr and Morrissey (2002) Am J Physiol Renal Physiol 283: F861-F875.

Twenty-four C57BL/6 male mice 12 weeks of age underwent left unilateral ureteral ligation twice at the level of the lower pole of kidney. After 3 days, eight mice were euthanized and kidneys from individual animals were harvested to assess kidney injury. The remaining mice were randomized into two groups: i) eight mice were injected subcutaneously with the ALK4-Fc:ActRIIB-Fc heterodimer at a dose of 10 mg/kg at day 3, day 7, day 10, and day 14 after surgery and a ii) eight mice were injected subcutaneously with vehicle control, phosphate buffered saline (PBS), at day 3, day 7, day 10, and day 14 after surgery. Both groups were sacrificed at day 17 in accordance with the relevant Animal Care Guidelines. Half kidneys from individual animals were collected for histology analysis (H&E, and Masson's Trichrome stain), from both the UUO kidney and contralateral kidney, and 1/4 kidneys were used for RNA extraction (RNeasy Midi Kit, Qiagen, Ill.).

Gene expression analysis on UUO kidney samples was performed to assess levels of various genes. QRT-PCR was performed on a CFX Connect™ Real-time PCR detection system (Bio-Rad, CA) to evaluate the expression of various fibrotic genes (Col1a1, Fibronectin, PAI-1, CTGF, and a-SMA), inflammatory genes (TNFa, and MCP1), cytokines (TGFβ1, TGFβ2, TGFβ3, and activin A), and kidney injury genes (NGAL. See FIG. 14. Treatment of mice with ALK4-Fc:ActRIIB-Fc heterodimer significantly suppressed the expression of fibrotic and inflammatory genes, inhibited the upregulation of TGFβ 1/2/3 and reduced kidney injury. Histology data confirmed that ALK4-Fc:ActRIIB-Fc heterodimer treatment significantly inhibited kidney fibrosis and reduced kidney injury in the UUO model.

Together, these data demonstrate that ALK4:ActRIIB heteromultimer treatment suppresses kidney fibrosis and inflammation and reduces kidney injury. Moreover, these data indicate that other ALK4:ActRIIB antagonists may be useful in the treatment or preventing of kidney disease including, for example, antagonists of ALK4 and/or ActRIIB-binding ligands, antagonists of ALK4 and/or ActRIIB receptors, antagonists of ALK4 and/or ActRIIB downstream signaling mediators (e.g., Smads), and antagonists of TGFβ superfamily co-receptors associated with ALK4 and/or ActRIIB.

We claim:

1. A soluble recombinant heteromultimer comprising an ALK4 polypeptide and an ActRIIB polypeptide, wherein the ALK4 polypeptide comprises an amino acid sequence that is at least 90% identical to amino acids 34-101 of SEQ ID NO: 9, and wherein the ActRIIB polypeptide comprises an amino acid sequence that is at least 90% identical to amino acids 29-109 of SEQ ID NO: 1, wherein the ActRIIB polypeptide does not comprise an aspartic acid (D) at the amino acid position corresponding to L79 of SEQ ID NO: 1; wherein the ALK4 and/or ActRIIB polypeptide is a fusion protein further comprising a heterologous domain, and wherein the heteromultimer binds to activin B.

2. The heteromultimer of claim 1, wherein the ALK4 polypeptide comprises an amino acid sequence that is at least 90%, 91%, 92%, 93%, 94%, 95%, 96%, 97%, 98%, 99%, or 100% identical to a polypeptide that:
   a) begins at any one of amino acids 24, 25, 26, 27, 28, 29, 30, 31, 32, 33, or 34 of SEQ ID NO: 9, and
   b) ends at any one of amino acids 101, 102, 103, 104, 105, 106, 107, 108, 109, 110, 111, 112, 113, 114, 115, 116, 117, 118, 119, 120, 121, 122, 123, 124, 125, or 126 of SEQ ID NO: 9.

3. The heteromultimer of claim 1, wherein the ActRIIB polypeptide comprises an amino acid sequence that is at least 90%, 91%, 92%, 93%, 94%, 95%, 96%, 97%, 98%, 99%, or 100% identical to a polypeptide that:
   a) begins at any one of amino acids 20, 21, 22, 23, 24, 25, 26, 27, 28, or 29 of SEQ ID NO: 1, and
   b) ends at any one of amino acids 109, 110, 111, 112, 113, 114, 115, 116, 117, 118, 119, 120, 121, 122, 123, 124, 125, 126, 127, 128, 129, 130, 131, 132, 133, or 134 of SEQ ID NO: 1.

4. The heteromultimer of claim 1, wherein the heterologous domain comprises an Fc immunoglobulin domain.

5. The heteromultimer of claim 4, wherein the Fc immunoglobulin domain comprises one or more amino acid modifications that promote heterodimer formation.

6. The heteromultimer of claim 4, wherein the immunoglobulin Fc domain comprises one or more amino acid modifications that inhibit homodimer formation.

7. The heteromultimer of claim 4, wherein the heterologous domain comprises an Fc immunoglobulin domain of IgG1 immunoglobulin.

8. The heteromultimer of claim 1, wherein the fusion protein further comprises a linker domain positioned between the ALK4 domain and the heterologous domain and/or a linker domain positioned between the ActRIIB domain and the heterologous domain.

9. The heteromultimer of claim 1, wherein the ALK4 polypeptide and/or ActRIIB polypeptide comprises one or more modified amino acid residues selected from the group consisting of: a glycosylated amino acid, a PEGylated amino acid, a farnesylated amino acid, an acetylated amino acid, a biotinylated amino acid, and an amino acid conjugated to a lipid moiety.

10. The heteromultimer of claim 1, wherein the ALK4 polypeptide and/or ActRIIB polypeptide is glycosylated and has a glycosylation pattern obtainable from a Chinese hamster ovary cell line.

11. The heteromultimer of claim 1, wherein the heteromultimer is an ALK4:ActRIIB heterodimer.

12. A pharmaceutical preparation comprising the heteromultimer of claim 1 and a pharmaceutically acceptable carrier.

13. The pharmaceutical preparation of claim 12, wherein the pharmaceutical preparation is substantially pyrogen-free.

14. The pharmaceutical preparation of claim 12, wherein the pharmaceutical preparation further comprises an additional active agent.

15. The pharmaceutical preparation of claim 12, wherein the pharmaceutical preparation comprises less than 10%, 9%, 8%, 7%, 6%, 5%, 4%, 3%, 2%, or less than 1% ALK4 homomultimers.

16. The pharmaceutical preparation of claim 12, wherein the pharmaceutical preparation comprises less than 10%, 9%, 8%, 7%, 6%, 5%, 4%, 3%, 2%, or less than 1% ActRIIB homomultimers.

17. The heteromultimer of claim 1, wherein the ALK4 polypeptide comprises an amino acid sequence that is at least 95% identical to amino acids 34-101 of SEQ ID NO: 9, and wherein the ActRIIB polypeptide comprises an amino acid sequence that is at least 95% identical to amino acids 29-109 of SEQ ID NO: 1.

18. The heteromultimer of claim 1, wherein the ALK4 polypeptide comprises the amino acid sequence corresponding to amino acids 34-101 of SEQ ID NO: 9, and wherein the ActRIIB polypeptide comprises the amino acid sequence corresponding to amino acids 29-109 of SEQ ID NO: 1.

19. The heteromultimer of claim 1, wherein the ALK4 polypeptide comprises an amino acid sequence that is at least 90% identical to the amino acid sequence of SEQ ID NO: 10, and wherein the ActRIIB polypeptide comprises an amino acid sequence that is at least 90% identical to the amino acid sequence of SEQ ID NO: 2.

20. The heteromultimer of claim 1, wherein the ALK4 polypeptide comprises the amino acid sequence of SEQ ID NO: 10, and wherein the ActRIIB polypeptide comprises the amino acid sequence of SEQ ID NO: 2.

21. The heteromultimer of claim 17, wherein the heterologous domain comprises an Fc immunoglobulin domain, wherein the Fc immunoglobulin domain is an IgG1 immunoglobulin domain.

22. The heteromultimer of claim 18, wherein the heterologous domain comprises an Fc immunoglobulin domain, wherein the Fc immunoglobulin domain is an IgG1 immunoglobulin domain.

23. The heteromultimer of claim 19, wherein the heterologous domain comprises an Fc immunoglobulin domain, wherein the Fc immunoglobulin domain is an IgG1 immunoglobulin domain.

24. The heteromultimer of claim 20, wherein the heterologous domain comprises an Fc immunoglobulin domain, wherein the Fc immunoglobulin domain is an IgG1 immunoglobulin domain.

25. The heteromultimer of claim 17, wherein the fusion protein further comprises a linker domain positioned between the ALK4 domain and the heterologous domain and/or a linker domain positioned between the ActRIIB domain and the heterologous domain.

26. The heteromultimer of claim 18, wherein the fusion protein further comprises a linker domain positioned between the ALK4 domain and the heterologous domain and/or a linker domain positioned between the ActRIIB domain and the heterologous domain.

27. The heteromultimer of claim 19, wherein the fusion protein further comprises a linker domain positioned between the ALK4 domain and the heterologous domain and/or a linker domain positioned between the ActRIIB domain and the heterologous domain.

28. The heteromultimer of claim 20, wherein the fusion protein further comprises a linker domain positioned between the ALK4 domain and the heterologous domain and/or a linker domain positioned between the ActRIIB domain and the heterologous domain.

29. The heteromultimer of claim 1, wherein the ALK4 polypeptide comprises an amino acid sequence that is at least 95% identical to the amino acid sequence of SEQ ID NO: 10, and wherein the ActRIIB polypeptide comprises an amino acid sequence that is at least 95% identical to the amino acid sequence of SEQ ID NO: 2.

30. The heteromultimer of claim 29, wherein the heterologous domain comprises an Fc immunoglobulin domain, wherein the Fc immunoglobulin domain is an IgG1 immunoglobulin domain.

31. The heteromultimer of claim 29, wherein the fusion protein further comprises a linker domain positioned between the ALK4 domain and the heterologous domain and/or a linker domain positioned between the ActRIIB domain and the heterologous domain.

* * * * *

SEQUENCE LISTING

<160> NUMBER OF SEQ ID NOS: 96

<210> SEQ ID NO 1
<211> LENGTH: 512

```
<212> TYPE: PRT
<213> ORGANISM: Homo sapiens

<400> SEQUENCE: 1

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400
```

```
Lys Ala Ala Asp Gly Pro Val Asp Glu Tyr Met Leu Pro Phe Glu Glu
                405                 410                 415

Glu Ile Gly Gln His Pro Ser Leu Glu Leu Gln Glu Val Val
            420                 425                 430

His Lys Lys Met Arg Pro Thr Ile Lys Asp His Trp Leu Lys His Pro
            435                 440                 445

Gly Leu Ala Gln Leu Cys Val Thr Ile Glu Glu Cys Trp Asp His Asp
450                 455                 460

Ala Glu Ala Arg Leu Ser Ala Gly Cys Val Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
                500                 505                 510

<210> SEQ ID NO 2
<211> LENGTH: 115
<212> TYPE: PRT
<213> ORGANISM: Homo sapiens

<400> SEQUENCE: 2

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 3
<211> LENGTH: 100
<212> TYPE: PRT
<213> ORGANISM: Homo sapiens

<400> SEQUENCE: 3

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95
```

```
Leu Pro Glu Ala
            100

<210> SEQ ID NO 4
<211> LENGTH: 512
<212> TYPE: PRT
<213> ORGANISM: Homo sapiens

<400> SEQUENCE: 4

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Ala
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
```

```
                355                 360                 365
Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 5
<211> LENGTH: 115
<212> TYPE: PRT
<213> ORGANISM: Homo sapiens

<400> SEQUENCE: 5

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 6
<211> LENGTH: 100
<212> TYPE: PRT
<213> ORGANISM: Homo sapiens

<400> SEQUENCE: 6

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
```

```
                    50                  55                  60

Cys Tyr Asp Arg Gln Glu Cys Val Ala Thr Glu Glu Asn Pro Gln Val
 65                  70                  75                  80

Tyr Phe Cys Cys Cys Glu Gly Asn Phe Cys Asn Glu Arg Phe Thr His
                 85                  90                  95

Leu Pro Glu Ala
        100

<210> SEQ ID NO 7
<211> LENGTH: 1536
<212> TYPE: DNA
<213> ORGANISM: Homo sapiens

<400> SEQUENCE: 7
atgacggcgc cctgggtggc cctcgccctc ctctggggat cgctgtgcgc cggctctggg      60
cgtggggagg ctgagacacg ggagtgcatc tactacaacg ccaactggga gctggagcgc     120
accaaccaga gcggcctgga gcgctgcgaa ggcgagcagg acaagcggct gcactgctac     180
gcctcctggc gcaacagctc tggcaccatc gagctcgtga agaagggctg ctggctagat     240
gacttcaact gctacgatag caggagtgt gtggccactg aggagaaccc ccaggtgtac     300
ttctgctgct gtgaaggcaa cttctgcaac gaacgcttca ctcatttgcc agaggctggg     360
ggcccggaag tcacgtacga gccaccccg acagccccca ccctgctcac ggtgctggcc     420
tactcactgc tgcccatcgg gggcctttcc ctcatcgtcc tgctggcctt ttggatgtac     480
cggcatcgca agcccccta cggtcatgtg acatccatg aggaccctgg gcctccacca     540
ccatcccctc tggtgggcct gaagccactg cagctgctgg agatcaaggc tcggggggcgc     600 tttggctgtg tctggaaggc ccagctcatg aatgactttg tagctgtcaa gatcttccca     660
ctccaggaca gcagtcgtg gcagagtgaa cgggagatct tcagcacacc tggcatgaag     720
cacgagaacc tgctacagtt cattgctgcc gagaagcgag gctccaacct cgaagtagag     780
ctgtggctca tcacggcctt ccatgacaag ggctcccctca cggattaccct caaggggaac     840 atcatcacat ggaacgaact gtgtcatgta gcagagacga tgtcacgagg cctctcatac     900
ctgcatgagg atgtgcctg gtgccgtggc gagggccaca agccgtctat tgcccacagg     960
gactttaaaa gtaagaatgt attgctgaag agcgacctca cagccgtgct ggctgacttt    1020
ggcttggctg ttcgatttga gccagggaaa cctccagggg acacccacgg acaggtaggc    1080
acgagacggt acatggctcc tgaggtgctc gagggagcca tcaacttcca gagagatgcc    1140
ttcctgcgca ttgacatgta tgccatgggg ttggtgctgt gggagcttgt gtctcgctgc    1200
aaggctgcag acggacccgt ggatgagtac atgctgccct ttgaggaaga gattggccag    1260 caccctttcgt tggaggagct gcaggaggtg gtggtgcaca agaagatgag gcccaccatt    1320
aaagatcact ggttgaaaca cccgggcctg gcccagcttt gtgtgaccat cgaggagtgc    1380
tgggaccatg atgcagaggc tcgcttgtcc gcgggctgtg tggaggagcg ggtgtccctg    1440
attcggaggt cggtcaacgg cactacctcg gactgtctcg tttccctggt gacctctgtc    1500
accaatgtgg acctgccccc taaagagtca agcatc                              1536

<210> SEQ ID NO 8
<211> LENGTH: 345
<212> TYPE: DNA
<213> ORGANISM: Homo sapiens

<400> SEQUENCE: 8
```

```
gggcgtgggg aggctgagac acgggagtgc atctactaca acgccaactg ggagctggag      60
cgcaccaacc agagcggcct ggagcgctgc gaaggcgagc aggacaagcg gctgcactgc     120
tacgcctcct ggcgcaacag ctctggcacc atcgagctcg tgaagaaggg ctgctggcta     180
gatgacttca actgctacga taggcaggag tgtgtggcca ctgaggagaa ccccaggtg      240 tacttctgct gctgtgaagg caacttctgc aacgaacgct tcactcattt gccagaggct     300
gggggcccgg aagtcacgta cgagccaccc ccgacagccc ccacc                    345
```

<210> SEQ ID NO 9
<211> LENGTH: 505
<212> TYPE: PRT
<213> ORGANISM: Homo sapiens

<400> SEQUENCE: 9

```
Met Ala Glu Ser Ala Gly Ala Ser Ser Phe Phe Pro Leu Val Val Leu
1               5                   10                  15

Leu Leu Ala Gly Ser Gly Gly Ser Gly Pro Arg Gly Val Gln Ala Leu
            20                  25                  30

Leu Cys Ala Cys Thr Ser Cys Leu Gln Ala Asn Tyr Thr Cys Glu Thr
        35                  40                  45

Asp Gly Ala Cys Met Val Ser Ile Phe Asn Leu Asp Gly Met Glu His
    50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
                85                  90                  95

Tyr Thr Asp Tyr Cys Asn Arg Ile Asp Leu Arg Val Pro Ser Gly His
            100                 105                 110

Leu Lys Glu Pro Glu His Pro Ser Met Trp Gly Pro Val Glu Leu Val
        115                 120                 125

Gly Ile Ile Ala Gly Pro Val Phe Leu Leu Phe Leu Ile Ile Ile Ile
    130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175

Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
        195                 200                 205

Leu Gln Glu Ile Ile Gly Lys Gly Arg Phe Gly Glu Val Trp Arg Gly
    210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Asp Asn
            260                 265                 270

Gly Thr Trp Thr Gln Leu Trp Leu Val Ser Asp Tyr His Glu His Gly
        275                 280                 285

Ser Leu Phe Asp Tyr Leu Asn Arg Tyr Thr Val Thr Ile Glu Gly Met
    290                 295                 300

Ile Lys Leu Ala Leu Ser Ala Ala Ser Gly Leu Ala His Leu His Met
305                 310                 315                 320
```

```
Glu Ile Val Gly Thr Gln Gly Lys Pro Gly Ile Ala His Arg Asp Leu
                325                 330                 335
Lys Ser Lys Asn Ile Leu Val Lys Lys Asn Gly Met Cys Ala Ile Ala
            340                 345                 350
Asp Leu Gly Leu Ala Val Arg His Asp Ala Val Thr Asp Thr Ile Asp
        355                 360                 365
Ile Ala Pro Asn Gln Arg Val Gly Thr Lys Arg Tyr Met Ala Pro Glu
    370                 375                 380
Val Leu Asp Glu Thr Ile Asn Met Lys His Phe Asp Ser Phe Lys Cys
385                 390                 395                 400
Ala Asp Ile Tyr Ala Leu Gly Leu Val Tyr Trp Glu Ile Ala Arg Arg
                405                 410                 415
Cys Asn Ser Gly Gly Val His Glu Glu Tyr Gln Leu Pro Tyr Tyr Asp
            420                 425                 430
Leu Val Pro Ser Asp Pro Ser Ile Glu Glu Met Arg Lys Val Val Cys
        435                 440                 445
Asp Gln Lys Leu Arg Pro Asn Ile Pro Asn Trp Trp Gln Ser Tyr Glu
    450                 455                 460
Ala Leu Arg Val Met Gly Lys Met Met Arg Glu Cys Trp Tyr Ala Asn
465                 470                 475                 480
Gly Ala Ala Arg Leu Thr Ala Leu Arg Ile Lys Lys Thr Leu Ser Gln
                485                 490                 495
Leu Ser Val Gln Glu Asp Val Lys Ile
            500                 505

<210> SEQ ID NO 10
<211> LENGTH: 103
<212> TYPE: PRT
<213> ORGANISM: Homo sapiens

<400> SEQUENCE: 10

Ser Gly Pro Arg Gly Val Gln Ala Leu Leu Cys Ala Cys Thr Ser Cys
1               5                   10                  15
Leu Gln Ala Asn Tyr Thr Cys Glu Thr Asp Gly Ala Cys Met Val Ser
            20                  25                  30
Ile Phe Asn Leu Asp Gly Met Glu His His Val Arg Thr Cys Ile Pro
        35                  40                  45
Lys Val Glu Leu Val Pro Ala Gly Lys Pro Phe Tyr Cys Leu Ser Ser
    50                  55                  60
Glu Asp Leu Arg Asn Thr His Cys Cys Tyr Thr Asp Tyr Cys Asn Arg
65                  70                  75                  80
Ile Asp Leu Arg Val Pro Ser Gly His Leu Lys Glu Pro Glu His Pro
                85                  90                  95
Ser Met Trp Gly Pro Val Glu
            100

<210> SEQ ID NO 11
<211> LENGTH: 1515
<212> TYPE: DNA
<213> ORGANISM: Homo sapiens

<400> SEQUENCE: 11
atggcggagt cggccggagc ctcctccttc ttccccttg ttgtcctcct gctcgccggc    60
agcggcgggt ccgggccccg gggggtccag gctctgctgt gtgcgtgcac cagctgcctc   120
caggccaact acacgtgtga gacagatggg gcctgcatgg tttccatttt caatctggat   180
```

```
gggatggagc accatgtgcg cacctgcatc cccaaagtgg agctggtccc tgccgggaag      240
cccttctact gcctgagctc ggaggacctg cgcaacaccc actgctgcta cactgactac      300
tgcaacagga tcgacttgag ggtgcccagt ggtcacctca aggagcctga gcacccgtcc      360
atgtggggcc cggtggagct ggtaggcatc atcgccggcc cggtgttcct cctgttcctc      420
atcatcatca ttgttttcct tgtcattaac tatcatcagc gtgtctatca aaccgccag       480 agactggaca tggaagatcc ctcatgtgag atgtgtctct ccaaagacaa gacgctccag      540
gatcttgtct acgatctctc cacctcaggg tctggctcag ggttacccct ctttgtccag      600
cgcacagtgg cccgaaccat cgttttacaa gagattattg gcaagggtcg gtttggggaa      660
gtatggcggg ccgctggagg gggtggtgat gtggctgtga aaatattctc ttctcgtgaa      720
gaacggtctt ggttcaggga agcagagata taccagacgg tcatgctgcg ccatgaaaac      780
atccttggat ttattgctgc tgacaataaa gataatggca cctggacaca gctgtggctt      840
gtttctgact atcatgagca cgggtccctg tttgattatc tgaaccggta cacagtgaca      900 attgaggga tgattaagct ggccttgtct gctgctagtg ggctggcaca cctgcacatg        960
gagatcgtgg gcacccaagg gaagcctgga attgctcatc gagacttaaa gtcaaagaac      1020
attctggtga agaaaaatgg catgtgtgcc atagcagacc tgggcctggc tgtccgtcat      1080
gatgcagtca ctgacaccat tgacattgcc ccgaatcaga gggtggggac caaacgatac      1140
atggcccctg aagtacttga tgaaaccatt aatatgaaac actttgactc ctttaaatgt      1200
gctgatattt atgccctcgg gcttgtatat tgggagattg ctcgaagatg caattctgga      1260
ggagtccatg aagaatatca gctgccatat tacgacttag tgccctctga cccttccatt      1320
gaggaaatgc gaaaggttgt atgtgatcag aagctgcgtc caacatccc caactggtgg        1380 cagagttatg aggcactgcg ggtgatgggg aagatgatgc gagagtgttg gtatgccaac      1440
ggcgcagccc gcctgacggc cctgcgcatc aagaagaccc tctcccagct cagcgtgcag      1500
gaagacgtga agatc                                                      1515

<210> SEQ ID NO 12
<211> LENGTH: 309
<212> TYPE: DNA
<213> ORGANISM: Homo sapiens

<400> SEQUENCE: 12
tccgggcccc gggggtcca ggctctgctg tgtgcgtgca ccagctgcct ccaggccaac        60
tacacgtgtg agacagatgg ggcctgcatg gtttccattt tcaatctgga tgggatggag      120
caccatgtgc gcacctgcat ccccaaagtg gagctggtcc ctgccgggaa gcccttctac      180
tgcctgagct cggaggacct gcgcaacacc cactgctgct acactgacta ctgcaacagg      240
atcgacttga gggtgcccag tggtcacctc aaggagcctg agcacccgtc catgtggggc      300
ccggtggag                                                             309

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly
```

```
<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Gly Gly
1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Gly Gly Gly Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Gly Gly Gly Gly
1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Gly Gly Gly
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Gly Gly Gly
1

<210> SEQ ID NO 19
<211> LENGTH: 546
<212> TYPE: PRT
<213> ORGANISM: Homo sapiens

<400> SEQUENCE: 19
```

```
Met Ala Glu Ser Ala Gly Ala Ser Ser Phe Phe Pro Leu Val Val Leu
1               5                   10                  15

Leu Leu Ala Gly Ser Gly Ser Gly Pro Arg Gly Val Gln Ala Leu
            20                  25                  30

Leu Cys Ala Cys Thr Ser Cys Leu Gln Ala Asn Tyr Thr Cys Glu Thr
            35                  40                  45

Asp Gly Ala Cys Met Val Ser Ile Phe Asn Leu Asp Gly Met Glu His
            50                  55                  60

His Val Arg Thr Cys Ile Pro Lys Val Glu Leu Val Pro Ala Gly Lys
65                      70                  75                  80

Pro Phe Tyr Cys Leu Ser Ser Glu Asp Leu Arg Asn Thr His Cys Cys
                85                  90                  95

Tyr Thr Asp Tyr Cys Asn Arg Ile Asp Leu Arg Val Pro Ser Gly His
                100                 105                 110

Leu Lys Glu Pro Glu His Pro Ser Met Trp Gly Pro Val Glu Leu Val
            115                 120                 125

Gly Ile Ile Ala Gly Pro Val Phe Leu Leu Phe Leu Ile Ile Ile Ile
            130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175

Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
            195                 200                 205

Leu Gln Glu Ile Ile Gly Lys Gly Arg Phe Gly Glu Val Trp Arg Gly
            210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Ala Asp
                260                 265                 270

Cys Ser Phe Leu Thr Leu Pro Trp Glu Val Val Met Val Ser Ala Ala
                275                 280                 285

Pro Lys Leu Arg Ser Leu Arg Leu Gln Tyr Lys Gly Arg Gly Arg
            290                 295                 300

Ala Arg Phe Leu Phe Pro Leu Asn Asn Gly Thr Trp Thr Gln Leu Trp
305                 310                 315                 320

Leu Val Ser Asp Tyr His Glu His Gly Ser Leu Phe Asp Tyr Leu Asn
                325                 330                 335

Arg Tyr Thr Val Thr Ile Glu Gly Met Ile Lys Leu Ala Leu Ser Ala
                340                 345                 350

Ala Ser Gly Leu Ala His Leu His Met Glu Ile Val Gly Thr Gln Gly
            355                 360                 365

Lys Pro Gly Ile Ala His Arg Asp Leu Lys Ser Lys Asn Ile Leu Val
            370                 375                 380

Lys Lys Asn Gly Met Cys Ala Ile Ala Asp Leu Gly Leu Ala Val Arg
385                 390                 395                 400

His Asp Ala Val Thr Asp Thr Ile Asp Ile Ala Pro Asn Gln Arg Val
                405                 410                 415
```

```
Gly Thr Lys Arg Tyr Met Ala Pro Glu Val Leu Asp Glu Thr Ile Asn
            420                 425                 430

Met Lys His Phe Asp Ser Phe Lys Cys Ala Asp Ile Tyr Ala Leu Gly
        435                 440                 445

Leu Val Tyr Trp Glu Ile Ala Arg Arg Cys Asn Ser Gly Gly Val His
    450                 455                 460

Glu Glu Tyr Gln Leu Pro Tyr Tyr Asp Leu Val Pro Ser Asp Pro Ser
465                 470                 475                 480

Ile Glu Glu Met Arg Lys Val Val Cys Asp Gln Lys Leu Arg Pro Asn
                485                 490                 495

Ile Pro Asn Trp Trp Gln Ser Tyr Glu Ala Leu Arg Val Met Gly Lys
            500                 505                 510

Met Met Arg Glu Cys Trp Tyr Ala Asn Gly Ala Ala Arg Leu Thr Ala
        515                 520                 525

Leu Arg Ile Lys Lys Thr Leu Ser Gln Leu Ser Val Gln Glu Asp Val
    530                 535                 540

Lys Ile
545

<210> SEQ ID NO 20
<211> LENGTH: 103
<212> TYPE: PRT
<213> ORGANISM: Homo sapiens

<400> SEQUENCE: 20

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu
            100

<210> SEQ ID NO 21
<211> LENGTH: 1638
<212> TYPE: DNA
<213> ORGANISM: Homo sapiens

<400> SEQUENCE: 21
atggcggagt cggccggagc ctcctccttc ttccccottg ttgtcctcct gctcgccggc        60
agcggcgggt ccgggccccg gggggtccag gctctgctgt gtgcgtgcac cagctgcctc       120
caggccaact acacgtgtga gacagatggg gcctgcatgg tttccatttt caatctggat       180
gggatggagc accatgtgcg cacctgcatc cccaaagtgg agctggtccc tgccggaaag       240
ccCttctact gcctgagctc ggaggacctg cgcaacaccc actgctgcta cactgactac       300
tgcaacagga tcgacttgag ggtgcccagt ggtcacctca aggagcctga gcacccgtcc       360
atgtggggcc cggtggagct ggtaggcatc atcgccggcc cggtgttcct cctgttcctc       420
atcatcatca ttgttttcct tgtcattaac tatcatcagc gtgtctatca caaccgccag       480
```

```
agactggaca tggaagatcc ctcatgtgag atgtgtctct ccaaagacaa gacgctccag      540
gatcttgtct acgatctctc cacctcaggg tctggctcag ggttacccct ctttgtccag      600
cgcacagtgg cccgaaccat cgttttacaa gagattattg caagggtcg gtttggggaa       660 gtatggcggg gccgctggag gggtggtgat gtggctgtga aaatattctc ttctcgtgaa      720
gaacggtctt ggttcaggga agcagagata taccagacgg tcatgctgcg ccatgaaaac     780
atccttggat ttattgctgc tgacaataaa gcagactgct cattcctcac attgccatgg     840
gaagttgtaa tggtctctgc tgccccaag ctgaggagcc ttagactcca atacaaggga      900 ggaagggaa gagcaagatt tttattccca ctgaataatg gcacctggac acagctgtgg     960
cttgtttctg actatcatga gcacgggtcc ctgtttgatt atctgaaccg gtacacagtg   1020
acaattgagg ggatgattaa gctggccttg tctgctgcta gtgggctggc acacctgcac   1080
atggagatcg tgggcaccca agggaagcct ggaattgctc atcgagactt aaagtcaaag   1140
aacattctgg tgaagaaaaa tggcatgtgt gccatagcag acctgggcct ggctgtccgt   1200
catgatgcag tcactgacac cattgacatt gccccgaatc agagggtggg gaccaaacga   1260
tacatgcccc ctgaagtact tgatgaaacc attaatatga aacactttga ctccttaaa   1320 tgtgctgata tttatgccct cgggcttgta tattgggaga ttgctcgaag atgcaattct   1380
ggaggagtcc atgaagaata tcagctgcca tattacgact tagtgccctc tgacccttcc   1440
attgaggaaa tgcgaaaggt tgtatgtgat cagaagctgc gtcccaacat ccccaactgg   1500
tggcagagtt atgaggcact gcgggtgatg gggaagatga tgcgagagtg ttggtatgcc   1560
aacggcgcag cccgcctgac ggccctgcgc atcaagaaga ccctctccca gctcagcgtg   1620
caggaagacg tgaagatc                                                  1638
```

<210> SEQ ID NO 22
<211> LENGTH: 309
<212> TYPE: DNA
<213> ORGANISM: Homo sapiens

<400> SEQUENCE: 22

```
tccgggcccc gggggtcca ggctctgctg tgtgcgtgca ccagctgcct ccaggccaac        60
tacacgtgtg agacagatgg ggcctgcatg gtttccattt tcaatctgga tgggatggag      120
caccatgtgc gcacctgcat ccccaaagtg gagctggtcc ctgccgggaa gcccttctac      180
tgcctgagct cggaggacct gcgcaacacc cactgctgct acactgacta ctgcaacagg      240
atcgacttga gggtgcccag tggtcacctc aaggagcctg agcacccgtc catgtggggc      300
ccggtggag                                                              309
```

<210> SEQ ID NO 23
<211> LENGTH: 225
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 23

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp

-continued

```
                35                  40                  45
Pro Glu Val Lys Phe Asn Trp Tyr Val Asp Gly Val Glu Val His Asn
 50                  55                  60
Ala Lys Thr Lys Pro Arg Glu Glu Gln Tyr Asn Ser Thr Tyr Arg Val
 65                  70                  75                  80
Val Ser Val Leu Thr Val Leu His Gln Asp Trp Leu Asn Gly Lys Glu
                 85                  90                  95
Tyr Lys Cys Lys Val Ser Asn Lys Ala Leu Pro Ala Pro Ile Glu Lys
                100                 105                 110
Thr Ile Ser Lys Ala Lys Gly Gln Pro Arg Glu Pro Gln Val Tyr Thr
            115                 120                 125
Leu Pro Pro Ser Arg Lys Glu Met Thr Lys Asn Gln Val Ser Leu Thr
130                 135                 140
Cys Leu Val Lys Gly Phe Tyr Pro Ser Asp Ile Ala Val Glu Trp Glu
145                 150                 155                 160
Ser Asn Gly Gln Pro Glu Asn Asn Tyr Lys Thr Thr Pro Pro Val Leu
                165                 170                 175
Lys Ser Asp Gly Ser Phe Phe Leu Tyr Ser Lys Leu Thr Val Asp Lys
            180                 185                 190
Ser Arg Trp Gln Gln Gly Asn Val Phe Ser Cys Ser Val Met His Glu
        195                 200                 205
Ala Leu His Asn His Tyr Thr Gln Lys Ser Leu Ser Leu Ser Pro Gly
210                 215                 220
Lys
225

<210> SEQ ID NO 24
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Thr His Thr Cys Pro Cys Pro Ala Pro Glu Leu Leu Gly Gly Pro
 1               5                  10                  15
Ser Val Phe Leu Phe Pro Pro Lys Pro Lys Asp Thr Leu Met Ile Ser
                 20                  25                  30
Arg Thr Pro Glu Val Thr Cys Val Val Val Asp Val Ser His Glu Asp
             35                  40                  45
Pro Glu Val Lys Phe Asn Trp Tyr Val Asp Gly Val Glu Val His Asn
 50                  55                  60
Ala Lys Thr Lys Pro Arg Glu Glu Gln Tyr Asn Ser Thr Tyr Arg Val
 65                  70                  75                  80
Val Ser Val Leu Thr Val Leu His Gln Asp Trp Leu Asn Gly Lys Glu
                 85                  90                  95
Tyr Lys Cys Lys Val Ser Asn Lys Ala Leu Pro Ala Pro Ile Glu Lys
                100                 105                 110
Thr Ile Ser Lys Ala Lys Gly Gln Pro Arg Glu Pro Gln Val Tyr Thr
            115                 120                 125
Leu Pro Pro Ser Arg Glu Glu Met Thr Lys Asn Gln Val Ser Leu Thr
130                 135                 140
Cys Leu Val Lys Gly Phe Tyr Pro Ser Asp Ile Ala Val Glu Trp Glu
145                 150                 155                 160
```

```
Ser Asn Gly Gln Pro Glu Asn Asn Tyr Asp Thr Thr Pro Pro Val Leu
            165                 170                 175

Asp Ser Asp Gly Ser Phe Phe Leu Tyr Ser Asp Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 25
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Tyr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
            165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 26
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 26

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Thr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 27
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

```
Thr Ile Ser Lys Ala Lys Gly Gln Pro Arg Glu Pro Gln Val Tyr Thr
            115                 120                 125

Leu Pro Pro Cys Arg Glu Glu Met Thr Lys Asn Gln Val Ser Leu Trp
        130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 28
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Cys Thr
        115                 120                 125

Leu Pro Pro Ser Arg Glu Glu Met Thr Lys Asn Gln Val Ser Leu Ser
    130                 135                 140

Cys Ala Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Val Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
```

<210> SEQ ID NO 29
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Phe Arg Pro Glu Val His Leu
        115                 120                 125

Leu Pro Pro Ser Arg Glu Glu Met Thr Lys Asn Gln Val Ser Leu Thr
    130                 135                 140

Cys Leu Ala Arg Gly Phe Tyr Pro Lys Asp Ile Ala Val Glu Trp Glu
145                 150                 155                 160

Ser Asn Gly Gln Pro Glu Asn Asn Tyr Lys Thr Thr Pro Ser Arg Gln
                165                 170                 175

Glu Pro Ser Gln Gly Thr Thr Thr Phe Ala Val Thr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Thr Ile Ser Leu
    210                 215                 220

Ser Pro Gly Lys
225

<210> SEQ ID NO 30
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn

```
                    50                  55                  60
Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
                115                 120                 125

Leu Pro Pro Ser Glu Glu Leu Ala Leu Asn Glu Leu Val Thr Leu
130                 135                 140

Thr Cys Leu Val Lys Gly Phe Tyr Pro Ser Asp Ile Ala Val Glu Trp
145                 150                 155                 160

Glu Ser Asn Gly Gln Glu Leu Pro Arg Glu Lys Tyr Leu Thr Trp Ala
                165                 170                 175

Pro Val Leu Asp Ser Asp Gly Ser Phe Phe Leu Tyr Ser Ile Leu Arg
                180                 185                 190

Val Ala Ala Glu Asp Trp Lys Lys Gly Asp Thr Phe Ser Cys Ser Val
                195                 200                 205

Met His Glu Ala Leu His Asn His Tyr Thr Gln Lys Ser Leu Asp Arg
                210                 215                 220

Ser Pro Gly Lys
225

<210> SEQ ID NO 31
<211> LENGTH: 225
<212> TYPE: PRT
<213> ORGANISM: Homo sapiens

<400> SEQUENCE: 31

Thr His Thr Cys Pro Pro Cys Pro Ala Pro Glu Leu Leu Gly Gly Pro
  1               5                  10                  15

Ser Val Phe Leu Phe Pro Pro Lys Pro Lys Asp Thr Leu Met Ile Ser
                 20                  25                  30

Arg Thr Pro Glu Val Thr Cys Val Val Val Asp Val Ser His Glu Asp
                 35                  40                  45

Pro Glu Val Lys Phe Asn Trp Tyr Val Asp Gly Val Glu Val His Asn
 50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
                115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
                180                 185                 190
```

Ser Arg Trp Gln Gln Gly Asn Val Phe Ser Cys Ser Val Met His Glu
            195                 200                 205

Ala Leu His Asn His Tyr Thr Gln Lys Ser Leu Ser Leu Ser Pro Gly
210                 215                 220

Lys
225

<210> SEQ ID NO 32
<211> LENGTH: 223
<212> TYPE: PRT
<213> ORGANISM: Homo sapiens

<400> SEQUENCE: 32

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 33
<211> LENGTH: 232
<212> TYPE: PRT
<213> ORGANISM: Homo sapiens

<400> SEQUENCE: 33

Glu Pro Lys Ser Cys Asp Thr Pro Pro Pro Cys Pro Arg Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Gln Phe Lys Trp Tyr Val
    50                  55                  60

```
Asp Gly Val Glu Val His Asn Ala Lys Thr Lys Pro Arg Glu Glu Gln
 65                  70                  75                  80

Tyr Asn Ser Thr Phe Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Thr Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Ser Gly Gln Pro Glu Asn Asn Tyr
                165                 170                 175

Asn Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Ile Phe
        195                 200                 205

Ser Cys Ser Val Met His Glu Ala Leu His Asn Arg Phe Thr Gln Lys
210                 215                 220

Ser Leu Ser Leu Ser Pro Gly Lys
225                 230

<210> SEQ ID NO 34
<211> LENGTH: 279
<212> TYPE: PRT
<213> ORGANISM: Homo sapiens

<400> SEQUENCE: 34

Glu Leu Lys Thr Pro Leu Gly Asp Thr Thr His Thr Cys Pro Arg Cys
  1               5                  10                  15

Pro Glu Pro Lys Ser Cys Asp Thr Pro Pro Cys Pro Arg Cys Pro
             20                  25                  30

Glu Pro Lys Ser Cys Asp Thr Pro Pro Cys Pro Arg Cys Pro Glu
         35                  40                  45

Pro Lys Ser Cys Asp Thr Pro Pro Cys Pro Arg Cys Pro Ala Pro
 50                  55                  60

Glu Leu Leu Gly Gly Pro Ser Val Phe Leu Phe Pro Lys Pro Lys
 65                  70                  75                  80

Asp Thr Leu Met Ile Ser Arg Thr Pro Glu Val Thr Cys Val Val Val
                 85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205
```

```
Ile Ala Val Glu Trp Glu Ser Ser Gly Gln Pro Glu Asn Asn Tyr Asn
        210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
                260                 265                 270

Leu Ser Leu Ser Pro Gly Lys
        275

<210> SEQ ID NO 35
<211> LENGTH: 229
<212> TYPE: PRT
<213> ORGANISM: Homo sapiens

<400> SEQUENCE: 35

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 36
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36
```

Thr His Thr Cys Pro Pro Cys Pro Ala Pro Glu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Gly Gly Ser Ala Gln Leu Glu Lys Glu Leu Gln Ala Leu Glu Lys
225                 230                 235                 240

Glu Asn Ala Gln Leu Glu Trp Glu Leu Gln Ala Leu Glu Lys Glu Leu
                245                 250                 255

Ala Gln Gly Ala Thr
            260

<210> SEQ ID NO 37
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Thr His Thr Cys Pro Pro Cys Pro Ala Pro Glu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu

```
                    85                  90                  95
Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
        130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Gly Gly Ser Ala Gln Leu Lys Lys Leu Gln Ala Leu Lys Lys
225                 230                 235                 240

Lys Asn Ala Gln Leu Lys Trp Lys Leu Gln Ala Leu Lys Lys Lys Leu
                245                 250                 255

Ala Gln Gly Ala Thr
            260

<210> SEQ ID NO 38
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Met Asp Ala Met Lys Arg Gly Leu Cys Cys Val Leu Leu Leu Cys Gly
1               5                   10                  15

Ala Val Phe Val Ser Pro
            20

<210> SEQ ID NO 39
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
```

```
                  85                  90                  95
Val Ala Thr Glu Glu Asn Pro Gln Val Tyr Phe Cys Cys Glu Gly
                100                 105                 110

Asn Phe Cys Asn Glu Arg Phe Thr His Leu Pro Glu Ala Gly Gly Pro
                115                 120                 125

Glu Val Thr Tyr Glu Pro Pro Thr Ala Pro Thr Gly Gly Gly Thr
            130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Asp Val Ser His Glu Asp Pro
            180                 185                 190

Glu Val Lys Phe Asn Trp Tyr Val Asp Gly Val Glu Val His Asn Ala
                195                 200                 205

Lys Thr Lys Pro Arg Glu Glu Gln Tyr Asn Ser Thr Tyr Arg Val Val
            210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Lys Glu Met Thr Lys Asn Gln Val Ser Leu Thr Cys
                275                 280                 285

Leu Val Lys Gly Phe Tyr Pro Ser Asp Ile Ala Val Glu Trp Glu Ser
        290                 295                 300

Asn Gly Gln Pro Glu Asn Asn Tyr Lys Thr Thr Pro Pro Val Leu Lys
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
                355                 360                 365

<210> SEQ ID NO 40
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
atggatgcaa tgaagagagg gctctgctgt gtgctgctgc tgtgtggagc agtcttcgtt      60
tcgcccggcg cctctgggcg tgggaggct gagacacggg agtgcatcta ctacaacgcc     120
aactgggagc tggagcgcac caaccagagc ggcctggagc gctgcgaagg cgagcaggac    180
aagcggctgc actgctacgc ctcctggcgc aacagctctg gcaccatcga gctcgtgaag    240
aagggctgct ggctagatga cttcaactgc tacgataggc aggagtgtgt ggccactgag    300
gagaaccccc aggtgtactt ctgctgctgt gaaggcaact tctgcaacga gcgcttcact    360
catttgccag aggctggggg cccggaagtc acgtacgagc cccccgac agcccccacc      420 ggtggtggaa ctcacacatg cccaccgtgc ccagcacctg aactcctggg gggaccgtca    480
```

```
gtcttcctct tccccccaaa acccaaggac accctcatga tctcccggac ccctgaggtc    540
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gcccccatcg agaaaaccat ctccaaagcc    780
aaagggcagc cccgagaacc acaggtgtac accctgcccc catcccggaa ggagatgacc    840
aagaaccagg tcagcctgac ctgcctggtc aaaggcttct atcccagcga catcgccgtg    900
gagtgggaga gcaatgggca gccggagaac aactacaaga ccacgcctcc cgtgctgaag    960
tccgacggct ccttcttcct ctatagcaag ctcaccgtgg acaagagcag gtggcagcag    1020
gggaacgtct tctcatgctc cgtgatgcat gaggctctgc acaaccacta cacgcagaag    1080
agcctctccc tgtctccggg taaa                                             1104
```

<210> SEQ ID NO 41
<211> LENGTH: 343
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240
```

```
Glu Pro Gln Val Tyr Thr Leu Pro Pro Ser Arg Lys Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Lys Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
                340

<210> SEQ ID NO 42
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Asp Ala Met Lys Arg Gly Leu Cys Cys Val Leu Leu Leu Cys Gly
1               5                   10                  15

Ala Val Phe Val Ser Pro Gly Ala Ser Gly Pro Arg Gly Val Gln Ala
            20                  25                  30

Leu Leu Cys Ala Cys Thr Ser Cys Leu Gln Ala Asn Tyr Thr Cys Glu
        35                  40                  45

Thr Asp Gly Ala Cys Met Val Ser Ile Phe Asn Leu Asp Gly Met Glu
    50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255
```

Val Tyr Thr Leu Pro Pro Ser Arg Glu Glu Met Thr Lys Asn Gln Val
                260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Asp Thr Thr Pro
290                 295                 300

Pro Val Leu Asp Ser Asp Gly Ser Phe Phe Leu Tyr Ser Asp Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly
        355

<210> SEQ ID NO 43
<211> LENGTH: 1065
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
atggatgcaa tgaagagagg ctctgctgtt gtgctgctgc tgtgtggagc agtcttcgtt      60
tcgcccggcg cctccgggcc ccggggggtc caggctctgc tgtgtgcgtg caccagctgc     120
ctccaggcca actacacgtg tgagacagat ggggcctgca tggtttccat tttcaatctg     180
gatgggatgg agcaccatgt gcgcacctgc atccccaaag tggagctggt ccctgccggg     240
aagcccttct actgcctgag ctcggaggac ctgcgcaaca cccactgctg ctacactgac     300
tactgcaaca ggatcgactt gagggtgccc agtggtcacc tcaaggagcc tgagcacccg     360
tccatgtggg gcccggtgga gaccggtggt ggaactcaca catgcccacc gtgcccagca     420
cctgaactcc tggggggacc gtcagtcttc ctcttccccc caaaacccaa ggacaccctc     480
atgatctccc ggacccctga ggtcacatgc gtggtggtgg acgtgagcca cgaagaccct     540
gaggtcaagt tcaactggta cgtggacggc gtggaggtgc ataatgccaa gacaaagccg     600
cgggaggagc agtacaacag cacgtaccgt gtggtcagcg tcctcaccgt cctgcaccag     660
gactggctga atggcaagga gtacaagtgc aaggtctcca acaaagccct cccagccccc     720
atcgagaaaa ccatctccaa agccaaaggg cagccccgag aaccacaggt gtacaccctg     780
cccccatccc gggaggagat gaccaagaac caggtcagcc tgacctgcct ggtcaaaggc     840
ttctatccca gcgacatcgc cgtggagtgg gagagcaatg ggcagccgga gaacaactac     900
gacaccacgc ctcccgtgct ggactccgac ggctccttct tcctctatag cgacctcacc     960
gtggacaaga gcaggtggca gcaggggaac gtcttctcat gctccgtgat gcatgaggct    1020
ctgcacaacc actacacgca gaagagcctc tccctgtctc cgggt                    1065

<210> SEQ ID NO 44
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
            35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Gly Thr His Thr Cys Pro
                100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
        130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
                180                 185                 190

Val Leu His Gln Asp Trp Leu Asn Gly Lys Glu Tyr Lys Cys Lys Val
            195                 200                 205

Ser Asn Lys Ala Leu Pro Ala Pro Ile Glu Lys Thr Ile Ser Lys Ala
        210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
                260                 265                 270

Glu Asn Asn Tyr Asp Thr Thr Pro Pro Val Leu Asp Ser Asp Gly Ser
            275                 280                 285

Phe Phe Leu Tyr Ser Asp Leu Thr Val Asp Lys Ser Arg Trp Gln Gln
        290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly
                325                 330

<210> SEQ ID NO 45
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
```

```
                20                  25                  30
Arg Glu Cys Ile Tyr Tyr Asn Ala Asn Trp Glu Leu Glu Arg Thr Asn
             35                  40                  45

Gln Ser Gly Leu Glu Arg Cys Glu Gly Glu Gln Asp Lys Arg Leu His
         50                  55                  60

Cys Tyr Ala Ser Trp Arg Asn Ser Ser Gly Thr Ile Glu Leu Val Lys
 65                  70                  75                  80

Lys Gly Cys Trp Leu Asp Asp Phe Asn Cys Tyr Asp Arg Gln Glu Cys
                 85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
            115                 120                 125

Glu Val Thr Tyr Glu Pro Pro Thr Ala Pro Thr Gly Gly Gly Thr
            130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
            195                 200                 205

Lys Thr Lys Pro Arg Glu Glu Gln Tyr Asn Ser Thr Tyr Arg Val Val
            210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Cys Arg Glu Glu Met Thr Lys Asn Gln Val Ser Leu Trp Cys
            275                 280                 285

Leu Val Lys Gly Phe Tyr Pro Ser Asp Ile Ala Val Glu Trp Glu Ser
            290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
            355                 360                 365

<210> SEQ ID NO 46
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gly Arg Gly Glu Ala Glu Thr Arg Glu Cys Ile Tyr Tyr Asn Ala Asn
1               5                   10                  15
```

-continued

```
Trp Glu Leu Glu Arg Thr Asn Gln Ser Gly Leu Glu Arg Cys Glu Gly
             20                  25                  30

Glu Gln Asp Lys Arg Leu His Cys Tyr Ala Ser Trp Arg Asn Ser Ser
         35                  40                  45

Gly Thr Ile Glu Leu Val Lys Lys Gly Cys Trp Leu Asp Asp Phe Asn
     50                  55                  60

Cys Tyr Asp Arg Gln Glu Cys Val Ala Thr Glu Glu Asn Pro Gln Val
 65                  70                  75                  80

Tyr Phe Cys Cys Cys Glu Gly Asn Phe Cys Asn Glu Arg Phe Thr His
                 85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Cys Arg Glu Glu Met Thr Lys
                245                 250                 255

Asn Gln Val Ser Leu Trp Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340
```

<210> SEQ ID NO 47
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Met Asp Ala Met Lys Arg Gly Leu Cys Cys Val Leu Leu Leu Cys Gly
  1               5                  10                  15

Ala Val Phe Val Ser Pro Gly Ala Ser Gly Pro Arg Gly Val Gln Ala
             20                  25                  30
```

```
Leu Leu Cys Ala Cys Thr Ser Cys Leu Gln Ala Asn Tyr Thr Cys Glu
            35                  40                  45

Thr Asp Gly Ala Cys Met Val Ser Ile Phe Asn Leu Asp Gly Met Glu
 50                  55                  60

His His Val Arg Thr Cys Ile Pro Lys Val Glu Leu Val Pro Ala Gly
 65                  70                  75                  80

Lys Pro Phe Tyr Cys Leu Ser Ser Glu Asp Leu Arg Asn Thr His Cys
                 85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
            115                 120                 125

Gly Gly Gly Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
            210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Cys Thr Leu Pro Pro Ser Arg Glu Glu Met Thr Lys Asn Gln Val
            260                 265                 270

Ser Leu Ser Cys Ala Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Val Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
            355

<210> SEQ ID NO 48
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ser Gly Pro Arg Gly Val Gln Ala Leu Leu Cys Ala Cys Thr Ser Cys
 1               5                  10                  15

Leu Gln Ala Asn Tyr Thr Cys Glu Thr Asp Gly Ala Cys Met Val Ser
```

```
                20                  25                  30
        Ile Phe Asn Leu Asp Gly Met Glu His His Val Arg Thr Cys Ile Pro
                    35                  40                  45

Lys Val Glu Leu Val Pro Ala Gly Lys Pro Phe Tyr Cys Leu Ser Ser
            50                  55                  60

Glu Asp Leu Arg Asn Thr His Cys Cys Tyr Thr Asp Tyr Cys Asn Arg
         65                  70                  75                  80

Ile Asp Leu Arg Val Pro Ser Gly His Leu Lys Glu Pro Glu His Pro
                            85                  90                  95

Ser Met Trp Gly Pro Val Glu Thr Gly Gly Thr His Thr Cys Pro
                        100                 105                 110

Pro Cys Pro Ala Pro Glu Leu Leu Gly Gly Pro Ser Val Phe Leu Phe
                    115                 120                 125

Pro Pro Lys Pro Lys Asp Thr Leu Met Ile Ser Arg Thr Pro Glu Val
                130                 135                 140

Thr Cys Val Val Val Asp Val Ser His Glu Asp Pro Glu Val Lys Phe
        145                 150                 155                 160

Asn Trp Tyr Val Asp Gly Val Glu Val His Asn Ala Lys Thr Lys Pro
                            165                 170                 175

Arg Glu Glu Gln Tyr Asn Ser Thr Tyr Arg Val Val Ser Val Leu Thr
                        180                 185                 190

Val Leu His Gln Asp Trp Leu Asn Gly Lys Glu Tyr Lys Cys Lys Val
                    195                 200                 205

Ser Asn Lys Ala Leu Pro Ala Pro Ile Glu Lys Thr Ile Ser Lys Ala
                210                 215                 220

Lys Gly Gln Pro Arg Glu Pro Gln Val Cys Thr Leu Pro Pro Ser Arg
        225                 230                 235                 240

Glu Glu Met Thr Lys Asn Gln Val Ser Leu Ser Cys Ala Val Lys Gly
                            245                 250                 255

Phe Tyr Pro Ser Asp Ile Ala Val Glu Trp Glu Ser Asn Gly Gln Pro
                        260                 265                 270

Glu Asn Asn Tyr Lys Thr Thr Pro Pro Val Leu Asp Ser Asp Gly Ser
                    275                 280                 285

Phe Phe Leu Val Ser Lys Leu Thr Val Asp Lys Ser Arg Trp Gln Gln
                290                 295                 300

Gly Asn Val Phe Ser Cys Ser Val Met His Glu Ala Leu His Asn His
        305                 310                 315                 320

Tyr Thr Gln Lys Ser Leu Ser Leu Ser Pro Gly Lys
                            325                 330

<210> SEQ ID NO 49
<211> LENGTH: 116
<212> TYPE: PRT
<213> ORGANISM: Homo sapiens

<400> SEQUENCE: 49

Ile Leu Gly Arg Ser Glu Thr Gln Glu Cys Leu Phe Phe Asn Ala Asn
        1               5                   10                  15

Trp Glu Lys Asp Arg Thr Asn Gln Thr Gly Val Glu Pro Cys Tyr Gly
                    20                  25                  30

Asp Lys Asp Lys Arg Arg His Cys Phe Ala Thr Trp Lys Asn Ile Ser
                35                  40                  45

Gly Ser Ile Glu Ile Val Lys Gln Gly Cys Trp Leu Asp Asp Ile Asn
            50                  55                  60
```

```
Cys Tyr Asp Arg Thr Asp Cys Val Glu Lys Lys Asp Ser Pro Glu Val
 65                  70                  75                  80

Tyr Phe Cys Cys Glu Gly Asn Met Cys Asn Glu Lys Phe Ser Tyr
                 85                  90                  95

Phe Pro Glu Met Glu Val Thr Gln Pro Thr Ser Asn Pro Val Thr Pro
            100                 105                 110

Lys Pro Pro Thr
        115

<210> SEQ ID NO 50
<211> LENGTH: 150
<212> TYPE: PRT
<213> ORGANISM: Rattus sp.

<400> SEQUENCE: 50

Met Thr Ala Pro Trp Ala Ala Leu Ala Leu Leu Trp Gly Ser Leu Cys
 1               5                  10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Pro
 50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Glu Gly Asn Phe Cys Asn Glu Arg
            100                 105                 110

Phe Thr His Leu Pro Glu Pro Gly Gly Pro Glu Val Thr Tyr Glu Pro
            115                 120                 125

Pro Pro Thr Ala Pro Thr Leu Leu Thr Val Leu Ala Tyr Ser Leu Leu
            130                 135                 140

Pro Ile Gly Gly Leu Ser
145                 150

<210> SEQ ID NO 51
<211> LENGTH: 150
<212> TYPE: PRT
<213> ORGANISM: Sus sp.

<400> SEQUENCE: 51

Met Thr Ala Pro Trp Ala Ala Leu Ala Leu Leu Trp Gly Ser Leu Cys
 1               5                  10                  15

Val Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Arg
 50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Glu Gly Asn Phe Cys Asn Glu Arg
            100                 105                 110
```

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
        130                 135                 140

Pro Ile Gly Gly Leu Ser
145                 150

<210> SEQ ID NO 52
<211> LENGTH: 150
<212> TYPE: PRT
<213> ORGANISM: Mus sp.

<400> SEQUENCE: 52

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
            115                 120                 125

Pro Pro Thr Ala Pro Thr Leu Leu Thr Val Leu Ala Tyr Ser Leu Leu
        130                 135                 140

Pro Ile Gly Gly Leu Ser
145                 150

<210> SEQ ID NO 53
<211> LENGTH: 150
<212> TYPE: PRT
<213> ORGANISM: Homo sapiens

<400> SEQUENCE: 53

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
130                 135                 140

Pro Ile Gly Gly Leu Ser
145                 150

<210> SEQ ID NO 54
<211> LENGTH: 150
<212> TYPE: PRT
<213> ORGANISM: Bos sp.

<400> SEQUENCE: 54

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
            35                  40                  45

Cys Glu Gly Glu Arg Asp Lys Arg Leu His Cys Tyr Ala Ser Trp Arg
        50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
130                 135                 140

Pro Val Gly Gly Leu Ser
145                 150

<210> SEQ ID NO 55
<211> LENGTH: 150
<212> TYPE: PRT
<213> ORGANISM: Xenopus sp.

<400> SEQUENCE: 55

Met Gly Ala Ser Val Ala Leu Thr Phe Leu Leu Leu Ala Thr Phe
1               5                   10                  15

Arg Ala Gly Ser Gly His Asp Glu Val Glu Thr Arg Glu Cys Ile Tyr
                20                  25                  30

Tyr Asn Ala Asn Trp Glu Leu Glu Lys Thr Asn Gln Ser Gly Val Glu
            35                  40                  45

Arg Leu Val Glu Gly Lys Lys Asp Lys Arg Leu His Cys Tyr Ala Ser
        50                  55                  60

Trp Arg Asn Asn Ser Gly Phe Ile Glu Leu Val Lys Lys Gly Cys Trp
65                  70                  75                  80

Leu Asp Asp Phe Asn Cys Tyr Asp Arg Gln Glu Cys Ile Ala Lys Glu
                85                  90                  95

Glu Asn Pro Gln Val Phe Phe Cys Cys Cys Glu Gly Asn Tyr Cys Asn
            100                 105                 110

Lys Lys Phe Thr His Leu Pro Glu Val Glu Thr Phe Asp Pro Lys Pro
        115                 120                 125

Gln Pro Ser Ala Ser Val Leu Asn Ile Leu Ile Tyr Ser Leu Leu Pro
130                 135                 140

```
Ile Val Gly Leu Ser Met
145                 150

<210> SEQ ID NO 56
<211> LENGTH: 150
<212> TYPE: PRT
<213> ORGANISM: Homo sapiens

<400> SEQUENCE: 56

Met Gly Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile
145                 150

<210> SEQ ID NO 57
<211> LENGTH: 154
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (8)..(8)
<223> OTHER INFORMATION: Thr, Ala or absent
<220> FEATURE:
<221> NAME/KEY: MOD_RES
<222> LOCATION: (121)..(121)
<223> OTHER INFORMATION: Pro, Ala, Val or Met

<400> SEQUENCE: 57

Met Thr Ala Pro Trp Ala Ala Xaa Leu Ala Leu Leu Trp Gly Ser Leu
1               5                   10                  15

Cys Ala Gly Ser Gly Arg Gly Glu Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Leu Cys Glu Gly Glu Gln Asp Lys Arg Leu His Cys Tyr Ala Ser
    50                  55                  60

Trp Arg Asn Ser Ser Gly Thr Ile Glu Leu Val Lys Lys Gly Cys Trp
65                  70                  75                  80

Leu Asp Asp Phe Asn Cys Tyr Asp Arg Gln Glu Cys Val Ala Thr Glu
                85                  90                  95

Glu Asn Pro Gln Val Tyr Phe Cys Cys Cys Glu Gly Asn Phe Cys Asn
```

```
                      100                 105                 110
Glu Arg Phe Thr His Leu Pro Glu Xaa Gly Gly Pro Glu Val Thr Tyr
            115                 120                 125

Glu Pro Lys Pro Pro Thr Ala Pro Thr Leu Leu Thr Val Leu Ala Tyr
        130                 135                 140

Ser Leu Leu Pro Ile Gly Gly Leu Ser Met
145                 150

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Gly Gly Ser
1               5

<210> SEQ ID NO 59
<211> LENGTH: 103
<212> TYPE: PRT
<213> ORGANISM: Homo sapiens

<400> SEQUENCE: 59

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu
            100

<210> SEQ ID NO 60
<211> LENGTH: 103
<212> TYPE: PRT
<213> ORGANISM: Unknown
<220> FEATURE:
<223> OTHER INFORMATION: Description of Unknown:
      Mole polypeptide

<400> SEQUENCE: 60

Ser Gly Pro Arg Gly Ile Gln Ala Leu Leu Cys Ala Cys Thr Ser Cys
1               5                   10                  15

Leu Gln Ala Asn Leu Thr Cys Glu Thr Asp Gly Ala Cys Met Val Ser
            20                  25                  30

Ile Phe Asn Leu Asp Gly Leu Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Phe Cys Asn Lys
65                  70                  75                  80
```

-continued

Ile Asp Leu Arg Val Pro Ser Gly His Val Lys Glu Pro Glu Arg Pro
                85                  90                  95

Ser Val Trp Gly Pro Val Glu
            100

<210> SEQ ID NO 61
<211> LENGTH: 103
<212> TYPE: PRT
<213> ORGANISM: Unknown
<220> FEATURE:
<223> OTHER INFORMATION: Description of Unknown:
      Hedgehog polypeptide

<400> SEQUENCE: 61

Ser Gly Pro Arg Gly Ile Gln Ala Leu Leu Cys Ala Cys Thr Ser Cys
1               5                   10                  15

Leu Gln Thr Asn Tyr Thr Cys Glu Thr Asp Gly Ala Cys Met Val Ser
                20                  25                  30

Ile Phe Asn Leu Asp Gly Met Glu His His Val Arg Thr Cys Ile Pro
            35                  40                  45

Lys Val Glu Leu Val Pro Ala Gly Lys Pro Phe Tyr Cys Leu Ser Ser
        50                  55                  60

Glu Asp Leu Arg Asn Thr His Cys Cys Tyr Thr Asp Phe Cys Asn Arg
65                  70                  75                  80

Ile Asp Leu Arg Val Pro Ser Gly His Pro Lys Glu Ser Glu Gln Ala
                85                  90                  95

Ser Met Trp Gly Pro Val Glu
            100

<210> SEQ ID NO 62
<211> LENGTH: 102
<212> TYPE: PRT
<213> ORGANISM: Gallus sp.

<400> SEQUENCE: 62

Ala Pro Gly Gly Ala Arg Ala Leu Thr Cys Leu Cys Ser Asp Cys Lys
1               5                   10                  15

Gln Ala Asn Ser Thr Cys Glu Thr Asp Gly Ala Cys Met Val Ser Val
                20                  25                  30

Phe Asn Leu Asp Gly Val Lys His His Val Arg Thr Cys Ile Pro Glu
            35                  40                  45

Ala Lys Leu Ile Pro Ala Gly Lys Pro Phe Tyr Cys Leu Ser Ser Glu
        50                  55                  60

Asp Leu Arg Asn Thr His Cys Cys Tyr Ser Asp Phe Cys Asn Lys Ile
65                  70                  75                  80

Asp Leu Met Val Pro Ser Gly His Leu Lys Asp Asn Glu Pro Pro Ser
                85                  90                  95

Ser Trp Gly Pro Val Glu
            100

<210> SEQ ID NO 63
<211> LENGTH: 103
<212> TYPE: PRT
<213> ORGANISM: Mus sp.

<400> SEQUENCE: 63

Ser Gly Pro Arg Gly Ile Gln Ala Leu Leu Cys Ala Cys Thr Ser Cys
1               5                   10                  15

Leu Gln Thr Asn Tyr Thr Cys Glu Thr Asp Gly Ala Cys Met Val Ser
            20                  25                  30

Ile Phe Asn Leu Asp Gly Val Glu His His Val Arg Thr Cys Ile Pro
            35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Ile Asp Phe Cys Asn Lys
65                  70                  75                  80

Ile Asp Leu Arg Val Pro Ser Gly His Leu Lys Glu Pro Ala His Pro
            85                  90                  95

Ser Met Trp Gly Pro Val Glu
            100

<210> SEQ ID NO 64
<211> LENGTH: 103
<212> TYPE: PRT
<213> ORGANISM: Sus sp.

<400> SEQUENCE: 64

Ser Gly Pro Arg Gly Ile Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
            35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Phe Cys Asn Lys
65                  70                  75                  80

Ile Asp Leu Arg Val Pro Ser Gly His Leu Lys Glu Pro Glu His Pro
            85                  90                  95

Ser Met Trp Gly Pro Val Glu
            100

<210> SEQ ID NO 65
<211> LENGTH: 103
<212> TYPE: PRT
<213> ORGANISM: Rattus sp.

<400> SEQUENCE: 65

Ser Gly Pro Arg Gly Ile Gln Ala Leu Leu Cys Ala Cys Thr Ser Cys
1               5                   10                  15

Leu Gln Thr Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
            35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Ile Asp Phe Cys Asn Lys
65                  70                  75                  80

Ile Asp Leu Arg Val Pro Ser Gly His Leu Lys Glu Pro Glu His Pro
            85                  90                  95

Ser Met Trp Gly Pro Val Glu
            100

<210> SEQ ID NO 66

<400> SEQUENCE: 66

000

<210> SEQ ID NO 67
<400> SEQUENCE: 67

000

<210> SEQ ID NO 68
<400> SEQUENCE: 68

000

<210> SEQ ID NO 69
<400> SEQUENCE: 69

000

<210> SEQ ID NO 70
<400> SEQUENCE: 70

000

<210> SEQ ID NO 71
<400> SEQUENCE: 71

000

<210> SEQ ID NO 72
<400> SEQUENCE: 72

000

<210> SEQ ID NO 73
<400> SEQUENCE: 73

000

<210> SEQ ID NO 74
<400> SEQUENCE: 74

000

<210> SEQ ID NO 75
<400> SEQUENCE: 75

000

<210> SEQ ID NO 76
<400> SEQUENCE: 76

000

<210> SEQ ID NO 77
<400> SEQUENCE: 77

000

<210> SEQ ID NO 78
<400> SEQUENCE: 78
000

<210> SEQ ID NO 79
<400> SEQUENCE: 79
000

<210> SEQ ID NO 80
<400> SEQUENCE: 80
000

<210> SEQ ID NO 81
<400> SEQUENCE: 81
000

<210> SEQ ID NO 82
<400> SEQUENCE: 82
000

<210> SEQ ID NO 83
<400> SEQUENCE: 83
000

<210> SEQ ID NO 84
<400> SEQUENCE: 84
000

<210> SEQ ID NO 85
<400> SEQUENCE: 85
000

<210> SEQ ID NO 86
<400> SEQUENCE: 86
000

<210> SEQ ID NO 87
<400> SEQUENCE: 87
000

<210> SEQ ID NO 88
<400> SEQUENCE: 88
000

<210> SEQ ID NO 89

<400> SEQUENCE: 89

000

<210> SEQ ID NO 90
<211> LENGTH: 344
<212> TYPE: PRT
<213> ORGANISM: Homo sapiens

<400> SEQUENCE: 90

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn Ser Ile Ser
305                 310                 315                 320

Glu Asp Thr Glu Glu Glu Glu Asp Glu Asp Gln Asp Tyr Ser Phe
                325                 330                 335

Pro Ile Ser Ser Ile Leu Glu Trp

<210> SEQ ID NO 91
<211> LENGTH: 317
<212> TYPE: PRT
<213> ORGANISM: Homo sapiens

<400> SEQUENCE: 91

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn
305                 310                 315

<210> SEQ ID NO 92
<211> LENGTH: 63
<212> TYPE: PRT
<213> ORGANISM: Homo sapiens

<400> SEQUENCE: 92

Gly Asn Cys Trp Leu Arg Gln Ala Lys Asn Gly Arg Cys Gln Val Leu

```
                1               5                   10                  15
            Tyr Lys Thr Glu Leu Ser Lys Glu Glu Cys Cys Ser Thr Gly Arg Leu
                            20                  25                  30

Ser Thr Ser Trp Thr Glu Glu Asp Val Asn Asp Asn Thr Leu Phe Lys
                            35                  40                  45

Trp Met Ile Phe Asn Gly Gly Ala Pro Asn Cys Ile Pro Cys Lys
                    50                  55                  60
```

<210> SEQ ID NO 93
<211> LENGTH: 25
<212> TYPE: PRT
<213> ORGANISM: Homo sapiens

<400> SEQUENCE: 93

```
Glu Thr Cys Glu Asn Val Asp Cys Gly Pro Gly Lys Lys Cys Arg Met
 1               5                   10                  15

Asn Lys Lys Asn Lys Pro Arg Cys Val
                20                  25
```

<210> SEQ ID NO 94
<211> LENGTH: 26
<212> TYPE: PRT
<213> ORGANISM: Homo sapiens

<400> SEQUENCE: 94

```
Lys Thr Cys Arg Asp Val Phe Cys Pro Gly Ser Ser Thr Cys Val Val
 1               5                   10                  15

Asp Gln Thr Asn Asn Ala Tyr Cys Val Thr
                20                  25
```

<210> SEQ ID NO 95
<211> LENGTH: 263
<212> TYPE: PRT
<213> ORGANISM: Homo sapiens

<400> SEQUENCE: 95

```
Met Arg Pro Gly Ala Pro Gly Pro Leu Trp Pro Leu Pro Trp Gly Ala
 1               5                   10                  15

Leu Ala Trp Ala Val Gly Phe Val Ser Ser Met Gly Ser Gly Asn Pro
                20                  25                  30

Ala Pro Gly Gly Val Cys Trp Leu Gln Gln Gly Gln Glu Ala Thr Cys
                35                  40                  45

Ser Leu Val Leu Gln Thr Asp Val Thr Arg Ala Glu Cys Cys Ala Ser
                50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
                100                 105                 110

Leu Gly Gly Arg Pro Arg Cys Glu Cys Ala Pro Asp Cys Ser Gly Leu
                115                 120                 125

Pro Ala Arg Leu Gln Val Cys Gly Ser Asp Gly Ala Thr Tyr Arg Asp
                130                 135                 140

Glu Cys Glu Leu Arg Ala Ala Arg Cys Arg Gly His Pro Asp Leu Ser
145                 150                 155                 160

Val Met Tyr Arg Gly Arg Cys Arg Lys Ser Cys Glu His Val Val Cys
                165                 170                 175
```

```
Pro Arg Pro Gln Ser Cys Val Val Asp Gln Thr Gly Ser Ala His Cys
            180                 185                 190

Val Val Cys Arg Ala Ala Pro Cys Pro Val Pro Ser Ser Pro Gly Gln
        195                 200                 205

Glu Leu Cys Gly Asn Asn Asn Val Thr Tyr Ile Ser Ser Cys His Met
    210                 215                 220

Arg Gln Ala Thr Cys Phe Leu Gly Arg Ser Ile Gly Val Arg His Ala
225                 230                 235                 240

Gly Ser Cys Ala Gly Thr Pro Glu Glu Pro Pro Gly Gly Glu Ser Ala
                245                 250                 255

Glu Glu Glu Glu Asn Phe Val
                260

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 96

His His His His His His
1               5
```